US007776523B2

(12) United States Patent
Garcia et al.

(10) Patent No.: US 7,776,523 B2

(45) Date of Patent: Aug. 17, 2010

(54) ENDOGENOUS RETROVIRUSES UP-REGULATED IN PROSTATE CANCER

(75) Inventors: Pablo D. Garcia, San Francisco, CA (US); Stephen F. Hardy, San Francisco, CA (US); Jaime Escobedo, Alamo, CA (US); Lewis T. Williams, Mill Valley, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 0 days.

(21) Appl. No.: 10/016,604

(22) Filed: Dec. 7, 2001

(65) Prior Publication Data

US 2010/0136522 A1 Jun. 3, 2010

Related U.S. Application Data

(60) Provisional application No. 60/251,830, filed on Dec. 7, 2000.

(51) Int. Cl.
*C12Q 1/70* (2006.01)
*C12Q 1/68* (2006.01)

(52) U.S. Cl. ................................................ 435/6; 435/5

(58) Field of Classification Search ................ 435/91.2, 435/6; 536/23.1, 23.72, 24.3, 24.33
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis et al. |
| 4,777,127 | A | 10/1988 | Suni et al. |
| 4,816,567 | A | 3/1989 | Cabilly et al. |
| 4,959,314 | A | 9/1990 | Mark et al. |
| 5,010,175 | A | 4/1991 | Rutter et al. |
| 5,124,246 | A | 6/1992 | Urdea et al. |
| 5,149,655 | A | 9/1992 | McCabe et al. |
| 5,206,152 | A | 4/1993 | Sukhatme |
| 5,219,740 | A | 6/1993 | Miller et al. |
| 5,422,120 | A | 6/1995 | Kim |
| 5,445,934 | A | 8/1995 | Fodor et al. |
| 5,530,101 | A | 6/1996 | Queen et al. |
| 5,556,752 | A | 9/1996 | Lockhart et al. |
| 5,578,832 | A | 11/1996 | Trulson et al. |
| 5,580,859 | A | 12/1996 | Felgner et al. |
| 5,593,839 | A | 1/1997 | Hubbell et al. |
| 5,599,695 | A | 2/1997 | Pease et al. |
| 5,631,734 | A | 5/1997 | Stern et al. |
| 5,707,829 | A | 1/1998 | Jacobs et al. |
| 5,800,992 | A | 9/1998 | Fodor et al. |
| 5,807,522 | A | 9/1998 | Brown et al. |
| 5,814,482 | A | 9/1998 | Dubensky, Jr. et al. |
| 5,858,723 | A | 1/1999 | Mueller-Lantzsch et al. |
| 5,939,598 | A | 8/1999 | Kucherlapati et al. |
| 6,747,137 | B1 | 6/2004 | Weinstock et al. |

FOREIGN PATENT DOCUMENTS

| | | |
|---|---|---|
| EP | 0345242 | 12/1989 |
| EP | 0505012 | 9/1992 |
| EP | 0509112 | 10/1992 |
| EP | 0524968 | 2/1993 |
| EP | 0689454 | 1/1996 |
| EP | 0721016 | 7/1996 |
| EP | 0835318 | 1/1997 |
| EP | 0799897 | 10/1997 |
| EP | 0735898 | 3/1999 |
| EP | 0761231 | 1/2000 |
| EP | 1074617 | 2/2001 |
| EP | 0785280 | 4/2003 |
| GB | 2200651 | 8/1988 |
| GB | 2220221 | 1/1990 |
| WO | WO 90/07936 | 7/1990 |
| WO | WO 90/11092 | 10/1990 |
| WO | WO 90/14837 | 12/1990 |
| WO | WO 91/02805 | 3/1991 |
| WO | WO 91/10741 | 7/1991 |
| WO | WO 91/14445 | 10/1991 |
| WO | WO 91/17823 | 11/1991 |
| WO | WO 92/02526 | 2/1992 |
| WO | WO 92/11033 | 7/1992 |
| WO | WO 93/25698 | 2/1993 |
| WO | WO 93/03769 | 3/1993 |
| WO | WO 93/10218 | 5/1993 |
| WO | WO 93/11230 | 6/1993 |
| WO | WO 93/13202 | 7/1993 |
| WO | WO 93/14778 | 8/1993 |
| WO | WO 93/19191 | 9/1993 |
| WO | WO 93/25234 | 12/1993 |

(Continued)

OTHER PUBLICATIONS

Barbulescu et al. Many human endogenous retrovirus K (HERV-K) proviruses are unique to humans. Current Biology (Aug. 1999) vol. 9, No. 861-868.*

Wang-Johanning et al. Detection of human endogenous retrovirus envelope, HERV-E 4-1, mRNA transcriptional activity in prostate adenocarcinoma by RT-PCR and in-situ hybridization. Proc. American Ass. Cancer Research (Mar. 1999) vol. 40, p. 424, #2801.*

Andersson et al. Differential expression of human endogenous retroviral sequences similar to mouse mammary tumor virus in normal peripheral blood mononuclear cells. AIDS Research and Human Retroviruses (1996) vol. 12, No. 9, pp. 833-840.*

Yin et al. Transcription of human endogenous retroviral sequences related to mouse MMTV in human breast and placenta: similar pattern in most malignant and nonmalignant breast tissues. AIDS Research and Hum Retroviruses (1997) vol. 13, No. Abstract only.*

(Continued)

*Primary Examiner*—Patrick J Nolan
*Assistant Examiner*—Louise Humphrey
(74) *Attorney, Agent, or Firm*—Mei Hong; Benjamin Spehlmann

(57) ABSTRACT

Human endogenous retroviruses of the HML-2 family show up-regulated expression in prostate tumors. This finding can be used in prostate cancer screening, diagnosis and therapy.

7 Claims, 61 Drawing Sheets

FOREIGN PATENT DOCUMENTS

| | | |
|---|---|---|
| WO | WO 94/02602 | 2/1994 |
| WO | WO 94/03622 | 2/1994 |
| WO | WO 94/12649 | 6/1994 |
| WO | WO 94/23697 | 10/1994 |
| WO | WO 94/28938 | 12/1994 |
| WO | WO 95/00655 | 1/1995 |
| WO | WO 95/07994 | 3/1995 |
| WO | WO 95/11984 | 5/1995 |
| WO | WO 95/13796 | 5/1995 |
| WO | WO 95/22058 | 8/1995 |
| WO | WO 95/30763 | 11/1995 |
| WO | WO 95/35505 | 12/1995 |
| WO | WO 96/17072 | 6/1996 |
| WO | WO 96/30498 | 10/1996 |
| WO | WO 96/33735 | 10/1996 |
| WO | WO 97/02357 | 1/1997 |
| WO | WO 97/25431 | 7/1997 |
| WO | WO 97/27317 | 7/1997 |
| WO | WO 97/29212 | 8/1997 |
| WO | WO 97/42338 | 11/1997 |
| WO | WO 98/24893 | 6/1998 |
| WO | WO 98/57659 | 12/1998 |
| WO | WO 99/11241 | 3/1999 |
| WO | WO 99/52549 | 10/1999 |
| WO | WO 00/07621 | 2/2000 |
| WO | WO 00/23105 | 4/2000 |
| WO | WO 00/62800 | 10/2000 |
| WO | WO 00/73801 | 12/2000 |
| WO | WO 01/21152 | 3/2001 |
| WO | WO 01/21207 | 3/2001 |
| WO | WO 01/42467 | 6/2001 |
| WO | WO 01/51623 | 7/2001 |
| WO | WO 01/57182 | 8/2001 |
| WO | WO 01/57270 | 8/2001 |
| WO | WO 01/57272 | 8/2001 |
| WO | WO 01/57274 | 8/2001 |
| WO | WO 01/57275 | 8/2001 |
| WO | WO 01/57276 | 8/2001 |
| WO | WO 01/57277 | 8/2001 |
| WO | WO 01/57278 | 8/2001 |
| WO | WO 01/60860 | 8/2001 |
| WO | WO 01/73032 | 10/2001 |
| WO | WO 01/75067 | 10/2001 |

OTHER PUBLICATIONS

Perkins et al. Breast Cancer in men. BMJ (2003) vol. 327, pp. 239-240.*
Stauffer et al. Digital expression profiles of human endogenous retroviral families in normal and cancerous tissues. Cancer Immunity (2004) vol. 4, pp. 1-18.*
Pascal et al. Correlation of mRNA and protein levels: Cell type-specific gene expression of cluster designation antigens in the prostate. BMC Genomics 2008, vol. 9, pp. 246-258.*
Guo et al. How is mRNA expression predictive for protein expression? A correlation study on human circulating monocytes. Acta Biochim Biophysica Sin (Shanghai). May 2008, vol. 40, No. 5, pp. 426-436.*
Chen et al. Discordant protein and mRNA expression in lung adenocarcinomas. Molecular and Cellular Proteomics 2002, vol. 1, pp. 304-313.*
Lichtinghagen et al. Different mRNA and protein expression of matrix metalloproteinases 2 and 9 and tissue inhibitor of metalloproteinases 1 in benign and malignant prostate tissue. European Urology 2002, vol. 42, pp. 398-406.*
Depil et al. Expression of a human endogenous retrovirus, HERV-K, in the blood cells of leukemia patients. Leukemia 2002, vol. 16, pp. 254-259.*
Herbst et al. Human endogenous retrovirus K transcripts in germ cell and trophoblastic tumors. APMIS 1998, vol. 106, pp. 216-220.*
Huang et al. Human endogenous retroviral pol RNA and protein detected and identified in the blood of individuals with schizophrenia. Schizophrenia Research 2006, vol. 83, pp. 193-199.*
Willer et al. Two Groups of Endogenous MMTV Related Retroviral env Transcripts Expressed in Human Tissues, Virus Genes 1997, vol. 15, No. 2, pp. 123-133.*
Mayer et al, XP002239083, (1999) Nature Genetics 21(3):257-258.
Huang et al, XP009009633, (1998) Oncogene 16(18):2311-19.
Löwer et al, XP002233322, (1996) Proc. Natl. Sci. USA 93(11):5177-84.
Magin et al, XP002239089, (2000) Virology 274(1):11-16.
Smith et al, XP009009588, (2001) American Journal of Human Genetics 69(4) Supplement:275.
Smith et al, XP009009589, (2001) Journal Of Urology 165(5) Supplement:136-7.
Wang-Johanning et al (2001) Clinical Cancer Research 7:1553-60.
Mariani-Costantini et al (1989) Journal of Virology 63(11) 4982-85.
Löwer et al (1996) Proc. Natl. Acad. Sci USA 93:5177-84.
Ono et al (1986) Journal of Virology 60(2):589-98.
Ono et al (1986) Journal of Virology 58(3):937-44.
Ono et al (1987) Journal of Virology 61(6):2059-62.
Shih et al (1991) Virology 182:495-502.
Löwer et al (1993) Proc. Natl. Acad. Sci USA 90:4480-84.
Boller et al (1993) Virology, 196:349-353.
Barbulescu et al (1999) Current Biology 9:861-868.
Mueller-Lantzsch et al (1993) Aids Research and Human Retroviruses 9(4):343-50.
Magin-Lachmann (2001) J. Virol. 75(21):10359-71.
McSharry (1999) Antiviral Res 43(1):1-21.
Schommer et al (1996) J Gen Virol 77:375-379.
Boese et al (2001) FEBS Lett 493(2-3):117-21.
Larsson (1989) Current Topics in Microbiology and Immunology 148:115 (1989).
Tönjes et al (1996) J. Aids Hum. Retrovir. 13 (Suppl 1): S261-S267.
Kuhelj et al (2001) J Biol Chem 276(20):16674-82.
Johnston et al (2001) Ann Neurol 50(4):434:42.
Hanahan et al (2000) Cell 100:57-70.
Genbank accession No. AB047240 (2003).
Sugimoto et al, Genomics (Mar. 2001) 72(2):137-44.
Andersson et al (1999) J. Gen. Virol. 80:255-260.
Töjes et al, XP002238923, (1999) J. Virol. 73(11):9187:9195.
Barbulescu et al, XP000953273, (1999) Current Biology, Current Science 9:861-68.
Mayer et al, XP009009741, (1997) Cytogenetics and Cell Genetics 79(1-2):157-61.
Löwer et al (1993) Virology 192:501-11.
Wang-Johanning et al, Proceedings of the American Association for Cancer Research 40:424 (1999).
Herbst et al (1996) American Journal of Pathology 149(5):1727-35.
Löwer et al (1995) Journal of Virology 69(1):141-9.
Mayer et al (1999) Nature Genetics 21:257-258.
Magin et al (1999) Journal of Virology 73(11):9496-9507.
Boese et al (2000) Oncogene 19:4328-36.
Berkhout et al (1999) Journal of Virology 73(3):2365-75.
Sverdlo (2000) BioEssays 22:161-71.
Seifarth et al (1998) Journal of Virology 72(10):8384:91.
Zsiros et al, (1998) Journal of General Virology 79:61-70.
Medstrand et al (1993) Journal of Virology 67(11):6778-87.
Medstrand et al, (1998) 72(12):9782-87.
Tönjes et al (1999) Journal of Virology 73(11):9187-195.
Urnovitz et al (1996) Clinical Microbiology Reviews 9(1):72-99.
Yang et al (1999) Proc. Natl. Acad. Sci. USA 96(23)13404-08.
Counterpart PCT Application, "PCT Notification of Transmittal of the International Search Report" (May 13, 2003).
Sauter, M. et al., "Human Endogenous Retrovirus K10: Expression of Gag Protein and Detection of Antibodies in Patients with Seminomas," Journal of Virology, vol. 69(1): 414-421 (Jan. 1995).
Goedert, J. et al., "High Prevalence of Antibodies against HERV-K10 in Patients with Testicular Cancer but not with AIDS," Cancer Epidemiology, Biomarkers & Prevention, vol. 8: 293-296 (Apr. 1999).

Kurdyukov, S. et al., "Full-sized HERV-K (HML-2) Human Endogenous Retroviral LTR Sequences on Human Chromosome 21: Map Locations and Evolutionary History," Gene, vol. 273(1): 51-61 (Jul. 2001).

Griffifths, D., "Minireview: Endogenous Retroviruses in the Human Genome Sequence," Genome Biology, vol. 2(6):reviews 1017.1-1017.5 (2001).

Tristem, M., "Identification and Characterization of Novel Human Endogenous Retrovirus Families by Phylogenetic Screening of the Human Genome Mapping Project Database," Journal of Virology, vol. 74(8): 3715-3730 (Apr. 2000).

Bussemakers, Marion J.G., et al., Biochemical and Biophysical Research Communications, vol. 182, No. 1, Jan. 15, 1992 pp. 318-324.

Lower, et al. "The viruses in all of us: Characteristics and biological significance of human endogenous retrovirus sequences" Proc. Natl. Acad. Sci. May 1996, 93: 5177-5184.

Magin-Lachmann et al. "Function requires interaction with a complex, folded RNA structure within its responsive element" 2001 J. Virol. 2001 75(21):10359-71.

McSharry, J.J. "Antiviral drug susceptibility assays: going with the flow," 1999 Antiviral Res 43(1):1-21.

Schommer et al. "Characterization of the human endogenous retrovirus K proteinase," 1996 J. Gen Virol. 77:375-379.

Boese et al. "The Rev/Rex homolog HERV-K cORF multimerizes via a C-terminal domain," 2001 FEBS Lett 493 (2-3):117-21.

Larsson, E. et al. "Human endogenous proviruses," (1989) Current Topics in Microbiology and Immunology 148:115.

Tönjes, R.R. et al. "HERV-K: the biologically most active human endogenous retrovirus family," 1996 J. Aids Hum. Retrovir. 13 (Suppl 1):S261-S267.

Kuhelj, R. et al. "Inhibition of human endogenous retrovirus-K10 protease in cell-free and cell-based assays," 2001 J. Biol Chem 276(20):16674-82.

Johnston, JB et al. "Monocyte activation and differentiation augment human endogenous retrovirus expression: implications for inflammatory brain diseases," 2001 Ann Neurol 50(4):434:42.

Hanahan, D. et al. "The hallmarks of cancer," 2000 Cell 100:57-70.

Genbank Accession No. AB047240 (2003).

Sugimoto et al., "Transcriptionally active HERV-K genes: identification, isolation and chromosomal mapping," Genomics (Mar. 2001) 72(2):137-44.

Andersson et al. "Diversity of Human Endogenour Retrovirus Class II-Like Sequences," 1999 Gen. Virol. 80:255-260.

Tönjes et al., "Genome-Wide Screening, Cloning, chromosomal Assignment, and Expression of Full-Length Human Endogenous Retrovirus Type K," 1999 J. Virol 73(11):9187-9195.

Barbulescu et al. "Many Human Endogenous Retrovirus K (HERV-K) Proviruses are Unique to Humans," Current Biology, Current Science 9:861-68.

Mayer J; Meese E; Mueller-Lantzsch N. Chromosomal assignment of human endogenous retrovirus K (HERV-K) env open reading frames.Cytogenetics and cell genetics 1997;79(1-2):157-61.

Mayer, J., Sauter, M., Racz, A., Scherer, D., Mueller-Lantzsch, N., Meese, E.,1999 An almost intact human endogenous retrovirus K on human chromosome 7. Nature Genetics 21, 257-258.

Huang, H. et al., "FRA7G extends over a broad region: coincidence of human endogenous retroviral sequences (HERV-H) and small polydispersed circular DNAs (spcDNA) and fragile sites," 1998 Oncogene 16(18):2311-19.

Ono, M. et al. "Stimulation of expression of the human endogenous retrovirus genome by female steroid hormones in human breast cancer cell line," T47D. J Virol. Jun. 1987; 61(6): 2059-2062.

Magin, et al. "Corf, the Rev/Rex Homologue of HTDV/HERV-K, Encodes an Arginine-Rich Nuclear Localization Signal That Exerts a trans-Dominant Phenotype When Mutated ," Virology, vol. 274, No. 1, Aug. 2000, pp. 11-16(6).

Smith et al. The American Society of Human Genetics, 51st Annual Meeting : Oct. 12-16, 2001, San Diego, California / 2001 program committee, Orr, Harry T, chair University of Chicago Press, 2001 69(4) p. 275.

Smith, "Human endogenous retrovirus HERV-K expression in prostate cancer," 2001 Journal of Urology, Baltimore, Maryland 165(5) Supplement: 136-7 pp. 136-137.

Wang-Johanning, F. et al. "Expression of human endogenous retrovirus K envelope transcripts in human breast cancer," 2001 Clin Cancer Res 7:1553-1560.

Mariani-Constantini, R. et al. "Ancestry of a human endogenous retrovirus family," 1989 J Virol. Nov. 1989; 63(11): 4982-4985.

Löwer, R. et al "The viruses in all of us: characteristics and biological significance of human endogenous retrovirus sequences," Proc Natl Acad Sci U S A. May 28, 1996;93(11):5177-84.

Ono, M. et al. "Nucleotide sequence of human endogenous retrovirus genome related to the mouse mammary tumor virus genome related to the mouse mammary tumor virus genome," 1986 Journal of Virology, 60(2):589-98.

Ono, M. et al. "Molecular cloning and long terminal repeat sequences of human endogenous retrovirus genes related to types A and B retrovirus genes," 1987 Journal of Virology 58(3):937-44.

Shih, A. et al. "Evolutionary implications of primate endogenous retroviruses," 1991 Virology, Jun; 182(2):495-502.

Löwer, R. et al. "Identification of human endogenous retroviruses with complex mRNA expression and particle formation," Proced. Nat'l Acad. Sci. USA May 15, 1993;90(10):4480-4.

Boller, K. et al. "Evidence that HERV-K is the endogenous retrovirus sequence that codes for the human teratocarcinoma-derived retrovirus HTDV," Virology. Sep. 1993;196(1):349-353.

Mueller-Lantzsch, N. et al. "Human endogenous retroviral element K10 (HERV-K10) encodes a full-length gag homologous 73-kDa protein and a functional protease. AIDS Res Hum Retroviruses," Apr. 1993;9(4):343-350.

Löwer, R. et al. "A general method for the identification of transcribed retrovirus sequences (R-U5 PCR) reveals the expression of the human endogenous retrovirus loci HERV-H and HERV-K in teratocarcinoma cells.Virology," Feb. 1993;192(2):501-11.

Wang-Johanning et al., 1999 Proceedings of the American Association for Cancer Research 40:424.

Herbst, H. et al. "Expression of human endogenous retrovirus K elements in germ cell and trophoblastic tumors. Am J Pathol," Nov. 1996; 149(5): 1727-1735.

Löwer, R. et al. "Identification of a Rev-related protein by analysis of spliced transcripts of the human endogenous retroviruses HTDV/HERV-K," J Virol. Jan. 1995;69(1):141-149.

Yang, J. "An ancient family of human endogenous retroviruses encodes a functional homolog of the HIV-1 Rev protein," Proc Natl Acad Sci U S A. Nov. 9, 1999;96(23):13404-8.

Magin, C. et al. "cORF and RcRE, the Rev/Rex and RRE/RxRE Homologues of the Human Endogenous Retrovirus Family HTDV/HERV-K," Journal of Virology, Nov. 1999, pp. 9496-9507, vol. 73, No. 11.

Boese, A. et al. "Human endogenous retrovirus protein cORF supports cell transformation and associates with the promyelocytic leukemia zinc finger protein," 2000 Oncogene 19: 4328-4336.

Berkhout, B. et al. "Identification of an active reverse transcriptase enzyme encoded by a human endogenous HERV-K retrovirus," 1999 J. Virol. 73:2365-2375.

Sverdlo, E. D. "Retroviruses and primate evolution." BioEssays. Feb. 2000;22(2):161-71.

Seifarth, W. et al. "Proviral structure, chromosomal location, and expression of HERV-K-T47D, a novel human endogenous retrovirus derived from T47D particles," J. Virol., Oct. 1998;72(10):8384-91.

Zsiros, J. et al. "Evolutionary relationships within a subgroup of HERV-K-related human endogenous retroviruses. The Journal of general virology," 1998;79 ( Pt 1) : 61-70.

Medstrand, P. et al. "Characterization of novel reverse transcriptase encoding human endogenous retroviral sequences similar to type A and type B retroviruses: differential transcription in normal human tissues," J Virol. Nov. 1993; 67(11): 6778-6787.

Medstrand, P et al. "Human-specific integrations of the HERV-K endogenous retrovirus family," Journal of virology 1998;72(12):9782-7.

Urnovitz, H. "Human endogenous retroviruses: nature, occurrence, and clinical implications in human disease. Clinical microbiology reviews," 1996;9(1):72-99.

Office Action for U.S. Appl. No. 10/497,786 dated Oct. 1, 2008.
De Parseval, "Human endogenous retroviruses: from infectious elements to human genes", Cytogenet Genome Res 110:318-332 (2005).
Mayer, "Human endogenous retroviruses in the primate lineage and their influence on host genomes" Cytogenet Genome Res 110:448-456 (2005).
Armbruester, "A Novel Gene from the Human Endogenous Retrovirus K Expressed in Transformed Cells", Clinical cancer research, vol. 8, 1800-1807, Jun. 2002.
Database EMBL, Nov. 6, 2001, Accession No. AAM75812.
Database EMBL, Oct. 12, 2001 Accession No. BI858348.
Database EMBL, Mar. 30, 1995, Accession No. X82271.
Office Action for Japanese Patent Application No. 2003-551280 dated Aug. 19, 2008, translated into English.
Viglianti, G., "Simian Immunodeficiency Virus displays complex Patterns of RNA Splicing" Journal of Virology, Sep. 1990, p. 4207-4216, vol. 64, No. 9.
Hatanaka, Masakazu, "ATL and AIDS", Nankodo Co., Ltd. 1994, pp. 93-103 (in Japanese, no translation available).
Office Action for U.S. Appl. No. 10/498,033 mailed Oct. 15, 2008.
Guinet, E., et al. "Do retroviruses preferentially integrate within highly plastic regions of the human genome?" Medical Hypotheses, (2003) 60(2) 293-297.
Alignment For Instant SEQ ID No. 55 ABG17449 Novel human diagnostic protein #17440.
Alignment For Instant SEQ ID No. 54 ABG19124 standard; protein; 1489 AA.
Supplementary European Search Report for EP Patent application No. 02807929.1 mailed Jun. 22, 2007.
Database Geneseq Mar. 26, 2001 "Human prostate cancer associated antigen nucleotide sequence SEQ ID:506." Accession No. GSN:AAF22927.
Database Geneseq Mar. 26, 2001 "Human prostate cancer associated antigen protein sequence SEQ ID No. 1220" Accession No. GSP:AAB63848.
Database EMBL Jun. 16, 1999 *Homo sapiens* genomic DNA, chromosome 22q11.1, clone KB1572G7 Accession No. AP000346.
Artamonova I., et al. "Nonrandom distribution of endogenous retroviral regulatory elements, HERV-KLTRS, on human Chr22" vol. 372, No. 3, May 2000 pp. 401-403.
Turner G., et al. "Insertional polymorphisms of full-length endogenous retroviruses in humans" Current Biology 2001 11;1531-1535.
Database Geneseq: ABV 21518 Sep. 13, 2002 Human prostate expression marker cDNA 21509—Integrated Biotechnological Information Services.
Database Geneseq: ABV22008 standard; Sep. 13, 2002 Human prostate expression marker cDNA 21999—Integrated Biotechnological Information Services.
Database Geneseq: ABV24390 standard: cDNA; 681 BP Sep. 16, 2002 Human prostate expression marker cDNA 24381.
Tomlins, Scott A. "Distinct classes of chromosomal rearrangements create oncogenic ETS gene fusions in prostate cancer" Nature vol. 448 Aug. 2007.
Dunham, I., "The DNA sequence of human chromosome 22" Nature vol. 402, Dec. 2, 1999 pp. 489-495.
Comments to the human chromosome 22 article, Nature 402, 489:1999 HERVd Oct. 5, 2001 Retrieved from http://herv.img.cas.cz/comments.
Reus, K., "Genomic Organization of the Human Endogenous Retrovirus HERV-K (HML-2.HOM) ERVK6) on Chromosome 7" Genomics 72, 314-320 (2001).
Slade, M., "Quantitative Polymerase Chain Reaction for the Detection of Micrometastases in Patients with Breast Cancer" Journal of clinical Oncology vol. 17, No. 3 Mar. 1999: pp. 870-879.
Hoon, D., "Detection of Occult Melanoma Cells in Blood with a Multiple-Marker Polymerase Chain Reaction Assay" Journal of Clinical Oncology, vol. 13, No. 8 Aug. 1995: pp. 2109-2116.
Yao, Kai-Ling , et al. "Reverse transcriptase-polymerase chain reaction (RT-PCR) to detect prostate cancer micrometastasis in the blood" Pienta, K.J. Diagnosis and Treatment of Genitourinary Malignancies, Copyright 1996. Cancer Treatment and Research 1996; vol. 88: 77-91.
Flockerzi, A., "Expression patterns of transcribed human endogenous retrovirus HERV-K(HML-2) loci in human tissues and the need for a HERV Transcriptome Project" BMC Genomics 2008 9:354.
Supplementary European Search Report for EP Patent Application No. 02786981.7 mailed Feb. 20, 2007.
Artamonova, I.I. et al., "Nonrandom Distribution of the Endogenous Retroviral Regulatory Elements HERV-K LTR on Human Chromosome 22," Doklady Biochemistry, vol. 372, 2000, pp. 87-89; translation, Shemyakin-Ovchinnikov Institute of Bioorganic Chemistry, Russian Academy of Sciences, Moscow, Russia.
Office Action dated Dec. 4, 2009 in U.S. Appl. No. 10/497,786, claiming priority to the present application.
Dunham, et al., (Nature (1999) 402: 489-495) alignment to SEQ ID 54 of U.S. Appl. No. 10/498,033, claiming priority to the present application.
Dunham et al., (Nature (1999) 402: 489-495) alignment to SEQ ID 55 of U.S. Appl. No. 10/498,033, claiming priority to the present application.
Giot et al., (U.S. Patent No. 6,753,314) alignment to SEQ ID 59 of U.S. Appl. No. 10/498,033, claiming priority to the present application.
Bandman et al. (WO200009709 A2) alignment to SEQ ID 61 of U.S. Appl. No. 10/498,033, claiming priority to the present application.
Barbulescu et al. (Curr. Biol. (1999) 9: 861-868) alignment to SEQ ID 64 of U.S. Appl. No. 10/498,033, claiming priority to the present application.
Chang et al., (WO9803192 A1) alignment to SEQ ID 67 of U.S. Appl. No. 10/498,033, claiming priority to the present application.
Office Action dated Jul. 1, 2009 in U.S. Appl. No. 10/497,786, claiming priority to the present application.
Office Action dated Jul. 7, 2009 in U.S. Appl. No. 10/498,033, claiming priority to the present application.
Office Action dated Apr. 28, 2010 in U.S. Appl. No. 10/498,033.
Seher et al., EMBL/GenBank database submission dated Nov. 1999.

* cited by examiner

```
                                  1                                                                              80
        ENV GENOMIC HERV MDA (1) ---------------------------------------------------------------ACATTTAAAGTTCTACA
    ENV GENOMIC HERV-K TAN. (1) ---------------------------------------------------------------ACATTTGAAGTTCTACA
        ENV GENOMIC AC025420 (1) ---------------------------------------------------------------ACATTTGAAGTTCTACA
        ENV GENOMIC AP000776 (1) ---------------------------------------------------------------ACATTTGAAGTTCTACA
         ENV GENOMIC HERV-K8 (1) --------------------------------------------------------------------------------
         ENV GENOMIC HERV-KI (1) ---------------------------------------------------------------ACATTTGAAGTTCTACA
         ENV HERV-K AF023261 (1) GGGGAGAGGTTTTGCTTGTGTTTCACCAGGAGAAAATCAGCTTCCTGTTTGGATACCCACTAGACATTTGAAGTTCTACA
            ENV GEN AL035086 (1) --------------------------------------------------------------------------------
        ENV GENOMIC AL035587 (1) ---------------------------------------------------------------AAATTTAAAGTTCTACA
        ENV GENOMIC AC012068 (1) ---------------------------------------------------------------------------CTACA
        ENV GENOMIC AF277315 (1) ------------------------------------------------------------------TTTAAAGTTCTACA
        ENV GENOMIC AF027650 (1) GGGGAGAGGTTTTGCTTGTGTTTCACCAGGAGAAAATCAGCTTCCTGTTTGGATACCCACTAGACATTTGA--TTCTACA
        ENV GENOMIC AC078899 (1) ---------------------------------------------------------------ACATTTGA--TTCTACA
        ENV GENOMIC HERV-KII (1) ---------------------------------------------------------------ACATTTGAAGTTCTACA
        ENV GENOMIC AC008813 (1) ----------------------------------------------------ATACCCACTAGACATTTAAAGTTCTACA
        ENV GENOMIC AC012309 (1) ------------------------------------------------------------TAGACATTTGAAGTTCTACA
        ENV GENOMIC AL121932 (1) ---------------------------------------------------------------ACATTTGAAGTTCTACA
        ENV GENOMIC AD000090 (1) ---------------------------------------------------------------ACATTTGAAGTTCTACA
           ENV GEN  AL160008 (1) --------------------------------------------------------------------------------
        ENV GENOMIC HEU32496 (1) ---GCGTAATCATTGAGGACAAGTCGACGAGAGATCCCGAGGACGTCTACAGTCAGCCTTACGACATTTGAAGTTCTACA
        ENV GENOMIC AC011467 (1) ------GGTTTTGCTTGTGTTTCACGAGGAGA-AAATCAGCTTCCTGTTTGGATGCCCACTAGACATTTGAAGTTCTACA
        ENV GENOMIC AF235103 (1) --------TTTTTCTTGTGTTTCACCAGGAGA-AAATCAGCTTCCTGTTTGGATACCCACTAGACATTTGAAGTTCTACA
        ENV GENOMIC AC026786 (1) --------TTTTGCTTGTGTTTAACCAGAAAATAAATCAGCTTCCAGTTTGGATACTTACAACTT---------------
        ENV GENOMIC AC034203 (1) ----------------------CACCAGGAGA-AAATCAGCTTCCTGTTTGGGTACCCACTAGACATTTGAAGTTCTACA
        ENV GENOMIC AC018809 (1) -----------------------------------------------------------------ATTTGAAGTTCTACA
ENV GENOMIC HERV-K102 AF164610 (1) ----------TTGCTTGTGTTTCACCAGGAGA-AAATCAGCTTCCTGTTTGGATACCCACTAGACATTTGAAGTTCTACA
   ENV GENOMIC FRAG. AF260253 (1) --------------------------------------------------------------------------------
                   CONSENSUS (1)                                                                ACATTTGAAGTTCTACA
```

FIG. 6-1

```
                                     161                                                                           240
ENV GENOMIC HERV MDA           (72) ------------CTCGCCAGGTAAACAAAATGGTGATATCAGAAGAACAGAAAAGTTGCCTTCCATCAAGGAAGCAGA
ENV GENOMIC HERV-K TAN.        (83) --------GTTGACTCACAAGATGAACAAAATGGTGACGTCAGAAGAACAGATGAAGTTGCCATCCACCAAGAAGGCAGA
ENV GENOMIC AC025420           (83) --------GTTGACTCACAAGATGAACAAAATGGTGACATCAGAA---CAGATGAAGTTGCCATCCACCAAGAAGGCAGA
ENV GENOMIC AP000776           (83) --------GTTGACTCACAAGATGAACAAAATGGTGACGTCAGAAGAACAGATGAAGTTGCCATCCACCAAGAAGGCAGA
ENV GENOMIC HERV-K8            (15) --------GTTGACTCACAAGATGAACAAAATGGTGACGTCAGAAGAACAGATGAAGTTGCCATCCACCAAGAAAGCAGA
ENV GENOMIC HERV-KI            (83) --------GTTGACTCACAAGATGAACAAAATGGTGACGTCAGAAGAAGAGATGAAGTTGCCATCCACCAAGAAGGCAGA
ENV HERV-K AF023261           (146) --------GTTGACTCACAAGATGAACAAAATGGTGACGTCAGAAGAACAGATGAAGTTGCCATCCACCAAGAAAGCAGA
ENV GEN AL035086                (1) --------------------------------------------------------------------------------
ENV GENOMIC AL035587           (83) --------ATCGACTCGCCAGGTAAATAAAATGGTGATATCAGAAGAACAGATGAAGTTGCCATCCACCAAGGAAGCGGA
ENV GENOMIC AC012068           (71) --------ATCACCTCGCCAGGTGAAGAAAATGGTGATATCAAAAGAACAGATGAAGTTGCCATCCACCAAGAAAGCGGA
ENV GENOMIC AF277315           (80) --------ATCGACTCGCCAGGTGAACAAAATGGTGGTATCAGAAGAACAGATGAAGTTGACATCCACCAAGGAAGTGGA
ENV GENOMIC AF027650          (144) --------ATTGACTCATAAGATGAAGAAAAAGGTCATGTCAGAAGAACAGATGAAGTTGCCTTCCACCAAGAAGACAGA
ENV GENOMIC AC078899           (81) --------ATTGACTCATAAGATGAAGAAAAAGGTCATGTCAGAAGAACAGATGAAGTTGCCATCCACCAAGAAGACAGA
ENV GENOMIC HERV-KII           (72) --------------------------------------------------------------------------------
ENV GENOMIC AC008813          (104) --------ATTGACTCACAAGATAAACAAAATGGTGATGTCAAAAAAACAGATGAAGTTGCCATCCACCACGAAGGCGGA
ENV GENOMIC AC012309           (86) --------ATCAACTCACAAGAT----AAAATGGTGATGTCAGAAGAATAGATGAAGTTGCCATTCACCAAGAAGGCAGA
ENV GENOMIC AL121932           (83) --------ATCGACTCACAAGATGAACAGAATGGTGATGTCAGAAGAATAGATGAAGTTGCCATCCACCAAGAAGACAAA
ENV GENOMIC AD000090           (88) CGAGAACCATCGACTCAGAAGATGAACAGAATGGTGATGTCAGAAGAACAGATGAAGTTGCCATCCACCAAGAAGGCAGA
ENV GEN  AL160008               (1) -----------------------------------------------ACAGATAAAGTTGTCATCCACCAAGAAAGCGGA
ENV GENOMIC HEU32496          (143) --------GTTGACTCACAGGATGAACAAAATGGTGACATCAGA---ACAGATGAAGTTGCCATCCACCAAGATGGCAGA
ENV GENOMIC AC011467          (128) --------------------------------------------------------------------------------
ENV GENOMIC AF235103          (142) --------ATCGACCCACCAGGTGAACAAAATGGTGATATCAGAAGAACAGATGAAGTTGCCATCCACCAAGAAAGCGGA
ENV GENOMIC AC026786           (58) -----------------------------------------------ACAAAAGAAGTTTCCATCTACCAAGAAAGCGGA
ENV GENOMIC AC034203          (123) --------ATCGACTCGCAGGATGAATAAAATGGTAATATCAGAAAAACAGATGAAATTGCCATCCACCAAAAAGGTGGA
ENV GENOMIC AC018809           (70) --------------------------------------------------------------------------------
ENV GENOMIC HERV-K102 AF164610(124) --------------------------------------------------------------------------------
ENV GENOMIC FRAG. AF260253      (1) --------------------------------------------------------------------------------
CONSENSUS                     (161)         T GACTCACAAGATGAA AAAATGGTGA  TCAGAAGAACAGATGAAGTTGCCATCCACCAAGAA GC GA
```

FIG. 6-3

```
                                         241                                                                            320
              ENV GENOMIC HERV MDA  (139) GTTGCCAATATAGGCACAATTAAAGAAGCTGACACAGTTAGCTAAAAAAAAAAGCCTAGAGAATACAAAGGTGACACCAA
        ENV GENOMIC HERV-K TAN.     (155) GCCGCCAACTTGGGCACAACTAAAGAAGCTGACGCAGTTAGCTACAAAATA---TCTAGAGAACACAAAGGTGACACAAA
              ENV GENOMIC AC025420  (152) GCCGCCGACTTGGGCACAACTAAAGAAGCTGACGCAGTTAGCTACAAAATA---TCTAGAGAACACAAAGGTGACACAAA
              ENV GENOMIC AP000776  (155) GCCGCCAACTTGGGCACAACTAAAGAAGCTGACGCAGTTAGCTACAAAATA---TCTAGAGAACACAAAGGTGACACAAA
               ENV GENOMIC HERV-K8  (87)  GCCGCCGACTTGGGCACAACTAAAGA-GCTGACGCAGTTAGCTACAAAATA---TCTAGAGAACACAAAGGTGACACAAA
               ENV GENOMIC HERV-KI  (155) GCCACCGACTTGGGCACAACTAAAGAAGCTGACACAGTTAGCTACAAAATA---TCTAGAGAACACAAAGGTGACACAAA
               ENV HERV-K AF023261  (218) GCCGCCGACTTGGGCACAACTAAAGAAGCTGACGCAGTTAGCTACAAAATA---TCTAGAGAACACAAAGGTGACACAAA
                  ENV GEN AL035086  (1)   ---------------------------------------------------------------CACAAAGGTGACACAAA
              ENV GENOMIC AL035587  (155) GCCACCGACTTGGGCCCAATTAAAGAAGCTGACACAGTTAGCTAAAAAAAG---CCTAAAGAACACAAGGGTAATGTGAA
              ENV GENOMIC AC012068  (143) GCCGCCGACCTGGGCCCAGCTAAAGAAGCTGACACAGTTAGCTGAAAAAAG---CCTGAAAAACATGAGGGTAACATAAA
              ENV GENOMIC AF277315  (152) GCCGCCGACCTGGGCCCAACTAAAGAAGTTGACACAGTTAGCTGAAAAAAG---CCTGAAGAAAACAAGGGTAACACAAA
              ENV GENOMIC AF027650  (216) GCCGCCGACTTGGGCACAATTAAAGAAGGTGACACCGTTAGCTAAAAAAAA--GCCTGGAGAACACAAAGGTGACACAAA
              ENV GENOMIC AC078899  (153) GCCGCCGACTTGGGCACAATTAAAGAAGGTGACACCGTTAGCTAAAAAAAA--GCCTGGAGAACACAAAGGTGACACAAA
              ENV GENOMIC HERV-KII  (72)  --------------------------------------------------------------------------------
              ENV GENOMIC AC008813  (176) GATGCCAACTTGGGCACAATTTAA-AAGCTGACACAGTTAGCTTAAAAAAG---CCTAGAGAACACAAAGGTGACACAAA
              ENV GENOMIC AC012309  (154) GCCGCCGACTTGGGCACAATTAAAGAAGCTGACACAGTTAGCTAAAAAAGG---CCTTGAGAACACAAAGGTGACACAAA
              ENV GENOMIC AL121932  (155) GCTGCTTGACTTGGGCACAATTAAAGAAGCTGACGCAGTTAGCTACAAAATG---TCTAGAGAACACAAAGGAGACACAAA
              ENV GENOMIC AD000090  (168) GCTGCTTGACTTGGGCACAATTAAAGAAGCTGACACAGTTAGCTACAAAATA---TCTAGAGAACACAAAGGTGACACAAA
                 ENV GEN  AL160008  (34)  GCCGCCGACTTGGGCACAATTAAAGAAGCTGACACAGTTAGCTGAAAAAAG---CCTAAAGAACACAAGGGTAATCCAAA
              ENV GENOMIC HEU32496  (212) GCCGCCGACTTGGGCACAACTAAAGAAGCTGACGCAGTTAGCTACAAAATA---TCTAGAGAACACAAAGGTGACACAAA
              ENV GENOMIC AC011467  (128) --------------------------------------------------------------------------------
              ENV GENOMIC AF235103  (214) GCCGCCAACCTGGGCCCAGCTAAAGAAGCTGACACAGTTAGCTGAAAAAAG---TCTGAAAAACACAAGGGTAACACAAA
              ENV GENOMIC AC026786  (91)  GCCGTCGACATGGGCCCAGCTAAAGAAGCTGACACAGTTAGCTGAAAAAAA--GCCTGGAAAACACAAGAGTAACACAAA
              ENV GENOMIC AC034203  (195) GCTGCCGACCTGGGCCCAGCTAAAGAAGCTGACACAGTTAGCTAAAAAAAG---CCTGGAAAACACAAGGGTAACACAAA
              ENV GENOMIC AC018809  (70)  --------------------------------------------------------------------------------
ENV GENOMIC HERV-K102 AF164610      (124) --------------------------------------------------------------------------------
      ENV GENOMIC FRAG. AF260253    (1)   --------------------------------------------------------------------------------
                         CONSENSUS  (241) GCCGCCGACTTGGGCACAA TAAAGAAGCTGACACAGTTAGCTA AAAA      CT GAGAACACAAAGGTGACACAAA
```

FIG. 6-4

```
                                      481                                                                        560
         ENV GENOMIC HERV MDA  (379)  AGATGTTAATAATAGTGCATGGG-TGCCTGGCCCCACAGATGACTGTTGCCCTGCCCAACCTGA---AGAAGGAATGATG
     ENV GENOMIC HERV-K TAN.   (392)  ATATGTTAATGATAGTGTATGGG-TACCTGGCCCCATAGATGATCGCTGCCCTGCCAAACCTGAGGAAGAAGGGATGATG
         ENV GENOMIC AC025420  (389)  ATATGTTAATGATAGTGTATGGG-TACATGGCCCCATAGATGATCGCTGCCCTGCCAAACCTGAGGAAGAAGGGATGATG
         ENV GENOMIC AP000776  (392)  ATATGTTAATGATAGTGTATGGG-TACCTGGCCCCATAGATGATCGCTGCCCTGCCAAACCTGAGGAAGAAGGGATGATG
          ENV GENOMIC HERV-K8  (291)  --------------------------------------------------------------------------------
          ENV GENOMIC HERV-KI  (392)  ATATGTTAATGATAGTGTATGGG-TACCTGGCCCCACAGATGATCGCTGCCCTGCCAAACCTGAGGAAGAAAGGATGATG
          ENV HERV-K AF023261  (455)  ATATGTTAATGATAGTGTATGGG-TACCTGGCCCCACAGATGATCACTGCCCTGCCAAACCTGAGGAAGAAGGGATGATG
             ENV GEN AL035086  (178)  ATATGTTAATAATAGTGCATGGG-TACCTGGCCCCACGGATGATCGTTGCCCTGCCCAACCCAAGGAAGAAGGAATGATG
         ENV GENOMIC AL035587  (392)  ATATGTTAATAATAGGGCATGGG-TACCAGGCCCCACAGACGATTGTTGCCCTGCCCAACCTAAAGAAGAAGGAATGATG
         ENV GENOMIC AC012068  (380)  ACATGTTAACAATAGTACATGGG-TACCAGACCCCACAGATGACCGTGGCCCTGCCCAACCTGAAGAAGAAGGAATGATG
         ENV GENOMIC AF277315  (389)  ATGTGTTAATAATAGTGCATGAG-TACCAGGCCCCACAGATGATTGTTGCCCTGCCCAACCTGAAAAAGAAGGAATGATG
         ENV GENOMIC AF027650  (454)  ATATGTTAATAATGGTGTATGGG-TACATGGCCCTACAGATGATCGTTGCCCTGCCAAACCCAAGGAAGAAGGAATGATG
         ENV GENOMIC AC078899  (391)  ATATGTTAATAATGGTGTATGGG-TACATGGCCCTACAGATGATCGTTGCCCTGCCAAACCCAAGGAAGAAGGAATGATG
         ENV GENOMIC HERV-KII  (100)  ATATGTTAATGATAGTGTATGGG-TACCTGGCCCCACAGATGATCGCTGCCCTGCCAAACCTGAGGAAGAAGGGATGATG
         ENV GENOMIC AC008813  (412)  ATACGTTAATAATAGTGTATGGG-TACCTGGCCCCACAGATGATCGTTGCCCTGCCAAACCTGAGGAAGAAGGAATGATG
         ENV GENOMIC AC012309  (391)  ATATGTTAATAACAGTGTATGGG-TACCTGGCCCCACAGATGATCACTGCCCTGCCAAACCTGAGGAAGAAGGAATGACG
         ENV GENOMIC AL121932  (389)  ATATGTTAATAATAGCGTGTGGC-TACCTGGCCCCACAGATGATTATTGCCCTGCCAAACCTGAGGAAGAAGGAATGATG
         ENV GENOMIC AD000090  (405)  ATATGTTAATGATAGTGTATGGG-TACCTGGTCCAACAGATGATCGTTGCCCTGCCAAACCTGAGGAAGAAGGGATGATG
             ENV GEN  AL160008 (271)  TTACGTTCATAGTAGTGTTTGGA-TGCCTGAGCCTACAGATTCTCGTGGGCCCTCTCACCCAGAGGAGGAAGGAATGTTA
         ENV GENOMIC HEU32496  (441)  --------------------------------------------------------------------------------
         ENV GENOMIC AC011467  (156)  ATATGTTAATGATAGTGTATGGG-TACATGGCCCCACAGATGATCGCTGCCCTGCCAAACCTGAGGAAGAAGGGATGATG
         ENV GENOMIC AF235103  (451)  ATATGTTAATAATAGTGCATGGG-TACCAGGCCCCACAGATGACCGTGGCCCTGCCCAACCTGAAGAAGAAGGAATGATG
         ENV GENOMIC AC026786  (329)  ATACGTTAATAACAGTGCATGGG-TACCAGGCCCCATGGATGACCGTGGCCCTGCCCAACCTGA---AGAAGGAATGATG
         ENV GENOMIC AC034203  (432)  ATATGTTAATAACAGTGTATGGG-TACCAGGCCCCACAGATAACCGTGGCCCTGCCCAACCTGAAGAAGAAGGAATGATG
         ENV GENOMIC AC018809  (98)   ATATGTTAATGATAGTGTATGGGGTACCTGGCCCCACAGATGATCGCTGCCCTGCCAAACCTGAGGAAGAAGGGATTATG
ENV GENOMIC HERV-K102 AF164610 (152)  ATATGTTAATGATAGTGTATGGG-TACCTGGACCCATAGATGATCGCTGCCCTGCCAAACCTGAGGAAGAAGGGATGATG
   ENV GENOMIC FRAG. AF260253  (1)    --------------------------------------------------------------------------------
                    CONSENSUS  (481)  ATATGTTAATAATAGTGTATGGG TACCTGGCCCCACAGATGATCGTTGCCCTGCCAAACCTGAGGAAGAAGGAATGATG
```

FIG. 6-7

```
                                          561                                                                            640
         ENV GENOMIC HERV MDA      (455) ACGAATATTTCCATTGGGTATCCTTATCCTCCTGTTTGCCTAGGGAAGGCACCAGGATGCTTAAT-GCCTACAACCCAAA
    ENV GENOMIC HERV-K TAN.        (471) ATAAATATTTCCATTGGGTATCATTATCCTCCTATTTGCCTAGGGAGAGCACCAGGATGTTTAAT-GCCTGCAGTCCAAA
         ENV GENOMIC AC025420      (468) ATAAATATCTCCATTGGGTATCATTATCCTCCTATTTGCCTAGGGAGAGCACCAGGATGTTTAAT-GCCTGCAGTCCAAA
         ENV GENOMIC AP000776      (471) ATAAATATTTCCATTGGGTATCGTTATCCTCCTATTTGCTTAGGGACAGCACCAGGATGTTTAAT-GCCTGCAGTCCAAA
          ENV GENOMIC HERV-K8      (291) --------------------------------------------------------------------------------
          ENV GENOMIC HERV-KI      (471) ATAAATATTTCCATTGGGTATCGTTATCCTCCTATTTGCCTAGGGAGAGCACCAGGATGTTTAAT-GCCTGCAGTCCAAA
          ENV HERV-K AF023261      (534) ATAAATATTTCCATTGGGTATCGTTATCCTCCTATTTGCTTAGGGAGAGCACCAGGATGTTTAAT-GCCTGCAGTCCAAA
             ENV GEN AL035086      (257) ATGATTATTTCCACTGGGTATTGTTATCCTCCTATTTGCCTGGGGAGGGCACCAGGATGCTTAAT-GCCTACAACCCAAA
         ENV GENOMIC AL035587      (471) ATAAATGTTTCCACTGGGTATCATTATCCTCCTATTTGCCTAGGGAAGGCACCAGGATGTTTAAT-GCCTACAACCCAAA
         ENV GENOMIC AC012068      (459) ATAAACATTTCCATTGGGTATCATTATCCTCCTATTTGTCTGGGAAAAGCACCAGGATGCTTAAT-GCCTACAAACCAAA
         ENV GENOMIC AF277315      (468) ATAAATATTTCCATTGGGTATCATTATCCTCCTATTTGCCTAGGGAAGGCACCAGGATATTTAAT-TCCTACAACCCAAA
         ENV GENOMIC AF027650      (533) ATAAATATCTCCACTGGATATCGCTATCCTCCTATTTGCCTAGGGAGAGCACTAGGATGTTTAAT-GCCTGCAATCCAAA
         ENV GENOMIC AC078899      (470) ATAAATATCTCCACTGGATATCGTTATCCTCCTATTTGCCTAGGGAGAGCACTAGGATGTTTAAT-GCCTGCAATCCAAA
         ENV GENOMIC HERV-KII      (179) ATAAATATTTCCATTGTGTATCGTTATCCTCCTATTTGCCTAGGGAGAGCACCAGGATGTTTAAT-GCCTGCAGTCCAAA
         ENV GENOMIC AC008813      (491) ATAAATATTTCCACTGGGTATCATTATCCTCCTATTTGCCTGGGGAGAGCACCAGGATGTTTAAT-GCCTGCAGTCAAAA
         ENV GENOMIC AC012309      (470) ATAAATATTTCTACTGGGTATCGTTATCCTCCTATTTGTCTAGGGAGAACACCAGGATGTTTAAT-GCCTACAATCCAAA
         ENV GENOMIC AL121932      (468) ATAAATATTTCCACTGGGTATTGTTATCCTCCTATTTGCCTAGGGAGAACACCAGGATGTTTAAT-GCCTGCAATCCAAA
         ENV GENOMIC AD000090      (484) ATAAATATTTTCATTGGGTATCATTATCCTCCTATTTGCCTGGGGAGAGCACCAGGATGTTTAAT-GCCTGCAGTCCAAA
             ENV GEN  AL160008     (350) ATAAATGTGTCCGTGGGTTATCAATTCCGCCCTGTTTGCATAGGGCTGGCTATCTGTTGCCTAAAAGGCTACCGACAAAC
         ENV GENOMIC HEU32496      (441) --------------------------------------------------------------------------------
         ENV GENOMIC AC011467      (235) ACAAATATTTCCACTGGGTATCATTATCCTCCTATTTGCCTAGGGAGAGCACTAGGATGCTTAAT-GCCTGCAGTCCAAA
         ENV GENOMIC AF235103      (530) ATAAACATTTCCATTGGGTATCATTATCCTCCTATTTGCCTGGGAAAAGCACCGGGATGCTTAAT-GCCTACAAACCAAA
         ENV GENOMIC AC026786      (405) ATAAACATTTCCATTGGGTATCATTATCCTCCTATTTGCCTGGAAAAAGCACCAGGATGCTTAAT-GCCTACAATCCAAA
         ENV GENOMIC AC034203      (511) ATAAACATTTCCATTGGGTATCATTATCCTCCTATTTGCTTGGGAAAAGCACCAGGATGCTTAAT-GCCTACTATCCAAA
         ENV GENOMIC AC018809      (178) ATAAATATTTCCACTGGGTATCGTTATCCTCCTATTTGCCTAGGGAGAGCACCAGGATGCTTAAT-GCCTGCAGTCCAAA
ENV GENOMIC HERV-K102 AF164610     (231) ATAAATATTTCCATTGGGTATCGTTATCCTCCTATTTGCCTAGGGAGAGCACCAGGATGTTTAAT-GCCTGCAGTCCAAA
    ENV GENOMIC FRAG. AF260253       (1) --------------------------------------------------------------------------------
                    CONSENSUS      (561) ATAAATATTTCCATTGGGTATC TTATCCTCCTATTTGCCTAGGGAGAGCACCAGGATGTTTAAT GCCTGCA TCCAAA
```

FIG. 6-8

```
                                           641                                                                             720
ENV GENOMIC HERV MDA               (534)  ATTGGTTGGTAGAAGTACCTACAGTCAGTGCTACCAGTAGATTTACTTATCACATGGTAAGTGGAATGTCACAGA-----
ENV GENOMIC HERV-K TAN.            (550)  ATTGGTTGGTAGAAGTACCTACTGTCAGTCCCATCTGTAGATTCACTTATCACATGGTAAGCGGGATGTCACTCAGGCCA
ENV GENOMIC AC025420               (547)  ATTGGTTGGTAGAAGTACCTACTGTCAGTCCCATCAGTAGATTCACTTATAACATGGTAAGCGGGATGTCACTCAGGCCA
ENV GENOMIC AP000776               (550)  ACTGGTTGGTAGAAGTACCTATTGTCAGTCCCATCAGTAGATTCACTTATCACATGGTAAGCGGGATGTCACTCAGGCCA
ENV GENOMIC HERV-K8                (291)  --------------------------------------------------------------------------------
ENV GENOMIC HERV-KI                (550)  ATTGGTTAGTAGAAGTACCTACTGTCAGTCCCATCAGTAGATTCACTTATCACATGGTAAGCGGGATGTCACTCAGGCCA
ENV HERV-K AF023261                (613)  ATTGGTTGGTAGAAGTACCTACTGTCAGTCCCATCAGTAGATTCACTTATCACATGGTAAGCGGGATGTCACTCAGGCCA
ENV GEN AL035086                   (336)  ATTGGTTGGTAGAAGTACCTACTGTCAGTGCCACCAGTGGATTTACTTATCACAGGGTAAGTGGAATGTCACTCAGGCCA
ENV GENOMIC AL035587               (550)  ACTGGTTGGTAGAAGTACCTACCGTCAGTGCCACCAGTAAATTTACTTATCACATGGTAAGTGGAATGTCACTCGGGCCA
ENV GENOMIC AC012068               (538)  ACTGGTTGGTAGAAGTACCTACTGTCAGTGCCACCAGTAAATTCACTTATCACATGGTAAGTGAAATGTCACTTGGGTCA
ENV GENOMIC AF277315               (547)  ATTGGTTGGTAGAAGTACCTACTGTCATTGCCAGCAATAGATTTACTTATCACATGGTAAGTGAAATGTCACTCGGGCCA
ENV GENOMIC AF027650               (612)  ATTGGTTGGTACAAGTACCTACTGTCAGTACCATCAGTAGATTCACTTATCACATGGTAAGGGGAATGTCACTCAGGCCA
ENV GENOMIC AC078899               (549)  ATTGGTTGGTACAAGTACCTACTGTCAGTACCATCAGTAGATTCACTTATCACATGGTAAGGGGAATGTCACTCAGGCCA
ENV GENOMIC HERV-KII               (258)  ATTGGTTGGTAGAAGTACCTACTGTCAGTCCTAACAGTAGATTCACTTATCACATGGTAAGCGGGATGTCACTCAGGCCA
ENV GENOMIC AC008813               (570)  ATTGGTTGGTAGAAGTACCTACTGTCGGTACCACCAGTAGATTCACTAATCACGCGGTAAGTGGAATGTCACTCAGGCCA
ENV GENOMIC AC012309               (549)  ATTGGTTGGTAGAAGTACTTACTTACTGTACCACCAGTAGATTCACTTATCACATGGTAAGCGGAATGTCACTCAGGCCA
ENV GENOMIC AL121932               (547)  ATTGGTTGGTAAACGTACCTACTTTCAGTACCACCAGTAGATTTACTTATCACATGGTAAGTGGAATGTCACTCAGGCCA
ENV GENOMIC AD000090               (563)  ATTGGTTGGTAGAAGTACCTACTGTCAGTCCCATCAGAAGATTCACTTATCACATGGTAAGCGGGATGTCGCTCAGGCCA
ENV GEN AL160008                   (429)  ATTGGCTAGTTAAGATTCCA------GGTCA--TAATCAAAGACCAGTATCC---------------TGTCATTTA-----
ENV GENOMIC HEU32496               (441)  --------------------------------------------------------------------------------
ENV GENOMIC AC011467               (314)  ATTGGTTGGTAGAAGTACCTACTGTCAGTCCCATCAGTAGATTCACTTATCACATGGTAAGTGGGATGTCACTCAGGCCA
ENV GENOMIC AF235103               (609)  ATTGGTTGGTAGAAGTACCTACTGTCAGTGCTACCAGTAAATTCACTTATCACA-GGTAAGTGAAATGTCACTCGGGTCA
ENV GENOMIC AC026786               (484)  ATTGGTTGGTATAAGTACCTACTGTCAATGCCACCAGTAAATTTACTTATCACATGGTAAGTGGAATGTCAATCGGGTCA
ENV GENOMIC AC034203               (590)  ATTGGTTGGTAGAAGTACCTACTGTCAGTGGCACCAGTAAATTTACTTATCATGTGATAAGTGGAATGTCACTCGGGTCA
ENV GENOMIC AC018809               (257)  ATTGGTTGTTAGAAGTACCTACTGTCAGTCCCATCAGTAGATTCACTTATCACACGGTAAGCAGGATGTCACTCAGGCCA
ENV GENOMIC HERV-K102 AF164610     (310)  ATTGGTTGGTAGAAGTACCTACTGTCAGTCCCATCAGTAGATTCACTTATCACATGGTAAGCGGGATGTCACTCAGGCCA
ENV GENOMIC FRAG. AF260253           (1)  --------------------------------------------------------------------------------
CONSENSUS                          (641)  ATTGGTTGGTAGAAGTACCTACTGTCAGT CCA CAGTAGATTCACTTATCACATGGTAAG GG ATGTCACTCAGGCCA
```

FIG. 6-9

```
                                        721                                                                            800
ENV GENOMIC HERV MDA            (609)   ----TAAATAATTTACAGGACCCTTCTTATCAAAGATCATTACAATGTAGGCCTAAGGGGAAGGCTTGCCCCAAGGAAAT
ENV GENOMIC HERV-K TAN.         (630)   CGGGTAAATTATTTACAAGACTTTTCTTATCAAAGATCATTAAAATTTAGACCTAAAGGGAAACCTTGCCCCAAGGAAAT
ENV GENOMIC AC025420            (627)   CGGGTAAATTATTTACAAGACTTTTCTTATCAAAGATCATTAAAATTTAGACCTAAAGGGAAACCTTGCCCCAAGGAAAT
ENV GENOMIC AP000776            (630)   CGGGTAAATTATTTACAAGACTTTTCTTATCAAAGATCATTAAAATTTAGACCTAAAGGGAAACCTTGCCCCAAGGAAAT
ENV GENOMIC HERV-K8             (291)   --------------------------------------------------------------------------------
ENV GENOMIC HERV-KI             (630)   CAGGTAAATTATTTACAAGACTTTTCTTATCAAAGATCATTAAAATTTAGACCTAAAAGGAAACCTTGCCTCAAGGAAAT
ENV HERV-K AF023261             (693)   CGGGTAAA------------------------------------------------------------------------
ENV GEN AL035086                (416)   CAGGTAAATTATTTGCAGGACCCTTCTTATCAAAGATGATTAAAATCTAGGCCTAAGGGGAAGCCTTGCCCCAAAGAAAT
ENV GENOMIC AL035587            (630)   CAGATAAATAATTTAGAGGACGCTTCTTATCAAAGATCATTAAAATCTGGGCCTAAGGGGAAGCCTTGCCCCAAGGAAAT
ENV GENOMIC AC012068            (618)   CAAATGAATAATTTACAGGACTCTTCGTATCAAAGATCATTAAGATTTAGGCCTAAGGGAAAATCTTGCCCCAAGGAAAT
ENV GENOMIC AF277315            (627)   CAGATAAATAATTTACAGGATCCTTCTTATCAAAGATCATTAAAATTTAGGCCTAAGAGGAAGCCTTGCCCCAAGGAAAT
ENV GENOMIC AF027650            (692)   CGGGTAAA------------------------------------------------------------------------
ENV GENOMIC AC078899            (629)   TGGGTAAATTATTTACAGGACTTTTCTTATCAAAGGTCATTAAAATTTAGGCCTAAAGGGAAACATTGCCCCAAGGAAAT
ENV GENOMIC HERV-KII            (338)   CGGGTAAATTATTTACAAGACTTTTCTTATCAAAGATCATTAAAATTTAGACCTAAAGGGAAACCTTGCCCCAAGGAAAT
ENV GENOMIC AC008813            (650)   CAGGTAAATTATTTACAAGACTTTTCTTATCAAAGATCATTAAAATTTAGGCCTAAAGGAAAGCCTTACCCCCAA-AAAA
ENV GENOMIC AC012309            (629)   CAGGTAAATTATTTACAGGACTTTTCTTATCAAAGATCATTAAAATGTAGGCCTAAAGGGAAACCTTGCCCCACGGAAAT
ENV GENOMIC AL121932            (627)   CAGGTAAATTATTTACAGGACTTTTCTTATCAAAGATCATTAAAATTTAGGCCTAAAGGGAAACCTTGCCCCAAGGAAAT
ENV GENOMIC AD000090            (643)   CAGGTAAATTATTTACAAGACTTTTCTTATCAAAGATCATTAAAATTTAGACCTAAAGGGAAACCTTGCCCCGAGGAAAT
ENV GEN AL160008                (482)   ----------TTTTACAA-AGTTTGGTTCAATTGGAACAGT----TTAAGCCCAGAAAAGAGAGGTGTCAACAAC----C
ENV GENOMIC HEU32496            (441)   --------------------------------------------------------------------------------
ENV GENOMIC AC011467            (394)   CGGGTAAATAATTTACAAGACTTTCCTTATCAAAGATCATTAAAATTTAGACCTAAAGGGCAACCTTGCCCCGAGGAAAT
ENV GENOMIC AF235103            (688)   CAAATAAATAATTTACAGGATTCTTCCTATAAAAGATCATTAAAATTTAGGCTTAAGGGAAAATCTTGCCCCAAGGAAAT
ENV GENOMIC AC026786            (564)   CAAATGAATAATTTACAGGATTCTTCCTATCAAAGATCATTAAAATTTAGGCCTAAGGGAAAACCATGCCCCAAGGAAAT
ENV GENOMIC AC034203            (670)   CAAATAAATAATTTACAAAATTCTTCCTATCAAAGATCATTAAAATTTAGGCCTAAAGGGAAACCATGCCCCGAGGAAAT
ENV GENOMIC AC018809            (337)   CGGGTAAATAATTTACAAGACTTTTCTTATCAAAGATCATTAAAATTTAGACCTAAAGGGAAACCTTGCCCCAAGAAAAT
ENV GENOMIC HERV-K102 AF164610  (390)   CGGGTAAATTATTTACAAGACTTTTCTTATCAAAGATCATTAAAATTTAGACCTAAAGGGAAACCTTGCCCCAAGGAAAT
ENV GENOMIC FRAG. AF260253        (1)   --------------------------------------------------------------------------------
CONSENSUS                       (721)   C GGTAAAT ATTTACA GACTTTTCTTATCAAAGATCATTAAAATTTAG CCTAAAGGGAAACCTTGCCCCAAGGAAAT
```

FIG. 6-10

```
                                      801                                                                           880
ENV GENOMIC HERV MDA          (685) TCCCAAAGAATCAAAAAGCCCAGAAGTCTTAGTCTGGGGAGAATGTGTGGCTGATACTGCAGTG-TAGTACAAAACAATG
ENV GENOMIC HERV-K TAN.       (710) TCCCAAAGAATCAAAAAATACAGAAGTTTTAGTTTGGGAAGAATGTGTGGCCAATAGTGCGGTGATATTACAAAACAATG
ENV GENOMIC AC025420          (707) TCCCAAAGAATCAAAAAATACAGAAGTTTTAGTTTGGGAAGAATGTGTGGCCAATAGTGTGGTGATATTACAAAACAATG
ENV GENOMIC AP000776          (710) TCCCAAAGAATCAAAAAATACAGAAGTTTTAGTTTGGGAAGAATGTGTGGCCAATAGTGCGGTGATATTACAAAACAATG
ENV GENOMIC HERV-K8           (291) --------------------------------------------------------------------------------
ENV GENOMIC HERV-KI           (710) TCCCAAAGAATCAAAAAATACAGAAGTTTTAGTTTAGGAAGAATGTGTGGCCAATAGTGCGGTGATATTACAAAACAATG
ENV HERV-K AF023261           (701) --------------------------------------------------------------------------------
ENV GEN AL035086              (496) TCCCAAAGGATCAAAAGGCCCAGAAGTTTTAGTTTGAGAAGAATGTGTGGCTGATAGGACGGTGATATTACAAAACAATG
ENV GENOMIC AL035587          (710) TCCCAAAGAATCAAAAAGCCCAGAAGCCTTAGTTTGGGAAGAATGTGTGGCTAATACTGCGGTGGTATTACAAAACAATG
ENV GENOMIC AC012068          (698) TCCAAAAGAATCAAAAGACCCAGAAGTCTTAGTTTGGGAAGAATGTGTGGCTGATACTGCAGTGGTACTACAAAACAATA
ENV GENOMIC AF277315          (707) TCCCAAAGAATCAAAAGGCCCAGAAGTCTTCAGTTTGGGAAGAATGTGTGGCTGATACTGCTGTGGTATTACAAAACAATG
ENV GENOMIC AF027650          (700) --------------------------------------------------------------------------------
ENV GENOMIC AC078899          (709) TCCCAAAGGATCAAAAGACATAGAAGTTTTAGTTTGGGAAGAATGTGTGGCCAAGAGTGCAGTGATATTACAAAATGATG
ENV GENOMIC HERV-KII          (418) TCCCAAAGAATCAAAAAATACAGAAGTTTTAGTTTGGGAAGAATGTGTGGCCAATAGTGCGGTGATATTACAAAACAATG
ENV GENOMIC AC008813          (729) TCCCAAAGGATCAAAAGACACAAAAGTTTTAGTTTGGGAAGAATGTGTGGCCAATAGTGCGGTGATATTACAAAATGATA
ENV GENOMIC AC012309          (709) TCCCAAGGTATCAAAAGACACAGAAGTTTTAGTTTAGGAAGAATGTGTGGCCAATAGTGTGGTGATATTACAAAATGATG
ENV GENOMIC AL121932          (707) TCCCAAAGGATCAAAAGACACAGAAGTTTTAGTTTTGGAAGAATGTGTGGCCAATAGAGCAGTGATATTACAAAACGATG
ENV GENOMIC AD000090          (723) TTCCAAAGGATCAAAAAATGTAGAAGCTTTAGTTTGGGAAGAATGTGTGGCCAATAGTGCAGTGATATTACAAAACAGTG
ENV GEN AL160008              (543) TCAATAATGGTCAAAGGATTTAGAAACATTGATTTGGAAGGATTGCATCACTGATCACACTGTGGTACTGCAAAATAATC
ENV GENOMIC HEU32496          (441) --------------------------------------------------------------------------------
ENV GENOMIC AC011467          (474) TCCCAAAGGATCAAAAAATACAGAAGTTTTAGTTTGGGAAGAATGTGTGGCCAATAGTTCAGTAATATTACAAAACAATG
ENV GENOMIC AF235103          (768) TCCAAAAGAATAAAAAGACTCAGAAGTCTTAGTTTGGGAAGAATGTGTGGCTGATACTGCGGTGGTATTACAAAACAATA
ENV GENOMIC AC026786          (644) TCCAAAAGAATCAAAAGACCCAGAAGTCTTAGTTTGGGAACAATGTGCGGCTGATACTGCAGTGGTACTACAAAACAATA
ENV GENOMIC AC034203          (750) TCCAAAAGAATCAAAAGACCCAAAAGTCTTAGTTTAGGAAGAATGTGTGGCTGATACTGCAGTGGTACTACAAAACAATA
ENV GENOMIC AC018809          (417) TCCCAAAGGATCAAAAAATACAGAAGCTTTAGTTTGGGAAGAATGTGTGGCCAATAGTGCGGTAATATTACAAAACAATG
ENV GENOMIC HERV-K102 AF164610 (470) TCCCAAAGAATCAAAAAATACAGAAGTTTTAGTTTGGGAAGAATGTGTGGCCAATAGTGCGGTGATATTACAAAACAATG
ENV GENOMIC FRAG. AF260253      (1) --------------------------------------------------------------------------------
CONSENSUS                     (801) TCCCAAAG ATCAAAA A CAGAAGTTTTAGTTTGGGAAGAATGTGTGGC AATAGTGC GTGATATTACAAAACAATG
```

FIG. 6-11

```
                                         881                                                                          960
           ENV GENOMIC HERV MDA   (764)  AATTTTGAACTATGATAGACTGGGTCCCTTGAGGCCAATTATATCATA-------------------------------ACTGTACA
      ENV GENOMIC HERV-K TAN.     (790)  AATTCGGAACTATTATAGATTGGGCACCTCGAGGTCAATTCTACCACA-------------------------------ATTGCTCA
         ENV GENOMIC AC025420     (787)  AATTTGGAACTATTATAGATTGGGCACCTCGAGGTCAATTCTACCACA-------------------------------ATTGCTCA
         ENV GENOMIC AP000776     (790)  AATTTGGAACTATTATAGATTGGGCACCTCGAGGTCAATTCTACCACA-------------------------------ATTGCTCA
          ENV GENOMIC HERV-K8     (291)  ---------------------------------------------------------------------------------------
          ENV GENOMIC HERV-KI     (790)  AATTCGGAACTATTATAGATTAGGCACCTCGAGGTCAATTCTACCACA-------------------------------ATTGCTCA
          ENV HERV-K AF023261     (701)  ---------------------------------------------------------------------------------------
             ENV GEN AL035086     (576)  AATTCGGAACCATTATAGATTGGGCACCTCGAGGTCAATTCTACTGCA-------------------------------ATTGCACA
         ENV GENOMIC AL035587     (790)  AATTTGGAACTACTATAATATTATATAATAGTTATATATTATATTATATTATATACAATTATATTATATATAATTGTATG
         ENV GENOMIC AC012068     (778)  AATTTGGAACTATTATAGACTAGGCCCCTCGAGGCCAATTATATTATG-------------------------------ACCGTATG
         ENV GENOMIC AF277315     (787)  AATTTGGAACTATTATAGACTGGGCCCCTCAAGGCCAATTATATTATG-------------------------------ATTGTACA
         ENV GENOMIC AF027650     (700)  ---------------------------------------------------------------------------------------
         ENV GENOMIC AC078899     (789)  AATTCAGAACTATTATAGATTGGGCAACTCAAGGTCAATTCTAACACA-------------------------------ATTGCACA
         ENV GENOMIC HERV-KII     (498)  AATTCGGAACTATTATAGATTGGGCACCTCGAGGTCAATTCTACCACA-------------------------------ATTGCTCA
         ENV GENOMIC AC008813     (809)  AATTCGGAACTATTATAGATTGGGCACCTCGAGGTCAATTCTACCACA-------------------------------ATTGCACA
         ENV GENOMIC AC012309     (789)  AATTTGGAACTATTATAGATTGGGCACCTCGAGGTCAATTCTACCACA-------------------------------ATTGCACA
         ENV GENOMIC AL121932     (787)  AATTTGGAACTGTTATAGATAGGGCACCTCGAGGTCAATTCTACCACA-------------------------------ATTGCACA
         ENV GENOMIC AD000090     (803)  AATTCCGAACTATTATAGATTGGGCACCTCGAGGTCAATTCTACCACA-------------------------------ATTGCACA
             ENV GEN  AL160008    (623)  CCTATGGAATCATCATTCATTGGG---------------------------------------------------------------
         ENV GENOMIC HEU32496     (441)  ---------------------------------------------------------------------------------------
         ENV GENOMIC AC011467     (554)  AATTCAGAACTATTATAGATTGGACATCTGGAGGTCAATTCTACCACA-------------------------------ATTGCTCA
         ENV GENOMIC AF235103     (848)  AATTTGGAACTATTATAAACTGGGCCGCTTGAGGCCAATTATATTATG-------------------------------ATAGTACA
         ENV GENOMIC AC026786     (724)  AATTTGGAACTATTATAGACTGGGCCCCTCGAGGCCAATTATATTATG-------------------------------ATTGTACG
         ENV GENOMIC AC034203     (830)  AGTTTGGAACTATTATAGACTGGGCCCCTCGAGGCCAGTTATATTATG-------------------------------ATTGTATG
         ENV GENOMIC AC018809     (497)  AATTTGGAACTATTATAGATTGGGCACCTTGAGGTCAATTCTACCACA-------------------------------ATTGCTCA
ENV GENOMIC HERV-K102 AF164610    (550)  AATTTGGAACTATTATAGATTGGGCACCTCGAGGTCAATTCTACCACA-------------------------------ATTGCTCA
     ENV GENOMIC FRAG. AF260253     (1)  ---------------------------------------------------------------------------------------
                        CONSENSUS (881)  AATTTGGAACTATTATAGATTGGGCACCTCGAGGTCAATTCTA CACA                                ATTGC CA
```

FIG. 6-12

```
                                   1121                                                                             1200
       ENV GENOMIC HERV MDA   (967) --------------------------------------------------------------------------------
   ENV GENOMIC HERV-K TAN.    (984) --------------------------------------------------------------------------------
       ENV GENOMIC AC025420   (981) --------------------------------------------------------------------------------
       ENV GENOMIC AP000776   (984) --------------------------------------------------------------------------------
         ENV GENOMIC HERV-K8  (291) --------------------------------------------------------------------------------
         ENV GENOMIC HERV-KI  (984) --------------------------------------------------------------------------------
         ENV HERV-K AF023261  (701) --------------------------------------------------------------------------------
            ENV GEN AL035086  (770) --------------------------------------------------------------------------------
       ENV GENOMIC AL035587  (1017) --------------------------------------------------------------------------------
       ENV GENOMIC AC012068   (981) --------------------------------------------------------------------------------
       ENV GENOMIC AF277315   (990) --------------------------------------------------------------------------------
       ENV GENOMIC AF027650   (700) --------------------------------------------------------------------------------
       ENV GENOMIC AC078899   (993) TTCAGCGAAGACTCCAAGATGGCAATCGCCACCTCGGATACCCTAACTCAGCATTTCCGGGTTCACCTTTCCTGTTCCCA
       ENV GENOMIC HERV-KII   (692) --------------------------------------------------------------------------------
       ENV GENOMIC AC008813  (1003) --------------------------------------------------------------------------------
       ENV GENOMIC AC012309   (983) --------------------------------------------------------------------------------
       ENV GENOMIC AL121932   (981) --------------------------------------------------------------------------------
       ENV GENOMIC AD000090   (997) --------------------------------------------------------------------------------
           ENV GEN  AL160008  (647) --------------------------------------------------------------------------------
       ENV GENOMIC HEU32496   (441) --------------------------------------------------------------------------------
       ENV GENOMIC AC011467   (683) --------------------------------------------------------------------------------
       ENV GENOMIC AF235103  (1051) --------------------------------------------------------------------------------
       ENV GENOMIC AC026786   (927) --------------------------------------------------------------------------------
       ENV GENOMIC AC034203  (1033) --------------------------------------------------------------------------------
       ENV GENOMIC AC018809   (691) --------------------------------------------------------------------------------
ENV GENOMIC HERV-K102 AF164610 (744) --------------------------------------------------------------------------------
    ENV GENOMIC FRAG. AF260253  (1) --------------------------------------------------------------------------------
                   CONSENSUS (1121)
```

FIG. 6-15

```
                                       1201                                                                            1280
       ENV GENOMIC HERV MDA    (967)   --------------------------------------------------------------------------------
   ENV GENOMIC HERV-K TAN.     (984)   --------------------------------------------------------------------------------
       ENV GENOMIC AC025420    (981)   --------------------------------------------------------------------------------
       ENV GENOMIC AP000776    (984)   --------------------------------------------------------------------------------
        ENV GENOMIC HERV-K8    (291)   --------------------------------------------------------------------------------
        ENV GENOMIC HERV-KI    (984)   --------------------------------------------------------------------------------
        ENV HERV-K AF023261    (701)   --------------------------------------------------------------------------------
           ENV GEN AL035086    (770)   --------------------------------------------------------------------------------
       ENV GENOMIC AL035587   (1017)   --------------------------------------------------------------------------------
       ENV GENOMIC AC012068    (981)   --------------------------------------------------------------------------------
       ENV GENOMIC AF277315    (990)   --------------------------------------------------------------------------------
       ENV GENOMIC AF027650    (700)   --------------------------------------------------------------------------------
       ENV GENOMIC AC078899   (1073)   CCACCCCGACTAACGCACATGCCCACTAGGGCGTGTCACACTCAGAAGTGTGAAACTCAACCGATCCCGCCCCTACCCCG
       ENV GENOMIC HERV-KII    (692)   --------------------------------------------------------------------------------
       ENV GENOMIC AC008813   (1003)   --------------------------------------------------------------------------------
       ENV GENOMIC AC012309    (983)   --------------------------------------------------------------------------------
       ENV GENOMIC AL121932    (981)   --------------------------------------------------------------------------------
       ENV GENOMIC AD000090    (997)   --------------------------------------------------------------------------------
          ENV GEN  AL160008    (647)   --------------------------------------------------------------------------------
       ENV GENOMIC HEU32496    (441)   --------------------------------------------------------------------------------
       ENV GENOMIC AC011467    (683)   --------------------------------------------------------------------------------
       ENV GENOMIC AF235103   (1051)   --------------------------------------------------------------------------------
       ENV GENOMIC AC026786    (927)   --------------------------------------------------------------------------------
       ENV GENOMIC AC034203   (1033)   --------------------------------------------------------------------------------
       ENV GENOMIC AC018809    (691)   --------------------------------------------------------------------------------
ENV GENOMIC HERV-K102 AF164610 (744)   --------------------------------------------------------------------------------
    ENV GENOMIC FRAG. AF260253   (1)   --------------------------------------------------------------------------------
                      CONSENSUS (1201)
```

FIG. 6-16

```
                                              1281                                                                          1360
        ENV GENOMIC HERV MDA      (967)   --------------------------------------------------------------------------------
     ENV GENOMIC HERV-K TAN.      (984)   --------------------------------------------------------------------------------
        ENV GENOMIC AC025420      (981)   --------------------------------------------------------------------------------
        ENV GENOMIC AP000776      (984)   --------------------------------------------------------------------------------
         ENV GENOMIC HERV-K8      (291)   --------------------------------------------------------------------------------
         ENV GENOMIC HERV-KI      (984)   --------------------------------------------------------------------------------
         ENV HERV-K AF023261      (701)   --------------------------------------------------------------------------------
            ENV GEN AL035086      (770)   --------------------------------------------------------------------------------
        ENV GENOMIC AL035587     (1017)   --------------------------------------------------------------------------------
        ENV GENOMIC AC012068      (981)   --------------------------------------------------------------------------------
        ENV GENOMIC AF277315      (990)   --------------------------------------------------------------------------------
        ENV GENOMIC AF027650      (700)   --------------------------------------------------------------------------------
        ENV GENOMIC AC078899     (1153)   ACCACTCCTCACCCAGCATCCATAAAAGCGCGCTGCACCTTTCGCACAGCGTGACTTCCCCTGGCGGACCAGTGAACCTC
        ENV GENOMIC HERV-KII      (692)   --------------------------------------------------------------------------------
        ENV GENOMIC AC008813     (1003)   --------------------------------------------------------------------------------
        ENV GENOMIC AC012309      (983)   --------------------------------------------------------------------------------
        ENV GENOMIC AL121932      (981)   --------------------------------------------------------------------------------
        ENV GENOMIC AD000090      (997)   --------------------------------------------------------------------------------
           ENV GEN  AL160008      (647)   --------------------------------------------------------------------------------
        ENV GENOMIC HEU32496      (441)   --------------------------------------------------------------------------------
        ENV GENOMIC AC011467      (683)   --------------------------------------------------------------------------------
        ENV GENOMIC AF235103     (1051)   --------------------------------------------------------------------------------
        ENV GENOMIC AC026786      (927)   --------------------------------------------------------------------------------
        ENV GENOMIC AC034203     (1033)   --------------------------------------------------------------------------------
        ENV GENOMIC AC018809      (691)   --------------------------------------------------------------------------------
ENV GENOMIC HERV-K102 AF164610    (744)   --------------------------------------------------------------------------------
   ENV GENOMIC FRAG. AF260253       (1)   --------------------------------------------------------------------------------
                  CONSENSUS      (1281)
```

FIG. 6-17

```
                                        1361                                                                          1440
          ENV GENOMIC HERV MDA   (967)  --------------------------------------------------------------------------------
     ENV GENOMIC HERV-K TAN.   (984)  --------------------------------------------------------------------------------
        ENV GENOMIC AC025420   (981)  --------------------------------------------------------------------------------
        ENV GENOMIC AP000776   (984)  --------------------------------------------------------------------------------
         ENV GENOMIC HERV-K8   (291)  --------------------------------------------------------------------------------
         ENV GENOMIC HERV-KI   (984)  --------------------------------------------------------------------------------
         ENV HERV-K AF023261   (701)  --------------------------------------------------------------------------------
            ENV GEN AL035086   (770)  --------------------------------------------------------------------------------
        ENV GENOMIC AL035587  (1017)  --------------------------------------------------------------------------------
        ENV GENOMIC AC012068   (981)  --------------------------------------------------------------------------------
        ENV GENOMIC AF277315   (990)  --------------------------------------------------------------------------------
        ENV GENOMIC AF027650   (700)  --------------------------------------------------------------------------------
        ENV GENOMIC AC078899  (1233)  ACCGGAGAGCTCAATAAAGAAGATTTTTGCCCTCTTTGTCTTGCCTCTTGGCCTTATTGATCCACGGTGCCTTTCCATTG
        ENV GENOMIC HERV-KII   (692)  --------------------------------------------------------------------------------
        ENV GENOMIC AC008813  (1003)  --------------------------------------------------------------------------------
        ENV GENOMIC AC012309   (983)  --------------------------------------------------------------------------------
        ENV GENOMIC AL121932   (981)  --------------------------------------------------------------------------------
        ENV GENOMIC AD000090   (997)  --------------------------------------------------------------------------------
           ENV GEN  AL160008   (647)  --------------------------------------------------------------------------------
        ENV GENOMIC HEU32496   (441)  --------------------------------------------------------------------------------
        ENV GENOMIC AC011467   (683)  --------------------------------------------------------------------------------
        ENV GENOMIC AF235103  (1051)  --------------------------------------------------------------------------------
        ENV GENOMIC AC026786   (927)  --------------------------------------------------------------------------------
        ENV GENOMIC AC034203  (1033)  --------------------------------------------------------------------------------
        ENV GENOMIC AC018809   (691)  --------------------------------------------------------------------------------
ENV GENOMIC HERV-K102 AF164610   (744)  --------------------------------------------------------------------------------
    ENV GENOMIC FRAG. AF260253     (1)  --------------------------------------------------------------------------------
                     CONSENSUS  (1361)
```

FIG. 6-18

```
                                        1521                                                                           1600
ENV GENOMIC HERV MDA           (1031)  TCAC-ACCACATTAGAATTTGTTCTGGAAATCAAGCTATAGGAACAAGAGATCGTAAGTCATATTATACTATCAACCTAA
ENV GENOMIC HERV-K TAN.        (1053)  TCAC-ACCACATTAGAATTTGGTCTGGAAATCAAACTTTAGAAACAAGAGATCGTAAGCCATTTTATACTATTGACCTGA
ENV GENOMIC AC025420           (1050)  TCAC-ACCACATTAGAATTTGGTCTGGAAATCAAACTTTAGAAACAAGAGATCGTAAGCCATTTTATACTGTTGACCTAA
ENV GENOMIC AP000776           (1053)  TCAC-ACCACATTAGAATTTGGTCTGGAAATCAAACTTTAGAAACAAGAGATCGTAAGCCATTTTATACTGTCGACCTAA
ENV GENOMIC HERV-K8             (291)  --------------------------------------------------------------------------------
ENV GENOMIC HERV-KI            (1053)  TCAC-ACCACATTAGAATTTGGTCTGGAAATCAAACTTTAGAAACAAGAGATCATAAGCCATTTTATACTATCGACCTAA
ENV HERV-K AF023261             (701)  --------------------------------------------------------------------------------
ENV GEN AL035086                (839)  TCGC-ACCACATTAGAATTTGGTCTGGAAATTAAGCTATAAAAACAAGAGATGGTAAGCCATCTTATACTATCGACCTAA
ENV GENOMIC AL035587           (1086)  TCGC-ACTACATTAGAATTTGGTCTGGAAATCAAGCTACAGAAACAAGAAATCGTAAGCCATATTATACTATCAACCTAA
ENV GENOMIC AC012068           (1046)  TCGT-ACCACATTAGAATTTGGTCTGGAAATCAAGTTATGGGAACAAGAAATCATAAGCCATATTATACTATTAACCTAA
ENV GENOMIC AF277315           (1059)  TCGC-ACCACATTAGAATTTGGTTTGGAAATGAAGCTATAGGAACAAGAGATCGTAAGCCATATTATACTATTAACCTAA
ENV GENOMIC AF027650            (700)  --------------------------------------------------------------------------------
ENV GENOMIC AC078899           (1393)  TCAT-ACCACATTAGAATTTGGTCTGGAAATCAAACTGTAGAAACAAGAGATCGTAAGCCATTTTATACTATCGACCTAA
ENV GENOMIC HERV-KII            (757)  TGAC-ACCACATTAGAATTTGGTCTGGAAATCAAACTTTAGAAACAAGAGATCGTAAGCCATTTTATACTATCGACCTAA
ENV GENOMIC AC008813           (1072)  TCAT-ACCGCATTAAAATTTGGTCTGGAAATCAAGCTATAGAAACAAGAGATCGTAAGCCATTTTATACTATCGACCTAA
ENV GENOMIC AC012309           (1052)  TCAT-ACCGCATTAGAATTTGATCTGGAAATCAAGCTATAGAAACAGGAGATCATAAGCCATTTTATACTATCGACCTAA
ENV GENOMIC AL121932           (1050)  TCATTACCATATTAGAATTTGGTCTAGAAATCAAGCTATAAAAACAAGAGATCATAAGCCGTGTTACACTATCAACCTAA
ENV GENOMIC AD000090           (1066)  TCAT-ACTACATTAGAATTTGGTCTGGAAATCAAACTTTAGAAACGAGA--TCATAAGCCATTTTATACTATCGACCTAA
ENV GEN  AL160008               (647)  --------------------------------------------------------------------------------
ENV GENOMIC HEU32496            (441)  --------------------------------------------------------------------------------
ENV GENOMIC AC011467            (727)  TCAT-ACCACATTAGGATTTGATCTGGAAATCAAACTTTAGAAACAAGAGATCATAAGCCATTTTATACTATCGATCTAA
ENV GENOMIC AF235103           (1120)  TCAT-ACCACATTAGAATTTGGTCTGGAAATCAAGTTATGGGAACAAGAAATCATAAACCATATTTTACTATTAACCTAA
ENV GENOMIC AC026786            (996)  TCCT-ACCACATTAAAATTTGGTATGGAAATCAAGTTATGGAAACAAGAAATCACAAGCCATATTACACTATTAACCTAA
ENV GENOMIC AC034203           (1102)  TCAT-ACCACACTAGAATTTGGTCTGAAAATCAAGTTATGGGAACAAAAAATCATAAGCCATATTATACTCTTAACCTAA
ENV GENOMIC AC018809            (760)  TCAT-ACCACATTAGGATTTGGTCTGGAAATCAAACTTTAGAAACAAGAGATCATCAGCCGTTTTATACTATCGACCTAA
ENV GENOMIC HERV-K102 AF164610  (813)  TCAC-ACCACATTAGAATTTGGTCTGGAAATCAAACTTTAGAAACAAGAGATTGTAAGCCATTTTATACTATCGACCTAA
ENV GENOMIC FRAG. AF260253        (1)  --------------------------------------------------------------------------------
CONSENSUS                      (1521)  TCA  ACCACATTAGAATTTGGTCTGGAAATCAA CT TAGAAACAAGAGATC TAAGCCAT TTATACTATC ACCTAA
```

FIG. 6-20

```
                                         1601                                                                           1680
         ENV GENOMIC HERV MDA    (1110)  ATTCCAGTCTGACAATTCCTTTGCAAAATTGTGTAAAACTCCCTTATATTGCTAGTTGTAGGAAAAACATAGTTATTAAA
    ENV GENOMIC HERV-K TAN.      (1132)  ATTCCAGTCTAACAGTTCCTTTACAAAGTTGCGTAAAGCCCCCTTATAT-GCTAGTTGTAGGAAATA--TAGTTATTAAA
         ENV GENOMIC AC025420    (1129)  ATTCCAGTCTAACAGTTCCTTTACAAAGTTGCGTAAAGCCCCCTTATAT-GCTAGTTGTAGGAAATA--TAGTTATTAAA
         ENV GENOMIC AP000776    (1132)  ATTCCAGTCTAACAGTTCCTTTACAAAGTTGCGTAAAGCCCCCTTATAT-GCTAGTTGTAGGAAATA--TAGTTATTAAA
          ENV GENOMIC HERV-K8     (291)  --------------------------------------------------------------------------------
          ENV GENOMIC HERV-KI    (1132)  ATTCCAGTCTAACACTTCCTTTACAAAGTTGCGTAAAGCCCCCTTATAT-GCTAGTTGTAGGAAATA--TAGTTATTAAA
          ENV HERV-K AF023261     (701)  --------------------------------------------------------------------------------
             ENV GEN AL035086     (918)  ATTCCAGTCTGACAATTCCTTTGCAAATTTGTGTAAAGCCCCCTTATAT-GCTAGTTGTAGGAAAAA--TAGTTATTAAC
         ENV GENOMIC AL035587    (1165)  ATTCCAATCTGACAATTCCTTTACAAAGTTGTGTAAAACCCCCTTATAT-GCTAGTTATAGAAAACA--TAGTTATTAAA
         ENV GENOMIC AC012068    (1125)  ATTACAATCTGACAATTCCTTTGCAAAGTTAGGTAAAACCCCCTTATAC-GCTAGTTGTAGGAAATA--TAGTTATTAAA
         ENV GENOMIC AF277315    (1138)  ATTCCAATCTGACAATTCCTTTGCAAAGTTGTGTAAGACCCCCTTATAT-GTTAGTTGTAGGAAAAA--TAGTTATTAAA
         ENV GENOMIC AF027650     (700)  --------------------------------------------------------------------------------
         ENV GENOMIC AC078899    (1472)  ATTCCAGTCTAACAGCTCCTTTACAAAGTTGTGTAAAGCCCCCTTATAT-GCTAGTTGTAGGAAATA--TAGTTATTAAA
         ENV GENOMIC HERV-KII     (836)  ATTCCAGTCTAACGGTTCCTTTACAAAGTTGCGTAAAGCCCTCTTATAT-GCTAGTTGTAGGAAATA--TAGTTATTAAA
         ENV GENOMIC AC008813    (1151)  ATTCCAGTCTAACAGTTCCTTTGCAAAGTTGTGTAAAGCCCCCTTATAT-GCTAGTTGTAGGAAATA--TAGTTATTAAA
         ENV GENOMIC AC012309    (1131)  ATTCAAGTCTAACGGTTTCTTTACAAAGTTGTATAAAGCGCCCTTATAT-GCTAGTTGTAGGAAATA--TAGTTATTAAA
         ENV GENOMIC AL121932    (1130)  ATTCCAGTCTAACGGTTCCTTCACAAAGTTGTGTAAAGCCCCCTTATAT-GCTAGTTGTAGGAAATA--TAGTTATTAAA
         ENV GENOMIC AD000090    (1143)  ATTCCAGTCTAACAGTTCCTTTACAAAGCTGTGTAAAGTCCCTTTATAT-GCTAGTTATAGGAAATA--TAGTTATTAAA
             ENV GEN  AL160008    (647)  --------------------------------------------------------------------------------
         ENV GENOMIC HEU32496     (441)  --------------------------------------------------------------------------------
         ENV GENOMIC AC011467     (806)  ATTCCAGTCTAACGGTTCCTTTACAAAGTTTCATAAAGCCCCCTTATAT-GCTAGTTGTAGGAAATA--TAGTTATTAAA
         ENV GENOMIC AF235103    (1199)  AATCCAATCCGACAATTCCTTTGCAAAGTTATGTAAAACCCCCTCATAT-GCTAGTTGTAGGAAACA--TAGTTATTAAA
         ENV GENOMIC AC026786    (1075)  ATTCCAATCTGACAATTCCTTTGCAAAGTTGTGTAAAACCCCCTTATAT-GCTAGTTGTAGGAAACA--TAGTTATTAAA
         ENV GENOMIC AC034203    (1181)  ATTCCAATCTGACAATTCCTTTGCAAAGTTGTGTAAAACCCCCTTATAT-GCTAGTTGTAGGAAACA--TAGTTATTAAA
         ENV GENOMIC AC018809     (839)  ATTCCAGTCTAACGGTTCCTTTACAAAGTTGTGTAAAGCCCCCTTATAT-GCTAGTTGTAGGAAATA--TAGTTATTAAA
ENV GENOMIC HERV-K102 AF164610    (892)  ATTCCAGTCTAACAGTTCCTTTACAAAGTTGCGTAAAGCCCCCTTATAT-GCTAGTTGTAGGAAATA--TAGTTATTAAA
   ENV GENOMIC FRAG. AF260253       (1)  --------------------------------------------------------------------------------
                    CONSENSUS    (1601)  ATTCCAGTCT ACA TTCCTTT CAAAGTTG GTAAAGCCCCCTTATAT GCTAGTTGTAGGAAATA  TAGTTATTAAA
```

FIG. 6-21

```
                                          1681                                                                           1760
          ENV GENOMIC HERV MDA   (1190)  CCTGATTCCCAAACCATA--ATCTGTGAAAATTGTGGAATGTTTACTTGCATTGATTTGACTTTTAATTGGCAGCACCGT
     ENV GENOMIC HERV-K TAN.     (1209)  CCAGACTCCCAGACTATA--ACCTGTGAAAATTGTAGATTGCTTACTTGCATTGATTCAACTTTTAATTGGCAACACCGT
          ENV GENOMIC AC025420   (1206)  CCAGACTCTCAAACTATA--ACCTGTGAAAATTGTAGATTGCTTACTTGCATTGATTCAACTTTTAATTGGCAACACCGT
          ENV GENOMIC AP000776   (1209)  CCAGACTCCCAGACTATA--ACCTGTGAAAATTGTAGATTGCTTACTTGCATTGATTCAACTTTTAATTGGCAACACCGT
            ENV GENOMIC HERV-K8  (291)   --------------------------------------------------------------------------------
            ENV GENOMIC HERV-KI  (1209)  CCAGACTCCCAGACTATA--ACCTGTGAAAATTGTAGATTGCTTACTTGCATTGATTCAACTTTTAATTGGCAACACCGT
            ENV HERV-K AF023261  (701)   --------------------------------------------------------------------------------
               ENV GEN AL035086  (995)   CCAGATTCCCAAACTATA--ACCTGTGAAAATTGTAGATTGTTTACTTGCATTGATTCAACTTTTAATTGGCAGCACTGT
          ENV GENOMIC AL035587   (1242)  CCAGATTCCCAAACTATA--ACCTGTGAAAACTGTAGATTGTTTACTTGCATTGATTTGACTTTTAATTGGCAGCGCCAT
          ENV GENOMIC AC012068   (1202)  CCAGATTCCCAAACTATA--ACCTGTGAAAACTGTAGATTGTTTACTTGCATTGATTCAACTTTCGACTGGCAGCATCAT
          ENV GENOMIC AF277315   (1215)  CCAGATTCCCAAACTATA--ACCTGTGAAAATTGTAGATTGTTTACTTGCATTGATTCGACTTCTGATTGGCAGCACCAT
          ENV GENOMIC AF027650   (700)   --------------------------------------------------------------------------------
          ENV GENOMIC AC078899   (1549)  CCAGACCCCCAAACTATA--ACCTGTGAAAATTGCAGATTGTTTACTAGCATTGATTCAACTTTTAATTGGCAGCACCGT
          ENV GENOMIC HERV-KII   (913)   CCAGACTCCCAAACTATA--ACCTGTGAAAATTGTAGATTGTTTACTTGCATTGATTCAACTTTTAATTGGCGGCACCGT
          ENV GENOMIC AC008813   (1228)  CCAGACTCCC----------------------------------------------------------------------
          ENV GENOMIC AC012309   (1208)  CCAGACTCCCAAACTATATAACCTGTGAAAATTGCAGATTGTTTACTTGCATTGATTCAACTTTCAATTGGCAGCACCGT
          ENV GENOMIC AL121932   (1207)  CCAGACTCCCAAACTATA--ACCTGTGAAAATTGCAGACTGTTTACTTGCATTGATTCGACTTTTAATTGGCAGCACTGT
          ENV GENOMIC AD000090   (1220)  CCAGACTCTCAAACTATA--ACCTGTGAAAACTGCAGATTGTTTACTTGCATTGATTCAACTTTTAATTGGCAACACCGT
              ENV GEN  AL160008  (647)   --------------------------------------------------------------------------------
          ENV GENOMIC HEU32496   (441)   --------------------------------------------------------------------------------
          ENV GENOMIC AC011467   (883)   CCAGACTTTCAAACTATA--ACCTGTGAAAACTGTAGATTGATTACTTACATTGATTCAACTTTTAATTGGCAGCACCGT
          ENV GENOMIC AF235103   (1276)  CCAGATTCCCAAACTATA--ACCTGTGAAAATTGTAGATTGTTTACTTGCATTGATTCAACTTTTGATTGGCAGCATCGT
          ENV GENOMIC AC026786   (1152)  CCAGATGTCCAAACTATA--ACCTGTGAAAATTGTAGATTGTTTACTTGCATTGATTCAACTTTTGATTGGCAGCATCGT
          ENV GENOMIC AC034203   (1258)  CCAGATTCCCAAACTATA--ACCTGTGAAAATTGTAGATTGTTTACTTGCATTGATTCAACTTTTGATTGGCAGCATCGT
          ENV GENOMIC AC018809   (916)   CCAGACTCTCAAACTATA--ACCTGTAAAAA--GTAGATAGTTTACTTGCATTGATTCGACTTTTAATCGGCAGCACCGT
ENV GENOMIC HERV-K102 AF164610   (969)   CCAGACTCCCAGACTATA--ACCTGTGAAAATTGTAGATTGCTTAGTTGCATTGATTCAACTTTTAATTGGCAACACCGT
     ENV GENOMIC FRAG. AF260253  (1)     --------------------------------------------------------------------------------
                      CONSENSUS  (1681)  CCAGA TCCCAAACTATA  ACCTGTGAAAATTGTAGATTGTTTACTTGCATTGATTCAACTTTTAATTGGCAGCACCGT
```

FIG. 6-22

| | | 1841 … 1920 |
|---|---|---|
| ENV GENOMIC HERV MDA | (1348) | TATTTTAACGGAAGTATTAAAAGGAATTCTAACTAGATCCAAAAGATTCATTTTTACTTTGATGGCAGTGATTATGGGCC |
| ENV GENOMIC HERV-K TAN. | (1367) | TATTTTGACTGAAGTATTAAAAGGTGTTTTAAATAGATCCAAAAGATTCATTTTTACTTTAATTGCAGTGATTATGGGAT |
| ENV GENOMIC AC025420 | (1364) | TATTTTGACTGAAGTATTAAAAGGTGTTTTAAATAGATCCAAAAGATTCATTTTTACTTTAATTGCAGTGATTATGGGAT |
| ENV GENOMIC AP000776 | (1367) | TATTTTGACTGAAGTATTAAAAGGTGTTTTAAATAGATCCAAAAGATTCATTTTTACTTTAATTGCAGTGATTATGGGAT |
| ENV GENOMIC HERV-K8 | (291) | -------------------------------------------------------------------------------- |
| ENV GENOMIC HERV-KI | (1367) | TATTTTGACTGAAGTATTAAAAGGTGTTTTAAATAGATCCAAAAGATTCATTTTTACTTTAATTGCAGTGATTATAGGAT |
| ENV HERV-K AF023261 | (701) | -------------------------------------------------------------------------------- |
| ENV GEN AL035086 | (1153) | TATTTTAACTGAAGTATTAAAAGGAGTTCTAAATAGATCCAAAAGATTCATTTTTACTTTGATTGCGGTGACTACGGGAT |
| ENV GENOMIC AL035587 | (1399) | TATTTTAACGGAAGTATTAAAAGGAATTCTAACTAGATCCAAAAGAT----TTTTACTTTGATTGCAGTGATTATGGGCC |
| ENV GENOMIC AC012068 | (1360) | TATCTTAACAGAAGTATTTAAAAGAGTTCTAACTAGATCTGAAACATTCATTTTTAGCTTGATTACAGTGATTATGGGTT |
| ENV GENOMIC AF277315 | (1373) | TATTTTAATGGAAGTATTAAAAGGAGTTCTAACTAGATCCAAAAGATTCATTTTTACTTTAATTGCAGTCATTATGGGTC |
| ENV GENOMIC AF027650 | (700) | -------------------------------------------------------------------------------- |
| ENV GENOMIC AC078899 | (1707) | TATTTTGACTGAGGTATTAAAAGACATTTTAAATAGATCCAAAAGATTCATTTTTACTTTAATTGCAGTGATTATGGGG- |
| ENV GENOMIC HERV-KII | (1071) | TATTTTGACTGAAGTATTAAAAGACATTTTAAATAGATCCAAAAGATTCATTTTTACCTTAATTGCAGTGATTATGGGAT |
| ENV GENOMIC AC008813 | (1238) | -------------------------------------------------------------------------------- |
| ENV GENOMIC AC012309 | (1368) | TATTTTGACTGAAGTATTAAAAGTCATTTTAAATAGATCCAAAAGATTCATTTTTACTTTAATTGCAGTGATTATGGGAT |
| ENV GENOMIC AL121932 | (1365) | TATTTTGACTGAAGTATTAAAAGGCATTTTAAATAGATCCAAAAGATTCGTTTTTACTTTAATTGCAGTGCTTATCGGAT |
| ENV GENOMIC AD000090 | (1378) | TATTTTGACTGAAGTATTAAAAGGCGTTTTAAATAGATCCAAAAGATTCATTTTTACTTTAATTACAGTGATTATGGGAT |
| ENV GEN AL160008 | (647) | -------------------------------------------------------------------------------- |
| ENV GENOMIC HEU32496 | (441) | -------------------------------------------------------------------------------- |
| ENV GENOMIC AC011467 | (1041) | TATTTTGACTGAAGTATTAAAAGGCATTTTAAATAGATCCAAAAGATTCATTTTTACTTTAATTGCAGTGATTATGGGAT |
| ENV GENOMIC AF235103 | (1434) | TATCTTAACAGAAGTATTAAAAGGAGTTCTAACTAGATCTAAAAGATTCATTTTTACTTTAATTGCAGTGATTATGGGTC |
| ENV GENOMIC AC026786 | (1310) | TATCTTAACAGAAGTATTAAAAGGAGTTCTAACTAAATCTAAAAGATTCATTTTTACTTTGATTGCAGTGATTATGGGTC |
| ENV GENOMIC AC034203 | (1403) | -------------------------------------------------------------------------------- |
| ENV GENOMIC AC018809 | (1072) | TATTTTGACTGAA-TATTAAAAGCCATTTTAAATAGATCCAAAAGATTCATTTTTACTTTAATTACAGTGCTTATGGGAT |
| ENV GENOMIC HERV-K102 AF164610 | (1127) | TATTTTGACTGAAGTATTAAAAGGTGTTTTAAATAGATCCAAAAGATTCATTTTTACTTTAATTGCAGTGATTATGGGAT |
| ENV GENOMIC FRAG. AF260253 | (1) | -------------------------------------------------------------------------------- |
| CONSENSUS | (1841) | TATTTT AC GAAGTATTAAAAGG  TT TAA TAGATCCAAAAGATTCATTTTTACTTTAATTGCAGTGATTATGGG |

FIG. 6-24

```
                                          2001                                                                         2080
        ENV GENOMIC HERV MDA    (1508) TGGCAAAAGAA-TTCCTCAAAATTGTGGAATTCTCAGATCCAA-ATAGATCAAAAATTGGCAAACCAAATTAATGATCTT
     ENV GENOMIC HERV-K TAN.    (1527) TGGCAAAAAAA-TTCTACAAGATTGTGGAATTCACA-ATCTAGTATTGATCAAAAATTGGCAAATCAAATTAATGATCTT
        ENV GENOMIC AC025420    (1524) TGGCAAAAAAA-TTCTACAAGATTGTGGAATTCACA-ATCTAGTATTGATCAAAAATTGGCAAATCAAATTAATGATCTT
        ENV GENOMIC AP000776    (1527) TGGCAAAAAAA-TTCTACAAGATTGTGGAATTCACA-ATCTAGTATTGATCAAAAATTGGCAAATCAAATTAATGATCTT
         ENV GENOMIC HERV-K8     (291) --------------------------------------------------------------------------------
         ENV GENOMIC HERV-KI    (1527) TGGCAAAAAAA-TTCTACAAGATTGTGGAATTCACA-ATCTAGTATTGATCAAAAATTGGCAAATCAAATTAATGATCTT
         ENV HERV-K AF023261     (701) --------------------------------------------------------------------------------
            ENV GEN AL035086    (1313) TGGCAAAAAAAATTCTACAAGATTGTGGAATTCACA-ATCTGGTATTGATCAAAAATTGGCAAATTAGATTAATGATCTT
        ENV GENOMIC AL035587    (1555) TGGCGAAAGAA-TTCCTCAAAATTGTGGAATTCTCAGACCCAA-ATAAATCAAAAATTGGCAAACGAAATTAATGATCTT
        ENV GENOMIC AC012068    (1520) TGGCAAAAGAA-TTCCTCGAAATTGTGGAATTCTCAGACTCAA-ACAGATCAAAAATTGACAAATCAAAGTAATGATCTT
        ENV GENOMIC AF277315    (1533) TGGCAAAAGAA-TTCCTCAAAATTGTGGAATTCTCAGACCCAA-ATAGATCAAAAATTGGCAAACCAAATTAATGACCTT
        ENV GENOMIC AF027650     (700) --------------------------------------------------------------------------------
        ENV GENOMIC AC078899    (1788) --GCAAAAGAA-TTCTACAAGATTGTGGAATTCACA-ATCTGGTATTGATCAAAAATTAGCAAATCAAATTAATGATTTT
        ENV GENOMIC HERV-KII    (1231) TGGCAAAAGAA-TTCTACAAGATTGTGGAATTCACA-ATCTAGTATTGATCAAAAATTGGCAAATCAAATTAATGATCTT
        ENV GENOMIC AC008813    (1238) --------------------------------------------------------------------------------
        ENV GENOMIC AC012309    (1528) TGGCAAAAGAA-TTCTACAAGATGGTGGAATTCACA-ATCTGGTATTGATCAAAAATTGGCAAATCAAATTAATGATCTT
        ENV GENOMIC AL121932    (1524) TGGCAAAAGAATTC------------------------------------------------------------------
        ENV GENOMIC AD000090    (1538) TGGCAAAAAAG-TTCTACAAGATTGTGGAATTCACA-ATCTAGTATTGATCAAAAATTGGCAAACCAAATTAATGATCTT
           ENV GEN  AL160008     (647) --------------------------------------------------------------------------------
        ENV GENOMIC HEU32496     (441) --------------------------------------------------------------------------------
        ENV GENOMIC AC011467    (1201) TGGCAAAAGAA-TTCCACAAGATTGTGGAATTCACA-ATCTGGTATTGATCAAAAATTGGCAAATCAAATTAATGATCTT
        ENV GENOMIC AF235103    (1594) TGGCAAAAGAA-TTCCTCAAAATTGTGGAATTCTCAGACTCAA-ATAGATCAAAAATTGGCAAATCAAATTAATGATCTT
        ENV GENOMIC AC026786    (1470) TGGCAAAAGAA-TTCCTCAAGACTGTGGAATTCTCAGACTCAA-ATAGATCAAAAATTAGCAAATCAAATTAATGATCTT
        ENV GENOMIC AC034203    (1403) --------------------------------------------------------------------------------
        ENV GENOMIC AC018809    (1231) TGGCAAAAAAA-TGCTACAAGATTGTGGAATTCACA-ATCTGGTATTGATCAAAAATTGGCAAATCAAATTAATGATTTT
ENV GENOMIC HERV-K102 AF164610  (1287) TGGCAAAAGAA-TTCTACAAGATTGTGGAATTCACA-ATCTAGTATTGATCAAAAATTGGCAAATCAAATTAATGATCTT
   ENV GENOMIC FRAG. AF260253      (1) --------------------------------------------------------------------------------
                   CONSENSUS    (2001) TGGCAAAA AA TTC  CAA ATTGTGGAATTC CA A C    AT GATCAAAAATTGGCAAATCAAATTAATGATCTT
```

FIG. 6-26

```
                                           2081                                                                        2160
           ENV GENOMIC HERV MDA    (1586) AGACAAACTGTCATTTGGATGGGAGA--GGCTCATGAGCTTGGAATATCTTTTTCAGTTACGATGTGACTGGAATACATC
      ENV GENOMIC HERV-K TAN.      (1605) AGACAAACTGTCATTTGGATGGGAGACAGACTCATGAGCTTAGAACATCGTTTCCAGTTACAATGTGACTGGAATACGTC
          ENV GENOMIC AC025420     (1602) AGACAAACTGTCATTTGGATGGGAGACAGGCTCATGAGCTTAGAACATCGTTTCCAGTTACAGTGTGACTGGAATACGTC
          ENV GENOMIC AP000776     (1605) AGACAAACTGTCATTTGGATGGGAGACAGACTCATGAGCTTAGAACATCGTTTCCAGTTACAATGTGACTGGAATACGTC
           ENV GENOMIC HERV-K8      (291) --------------------------------------------------------------------------------
           ENV GENOMIC HERV-KI     (1605) AAAAAAACTGTCATTTGGATAGGAGACAGACTCATGAGCTTAGAACATCGTTTCACGTTACAATGTGACTGGAATACGTC
           ENV HERV-K AF023261      (701) --------------------------------------------------------------------------------
              ENV GEN AL035086     (1392) AGACAAAATGTCATTTGGATGGGAGATAAGCTCGTGAGCTTGGAACATCATTTTCAGTTACAGTGTGACTGGAATACGTC
          ENV GENOMIC AL035587     (1633) AGACAAACTGTCATTTGGCTGGGAAATAGGCTCATGAGCTTGGAATATCTTTTTCAGTTACAGTGTGACTGGAATATGTC
          ENV GENOMIC AC012068     (1598) AGACAAACTGTCATTTGGATGGGAGATAGGCTCATAAGTTTGGAATATCTTTTTCAGTTACAGTGTGACTGGAATATGTC
          ENV GENOMIC AF277315     (1611) AGACAAACTGTCATTTGGATGCGAGATAGGCTCATGAGCTTGAAATATCTTTTTCAGTTACAGTGTGACTGGAATACGTC
          ENV GENOMIC AF027650      (700) --------------------------------------------------------------------------------
          ENV GENOMIC AC078899     (1864) AGACAAACTGTCATTTGGATGGGAGATAGGCTTATGAGCTTAGAACATCATTTCCAGTTACAGTGTGAATGGAATACTTC
          ENV GENOMIC HERV-KII     (1309) AGACAAACTGTCATTTGGATGGGAGACAGACTCATGAGCTTAGAACATTGTTTCCAGTTACAGTGTGACTGGAATACGTC
          ENV GENOMIC AC008813     (1238) --------------------------------------------------------------------------------
          ENV GENOMIC AC012309     (1606) AGAC----TGTCATTTGGATGGGAGATAGGCTCATGAGCTTAGAACATCATTTCCAGTTACAGTGTGACTGGAATACGTC
          ENV GENOMIC AL121932     (1538) --------------------------------------------------------------------------------
          ENV GENOMIC AD000090     (1616) AGACAAACTGTCATTTGGATGGGAGACAGGCTCATGAGCTTAGAACATCGTTTCCAGTTACAGTGTGACTGGAATACGTC
               ENV GEN  AL160008    (647) --------------------------------------------------------------------------------
          ENV GENOMIC HEU32496      (441) --------------------------------------------------------------------------------
          ENV GENOMIC AC011467     (1279) AGACAAACTGTCATTTGGGTGGGAGACAGACTCATGAGCTTAGAACATCATTTCCAGTTACGATGTGACTGGAATATCTC
          ENV GENOMIC AF235103     (1672) AGACAAACTGTCATTTGGATGGGAGATAGGCTCATAAGTTTGGAATATCTTTTTCAGTTACTGTGTGACTACAATACATC
          ENV GENOMIC AC026786     (1548) AGACAAACTGTCATTTGGATGGGAGATAGGCTCATGAGCCTGGAATATCTTTTTCAGTTA--GTGTGACTGGACTACGTC
          ENV GENOMIC AC034203     (1403) --------------------------------------------------------------------------------
          ENV GENOMIC AC018809     (1309) AGACAAACTGTCATTTGGATGGGAGACAGGCTCATGAGCTTAGAACATCGTTTCCAGTTACAATGTGACTGGAATATGTC
 ENV GENOMIC HERV-K102 AF164610    (1365) AGACAAACTGTCATTTGGATGGGAGACAGACTCATGAGCTTAGAACATCGTTTCCAGTTACAATGTGACTGGAATACGTC
     ENV GENOMIC FRAG. AF260253       (1) --------------------------------------------------------------------------------
                     CONSENSUS     (2081) AGACAAACTGTCATTTGGATGGGAGA AG CTCATGAGCTT GAA ATC TTT CAGTTACA TGTGACTGGAATACGTC
```

FIG. 6-27

```
                                          2161                                                                          2240
ENV GENOMIC HERV MDA             (1664)  AGATTTTTGTGTTACACCACAAGCCTATAATGAGTCTGAGCATCACTGGGACATGGTTAGATGCCATCTGCAAGGAGGAG
ENV GENOMIC HERV-K TAN.          (1685)  AGATTTTTGTATTACACCCCAAATTTATAATGAGTCTGAGCATCACTGGGACATGGTTAGACGCCATCTACAGGGAAGAG
ENV GENOMIC AC025420             (1682)  AGATTTTTGTATTACACCCCAAATTTATAATGAGTCTGAGCATCACTGGGACATGGTTAGACGCCATCTACAGGGAAGAG
ENV GENOMIC AP000776             (1685)  AGATTTTTGTATTACACCCCAAATTTATAATGAGTCTGAGCATCACTGGGACATGGTTAGACGCCATCTACAGGGAAGAG
ENV GENOMIC HERV-K8               (291)  --------------------------------------------------------------------------------
ENV GENOMIC HERV-KI              (1685)  AGATTTTTGTATTACACCCCAAATTTATAATGAGTCTGAGCATCACTAGGACATAGTTAGACGCCATCTACAAGGAAGAG
ENV HERV-K AF023261               (701)  --------------------------------------------------------------------------------
ENV GEN AL035086                 (1472)  AGATTTTTGTATTACACCCCAAGCCTGTAATGAGTCTGAGCCTCACTGGGACATGGTTAGATGCCATCTACAAGGAAGAG
ENV GENOMIC AL035587             (1713)  AGATTTTTGTATTACACCCCAAGCCTATAATGAGTCTGAGCATCACTGGGACATGGTTAGATGCCATCTACAGGGAAGAG
ENV GENOMIC AC012068             (1678)  AGATTTTTGTATTACACTTCAAGCCTATAATGAATCTAAACATCACTGGGACATGGTTAGATGCCATCTACAAGGAAGAG
ENV GENOMIC AF277315             (1691)  AGATTTTTGTATTACACCCCGAGCCTACAATGAGTCTGAGCATCACTGGGCCATGGTTAGATGCCATCTACAAGGAAGAG
ENV GENOMIC AF027650              (700)  --------------------------------------------------------------------------------
ENV GENOMIC AC078899             (1944)  AGATTTTTGTATTACACCCCGAGTTTATAATGAGTCTGAGCATCACTGGGACATGGTTAGACGCCATCTACAAGGAAAAG
ENV GENOMIC HERV-KII             (1389)  AGATTTTTGTATTACACCCCAAATTTATAATGAGTCTGAGCATCACTGGGACATGGTTAGACGCCATCTACAGGGAAGAG
ENV GENOMIC AC008813             (1238)  --------------------------------------------------------------------------------
ENV GENOMIC AC012309             (1682)  AGATTTTTGTATTACACCTGGAGTTTATAATGAGTCTGAGCATCACTGGGACATGGTTAGATGCCGTCTACAGGGAAGAA
ENV GENOMIC AL121932             (1538)  --------------------------------------------------------------------------------
ENV GENOMIC AD000090             (1696)  AGATTTTTGTATTACACCCCAAGTTTATAATGAGTCTGAGCATCACTGGGACATGGTTAGACGCCATCTACAGGGAAGAG
ENV GEN AL160008                  (647)  --------------------------------------------------------------------------------
ENV GENOMIC HEU32496              (441)  --------------------------------------------------------------------------------
ENV GENOMIC AC011467             (1359)  AGATTTTTGTATTACACCCCAAATTTATAATGAGTCTGAGCATCACTGGGACATGGTTAGATGCCATCTACAGGGAGGAG
ENV GENOMIC AF235103             (1752)  AGATTTTTGTATTACACCTCAAGCCTATAATGAATCTGAACATCACTGGGACATGGTTAGATGCCATCTACAAGGAAGAG
ENV GENOMIC AC026786             (1626)  AGATTTTTGTATTACACCTCGAGCCTATAATGAATCTGAACATCACTGGGACATGGTTAAACGCCGTCTACAAGGAAGAG
ENV GENOMIC AC034203             (1403)  --------------------------------------------------------------------------------
ENV GENOMIC AC018809             (1389)  AGATTTTTGTATTACACCCCAAGT-TGTAATGAGTCTGAGCATCACTGGGACATGGTTAGACGCCATCTACAGGCAAGAG
ENV GENOMIC HERV-K102 AF164610   (1445)  AGATTTTTGTATTACACCCCAAATTTATAATGAGTCTGAGCATCACTGGGACATGGTTAGACGCCATCTACAGGGAAGAG
ENV GENOMIC FRAG. AF260253          (1)  ----------------------------------------------------CTGGTAAGAGCTAGTCTACAGGAGAGAG
CONSENSUS                        (2161)  AGATTTTTGTATTACACC CAA   TATAATGAGTCTGAGCATCACTGGGACATGGTTAGA GCCATCTACA GGAAGAG
```

FIG. 6-28

```
                                            2321                                                                           2400
           ENV GENOMIC HERV MDA  (1824) TAAATTTGGTGCCAGGAACGGAGACAATCGTGAAAGCTGCTGATAGCCTCACAAATCTTAAGCCAGTCACTTGGGTTAAA
        ENV GENOMIC HERV-K TAN.  (1831) TAAATTTGGTGCCAGGAACTGAGGCAATTGCAGGAGTTGCTGATGGCCTCGCAAATCTTAACCCTGTCACTTGGGTTAAG
           ENV GENOMIC AC025420  (1828) TAAATTTGGTGCCAGGAACTGAGGCAATTGCAGGAGTTGCTGATGGCCTCGCAAATCTTAACCCTGTCACTTGGGTTAAG
           ENV GENOMIC AP000776  (1831) TAAATTTGGTGCCAGGAACTGAGGCAATTGCAGGAGTTGCTGATGGCCTCGCAAATCTTAACCCTGTCACTTGGGTTAAG
             ENV GENOMIC HERV-K8  (291) --------------------------------------------------------------------------------
             ENV GENOMIC HERV-KI (1831) TAAATTTAGTGCCAGGAACTGAGGCAATTGCAGGAGTTGCTGATGGCCTCGCAAATCTTAACCCTGTCACTT-----AAG
              ENV HERV-K AF023261 (701) --------------------------------------------------------------------------------
                 ENV GEN AL035086 (1618) TAAATTTGGTGCCAGGAACTGAAGCAATTACGGAAGCTACTGATGGCCTCGCAAATCTTAACCCAGTCACTTGGGTTAAA
           ENV GENOMIC AL035587  (1859) TAAATTTGG------GAACTGAGGCAATCGTGAAAGCTACTGATGGCCTCACAAATCTTAACACTGTCACTTGGTTAAAA
           ENV GENOMIC AC012068  (1824) TAAATCTGGTGCCAGAAACTGAGGCAACGGTGAAAGCTGTTGATAGCCTCACAAATCTTAACCCTGTCACTTGGGTTAAA
           ENV GENOMIC AF277315  (1837) TAAATCTGGTGCCAGAAACTGAGGCAATCGTGAAAGCTGCTGATGGCCTCACAAATCTTAATGCCGTCACTTGGGTTAAA
           ENV GENOMIC AF027650   (700) --------------------------------------------------------------------------------
           ENV GENOMIC AC078899  (2090) TAAATTTGGTACCGGGAACTGAGGCAATCATGGGAGTTGCTGACTGCCTCTCAAATCTTAACCCTGTCACTTGGGTTAAG
           ENV GENOMIC HERV-KII  (1535) TAAATTTGATGCCAGGAACTGAGGCAATTGCAGGAGTTGCTGATGGCCTCGCAAATCTTAACCCTGTCACTTGGGTTAAG
           ENV GENOMIC AC008813  (1238) --------------------------------------------------------------------------------
           ENV GENOMIC AC012309  (1826) TAAATTTGGTACCAGGAACTGAGGCAATCATGG-AGTTGCTGATGGTCTCACAAATCTTAACCCTGTCACTTGGGTTAAG
           ENV GENOMIC AL121932  (1538) --------------------------------------------------------------------------------
           ENV GENOMIC AD000090  (1842) TAAATTTGGTGCCAGGAACTGAGGCAATTGCAGGAGTTGCTGATGGCCTCGTAAATCTTAACCCTGTCACTTGGGTTAAG
                ENV GEN AL160008  (647) --------------------------------------------------------------------------------
           ENV GENOMIC HEU32496   (441) --------------------------------------------------------------------------------
           ENV GENOMIC AC011467  (1505) TAAATTTGGTGCCGGGAACTGAGGCAATCGCAGGAGTTGCTGCTGGCCTCTCAAATCTTAACCCTGTCACTTGGGTTAAG
           ENV GENOMIC AF235103  (1898) TAAATTTGGTGCCAGAAACTGAGGCAATGGAAAAAGCTGTTGATAGCCTCACGAATCTTAAACCTGTCACTTGGGTTAAA
           ENV GENOMIC AC026786  (1772) TAAATCTGGTGCCAGAAACTGAGACAATGGTAAAAGCTGTTGATAGCCTCACAAATCTTAACCCTGTCACTTGGGTTAAA
           ENV GENOMIC AC034203  (1403) --------------------------------------------------------------------------------
           ENV GENOMIC AC018809  (1534) TAAATTTGGTGCCAGGAACTGAGGCAATCGCAGGAGTTGCTGATGGCCTCACAAATCTTAACCCTGTCACTTGGGTTAAG
ENV GENOMIC HERV-K102 AF164610  (1591) TAAATTTGGTGCCAGGAACTGAGGCAATTGCAGGAGTTGCTGATGGCCTCGCAAATCTTAACCCTGTCACTTGGGTTAAG
     ENV GENOMIC FRAG. AF260253    (79) ---AATTGGTGCA--GAACTGAGGCAATGCAGA---GTGCTGATGGCCTCGCAAATCTTAACCCTGTCACTTGGGTTAGG
                       CONSENSUS (2321) TAAATTTGGTGCCAGGAACTGAGGCAAT G     AG TGCTGATGGCCTC CAAATCTTAACCCTGTCACTTGGGTTAA
```

FIG. 6-30

```
                                          2401                                                                          2480
           ENV GENOMIC HERV MDA  (1904) AGCATCAGAAGTTTCACTATTGTAAATTTCATATTAATCCTTGTATGCCTGTTCTGTCTGTTGTT--AGTCTACAGGTGT
      ENV GENOMIC HERV-K TAN.  (1911) ACCATTGGAAGTACTACGATTATAAATCTCATATTAATCCTTGTGTGCCTGTTTTGTCTGTTGTT--AGTCTGCAGGTGT
           ENV GENOMIC AC025420  (1908) ACCATTGGAAGTACTACGATTATAAATCTCATATTAATCCTTGTGTGCCTGTTTTGTCTGTTGTT--AGTCTGCAGGTGT
           ENV GENOMIC AP000776  (1911) ACCATTGGAAGTACTACAATTATAAATCTCATATTAATCCTTGTGTGCCTGTTTTGTCTGTTGTT--AGTCTGCAGGTGT
            ENV GENOMIC HERV-K8   (291) --------------------------------------------------------------------------------
            ENV GENOMIC HERV-KI  (1906) ACCATCGGAAGTACTACAATTATAAATCTCATATTAATCCTTGTGTGCCTGTTTTGTCTGTTGTT--AGTCTGCAGCTGT
            ENV HERV-K AF023261   (701) --------------------------------------------------------------------------------
                ENV GEN AL035086 (1698) ACCATCAGAAGTTTCCATTATTATAAATTTCATATTAATCCTTGTGTGCCTGTTCTGTCTGTTGTT--AGTCTGCAGGTGT
           ENV GENOMIC AL035587  (1933) ACCATCAGAAGTTTCCACTATTGTAAATTTCATATTAATCCTTGTATGCCTGTTCTGTCTGTTGTT--AGTCCACAGGTGT
           ENV GENOMIC AC012068  (1904) ACCACTGGAAATTTCCACTGTTGCAAATTTTGTATTAATTCTTGTACGTCTGTCCTGTCTGTTGTT--AGTCTACAGGTGT
           ENV GENOMIC AF277315  (1917) ACTATCAGAAGTTTCCACTATTGTAAATTTCATATTAATCCTTGTATGTCTGTTCTGTCTGTTGTT--AGTCTACAGGTGT
           ENV GENOMIC AF027650   (700) --------------------------------------------------------------------------------
           ENV GENOMIC AC078899  (2170) ACCATCAGAAGTACTACTATTATAAATTTCATATTAATCCTTGTGTGCCTGTTCTGTCTGTTGTT--AGTCTGCAGGTGT
           ENV GENOMIC HERV-KII  (1615) ACCATCGGAAGTACTATGATTATAAATCTCATATTAATCCTTGTGTGCCTGTTTTGTCTGTTGTT--AGTCTGCAGGTGT
           ENV GENOMIC AC008813  (1238) --------------------------------------------------------------------------------
           ENV GENOMIC AC012309  (1905) ACCATCGGAAGTTTCTACTATTGTAAATTTCCTATTAATCCTTGTGTGCCTGTTCTGTCTGTTGTT--AGTCTGCAGGTGT
           ENV GENOMIC AL121932  (1538) --------------------------------------------------------------------------------
           ENV GENOMIC AD000090  (1922) ACCATCGGAAGTACTATATATTATAAATTTCATATTAATCCTTGTGTGCCTGTTCTGTCTGTTGTT--AGTCTGCAGGGGT
               ENV GEN  AL160008  (647) --------------------------------------------------------------------------------
           ENV GENOMIC HEU32496   (441) --------------------------------------------------------------------------------
           ENV GENOMIC AC011467  (1585) ACCATTGGAAGTACTACTATTATAAATTTCATATTAATCCTTGTGTGGCTGTTTTGTCTGTTGTT--ACTCTGCAGGTGT
           ENV GENOMIC AF235103  (1978) ACCATTGGAAATTTCCACTATTGCAAATTTTGTATTAATCCTTGTATGTCTGTCCTCTCTATTGTT--AGTCTACAGGTGT
           ENV GENOMIC AC026786  (1852) ACCACTGGAAATTTCCACTATTACAAATTTTGTATTAATCCTTGTATGTCTGTCCTTTCTATTATT--AGTCTACAGGTGT
           ENV GENOMIC AC034203  (1403) --------------------------------------------------------------------------------
           ENV GENOMIC AC018809  (1614) ACGATTGGAAGTACTACGATTATAAATTTCATATTAATCCTTGTGTGCCTGTTTTGTCTGTTGTTCAAGTCTGCAGGTGT
ENV GENOMIC HERV-K102 AF164610  (1671) ACCATTGGAAGTACTACGATTATAAATCTCATATTAATCCTTGTGTGCCTGTTTTGTCTGTTGTT--AGTCTGCAGGTGT
   ENV GENOMIC FRAG. AF260253   (151) ATGCATCGAAGTAGTACGAT-GTAAATCTCATATTAATCATTGTGTGCCTGTTTTGTCTGTTGTT--GGTCTGCAGGTGT
                      CONSENSUS (2401) ACCAT  GAAGT C AC ATT TAAAT TCATATTAATCCTTGT TGCCTGTT TGTCTGTTGTT  AGTCT CAGGTGT
```

FIG. 6-31

| Sequence | Start | 2481 … 2560 |
|---|---|---|
| ENV GENOMIC HERV MDA | (1982) | ATCCAGCAGCTCCAAAGAGACAGCAACCAGCAAGAATGGGCCATAGTGACGATGGTGGTTTTGTCAAAAAGAAAAGGGGG |
| ENV GENOMIC HERV-K TAN. | (1989) | ACCCAACAGCTCCGAAGAGACAGCGACCATCGAGAACGGGCCATGATGACGATGGCGGTTTTGTCGAAAAGAAAAGGGGG |
| ENV GENOMIC AC025420 | (1986) | ACCCAACAGCTCCGAAGAGACAGCGACCATCGAGAACGGGCCATGATGACGATGGTGGTTTTGTCGAAAAGAAAAGGGGG |
| ENV GENOMIC AP000776 | (1989) | ACCCAACAGCTCTGAAGAGACAGCAACCATCGAGAACGGGCCATGATGACGATGGCGGTTTTGTCAAAAAGAAAAGGGGG |
| ENV GENOMIC HERV-K8 | (291) | -------------------------------------------------------------------------------- |
| ENV GENOMIC HERV-KI | (1984) | ACCCAACAGCTCCGAAGAGACAGCGACCATCGAGAACAGGCCATGATGACGATAGTGGTTTTGTCGAAAAGAAAAGGGGG |
| ENV HERV-K AF023261 | (701) | -------------------------------------------------------------------------------- |
| ENV GEN AL035086 | (1776) | ACCCAGCAGCTCCGAAGAGACAGCGACCATCAAGAACGGGCCATGATGACGATGGCAGTTTTGTCAAAAACAAAAGGGAG |
| ENV GENOMIC AL035587 | (2011) | ATCCACCAGCTCCGAAGAGACAGCGACCAGCAAGAACGGGCCATAACGACGATGGCAGTTTTGTCAAA-----AAGGGGG |
| ENV GENOMIC AC012068 | (1982) | ATCCAGCAGCTCCGGAGAGACAGCAACCAGCGAGAACGGGCCATGATGACTATGGCAGTTTTGTCAAAAAGAAAAGGGAC |
| ENV GENOMIC AF277315 | (1995) | ATCCAACAGCTCCGAAGAGACAGTGACCAGCGAAAACGGGCCGTGATGATGATGGTGGTTTTGTCAGAAAGAAAAGGGGG |
| ENV GENOMIC AF027650 | (700) | -------------------------------------------------------------------------------- |
| ENV GENOMIC AC078899 | (2248) | ACCCAGCAGCTCCAAAGAGACAGGGACCATCAAGAACGGGCCATGATAACGATGGTGGTTTTGTCAAAAATAAAAGGGGG |
| ENV GENOMIC HERV-KII | (1693) | ACCCAACAGCTCCGAAGAGACAGCGACCATCGAGAACGGGCCATGATGACGATGGCGGTTTTGTCGAAAAGAAAAGGGGG |
| ENV GENOMIC AC008813 | (1238) | -------------------------------------------------------------------------------- |
| ENV GENOMIC AC012309 | (1983) | ACCCAACAGCTCCAAAGAGACAGCGACCATCGAGAACGGGCCATGATGACGATGGCGGTTTTGTCCAAAAGAAAAGGGGG |
| ENV GENOMIC AL121932 | (1538) | -------------------------------------------------------------------------------- |
| ENV GENOMIC AD000090 | (2000) | ACCCAACAGCTCCGAAGAGACAGCGACCATCGAGAAAGAGCCATGATGACGATGGCGGTTTTGTTGAAAAGAAAAGGGGG |
| ENV GEN AL160008 | (647) | -------------------------------------------------------------------------------- |
| ENV GENOMIC HEU32496 | (441) | -------------------------------------------------------------------------------- |
| ENV GENOMIC AC011467 | (1663) | ACCCAACAGCTCCGAAGAGACAGCGACCATCCAGAA-------------------------------------------- |
| ENV GENOMIC AF235103 | (2056) | ATCCAGCAGCTCCGGAGAGACAGCGGCTAGCGAGAACGGACCATGATGATGATGGCGGTTTTGTCAAAAAGAAAAGGGGG |
| ENV GENOMIC AC026786 | (1930) | ATACAACAGCTCCGGAGAGACAGCGACCAGCGAGAACGGGTCATGATGACGATGGCGGTTTTGTCAAAAAGAAAAGGGGG |
| ENV GENOMIC AC034203 | (1403) | -------------------------------------------------------------------------------- |
| ENV GENOMIC AC018809 | (1694) | ACCCAACAGCTCTGAAGAGACAGCGACCATCAAGAACGGGCCATGATGATGATGGCAGTTTTGTCGAAAAGAAAAGGGGG |
| ENV GENOMIC HERV-K102 AF164610 | (1749) | ACCCAACAGCTCCGAAGAGACAGCGACCATCGAGAACGGGCCATGATGACGATGGCGGTTTTGTCGAAAAGAAAAGGGGG |
| ENV GENOMIC FRAG. AF260253 | (228) | ACCCAACAGCTCGGAAGAGACAGCGACCATCGAGAACGGGCCATGATGACGATGGCGGTTTTGTCGAAAAGAAAAGGGGG |
| CONSENSUS | (2481) | A CCA CAGCTCCGAAGAGACAGCGACCA C AGAACGGGCCATGATGACGATGG GGTTTTGTC AAAAGAAAAGGGGG |

FIG. 6-32

```
                                            2641                                                             2707
ENV GENOMIC HERV MDA               (2136)   TGATCTGTACTAA------------------------------------------------------
ENV GENOMIC HERV-K TAN.            (2146)   TGTTATGTACTAA------------------------------------------------------
ENV GENOMIC AC025420               (2143)   TGTTATGTACTAA------------------------------------------------------
ENV GENOMIC AP000776               (2146)   TGTTATGTACTAA------------------------------------------------------
ENV GENOMIC HERV-K8                 (291)   -------------------------------------------------------------------
ENV GENOMIC HERV-KI                (2141)   TGTTATGTACTAA------------------------------------------------------
ENV HERV-K AF023261                 (701)   -------------------------------------------------------------------
ENV GEN AL035086                   (1931)   TGATCTGTACTAA------------------------------------------------------
ENV GENOMIC AL035587               (2146)   -------------------------------------------------------------------
ENV GENOMIC AC012068               (2138)   TGAAAAAGACCTGTACTTTGAACAATT----------------------------------------
ENV GENOMIC AF277315               (2152)   TGACCTGTA----------------------------------------------------------
ENV GENOMIC AF027650                (700)   -------------------------------------------------------------------
ENV GENOMIC AC078899               (2405)   TGTTCTGTACTAAGAGAAATTCTTCTGCCTTGAGATGCTGTTAA-----------------------
ENV GENOMIC HERV-KII               (1850)   TGTTCTGTACTAA------------------------------------------------------
ENV GENOMIC AC008813               (1238)   -------------------------------------------------------------------
ENV GENOMIC AC012309               (2133)   TGTTCTGTACCAAG-----------------------------------------------------
ENV GENOMIC AL121932               (1538)   -------------------------------------------------------------------
ENV GENOMIC AD000090               (2157)   TGTTCTGTACTAA------------------------------------------------------
ENV GEN  AL160008                   (647)   -------------------------------------------------------------------
ENV GENOMIC HEU32496                (441)   -------------------------------------------------------------------
ENV GENOMIC AC011467               (1699)   -------------------------------------------------------------------
ENV GENOMIC AF235103               (2212)   TGAAAAAGACCTGTACTTTGAACAATTGCTTTGCTCAGATGTTGTTAATTTGTAGTTTT--------
ENV GENOMIC AC026786               (2086)   TGAAAAAGACCTGTACTTTAAACAATTGCTTTGCTGAGATGTTGTTAATTTGTAGCTTTCCCCAGCC
ENV GENOMIC AC034203               (1403)   -------------------------------------------------------------------
ENV GENOMIC AC018809               (1846)   TGCTCTGTACTAAG-----------------------------------------------------
ENV GENOMIC HERV-K102 AF164610     (1906)   TGTTATGTGTTAAGAAAAATTCTT-------------------------------------------
ENV GENOMIC FRAG. AF260253          (385)   TGTTCTGTACTAA------------------------------------------------------
CONSENSUS                          (2641)   TG   TGTAC
```

FIG. 6-34

```
                                       1                                                         60
GI_4185938_EMB_CAA76878.1_        (1)  -----MGQTKSKIKSKYASYLSFIKILLKRGGVKVSTKNLIKLFQIIEQFCPWFPEQGTL
GI_4185942_EMB_CAA76881.1_        (1)  -----MGQTKSKIKSKYASYLSFIKILLKRGGVKVSTKNLIKLFQIIEQFCPWFPEQGTL
GI_4185946_EMB_CAA76884.1_        (1)  -----MGQTKSKIKSKYASYLSFIKILLKRGGVKVSTKNLIKLFQIIEQFCPWFPEQGTL
GI_5931704_EMB_CAB56602.1_        (1)  -------MGQTKTKSKYASYLSFIKILLKRGGVRVSTKNLIKLFQTTEQFCPWFPEQGNL
            GAG OF AB047240       (1)  -----MGQTKSKTKSKYASYLSFIKILLKRGGVRVSTKNLIKLFQIIEQFCPWFPEQGTL
       TRANSLATION OF ORF99       (1)  YKKAGLGQTKSKTKSKYASYLSFIKILLKRGGVRVSTKNLIKLFQIIEQFCPWFPEQGTL
TRANSLATION OF G226TOP-LINK       (1)  ------------------------------------------------------------
TRANSLATION OF G591TOP-LINK       (1)  ------------------------------------------------------------
   TRANSLATION OF LNCAP-GAG       (1)  -----MGQTKSKTKSKYASYLSFIKILLKRGGVRVSTKNLIKLFQIIEQFCPWFPEQGTL
                 GAG106-135       (1)  ------------------------------------------------------------
                 GAG186-215       (1)  ------------------------------------------------------------
                   GAG46-75       (1)  --------------------------------------------------CPWFPEQGTL
                     PDG-G1       (1)  ------------------------------------------------------------
                     PGD-G2       (1)  ------------------------------------------------------------
                     PGD-G3       (1)  ------------------------------------------------------------
                  CONSENSUS       (1)                                                    CPWFPEQG L

                                       61                                                       120
GI_4185938_EMB_CAA76878.1_       (56)  DLKDWKRIGKELKQAGRKGNIIPLTVWNDWAIIKAALEPFQTEEDSVSVSDAPGSCIIDC
GI_4185942_EMB_CAA76881.1_       (56)  DLKDWKRIGKELKQAGRKGNIIPLTVWNDWAIIKAALEPFQTEEDSVSVSDAPGSCIIDC
GI_4185946_EMB_CAA76884.1_       (56)  DLKDWKRIGKELKQAGRKGNIIPLTVWNDWAIIKAALEPFQTEEDSVSVSDAPGSCIIDC
GI_5931704_EMB_CAB56602.1_       (54)  DLEDWKRIGKELKQAGRKGNIIPLTVWNDWPIIKAALEPFQTEDS-VSVSDAPGSCIIDC
            GAG OF AB047240      (56)  DLKDWKRIGEELKQAGRKGNIIPLTVWNDWAIIKAALEPFQTKEDSVSVSDAPGSCVIDC
       TRANSLATION OF ORF99      (61)  DLKDWKRIGEELKQAGRKGNIIPLTVWNDWAIIKAALEPFQTKEDSVSVSDAPGSCVIDC
TRANSLATION OF G226TOP-LINK       (1)  ------------------------------------------------------------
TRANSLATION OF G591TOP-LINK       (1)  ------------------------------------------------------------
   TRANSLATION OF LNCAP-GAG      (56)  DLKDWKRIGEELKQAGRKGNIIPLTVWNDWAIIKAALEPFQTKEDSVSVSDAPGSCVIDC
                 GAG106-135       (1)  --------------------------------------------------DAPGSCIIDC
                 GAG186-215       (1)  ------------------------------------------------------------
                   GAG46-75      (11)  DLKDWKRIGKELKQAGRKGN----------------------------------------
                     PDG-G1       (1)  ---DWKRIGKELKQAGRKG-----------------------------------------
                     PGD-G2       (1)  ------------------------------------------------------------
                     PGD-G3       (1)  ------------------------------------------------------------
                  CONSENSUS      (61)  DL DWKRIG ELKQAGRKGN                              DAPGSCIIDC
```

FIG. 7-1

```
                                       121                                                        180
    GI_4185938_EMB_CAA76878.1_  (116) NENTRKKSQKETEGLHCEYVAEPVMAQSTQNVDYNQLQEVIYPETLKLEGKGPELVGPSE
    GI_4185942_EMB_CAA76881.1_  (116) NENTRKKSQKETESLHCEYVAEPVMAQSTQNVDYNQLQEVIYPETLKLEGKGPELVGPSE
    GI_4185946_EMB_CAA76884.1_  (116) NENTRKKSQKETEGLHCEYVAEPVMAQSTQNVDYNQLQEVIYPETLKLEGKGPELVGPSE
    GI_5931704_EMB_CAB56602.1_  (113) NEKTRKKSQKETETLHCEYVAEPLMAQSTQNVDYNQLQEVIYPETLKLEGKGPELVGPLE
              GAG OF AB047240   (116) NEKTGRKSQKETESLHCEYVTEPVMAQSTQNVDYNQLQGVIYPETLKLEGKGPELVGPSE
          TRANSLATION OF ORF99  (121) NEKTGRKSQKETESLHCEYVTEPVMAQSTQNVDYNQLQGVIYPETLKLEGKGPELVGPSE
 TRANSLATION OF G226TOP-LINK    (1) ------------------------------------------------------------
 TRANSLATION OF G591TOP-LINK    (1) ------------------------------------------------------------
    TRANSLATION OF LNCAP-GAG    (116) NEKTGRKSQKETESLHCEYVTEPVMAQSTQNVDYNQLQGVIYPETLKLEGKGPELVGPSE
                 GAG106-135     (11) NENTRKKSQKETEGLHCEYV----------------------------------------
                 GAG186-215      (1) ------------------------------------------------------------
                   GAG46-75     (31) ------------------------------------------------------------
                     PDG-G1     (17) ------------------------------------------------------------
                     PGD-G2      (1) ------------------------------------------------------------
                     PGD-G3      (1) ------------------------------------------------------------
                  CONSENSUS    (121) NE T KKSQKETE LHCEYV

                                       181                                                        240
    GI_4185938_EMB_CAA76878.1_  (176) SKPRGTSPLPAGQVPVTLQPQKQVKENKTQPPVAYQYWPPAELQYRPPPESQYGYPGMPP
    GI_4185942_EMB_CAA76881.1_  (176) SKPRGTSRLPAGQVPVTLQPQTQVKENKTQPPVAYQYWPPAELQYRPPVESQYGYPGMPP
    GI_4185946_EMB_CAA76884.1_  (176) SKPRGTSPLPAGQVPVTLQPQKQVKENKTQPPVAYQYWPPAELQYRPPPESQYGYPGMPP
    GI_5931704_EMB_CAB56602.1_  (173) SKPRGPSPLSAGQVTVTLQPQAQVRENKTQLPVAYQYWPPAELQYRPPPESQYGYLGMPP
              GAG OF AB047240   (176) SKPRGPSPLPAGQVPVTLQPQTQVKENKTQPPVAYQYWPPAELQYLPPPESQYGYPGMPP
          TRANSLATION OF ORF99  (181) SKPRGPSPLPAGQVPVTLQPQTQVKENKTQPPVAYQYWPPAELQYLPPPESQYGYPGMPP
 TRANSLATION OF G226TOP-LINK    (1) --------------------------------------------------SQYGYPGMPP
 TRANSLATION OF G591TOP-LINK    (1) ------------------------------------------------------------
    TRANSLATION OF LNCAP-GAG    (176) SKPRGPSPLPAGQVPVTLQPQTQVKENKTQPPVAYQYWPPAELQYLPPPESQYGYPGMPP
                 GAG106-135     (31) ------------------------------------------------------------
                 GAG186-215      (1) ----------AGQVPVTLQPQKQVKENKTQPPVAYQYWPP--------------------
                   GAG46-75     (31) ------------------------------------------------------------
                     PDG-G1     (17) ------------------------------------------------------------
                     PGD-G2      (1) ------------------------------------------------------------
                     PGD-G3      (1) ------------------------------------------------------------
                  CONSENSUS    (181)           AGQV VTLQPQ QVKENKTQ PVAYQYWPP          SQYGY GMPP
```

FIG. 7-2

```
                                      241                                                        300
GI_4185938_EMB_CAA76878.1_     (236)  APQGRAPYPQPPTRRLNPTAPPSRQGSKLHEIIDKSRKEGDTEAWQFPVTLEPMPPGEGA
GI_4185942_EMB_CAA76881.1_     (236)  APQGRAPYPQPPTRRLNPTAPPSRRGSELHEIIDKSRKEGDTEAWQFPVMLEPMPPGEGA
GI_4185946_EMB_CAA76884.1_     (236)  APQGRAPYPQPPTRRLNPTAPPSRQGSKLHEIIDKSRKEGDTEAWQFPVTLEPMPPGEGA
GI_5931704_EMB_CAB56602.1_     (233)  APQDREPYPQPPTRRQCYGTT---------------------------------------
              GAG OF AB047240  (236)  ALQGRAPYPQPPTVRLNPTASRSGQGGTLHAVIDEARKQGDLEAWRFLVILQLVQAGEET
          TRANSLATION OF ORF99 (241)  ALQGRAPYPQPPTVRLNPTASRSGQGGTLHAVIDEARKQGDLEAWRFLVILQLVQAGEET
  TRANSLATION OF G226TOP-LINK  (11)   APQGRAPYPQPPTRRLNPTA----------------------------------------
  TRANSLATION OF G591TOP-LINK  (1)    ------------------------------------------------------------
     TRANSLATION OF LNCAP-GAG  (236)  ALQGRAPYPQPPTVRLNPTASRSGQGGTLHAVIDEARKQGDLEAWRFLVILQLVQAGEET
                  GAG106-135   (31)   ------------------------------------------------------------
                  GAG186-215   (31)   ------------------------------------------------------------
                    GAG46-75   (31)   ------------------------------------------------------------
                      PDG-G1   (17)   ------------------------------------------------------------
                      PGD-G2   (1)    --------------------------SKLHEIIDKSRKEGDT------------------
                      PGD-G3   (1)    ------------------------------------------------------------
                   CONSENSUS   (241)  A Q R PYPQPPT R

                                      301                                                        360
GI_4185938_EMB_CAA76878.1_     (296)  QEGEPPTVEARYKSFSIKKLKDMKEGVKQYGPNSPYMRTLLDSIAHGHRLIPYDWEILAK
GI_4185942_EMB_CAA76881.1_     (296)  QEGEPPTVEARYKSFSIKMLKDMKEGVKQYGPNSPYMRTLLDSIAHGHRLIPYDWEILAK
GI_4185946_EMB_CAA76884.1_     (296)  QEGEPPTVEARYKSFSIKKLKDMKEGVKQYGPNSPYMRTLLDSIAHGHRLIPYDWEILAK
GI_5931704_EMB_CAB56602.1_     (254)  ------------------------------------------------------------
              GAG OF AB047240  (296)  QVGAPARAETRCEPFTMKMLKDIKEGVKQYGSNSPYIRTLLDSIAHGNRLTPYDWESLAK
          TRANSLATION OF ORF99 (301)  QVGAPARAETRCEPFTMKMLKDIKEGVKQYGSNSPYIRTLLDSIAHGNRLTPYDWESLAK
  TRANSLATION OF G226TOP-LINK  (31)   ------------------------------------------------------------
  TRANSLATION OF G591TOP-LINK  (1)    ------------------------------------------------------------
     TRANSLATION OF LNCAP-GAG  (296)  QVGAPARAETRCEPFTMKMLKDIKEGVKQYGSNSPYIRTLLDSIAHGNRLTPYDWESLAK
                  GAG106-135   (31)   ------------------------------------------------------------
                  GAG186-215   (31)   ------------------------------------------------------------
                    GAG46-75   (31)   ------------------------------------------------------------
                      PDG-G1   (17)   ------------------------------------------------------------
                      PGD-G2   (17)   ------------------------------------------------------------
                      PGD-G3   (1)    ------------------------------------------------------------
                   CONSENSUS   (301)
```

FIG. 7-3

| | | 361 420 |
|---|---|---|
| GI_4185938_EMB_CAA76878.1_ | (356) | SSLSPSQFLQFKTWWIDGVQEQVRRNRAANPPVNIDADQLLGIGQNWSTISQQALMQNEA |
| GI_4185942_EMB_CAA76881.1_ | (356) | SSLSPSQFLQFKTWWIDGVQEQVRRNRAANPPVNIDADQLLGIGQNWSTISQQALMQNEA |
| GI_4185946_EMB_CAA76884.1_ | (356) | SSLSPSQFLQFKTWWIDGVQEQVRRNRAANPPVNIDADQLLGIGQNWSTISQQALMQNEA |
| GI_5931704_EMB_CAB56602.1_ | (254) | ------------------------------------------------------------ |
| GAG OF AB047240 | (356) | SSLSSSQYLQFKTWWIDGVQEQVRKNQATKPTVNIDADQLLGTGPNWSTINQQSVMQNEA |
| TRANSLATION OF ORF99 | (361) | SSLSSSQYLQFKTWWIDGVQEQVRKNQATKPTVNIDADQLLGTGPNWSTINQQSVMQNEA |
| TRANSLATION OF G226TOP-LINK | (31) | ------------------------------------------------------------ |
| TRANSLATION OF G591TOP-LINK | (1) | ------------------------------------------------------------ |
| TRANSLATION OF LNCAP-GAG | (356) | SSLSSSQYLQFKTWWIDGVQEQVRKNQATKPTVNIDADQLLGTGPNWSTINQQSVMQNEA |
| GAG106-135 | (31) | ------------------------------------------------------------ |
| GAG186-215 | (31) | ------------------------------------------------------------ |
| GAG46-75 | (31) | ------------------------------------------------------------ |
| PDG-G1 | (17) | ------------------------------------------------------------ |
| PGD-G2 | (17) | ------------------------------------------------------------ |
| PGD-G3 | (1) | ------------------------------------------------------------ |
| CONSENSUS | (361) | |

| | | 421 480 |
|---|---|---|
| GI_4185938_EMB_CAA76878.1_ | (416) | IEQVRAICLRAWEKIQDPGSTCPSFNTVRQGSKEPYPDFVARLQDVAQKSIADEKARKVI |
| GI_4185942_EMB_CAA76881.1_ | (416) | IEQVRAICLRAWEKIQDPGSTCPSFNTVRQGSKEPYPDFVARLQDVAQKSIANEKARKVI |
| GI_4185946_EMB_CAA76884.1_ | (416) | IEQVRAICLRAWEKIQDPGSTCPSFNTVRQGSKEPYPDFVARLQDVAQKSIADEKARKVI |
| GI_5931704_EMB_CAB56602.1_ | (254) | ------------------------------------------------------------ |
| GAG OF AB047240 | (416) | IEQVRAICLRAWGKIQDPGTAFP-INSIRQGSKEPYPDFVARLQDAAQKSITDDNARKVI |
| TRANSLATION OF ORF99 | (421) | IEQVRAICLRAWGKIQDPGTAF-PINSIRQGSKEPYPDFVARLQDAAQKSITDDNARKVI |
| TRANSLATION OF G226TOP-LINK | (31) | ------------------------------------------------------------ |
| TRANSLATION OF G591TOP-LINK | (1) | ------------------------------------------------------------ |
| TRANSLATION OF LNCAP-GAG | (416) | IEQVRAICLRAWGKIQDPGTAFP-INSIRQGSKEPYPDFVARLQDAAQKSITDDNARKVI |
| GAG106-135 | (31) | ------------------------------------------------------------ |
| GAG186-215 | (31) | ------------------------------------------------------------ |
| GAG46-75 | (31) | ------------------------------------------------------------ |
| PDG-G1 | (17) | ------------------------------------------------------------ |
| PGD-G2 | (17) | ------------------------------------------------------------ |
| PGD-G3 | (1) | ------------------------------------------------------------ |
| CONSENSUS | (421) | |

FIG. 7-4

```
                                       481                                                        540
   GI_4185938_EMB_CAA76878.1_   (476)  VELMAYENANPECQSAIKPLKGKVPAGSDVISEYVKACDGIGGAMYKAMLMAQAITGVVL
   GI_4185942_EMB_CAA76881.1_   (476)  VELMAYENPNPECQSAIKPLKGKVPAGSDVISEYVKACDGMGGAMHKAMLMAQAITGVVL
   GI_4185946_EMB_CAA76884.1_   (476)  VELMAYENANPECQSAIKPLKGKVPAGSDVISEYVKACDGIGGAMHKAMLMAQAITGVVL
   GI_5931704_EMB_CAB56602.1_   (254)  ------------------------------------------------------------
             GAG OF AB047240    (475)  VELMAYENANPECQSAIKPLKGKVPAGVDVITEYVKACDGIGGAMHKAMLMAQAMRGLTL
         TRANSLATION OF ORF99   (480)  VELMAYENANPECQSAIKPLKGKVPAGVDVITEYVKACDGIGGAMHKAMLMAQAMRGLTL
 TRANSLATION OF G226TOP-LINK     (31)  ------------------------------------------------------------
 TRANSLATION OF G591TOP-LINK      (1)  ------------------------------------------------------------
    TRANSLATION OF LNCAP-GAG    (475)  VELMAYENANPECQSAIKPLKGKVPAGVDVITEYVKACDGIGGAMHKAMLMAQAMRGLTL
                 GAG106-135      (31)  ------------------------------------------------------------
                 GAG186-215      (31)  ------------------------------------------------------------
                   GAG46-75      (31)  ------------------------------------------------------------
                     PDG-G1      (17)  ------------------------------------------------------------
                     PGD-G2      (17)  ------------------------------------------------------------
                     PGD-G3       (1)  ------------------------------------------------------------
                  CONSENSUS     (481)

                                       541                                                        600
   GI_4185938_EMB_CAA76878.1_   (536)  GGQVRTFGRKCYNCGQIGHLKKNCPVLNKQNITIQATTTG-REPPDLCPRCKKGKHWASQ
   GI_4185942_EMB_CAA76881.1_   (536)  GGQVRTFGGKCYNCGQIGHLKKNCPVLNKQNITIQATTTG-REPPDLCPRCKKGKHWASQ
   GI_4185946_EMB_CAA76884.1_   (536)  GGQVRTFGRKCYNCGQIGHLKKNCPVLNKQNITIQATTTG-REPPDLCPRCKKGKHWASQ
   GI_5931704_EMB_CAB56602.1_   (254)  ------------------------------------------------------------
             GAG OF AB047240    (535)  GGQVRTFGKKCYNCGQIGHLKRSCPVLNKQNIINQAITAKNKKPSGLCPKCGKGKHWANQ
         TRANSLATION OF ORF99   (540)  GGQVRTFGKKCYNCGQIGHLKRSCPVLNKQNIINQAITAKNKKPSGLCPKCGKGKHWANQ
 TRANSLATION OF G226TOP-LINK     (31)  ------------------------------------------------------------
 TRANSLATION OF G591TOP-LINK      (1)  --------------------------------------------------------WASQ
    TRANSLATION OF LNCAP-GAG    (535)  GGQVRTFGKKCYNCGQIGHLKRSCPVLNKQNIINQAITAKNKKPSGLCPKCGKGKHWANQ
                 GAG106-135      (31)  ------------------------------------------------------------
                 GAG186-215      (31)  ------------------------------------------------------------
                   GAG46-75      (31)  ------------------------------------------------------------
                     PDG-G1      (17)  ------------------------------------------------------------
                     PGD-G2      (17)  ------------------------------------------------------------
                     PGD-G3       (1)  ------------------------------------------------------------
                  CONSENSUS     (541)
```

FIG. 7-5

```
                                    601                                                        660
  GI_4185938_EMB_CAA76878.1_  (595) CRSKFDKNGQPLSGNEQRGQPQAPQQTGAFPIQPFVPQGFQGQQP-PLSQVFQGISQLPQ
  GI_4185942_EMB_CAA76881.1_  (595) CRSKFDKNGQPLSGNEQRGQPQAPQQTGAFPIQPFVPHGFQGQQP-PLSQVFQGISQLPQ
  GI_4185946_EMB_CAA76884.1_  (595) CRSKFDKNGQPLSGNEQRGQPQAPQQTGAFPIQPFVPQGFQGQQP-PLSQVFQGISQLPQ
  GI_5931704_EMB_CAB56602.1_  (254) ------------------------------------------------------------
             GAG OF AB047240  (595) CHSKFDKDGQPLSGNRKRGQPQAPQQTGAFPVQLFVPQGFQGQQPLQKIPPLQGVSQLQQ
         TRANSLATION OF ORF99 (600) CHSKFDKDGQPLSGNRKRGQPQAPQQTGAFPVQLFVPQGFQGQQPLQKIPPLQGVSQLQQ
TRANSLATION OF G226TOP-LINK    (31) ------------------------------------------------------------
TRANSLATION OF G591TOP-LINK     (5) CRSKFDKNGQPLSGNEQRGQPQAPQQ----------------------------------
   TRANSLATION OF LNCAP-GAG   (595) CHSKFDKDGQPLSGNRKRGQPQAPQQTGAFPVQLFVPQGFQGQQPLQKIPPLQGVSQLQQ
                 GAG106-135    (31) ------------------------------------------------------------
                 GAG186-215    (31) ------------------------------------------------------------
                   GAG46-75    (31) ------------------------------------------------------------
                     PDG-G1    (17) ------------------------------------------------------------
                     PGD-G2    (17) ------------------------------------------------------------
                     PGD-G3     (1) CRSKFDKNGQPLSGNE--------------------------------------------
                  CONSENSUS   (601) C SKFDK GQPLSGN
```

```
                                    661         673
  GI_4185938_EMB_CAA76878.1_  (654) YNNCPPPQAAVQQ
  GI_4185942_EMB_CAA76881.1_  (654) YNNCPPPQAAVQQ
  GI_4185946_EMB_CAA76884.1_  (654) YNNCPPPQAAVQQ
  GI_5931704_EMB_CAB56602.1_  (254) -------------
             GAG OF AB047240  (655) SNSCPAPQQAAPQ
         TRANSLATION OF ORF99 (660) SNSCPAPQQAAPQ
TRANSLATION OF G226TOP-LINK    (31) -------------
TRANSLATION OF G591TOP-LINK    (31) -------------
   TRANSLATION OF LNCAP-GAG   (655) SNSCPAPQQAAPQ
                 GAG106-135    (31) -------------
                 GAG186-215    (31) -------------
                   GAG46-75    (31) -------------
                     PDG-G1    (17) -------------
                     PGD-G2    (17) -------------
                     PGD-G3    (17) -------------
                  CONSENSUS   (661)
```

FIG. 7-6

```
                                              1                                                         60
            GI_4185939_EMB_CAA76879.1_   (1)  MLTDLRAVN---AVIQPMGPLQPGLPSPAMIPKDWPLIIIDLKDCFFTIPLAEQDCEKFA
            GI_4185943_EMB_CAA76882.1_   (1)  MLTDLRAVNAVNAVIQPMGPLQPGLPSLAMIPKDWPLIIIDLKDCFFTIPLAEQDCEKFA
            GI_4185947_EMB_CAA76885.1_   (1)  MLTDLRAVN---AVIQPMGPLQPGLPSPAMIPKDWPLIIIDLKDCFFTIPLAEQDCEKFA
            GI_5931705_EMB_CAB56603.1_   (1)  -----------------------------MIPKDWPLIIIDLKDCFFTIPLAEQDCEKFA
                       ENV OF AB047240   (1)  ------------------------------------------------------------
           TRANSLATION OF P386TOP-LINK   (1)  ------------------------------------------------------------
            TRANSLATION OF POL349-LINK   (1)  ------------------------------------------------------------
                  LNCAP-GENOMEA-POLORF   (1)  ------------------------------------------------------------
TRANSLATION OF LNCAP-POL-GENA-GOODA      (1)  ------------------------------------------------------------
              TRANSLATION OF ORF111-10   (1)  ------------------------------------------------------------
                                PGD-P1   (1)  ------------------------------------------------------------
                                PGD-P2   (1)  ------------------------------------------------------------
                                 PGDP3   (1)  ------------------------------------------------------------
                             CONSENSUS   (1)

                                              61                                                       120
            GI_4185939_EMB_CAA76879.1_  (58)  FTIPAINNKEPATRFQWKVLPQGMLNSPTICQTFVGRALQPVREKFSDCYIIHCIDDILC
            GI_4185943_EMB_CAA76882.1_  (61)  FTIPAINNKEPATRFQWKVLPQGMLNSPTICQTFVGRALQPVREKFSDCYIIHYIDDILC
            GI_4185947_EMB_CAA76885.1_  (58)  FTIPAINNKEPATRFQWKVLPQGMLNSPTICQTFVGRALQPVREKFSDCYIIHCIDDILC
            GI_5931705_EMB_CAB56603.1_  (32)  FTIPAINNKEPATRFQWKVLPQGMLNSPTLCQTFVGRALQPVRDKFSDCYIIHYFDDILC
                       ENV OF AB047240   (1)  ------------------------------------------------------------
           TRANSLATION OF P386TOP-LINK   (1)  ------------------------------------------------------------
            TRANSLATION OF POL349-LINK   (1)  ------------------------------------------------------------
                  LNCAP-GENOMEA-POLORF   (1)  ------------------------------------------------------------
TRANSLATION OF LNCAP-POL-GENA-GOODA      (1)  ------------------------------------------------------------
              TRANSLATION OF ORF111-10   (1)  ------------------------------------------------------------
                                PGD-P1   (1)  ------------------------------------------------------------
                                PGD-P2   (1)  ------------------------------------------------------------
                                 PGDP3   (1)  ------------------------------------------------------------
                             CONSENSUS  (61)
```

FIG. 8-1

| | | 121 180 |
|---|---|---|
| GI_4185939_EMB_CAA76879.1_ | (118) | AAETKDKLIDCYTFLQAEVANAGLAIASDKIQTSTPFHYLGMQIENRKIKPQKIEIRKDT |
| GI_4185943_EMB_CAA76882.1_ | (121) | AAEMKDKLIDCYTFLQAEVANAGLAIASDKIQTSTPFHYLEMQIENRKIKPPKIEIRKDT |
| GI_4185947_EMB_CAA76885.1_ | (118) | AAETKDKLIDCYTFLQAEVANAGLAIASDKIQTSTPFHYLGMQIENRKIKPQKIEIRKDT |
| GI_5931705_EMB_CAB56603.1_ | (92) | AAETKDKLIDCYTFLQAEVANAGLAIASDKIQTSTPFHYLGMQIENRKIKPQKIEIRKDT |
| ENV OF AB047240 | (1) | ------------------------------------------------------------ |
| TRANSLATION OF P386TOP-LINK | (1) | ------------------------------------------------------------ |
| TRANSLATION OF POL349-LINK | (1) | ------------------------------------------------------------ |
| LNCAP-GENOMEA-POLORF | (1) | ------------------------------------------------------------ |
| TRANSLATION OF LNCAP-POL-GENA-GOODA | (1) | ------------------------------------------------------------ |
| TRANSLATION OF ORF111-10 | (1) | ------------------------------------------------------------ |
| PGD-P1 | (1) | -------------------------------------------IENRKIKPQKIEIRKD- |
| PGD-P2 | (1) | ------------------------------------------------------------ |
| PGDP3 | (1) | ------------------------------------------------------------ |
| CONSENSUS | (121) | |

| | | 181 240 |
|---|---|---|
| GI_4185939_EMB_CAA76879.1_ | (178) | LKTLNDFQKLLGDINWIRPTLGIPTYAMSNLFSILRGDSDLNSKRMLTPEATKEIKLVEE |
| GI_4185943_EMB_CAA76882.1_ | (181) | LKTLNDFQKLLGDINWIRPTLGIPTYAMSNLFSILRGDSDLNSKRMLTPEATKEIKLVEE |
| GI_4185947_EMB_CAA76885.1_ | (178) | LKTLNDFQKLLGDINWIRPTLGIPTYAMSNLFSILRGDSDLNSKRMLTPEATKEIKLVEE |
| GI_5931705_EMB_CAB56603.1_ | (152) | LKTLNDFQKLLGDINWIRPTLGIPTYAMSNLFSILRGDSDLNSKRMLTPEATKEIKLVEE |
| ENV OF AB047240 | (1) | ------------------------------------------------------------ |
| TRANSLATION OF P386TOP-LINK | (1) | ------------------------------------------------------------ |
| TRANSLATION OF POL349-LINK | (1) | ------------------------------------------------------------ |
| LNCAP-GENOMEA-POLORF | (1) | ------------------------------------------------------------ |
| TRANSLATION OF LNCAP-POL-GENA-GOODA | (1) | ------------------------------------------------------------ |
| TRANSLATION OF ORF111-10 | (1) | ------------------------------------------------------------ |
| PGD-P1 | (17) | ------------------------------------------------------------ |
| PGD-P2 | (1) | ------------------------------------------------------------ |
| PGDP3 | (1) | ------------------------------------------------------------ |
| CONSENSUS | (181) | |

FIG. 8-2

```
                                             241                                                        300
     GI_4185939_EMB_CAA76879.1_       (238)  KIQSAQINRIDPLAPLQLLLIFATAHSPTGIIIQNTDLVEWSFLPHSTVKTFTLYLDQIAT
     GI_4185943_EMB_CAA76882.1_       (241)  KIQSAQINRIDPLAPLQLLLIFATAHSPTGIIIQNTDLVEWSFLPHSTVKTFTLYLDQMAT
     GI_4185947_EMB_CAA76885.1_       (238)  KIQSAQINRIDPLAPLQLLLIFATAHSPTGIIIQNTDLVEWSFLPHSTVKTFTLYLDQIAT
     GI_5931705_EMB_CAB56603.1_       (212)  KIQSAQINRIDPLAPLQLLLIFATAHSPTGIIIQNTDLVEWSFLPHSTVKTFTLYLDQIAT
                ENV OF AB047240         (1)  ---------------------------------------------------------MAT
     TRANSLATION OF P386TOP-LINK        (1)  ------------------------------------------------------------
      TRANSLATION OF POL349-LINK        (1)  ------------------------------------------------------------
           LNCAP-GENOMEA-POLORF         (1)  ----------DHLAPLQILLIFGTAHSLTAIIVQNTDLVDWSFLPHSTIKTFTLYLDQMAT
TRANSLATION OF LNCAP-POL-GENA-GOODA     (1)  ----------DHLAPLQILLIFGTAHSLTAIIVQNTDLVDWSFLPHSTIKTFTLYLDQMAT
        TRANSLATION OF ORF111-10        (1)  ----YKKAGSDHLAPLQILLIFGTAHSLTAIIVQNTDLVDWSFLPHSTIKTFTLYLDQMAT
                         PGD-P1        (17)  ------------------------------------------------------------
                         PGD-P2         (1)  ------------------------------------------------------------
                          PGDP3         (1)  ------------------------------------------------------------
                      CONSENSUS       (241)            D LAPLQLLIFATAHS TGIIIQNTDLVEWSFLPHSTVKTFTLYLDQMAT

                                             301                                                        360
     GI_4185939_EMB_CAA76879.1_       (298)  LIGQTRLRIIKLCGNDPDKIVVPLTKEQVRQAFINSGAWKIGLANFVGIIDNHYPKTKIF
     GI_4185943_EMB_CAA76882.1_       (301)  LIGQTRLRIIKLCGNDPDKIVVPLTKEQVRQAFINSGAWQIGLANFVGIIDNHYPKTKIF
     GI_4185947_EMB_CAA76885.1_       (298)  LIGQTRLRIIKLCGNDPDKIVVPLTKEQVRQAFINSGAWKIGLANFVGIIDNHYPKTKIF
     GI_5931705_EMB_CAB56603.1_       (272)  LIGPTRLRIIKLCGNDPDKIVVPLTKEQVRQAFINSGAWQIGLANFVGIIDNHYPKTKIF
                ENV OF AB047240         (4)  LIGQGRLRIITLCGNDPDKITVPFNKQQVRQAFISSGAWQIGLANFLGIIDNHYPKTKIF
     TRANSLATION OF P386TOP-LINK        (1)  ------------------------------------------------------------
      TRANSLATION OF POL349-LINK        (1)  ---------------------------------------------------NHYPKTKIF
           LNCAP-GENOMEA-POLORF        (51)  LIGQGRLRIITLCGNDPDKITVPFNKQQVRQAFISSGAWQIGLANFLGIIDNHYPKTKIF
TRANSLATION OF LNCAP-POL-GENA-GOODA    (51)  LIGQGRLRIITLCGNDPDKITVPFNKQQVRQAFISSGAWQIGLANFLGIIDNHYPKTKIF
        TRANSLATION OF ORF111-10       (57)  LIGQGRLRIITLCGNDPDKITVPFNKQQVRQAFISSGAWQIGLANFLGIIDNHYPKTKIF
                         PGD-P1        (17)  ------------------------------------------------------------
                         PGD-P2         (1)  ------------------------------------------------------------
                          PGDP3         (1)  ------------------------------------------------------------
                      CONSENSUS       (301)  LIGQ RLRII LCGNDPDKI VP  K QVRQAFI SGAW IGLANFLGIIDNHYPKTKIF
```

FIG. 8-3

```
                                           361                                                        420
       GI_4185939_EMB_CAA76879.1_   (358) QFLKLTTWILPKITRREPLENALTVFTDGSSNGKAAYTGPKERVIKTPYQSAQRAELVAV
       GI_4185943_EMB_CAA76882.1_   (361) QFLKMTTWILPKITRREPLENALTVFTDGSSNGKAAYTGPKERVIKTQYQSAQRAELVAV
       GI_4185947_EMB_CAA76885.1_   (358) QFLKLTTWILPKITRREPLENALTVFTDGSSNGKAAYTGPKERVIKTPYQSAQRAELVAV
       GI_5931705_EMB_CAB56603.1_   (332) QFLKLTTWILPKITRREPLENALTVFTDGSSNGKVAYTGPKERVIKTPYQSAQRAELVAV
                  ENV OF AB047240    (64) QFLKLTTWILPKITRREPLENALTVFTDGSSNGKAAYTGPKERVIKTPYQSAQRAELVAV
     TRANSLATION OF P386TOP-LINK      (1) ----------------------------GSSNGKAAYTGPKERVIKTPYQSAQRAELV--
      TRANSLATION OF POL349-LINK     (10) QFLKLTTWILPKITRREP------------------------------------------
           LNCAP-GENOMEA-POLORF     (111) QFLKLTTWILPKITRREPLENALTVFTDGSSNGKAAYTGPKERVIKTPYQSAQRAELVAV
TRANSLATION OF LNCAP-POL-GENA-GOODA (111) QFLKLTTWILPKITRREPLENALTVFTDGSSNGKAAYTGPKERVIKTPYQSAQRAELVAV
        TRANSLATION OF ORF111-10    (117) QFLKLTTWILPKITRREPLENALTVFTDGSSNGKAAYTGPKERVIKTPYQSAQRAELVAV
                          PGD-P1     (17) ------------------------------------------------------------
                          PGD-P2      (1) ---------------------------------KAAYTGPKERVIKTPC-----------
                           PGDP3      (1) ------------------------------------------------------------
                       CONSENSUS    (361) QFLKLTTWILPKITRREPLENALTVFTDGSSNGKAAYTGPKERVIKTPYQSAQRAELVAV

                                           421                                                        480
       GI_4185939_EMB_CAA76879.1_   (418) ITVLQDFDQPINIISDSAYVVQATRDVETALIKYSMDDQLNQLFNLLQQTVRKRNFPFYI
       GI_4185943_EMB_CAA76882.1_   (421) ITVLQDFDQPINIISDSAYVVQATRDVETALIKYSMDDQLNQLFNLLQQTVRKRNFPFYI
       GI_4185947_EMB_CAA76885.1_   (418) ITVLQDFDQPINIISDSAYVVQATRDVETALIKYSMDDQLNQLFNLLQQTVRKRNFPFYI
       GI_5931705_EMB_CAB56603.1_   (392) ITVLQDFDQPINIISDSAYVVQATRDVETALIKYSMDDQLNQLFNLLQQTVRKRNFPFYI
                  ENV OF AB047240   (124) ITVLQDFDQPINIISDSAYVVQATRDVETALIKYSTDDHLNQLFNLLQQTVRKRNFPFYI
     TRANSLATION OF P386TOP-LINK     (31) ------------------------------------------------------------
      TRANSLATION OF POL349-LINK     (28) ------------------------------------------------------------
           LNCAP-GENOMEA-POLORF     (171) ITVLQDFDQPINIISDSAYVVQATRDVETALIKYSTDDHLNQLFNLLQQTVRKRNFPFYI
TRANSLATION OF LNCAP-POL-GENA-GOODA (171) ITVLQDFDQPINIISDSAYVVQATRDVETALIKYSTDDHLNQLFNLLQQTVRKRNFPFYI
        TRANSLATION OF ORF111-10    (177) ITVLQDFDQPINIISDSAYVVQATRDVETALIKYSTDDHLNQLFNLLQQTVRKRNFPFYI
                          PGD-P1     (17) ------------------------------------------------------------
                          PGD-P2     (17) ------------------------------------------------------------
                           PGDP3      (1) ------------------------------------------------------------
                       CONSENSUS    (421) ITVLQDFDQPINIISDSAYVVQATRDVETALIKYS DD LNQLFNLLQQTVRKRNFPFYI
```

FIG. 8-4

```
                                             481                                                        540
GI_4185939_EMB_CAA76879.1_          (478) THIRAHTNLPGPLTKANEQADLLVSSALIKAQELHALTHVNAAGLKNKFDVTWKQAKDIV
GI_4185943_EMB_CAA76882.1_          (481) THIRAHTNLPGPLTKANEQADLLVSSALIKAQELHALTHVNVAGLKNKFDVTWKQAKDIV
GI_4185947_EMB_CAA76885.1_          (478) THIRAHTNLPGPLTKANEQADLLVSSALIKAQELHALAHVNAAGLKNKFDVTWKQAKDIV
GI_5931705_EMB_CAB56603.1_          (452) THIRAHTNLPGPLTKANEQADLLVSSAFIKAQELHALTHVNAAGLKNKFDVTWKQAKDIV
ENV OF AB047240                     (184) THIRAHTNLPGPLTKANEQADLLVSSAFIKAQELLALTHVNAAGLKNKFDVTWKQAKDIV
TRANSLATION OF P386TOP-LINK          (31) ------------------------------------------------------------
TRANSLATION OF POL349-LINK           (28) ------------------------------------------------------------
LNCAP-GENOMEA-POLORF                (231) THIRAHTNLPGPLTKANEQADLLVSSAFIKAQELLALTHVNAAGLKNKFDVTWKQAKDIV
TRANSLATION OF LNCAP-POL-GENA-GOODA (231) THIRAHTNLPGPLTKANEQADLLVSSAFIKAQELLALTHVNAAGLKNKFDVTWKQAKDIV
TRANSLATION OF ORF111-10            (237) THIRAHTNLPGPLTKANEQADLLVSSAFIKAQELLALTHVNAAGLKNKFDVTWKQAKDIV
PGD-P1                               (17) ------------------------------------------------------------
PGD-P2                               (17) ------------------------------------------------------------
PGDP3                                 (1) ------------------------------------------------------------
CONSENSUS                           (481) THIRAHTNLPGPLTKANEQADLLVSSA IKAQEL ALTHVNAAGLKNKFDVTWKQAKDIV

                                             541                                                        600
GI_4185939_EMB_CAA76879.1_          (538) QHCTQCQVLHLPTQEAGVNPRGLCPNALWQMDVTHVPSFGRLSYVHVTVDTYSHFIWATC
GI_4185943_EMB_CAA76882.1_          (541) QHCTQCQVLHLPTQEAGVNPRGLCPNALWQMDVTHVSSFGRLSYIHVTVDTYSHFIWATC
GI_4185947_EMB_CAA76885.1_          (538) QHCTQCQVLHLPTQEAGVNPRGLCPNALWQMDVTHVPSFGRLSYVHVTVDTYSHFIWATC
GI_5931705_EMB_CAB56603.1_          (512) QHCTQCQVLDLPTQEAGVNPEVCVLMHYGKWMSHMYLHLGRLSYVHVTVDTYSHFMCATC
ENV OF AB047240                     (244) QHCTQCQVLHLSTQEAGVNPRGLCPNALWQMDGTHVPSFGRLSYVHVTVDTYSHFIWATC
TRANSLATION OF P386TOP-LINK          (31) ------------------------------------------------------------
TRANSLATION OF POL349-LINK           (28) ------------------------------------------------------------
LNCAP-GENOMEA-POLORF                (291) QHCTQCQVLHLSTQEAGVNPRGLCPNALWQMDGTHVPSFGRLSYVHVTVDTYSHFIWATC
TRANSLATION OF LNCAP-POL-GENA-GOODA (291) QHCTQCQVLHLSTQEAGVNPRGLCPNALWQMDGTHVPSFGRLSYVHVTVDTYSHFIWATC
TRANSLATION OF ORF111-10            (297) QHCTQCQVLHLSTQEAGVNPRGLCPNALWQMDGTHVPSFGRLSYVHVTVDTYSHFIWATC
PGD-P1                               (17) ------------------------------------------------------------
PGD-P2                               (17) ------------------------------------------------------------
PGDP3                                 (1) ------------------------------------------------------------
CONSENSUS                           (541) QHCTQCQVLHL TQEAGVNPRGLCPNALWQMD THV SFGRLSYVHVTVDTYSHFIWATC
```

FIG. 8-5

```
                                            601                                                       660
GI_4185939_EMB_CAA76879.1_           (598) QTGESTSHVKKHLLSCFAVMGVPEKIKTDNGPGYCSKAFQKFLSQWKISHTTGIPYNSQG
GI_4185943_EMB_CAA76882.1_           (601) QTGESTSHVKKHLLSCFAVMGVPEKIKTDNGPGYCSKAFQKFLSQWKISHTTGIPYNSQG
GI_4185947_EMB_CAA76885.1_           (598) QTGESTSHVKKHLLSCFAVMGVPEKIKTDNGPGYCSKAFQKFLSQWKISHTTGIPYNSQG
GI_5931705_EMB_CAB56603.1_           (572) QTGESTSHVKKHLLSCFAVMGVPEKIKTDNGPGYCSKAFQKFLSQWKISHTTGIPYNSQG
ENV OF AB047240                      (304) QTGESTSHVKKHLLSCFAVMGVPEKIKTDNGPGYCSKAFQKFLSQWKISHTTGIPYNSQG
TRANSLATION OF P386TOP-LINK           (31) ------------------------------------------------------------
TRANSLATION OF POL349-LINK            (28) ------------------------------------------------------------
LNCAP-GENOMEA-POLORF                 (351) QTGESTSHVKKHLLSCFAVMGVPEKIKTDNGPGYCSKAFQKFLSQWKISHTTGIPYNSQG
TRANSLATION OF LNCAP-POL-GENA-GOODA  (351) QTGESTSHVKKHLLSCFAVMGVPEKIKTDNGPGYCSKAFQKFLSQWKISHTTGIPYNSQG
TRANSLATION OF ORF111-10             (357) QTGESTSHAKKHLLSCFAVMGVPEKIKTDNGPGYCSKAFQKFLSQWKISHTTGIPYNSQG
PGD-P1                                (17) ------------------------------------------------------------
PGD-P2                                (17) ------------------------------------------------------------
PGDP3                                  (1) ------------------------------------------------------------
CONSENSUS                            (601) QTGESTSHVKKHLLSCFAVMGVPEKIKTDNGPGYCSKAFQKFLSQWKISHTTGIPYNSQG

                                            661                                                       720
GI_4185939_EMB_CAA76879.1_           (658) QAIVERTNRTLKTQLVKQKEGGDSKECTTPQMQLNLALYTLNFLNIYRNQTTTSAEQHLT
GI_4185943_EMB_CAA76882.1_           (661) QAIVERTNRTLKTQLVKQKEGGDSKECTTPQMQLNLALYTLNFLNIYRNQTTTSAEQHLT
GI_4185947_EMB_CAA76885.1_           (658) QAIVERTNRTLKTQLVKQKEGGDSKECTTPQMQLNLALYTLNFLNIYRNQTTTSAEQHLT
GI_5931705_EMB_CAB56603.1_           (632) QAIVERTNRTLKTQLVKQKEGGDSKECTTPQMQLNLALYTLNFLNIYRNQTTTSAE-HLT
ENV OF AB047240                      (364) QAIVERTNRTLKTQLVKQKEGGDSKECTTPQMQLNLALYTLNFLNIYRNQTTTSAKQHLT
TRANSLATION OF P386TOP-LINK           (31) ------------------------------------------------------------
TRANSLATION OF POL349-LINK            (28) ------------------------------------------------------------
LNCAP-GENOMEA-POLORF                 (411) QAIVERTNRTLKTQLVKQKEGGDSKECTTPQMQLNLALYTLNFLNIYRNQTTTSAKQHLT
TRANSLATION OF LNCAP-POL-GENA-GOODA  (411) QAIVERTNRTLKTQLVKQKEGGDSKECTTPQMQLNLALYTLNFLNIYRNQTTTSAKQHLT
TRANSLATION OF ORF111-10             (417) QAIVERTNRTLKTQLVKQKEGGDSKECTTPQMQLNLALYTLNFLNIYRNQTTTSAKQHLT
PGD-P1                                (17) ------------------------------------------------------------
PGD-P2                                (17) ------------------------------------------------------------
PGDP3                                  (1) ---------------------------------------------------------HLT
CONSENSUS                            (661) QAIVERTNRTLKTQLVKQKEGGDSKECTTPQMQLNLALYTLNFLNIYRNQTTTSA QHLT
```

FIG. 8-6

```
                                         721                                                        780
          GI_4185939_EMB_CAA76879.1_  (718) GKKNSPHEGKLIWWKDSKNKTWEIGKVITWGRGFACVSPGENQLPVWIPTRHLKFYNEPI
          GI_4185943_EMB_CAA76882.1_  (721) GKKNSPHEGKLIWWKDNKNKTWEIGKVITWGRGFACVSPGENQLPVWIPTRHLKFYNEPI
          GI_4185947_EMB_CAA76885.1_  (718) GKKNSPHEGKLIWWKDNKNKTWEIGKVITWGRGFACVSPGENQLPVWIPTRHLKFYNEPI
          GI_5931705_EMB_CAB56603.1_  (691) GKKNSPHEGKLI------------------------------------------------
                     ENV OF AB047240  (424) GKKHSPHEGKLIWWKDNKNKTWEIGKVITWGRGFACVSPGENQLPVWIPTRHLKFYNEPI
        TRANSLATION OF P386TOP-LINK   (31) ------------------------------------------------------------
         TRANSLATION OF POL349-LINK   (28) ------------------------------------------------------------
               LNCAP-GENOMEA-POLORF  (471) GKKHSPHEGKLIWWKDNKNKTWEIGKVITWGRGFACVSPGENQLPVWIPTRHLKFYNEPI
TRANSLATION OF LNCAP-POL-GENA-GOODA  (471) GKKHSPHEGKLIWWKDNKNKTWEIGKVITWGRGFACVSPGENQLPVWIPTRHLKFYNEPI
         TRANSLATION OF ORF111-10    (477) GKKHSPHEGKLIWWKDNKNKTWEIGKVITWGRGFACVSPGENQLPVWIPTRHLKFYNEPI
                             PGD-P1   (17) ------------------------------------------------------------
                             PGD-P2   (17) ------------------------------------------------------------
                              PGDP3    (4) GKKNSPHEGKLIC-----------------------------------------------
                          CONSENSUS  (721) GKK SPHEGKLIWWKD KNKTWEIGKVITWGRGFACVSPGENQLPVWIPTRHLKFYNEPI

                                         781                                                        840
          GI_4185939_EMB_CAA76879.1_  (778) RDAKKSTSAETETS----------------------------------------------
          GI_4185943_EMB_CAA76882.1_  (781) GDAKKSTSAETETP----------------------------------------------
          GI_4185947_EMB_CAA76885.1_  (778) RDAKKSTSAETETS----------------------------------------------
          GI_5931705_EMB_CAB56603.1_  (703) ------------------------------------------------------------
                     ENV OF AB047240  (484) GDAKKRASTEMVTPVTWMDNPIEVYVNDSVWVPGPTDDRCPAKPEEEGMMINISIVYRYP
        TRANSLATION OF P386TOP-LINK   (31) ------------------------------------------------------------
         TRANSLATION OF POL349-LINK   (28) ------------------------------------------------------------
               LNCAP-GENOMEA-POLORF  (531) GDAKKRASTEMVTPVTWMDNPIEVYVNDSVWVPGPTDDRCPAKPEEEGMMINISIVYRYP
TRANSLATION OF LNCAP-POL-GENA-GOODA  (531) GDAKKRASTEMVTPVTWMDNPIEVYVNDSVWVPGPTDDRCPAKPEEEGMMINISIVYRYP
         TRANSLATION OF ORF111-10    (537) GDAKKRASTEMVTPVTWMDNPIEVYVNDSVWVPGPTDDRCPAKPEEEGMMINISIVYRYP
                             PGD-P1   (17) ------------------------------------------------------------
                             PGD-P2   (17) ------------------------------------------------------------
                              PGDP3   (17) ------------------------------------------------------------
                          CONSENSUS  (781)  DAKK  S E  T
```

FIG. 8-7

```
                                                 841                                                        900
GI_4185939_EMB_CAA76879.1_               (792) ------------------------------------------------------------
GI_4185943_EMB_CAA76882.1_               (795) ------------------------------------------------------------
GI_4185947_EMB_CAA76885.1_               (792) ------------------------------------------------------------
GI_5931705_EMB_CAB56603.1_               (703) ------------------------------------------------------------
ENV OF AB047240                          (544) PICLGRAPGCLMPAVQNWLVEVPTVSPNSRFTYHMVSGMSLRPRVNYLQDFSYQRSLKFR
TRANSLATION OF P386TOP-LINK               (31) ------------------------------------------------------------
TRANSLATION OF POL349-LINK                (28) ------------------------------------------------------------
LNCAP-GENOMEA-POLORF                     (591) PICLGRAPGCLMPAVQNWLVEVPTVSPNSRFTYHMVSGMSLRPRVNYLQDFSYQRSLKFR
TRANSLATION OF LNCAP-POL-GENA-GOODA      (591) PICLGRAPGCLMPAVQNWLVEVPTVSPNSRFTYHMVSGMSLRPRVNYLQDFSYQRSLKFR
TRANSLATION OF ORF111-10                 (597) PICLGRAPGCLMPAVQNWLVEVPTVSPNSRFTYHMVSGMSLRPRVNYLQDFSYQRSLKFR
PGD-P1                                    (17) ------------------------------------------------------------
PGD-P2                                    (17) ------------------------------------------------------------
PGDP3                                     (17) ------------------------------------------------------------
CONSENSUS                                (841)

                                                 901                                                        960
GI_4185939_EMB_CAA76879.1_               (792) ------------------------------------QSSTVDSQDEQNGDVRRTDEVAIH
GI_4185943_EMB_CAA76882.1_               (795) ------------------------------------QSSTVDSQDEQNGDVRRTDEVAIH
GI_4185947_EMB_CAA76885.1_               (792) ------------------------------------QSSTVDSQDEQNGDVRRTDEVAIH
GI_5931705_EMB_CAB56603.1_               (703) ------------------------------------------------------------
ENV OF AB047240                          (604) PKGKPCPKEIPKESKNTEVLVWEECVANSAVILQNNEFGTIIDWAPRGQFYHNCSGQTQS
TRANSLATION OF P386TOP-LINK               (31) ------------------------------------------------------------
TRANSLATION OF POL349-LINK                (28) ------------------------------------------------------------
LNCAP-GENOMEA-POLORF                     (651) PKGKPCPKEIPKESKNTEVLVWEECVANSAVILQNNEFGTIIDWAPRGQFYHNCSGQTQS
TRANSLATION OF LNCAP-POL-GENA-GOODA      (651) PKGKPCPKEIPKESKNTEVLVWEECVANSAVILQNNEFGTIIDWAPRGQFYHNCSGQTQS
TRANSLATION OF ORF111-10                 (657) PKGKPCPKEIPKESKNTEVLVWEECVANSAVILQNNEFGTIIDWAPRGQFYHNCSGQTQS
PGD-P1                                    (17) ------------------------------------------------------------
PGD-P2                                    (17) ------------------------------------------------------------
PGDP3                                     (17) ------------------------------------------------------------
CONSENSUS                                (901)                                         TI
```

FIG. 8-8

```
                                            961                                                       1020
GI_4185939_EMB_CAA76879.1_          (816)  QEGRAANLGTTKEADAVSYKISREHKGDTNPREYAACSLDDCINGGKSPYACRSSCS---
GI_4185943_EMB_CAA76882.1_          (819)  QESRAADLGTTKEADAVSYKISREHKGDTNPREYAACGLDDCINGGKSPYACRSSCS---
GI_4185947_EMB_CAA76885.1_          (816)  QEGRAANLGTTKEADAVSYKISREHKGDTNPREYAACSLDDCINGGKSPYACRSSCS---
GI_5931705_EMB_CAB56603.1_          (703)  ------------------------------------------------------------
ENV OF AB047240                     (664)  CPSAQVSPAVDSDLTESLDKHKHKKLQSFYPWEWGEKGISTPRPEIISPVSGPEHPELWR
TRANSLATION OF P386TOP-LINK          (31)  ------------------------------------------------------------
TRANSLATION OF POL349-LINK           (28)  ------------------------------------------------------------
LNCAP-GENOMEA-POLORF                (711)  CPSAQVSPAVDSDLTESLDKHKHKKLQSFYPWEWGEKGISTPRPEIISPVSGP-------
TRANSLATION OF LNCAP-POL-GENA-GOODA (711)  CPSAQVSPAVDSDLTESLDKHKHKKLQSFYPWEWGEKGISTPRPEIISPVSGPEHPELWR
TRANSLATION OF ORF111-10            (717)  CPSAQVSPAVDSDLTESLDKHKHKKLQSFYPWEWGEKGISTPRPEIISPVSGPEHPELWR
PGD-P1                               (17)  ------------------------------------------------------------
PGD-P2                               (17)  ------------------------------------------------------------
PGDP3                                (17)  ------------------------------------------------------------
CONSENSUS                           (961)          A   D      K          P EWG   I        SP S

                                            1021         1035
GI_4185939_EMB_CAA76879.1_          (873)  ---------------
GI_4185943_EMB_CAA76882.1_          (876)  ---------------
GI_4185947_EMB_CAA76885.1_          (873)  ---------------
GI_5931705_EMB_CAB56603.1_          (703)  ---------------
ENV OF AB047240                     (724)  LWPDTTLEFGLEIKL
TRANSLATION OF P386TOP-LINK          (31)  ---------------
TRANSLATION OF POL349-LINK           (28)  ---------------
LNCAP-GENOMEA-POLORF                (764)  ---------------
TRANSLATION OF LNCAP-POL-GENA-GOODA (771)  LWPDTTLEFGLEIKL
TRANSLATION OF ORF111-10            (777)  LWPDTTLEFGLEIKL
PGD-P1                               (17)  ---------------
PGD-P2                               (17)  ---------------
PGDP3                                (17)  ---------------
CONSENSUS                          (1021)
```

FIG. 8-9

```
                                     1                                                          60
GI_4185940_EMB_CAA76880.1_       (1) ------------------------------------------------------------
GI_4185944_EMB_CAA76883.1_       (1) ------------------------------------------------------------
GI_4185948_EMB_CAA76886.1_       (1) ------------------------------------------------------------
GI_5931706_EMB_CAB56604.1_       (1) ------------------------------------------------------------
            ENV OF AB047240      (1) MATLIGQGRLRIITLCGNDPDKITVPFNKQQVRQAFISSGAWQIGLANFLGIIDNHYPKT
TRANSLATION OF E207TOP-LINK      (1) ------------------------------------------------------------
 TRANSLATION OF ENV287-LINK      (1) ------------------------------------------------------------
  TRANSLATION OF T20.22A-23      (1) ------------------------------------------------------------
                     PGD-E1      (1) ------------------------------------------------------------
                     PGD-E2      (1) ------------------------------------------------------------
                     PGD-E3      (1) ------------------------------------------------------------
                  CONSENSUS      (1)

                                     61                                                        120
GI_4185940_EMB_CAA76880.1_       (1) ------------------------------------------------------------
GI_4185944_EMB_CAA76883.1_       (1) ------------------------------------------------------------
GI_4185948_EMB_CAA76886.1_       (1) ------------------------------------------------------------
GI_5931706_EMB_CAB56604.1_       (1) ------------------------------------------------------------
            ENV OF AB047240     (61) KIFQFLKLTTWILPKITRREPLENALTVFTDGSSNGKAAYTGPKERVIKTPYQSAQRAEL
TRANSLATION OF E207TOP-LINK      (1) ------------------------------------------------------------
 TRANSLATION OF ENV287-LINK      (1) ------------------------------------------------------------
  TRANSLATION OF T20.22A-23      (1) ------------------------------------------------------------
                     PGD-E1      (1) ------------------------------------------------------------
                     PGD-E2      (1) ------------------------------------------------------------
                     PGD-E3      (1) ------------------------------------------------------------
                  CONSENSUS     (61)
```

FIG. 9-1

```
                                     121                                                        180
GI_4185940_EMB_CAA76880.1_      (1) ------------------------------------------------------------
GI_4185944_EMB_CAA76883.1_      (1) ------------------------------------------------------------
GI_4185948_EMB_CAA76886.1_      (1) ------------------------------------------------------------
GI_5931706_EMB_CAB56604.1_      (1) ------------------------------------------------------------
           ENV OF AB047240    (121) VAVITVLQDFDQPINIISDSAYVVQATRDVETALIKYSTDDHLNQLFNLLQQTVRKRNFP
TRANSLATION OF E207TOP-LINK     (1) ------------------------------------------------------------
 TRANSLATION OF ENV287-LINK     (1) ------------------------------------------------------------
  TRANSLATION OF T20.22A-23     (1) ------------------------------------------------------------
                     PGD-E1     (1) ------------------------------------------------------------
                     PGD-E2     (1) ------------------------------------------------------------
                     PGD-E3     (1) ------------------------------------------------------------
                  CONSENSUS   (121)
```

```
                                     181                                                        240
GI_4185940_EMB_CAA76880.1_      (1) ------------------------------------------------------------
GI_4185944_EMB_CAA76883.1_      (1) ------------------------------------------------------------
GI_4185948_EMB_CAA76886.1_      (1) ------------------------------------------------------------
GI_5931706_EMB_CAB56604.1_      (1) ------------------------------------------------------------
           ENV OF AB047240    (181) FYITHIRAHTNLPGPLTKANEQADLLVSSAFIKAQELLALTHVNAAGLKNKFDVTWKQAK
TRANSLATION OF E207TOP-LINK     (1) ------------------------------------------------------------
 TRANSLATION OF ENV287-LINK     (1) ------------------------------------------------------------
  TRANSLATION OF T20.22A-23     (1) ------------------------------------------------------------
                     PGD-E1     (1) ------------------------------------------------------------
                     PGD-E2     (1) ------------------------------------------------------------
                     PGD-E3     (1) ------------------------------------------------------------
                  CONSENSUS   (181)
```

FIG. 9-2

```
                                       241                                                        300
GI_4185940_EMB_CAA76880.1_        (1)  ------------------------------------------------------------
GI_4185944_EMB_CAA76883.1_        (1)  ------------------------------------------------------------
GI_4185948_EMB_CAA76886.1_        (1)  ------------------------------------------------------------
GI_5931706_EMB_CAB56604.1_        (1)  ------------------------------------------------------------
           ENV OF AB047240      (241)  DIVQHCTQCQVLHLSTQEAGVNPRGLCPNALWQMDGTHVPSFGRLSYVHVTVDTYSHFIW
TRANSLATION OF E207TOP-LINK       (1)  ------------------------------------------------------------
 TRANSLATION OF ENV287-LINK       (1)  ------------------------------------------------------------
  TRANSLATION OF T20.22A-23       (1)  ------------------------------------------------------------
                     PGD-E1       (1)  ------------------------------------------------------------
                     PGD-E2       (1)  ------------------------------------------------------------
                     PGD-E3       (1)  ------------------------------------------------------------
                  CONSENSUS     (241)

                                       301                                                        360
GI_4185940_EMB_CAA76880.1_        (1)  ------------------------------------------------------------
GI_4185944_EMB_CAA76883.1_        (1)  ------------------------------------------------------------
GI_4185948_EMB_CAA76886.1_        (1)  ------------------------------------------------------------
GI_5931706_EMB_CAB56604.1_        (1)  ------------------------------------------------------------
           ENV OF AB047240      (301)  ATCQTGESTSHVKKHLLSCFAVMGVPEKIKTDNGPGYCSKAFQKFLSQWKISHTTGIPYN
TRANSLATION OF E207TOP-LINK       (1)  ------------------------------------------------------------
 TRANSLATION OF ENV287-LINK       (1)  ------------------------------------------------------------
  TRANSLATION OF T20.22A-23       (1)  ------------------------------------------------------------
                     PGD-E1       (1)  ------------------------------------------------------------
                     PGD-E2       (1)  ------------------------------------------------------------
                     PGD-E3       (1)  ------------------------------------------------------------
                  CONSENSUS     (301)
```

FIG. 9-3

```
                                   361                                                        420
GI_4185940_EMB_CAA76880.1_     (1) --------------------------MQRKAPPRRRRHRNRAPLTHKMNKMVTSEEQMKL
GI_4185944_EMB_CAA76883.1_     (1) --------------------------MQRKAPPRRRRHRNRAPLTHKMNKMVTSEEQMKL
GI_4185948_EMB_CAA76886.1_     (1) --------------------------MQRKAPPRRRRHRNRAPLTHKMNKMVTSEEQMKL
GI_5931706_EMB_CAB56604.1_     (1) ------------------------------------------------------------
ENV OF AB047240              (361) SQGQAIVERTNRTLKTQLVKQKEGGDSKECTTPQMQLNLALYTLNFLNIYRNQTTTSAKQ
TRANSLATION OF E207TOP-LINK    (1) ------------------------------------------------------------
TRANSLATION OF ENV287-LINK     (1) ------------------------------------------------------------
TRANSLATION OF T20.22A-23      (1) --------------------MNPSEMQRKAPPRRRRHRNRAPLTHKMNKMVTSEEQMKL
PGD-E1                         (1) ------------------------------------------------------------
PGD-E2                         (1) ------------------------------------------------------------
PGD-E3                         (1) ------------------------------------------------------------
CONSENSUS                    (361)

                                   421                                                        480
GI_4185940_EMB_CAA76880.1_    (35) PSTKKAEPPTWAQLKKLTQLATKYLENTKVTQTPESMLLAALMIVSMVVSLPMPAGAAAA
GI_4185944_EMB_CAA76883.1_    (35) PSTKKAEPPTWAQLKKLTQLATKYLENTKVTQTPESMLLAALMIVSMVVSLPMPAGAAAA
GI_4185948_EMB_CAA76886.1_    (35) PSTKKAEPPTWAQLKKLTQLATKYLENTKVTQTPESMLLAALMIVSMVVSLPMPAGAAAA
GI_5931706_EMB_CAB56604.1_     (1) ------------------------------------------------------------
ENV OF AB047240              (421) HLTGKKHSPHEGKLIWWKDNKNKTWEIGKVITWGRGFACVSPGENQLPVWIPTRHLKFYN
TRANSLATION OF E207TOP-LINK    (1) ------------------------------------------------------------
TRANSLATION OF ENV287-LINK     (1) ------------------------------------------------------------
TRANSLATION OF T20.22A-23     (40) PSTKKAEPPTWAQLKKLTQLATKYLENTKVTQTPESMLLAALMIVSMVVSLPMPAGAAAA
PGD-E1                         (1) ------------------------------------------------------------
PGD-E2                         (1) ------------------------------------------------------------
PGD-E3                         (1) ------------------------------------------------------------
CONSENSUS                    (421)
```

FIG. 9-4

```
                                481                                                        540
GI_4185940_EMB_CAA76880.1_    (95) NYTYWAYVPFPP-LIRAVTWMDNPTEVYVNDSVWVPGPIDDRCPAKPEEEGMMINISIGY
GI_4185944_EMB_CAA76883.1_    (95) NYTYWAYVPFPP-LIRAVTWMDNPIEVYVNDSVWVPGPTDDHCPAKPEEEGMMINISIGY
GI_4185948_EMB_CAA76886.1_    (95) NYTYWAYVPFPP-LIRAVTWMDNPTEVYVNDSVWVPGPIDDRCPAKPEEEGMMINISIGY
GI_5931706_EMB_CAB56604.1_     (1) -------------MVTPVTWMDNPIEVYVNDSVWVPGPTDDRCPAKPEEEGMMINISIGY
           ENV OF AB047240   (481) EPIGDAKKRASTEMVTPVTWMDNPIEVYVNDSVWVPGPTDDRCPAKPEEEGMMINISIVY
TRANSLATION OF E207TOP-LINK    (1) ------------------------------------------------------------
TRANSLATION OF ENV287-LINK     (1) ------------------------------------------------------------
 TRANSLATION OF T20.22A-23   (100) NYTYWAYVPFPP-LIRAVTWMDNPTEVYVNDSVWVPGPIDDRCPAKPEEEGMMINISIGY
                    PGD-E1     (1) ------------------------------------------------------------
                    PGD-E2     (1) ------------------------------------------------------------
                    PGD-E3     (1) ------------------------------------------------------------
                 CONSENSUS   (481)              LI  VTWMDNP EVYVNDSVWVPGP DD CPAKPEEEGMMINISI Y

                                541                                                        600
GI_4185940_EMB_CAA76880.1_   (154) HYPPICLGRAPGCLMPAVQNWLVEVPTVSPICRFTYHMVSGMSLRPRVNYLQDFSYQRSL
GI_4185944_EMB_CAA76883.1_   (154) RYPPICLGRAPGCLMPAVQNWLVEVPTVSPISRFTYHMVSGMSLRPRVNYLQDFSYQRSF
GI_4185948_EMB_CAA76886.1_   (154) HYPPICLGRAPGCIMPAVQNWLVEVPTVSPICRFTYHMVSGMSLRPRVNYLQDFSYQRSL
GI_5931706_EMB_CAB56604.1_    (48) HYPPICLGRAPGCLMPAVQNWLVEVPTVSPNSRFTYHMVSGMSLRPRVNCLQDFSYQRSL
           ENV OF AB047240   (541) RYPPICLGRAPGCLMPAVQNWLVEVPTVSPNSRFTYHMVSGMSLRPRVNYLQDFSYQRSL
TRANSLATION OF E207TOP-LINK    (1) -----------------------------------------------------FSYQRSL
TRANSLATION OF ENV287-LINK     (1) ------------------------------------------------------------
 TRANSLATION OF T20.22A-23   (159) HYPPICLGRAPGCLMPAVQNWLVEVPTVSPICRFTYHMVSGMSLRPRVNYLQDFSYQRSL
                    PGD-E1     (1) ------------------------------------------------------------
                    PGD-E2     (1) ------------------------------------------------------------
                    PGD-E3     (1) ------------------------------------------------------------
                 CONSENSUS   (541)  YPPICLGRAPGCLMPAVQNWLVEVPTVSP  RFTYHMVSGMSLRPRVN LQDFSYQRSL
```

FIG. 9-5

```
                                    601                                                        660
GI_4185940_EMB_CAA76880.1_    (214) KFRPKGKPCPKEIPKESKNTEVLVWEECVANSAVILQNNEFGTIIDWAPRGQFYHNCSGQ
GI_4185944_EMB_CAA76883.1_    (214) KFRPKGKPCPKEIPKESKNTEVLVWEECVANSAVILQNNEFGTIIDWAPRGQFYHNCSGQ
GI_4185948_EMB_CAA76886.1_    (214) KFRPKGKPCPKEIPKESKNTEVLVWEECVANSAVILQNNEFGTIIDWAPRGQFYHNCSGQ
GI_5931706_EMB_CAB56604.1_    (108) KFRPKGKTCPKEIPKGSKNTEVLVWEECVANSVVILQNNEFGTIIDWAPRGQFYHNCSGQ
           ENV OF AB047240    (601) KFRPKGKPCPKEIPKESKNTEVLVWEECVANSAVILQNNEFGTIIDWAPRGQFYHNCSGQ
TRANSLATION OF E207TOP-LINK     (8) KFRPKGKPCPKEIPKESKNTEVL-------------------------------------
 TRANSLATION OF ENV287-LINK     (1) ------------------------------------------------------------
  TRANSLATION OF T20.22A-23   (219) KFRPKGKPCPKEIPKESKNTEVLVWEECVANSAVILQNNEFGTIIDWAPRGQFYHNCSGQ
                     PGD-E1     (1) --RPKGKPCPKEIPKESC------------------------------------------
                     PGD-E2     (1) ------------------------------------------------------------
                     PGD-E3     (1) ------------------------------------------------------------
                  CONSENSUS   (601) KFRPKGKPCPKEIPKESKNTEVLVWEECVANS VILQNNEFGTIIDWAPRGQFYHNCSGQ

                                    661                                                        720
GI_4185940_EMB_CAA76880.1_    (274) TQSCQSAQVSPAVDSDLTESLDKHKHKKLQSFYPWEWGEKGISTPRPKIVSPVSGPEHPE
GI_4185944_EMB_CAA76883.1_    (274) TQSCPSAQVSPAVDSDLTESLDKHKHKKLQSFYPWEWGEKGISTPRPKIISPVSGPEHPE
GI_4185948_EMB_CAA76886.1_    (274) TQSCPSAQVSPAVDSDLTESLDKHKHKKLQSFYPWEWGEKGISTPRPKIVSPVSGPEHPE
GI_5931706_EMB_CAB56604.1_    (168) TQSCPSAQVSPAVDSDLTESLDKHKHKKLQSFYLWEWEEKGISTPRPKIISPVSGPEHPE
           ENV OF AB047240    (661) TQSCPSAQVSPAVDSDLTESLDKHKHKKLQSFYPWEWGEKGISTPRPEIISPVSGPEHPE
TRANSLATION OF E207TOP-LINK    (31) ------------------------------------------------------------
 TRANSLATION OF ENV287-LINK     (1) --------------SDLTESLDKHKHKKLQSFYPWEWGEKGI------------------
  TRANSLATION OF T20.22A-23   (279) TQSCPSAQVSPAVDSDLTESLDKHKHKKLQSFYPWEWGEKGISTPRPKIVSPVSGPEHPE
                     PGD-E1    (17) ------------------------------------------------------------
                     PGD-E2     (1) ------------------------------------------------------------
                     PGD-E3     (1) ------------------------------------------------------------
                  CONSENSUS   (661) TQSC SAQVSPAVDSDLTESLDKHKHKKLQSFYPWEWGEKGISTPRP IISPVSGPEHPE
```

FIG. 9-6

```
                                     721                                                        780
GI_4185940_EMB_CAA76880.1_    (334) LWRLTVASHHIRIWSGNQTLETRDRKPFYTIDLNSSLTVPLQSCVKPPYMLVVGNIVIKP
GI_4185944_EMB_CAA76883.1_    (334) LWRLTVASHHIRIWSGNQTLETRDRKPFYTVDLNSSVTVPLQSCIKPPYMLVVGNIVIKP
GI_4185948_EMB_CAA76886.1_    (334) LWRLTVASHHIRIWSGNQTLETRDRKPFYTIDLNSSLTVPLQSCVKPPYMLVVGNIVIKP
GI_5931706_EMB_CAB56604.1_    (228) LWRLTVASHHIRIWSGNQTLETRYRKPFYTIDLNSILTVPLQSCVKPPYMLVVGNIVIKP
              ENV OF AB047240 (721) LW---------RL---------------------W---------------------P---
 TRANSLATION OF E207TOP-LINK   (31) ------------------------------------------------------------
 TRANSLATION OF ENV287-LINK    (29) ------------------------------------------------------------
 TRANSLATION OF T20.22A-23    (339) LWRLTVASHHIRIWSGNQTLETRDRKPFYTIDLNSSLTVPLQSCVKPPYMLVVGNIVIKP
                       PGD-E1  (17) ------------------------------------------------------------
                       PGD-E2   (1) --------------------------------LNSSLTVPLQSCVKPC------------
                       PGD-E3   (1) ------------------------------------------------------------
                    CONSENSUS (721) LW         RI                   LNS LTVPLQSCVKP

                                     781                                                        840
GI_4185940_EMB_CAA76880.1_    (394) DSQTITCENCRLLTCIDSTFNWQHRILLVRAREGVWIPVSMDRPWEASPSVHILTEVLKG
GI_4185944_EMB_CAA76883.1_    (394) DSQTITCENCRLLTCIDSTFNWQHRILLVRAREGVWIPVSMDRPWETSPSIHTLTEVLKG
GI_4185948_EMB_CAA76886.1_    (394) DSQTITCENCRLLTCIDSTFNWQHRILLVRAREGVWIPVSMDRPWEASPSVHILTEVLKG
GI_5931706_EMB_CAB56604.1_    (288) ASQTITCENCRLFTCIDSTFNWQHRILLVRAREGMWIPVSTDRPWEASPSIHILTEILKG
              ENV OF AB047240 (727) ----------------DITLEFGLEIKL--------------------------------
 TRANSLATION OF E207TOP-LINK   (31) ------------------------------------------------------------
 TRANSLATION OF ENV287-LINK    (29) ------------------------------------------------------------
 TRANSLATION OF T20.22A-23    (399) DSQTITCENCRLLTCIDSTFNWQHRILLVRAREGVWIPVSMDRPWEASPSVHILTEVLKG
                       PGD-E1  (17) ------------------------------------------------------------
                       PGD-E2  (17) ------------------------------------------------------------
                       PGD-E3   (1) ------------------------------------------------------------
                    CONSENSUS (781)                 DST  W   I L
```

FIG. 9-7

```
                                   841                                                        900
GI_4185940_EMB_CAA76880.1_  (454) VLNRSKRFIFTLIAVIMGLIAVTATAAVAGVALHSSVQSVNFVNDWQKNSTRLWNSQSSI
GI_4185944_EMB_CAA76883.1_  (454) VLNRSKRFIFTLIAVIMGLIAVTATAAVAGVALHSSVQSVNFVNDWQKNSTRLWNSQSSI
GI_4185948_EMB_CAA76886.1_  (454) VLNRSKRFIFTLIAVIMGLIAVTATAAVAGVALHSSVQSVNFVNDWQKNSTRLWNSQSSI
GI_5931706_EMB_CAB56604.1_  (348) VLNRSKRFIFTLIAVIMGLIAVTATAAVAGVALHSSVQSVNFVNYWQKNSTRLWNSQSSI
           ENV OF AB047240  (739) ------------------------------------------------------------
TRANSLATION OF E207TOP-LINK  (31) ------------------------------------------------------------
 TRANSLATION OF ENV287-LINK  (29) ------------------------------------------------------------
  TRANSLATION OF T20.22A-23 (459) VLNRSKRFIFTLIAVIMGLIAVTATAAVAGVALHSSVQSVNFVNDWQKNSTRLWNSQSSI
                     PGD-E1  (17) ------------------------------------------------------------
                     PGD-E2  (17) ------------------------------------------------------------
                     PGD-E3   (1) ------------------------------------------------------------
                  CONSENSUS (841)

                                   901                                                        960
GI_4185940_EMB_CAA76880.1_  (514) DQKLANQINDLRQTVIWMGDRLMSLEHRFQLQCDWNTSDFCITPQIYNESEHHWDMVRRH
GI_4185944_EMB_CAA76883.1_  (514) DQKLANQINDLRQTVIWMGDRLMSLEHRFQLQCDWNTSDFSITPQIYNESEHHWDMVRRH
GI_4185948_EMB_CAA76886.1_  (514) DQKLANQINDLRQTVIWMGDRLMSLEHRFQLQCDWNTSDFCITPQIYNESELHWDMVRRH
GI_5931706_EMB_CAB56604.1_  (408) DQKLASQINDLRQTVIWMGDRLMTLEHHFQLQCDWNTSDFCITPQIYNESEHHWDMVRRH
           ENV OF AB047240  (739) ------------------------------------------------------------
TRANSLATION OF E207TOP-LINK  (31) ------------------------------------------------------------
 TRANSLATION OF ENV287-LINK  (29) ------------------------------------------------------------
  TRANSLATION OF T20.22A-23 (519) DQKLANQINDLRQTVIWMGDRLMSLEHRFQLQCDWNTSDFCITPQIYNESEHHWDMVRRH
                     PGD-E1  (17) ------------------------------------------------------------
                     PGD-E2  (17) ------------------------------------------------------------
                     PGD-E3   (1) ------------------------------------------------------------
                  CONSENSUS (901)
```

FIG. 9-8

```
                                     961                                                      1020
   GI_4185940_EMB_CAA76880.1_  (574) LQGREDNLTLDISKLKEQIFEASKAHLNLVPGTEAIAGVADGLANLNPVTWVKTIGSTTI
   GI_4185944_EMB_CAA76883.1_  (574) LQGREDNLTLDISKLKEQIFEASKAHLNLVPGTEAIAGVADGLANLNPVTWVKTIGSTTI
   GI_4185948_EMB_CAA76886.1_  (574) LQGREDNLTLDISKLKEQIFEASKAHLNLVPGTEAIAGVADGLANLNPVTWVKTIGSTTI
   GI_5931706_EMB_CAB56604.1_  (468) LQGREDNLTLDISKLKEQIFEASKAHLNLVPGTEAIAGVADGLANLNPVTWIKTIRSTMI
              ENV OF AB047240  (739) ------------------------------------------------------------
TRANSLATION OF E207TOP-LINK     (31) ------------------------------------------------------------
 TRANSLATION OF ENV287-LINK     (29) ------------------------------------------------------------
  TRANSLATION OF T20.22A-23    (579) LQGREDNLTLDISKLKEQIFEASKAHLNLVPGTEAIAGVADGLANLNPVTWVKTIGSTTI
                       PGD-E1   (17) ------------------------------------------------------------
                       PGD-E2   (17) ------------------------------------------------------------
                       PGD-E3    (1) ------------------------------------------------------------
                    CONSENSUS  (961)

                                     1021                                                      1081
   GI_4185940_EMB_CAA76880.1_  (634) INLILILVCLFCLLLVCRCTQQLRRDSDHRERAMMTMAVLSKRKGGNVGKSKRDQIVTVSV
   GI_4185944_EMB_CAA76883.1_  (634) INLILILVCLFCLLLVCRCTQQLRRDSDHRERAMMTMAVLSKRKGGNVGKSKRDQIVTVSV
   GI_4185948_EMB_CAA76886.1_  (634) INLILILVCLFCLLLVCRCTQQLRRDSDHRERAMMTMAVLSKRKGGNVGKSKRDQIVTVSV
   GI_5931706_EMB_CAB56604.1_  (528) INLILIVVCLFCLLLVCRCTQQLRRDSDIENGP----------------------------
              ENV OF AB047240  (739) -------------------------------------------------------------
TRANSLATION OF E207TOP-LINK     (31) -------------------------------------------------------------
 TRANSLATION OF ENV287-LINK     (29) -------------------------------------------------------------
  TRANSLATION OF T20.22A-23    (639) INLILILVCLFCLLLVCRCTQQLRRDSDHRERAMMTMAVLSKRKGGNVGKSKRDQIVTVSV
                       PGD-E1   (17) -------------------------------------------------------------
                       PGD-E2   (17) -------------------------------------------------------------
                       PGD-E3    (1) -----------------RCTQQLRRDSDHRERA----------------------------
                    CONSENSUS (1021)                  RCTQQLRRDSD
```

FIG. 9-9

SEQUENCE LISTING

<160> NUMBER OF SEQ ID NOS: 225

<210> SEQ ID NO 1
<211> LENGTH: 89
<212> TYPE: DNA
<213> ORGANISM: Homo sapiens

<400> SEQUENCE: 1
ctttgtctct gtgtcttttt cttttccaaa tctctcgtcc caccttacga gaaacaccca 60
caggtgtgta ggggcaaccc acccctaca 89

<210> SEQ ID NO 2
<211> LENGTH: 560
<212> TYPE: DNA
<213> ORGANISM: Homo sapiens

<400> SEQUENCE: 2
tgtggggaaa agcaagagag atcagattgt tactgtgtct gtgtagaaag aagtagacat 60
aggagactcc attttgttat gtactaagaa aaattcttct gccttgagat tctgttaatc 120
tatgacctta cccccaaccc cgtgctctct gaaacatgtg ctgtgtccac tcagggttaa 180
atggattaag ggcggtgcag gatgtgcttt gttaaacaga tgcttgaagg cagcatgctc 240
cttaagagtc atcaccactc cctaatctca agtacccagg gacacaaaaa ctgcggaagg 300
ccgcagggac ctctgcctag gaaagccagg tattgtccaa cgtttctccc catgtgatag 360
cctgaaatat ggcctcgtgg gaagggaaag acctgaccgt cccccagccc gacacccgta 420
aagggtctgt gctgaggagg attagtaaaa gaggaaggaa tgcctcttgc agttgagaca 480
agaggaaggc atctgtctcc tgcctgtccc tgggcaatgg aatgtctcgg tataaaaccc 540
gattgtatgc tccatctact 560

<210> SEQ ID NO 3
<211> LENGTH: 319
<212> TYPE: DNA
<213> ORGANISM: Homo sapiens

<400> SEQUENCE: 3
gagataggga aaaaccgcct tagggctgga ggtgggacct gcgggcagca atactgcttt 60
gtaaagcact gagatgttta tgtgtatgca tatctaaaag cacagcactt aatcctttac 120
attgtctatg atgcaaagac ctttgttcac atgtttgtct gctgaccctc tccccacaat 180
tgtcttgtga ccctgacaca tccccctctt cgagaaacac ccacagatga tcagtaaata 240
ctaagggaac tcagaggctg gcgggatcct ccatatgctg aacgctggtt ccccgggtcc 300
ccttctttct ttctctata 319

<210> SEQ ID NO 4
<211> LENGTH: 408
<212> TYPE: DNA
<213> ORGANISM: Homo sapiens

<400> SEQUENCE: 4
gagataggga aaaaccgcct tagggctgga ggtgggacct gcgggcagca atactgcttt 60
gtaaagcact gagatgttta tgtgtatgca tatctaaaag cacagcactt aatcctttac 120
attgtctatg atgcaaagac ctttgttcac atgtttgtct gctgaccctc tccccacaat 180
tgtcttgtga ccctgacaca tccccctctt cgagaaacac ccacagatga tcagtaaata 240

-continued

```
ctaagggaac tcagaggctg gcgggatcct ccatatgctg aacgctggtt ccccgggtcc    300

ccttctttct ttctctatac tttgtctctg tgtctttttc ttttccaaat ctctcgtccc    360

accttacgag aaacacccac aggtgtgtag gggcaaccca cccctaca                 408


<210> SEQ ID NO 5
<211> LENGTH: 879
<212> TYPE: DNA
<213> ORGANISM: Homo sapiens

<400> SEQUENCE: 5

tgtggggaaa agcaagagag atcagattgt tactgtgtct gtgtagaaag aagtagacat     60

aggagactcc attttgttat gtactaagaa aaattcttct gccttgagat tctgttaatc    120

tatgacctta cccccaaccc cgtgctctct gaaacatgtg ctgtgtccac tcagggttaa    180

atggattaag ggcggtgcag gatgtgcttt gttaaacaga tgcttgaagg cagcatgctc    240

cttaagagtc atcaccactc cctaatctca agtacccagg gacacaaaaa ctgcggaagg    300

ccgcagggac ctctgcctag gaaagccagg tattgtccaa cgtttctccc catgtgatag    360

cctgaaatat ggcctcgtgg gaagggaaag acctgaccgt cccccagccc gacacccgta    420

aagggtctgt gctgaggagg attagtaaaa gaggaaggaa tgcctcttgc agttgagaca    480

agaggaaggc atctgtctcc tgcctgtccc tgggcaatgg aatgtctcgg tataaaaccc    540

gattgtatgc tccatctact gagataggga aaaaccgcct tagggctgga ggtgggacct    600

gcgggcagca atactgcttt gtaaagcact gagatgttta tgtgtatgca tatctaaaag    660

cacagcactt aatcctttac attgtctatg atgcaaagac ctttgttcac atgtttgtct    720

gctgaccctc tccccacaat tgtcttgtga ccctgacaca tccccctctt cgagaaacac    780

ccacagatga tcagtaaata ctaagggaac tcagaggctg gcgggatcct ccatatgctg    840

aacgctggtt ccccgggtcc ccttctttct ttctctata                           879


<210> SEQ ID NO 6
<211> LENGTH: 108
<212> TYPE: DNA
<213> ORGANISM: Homo sapiens

<400> SEQUENCE: 6

tctggtgccc aacgtggagg cttttctcta gggtgaaggt acgctcgagc gtggtcattg     60

aggacaagtc gacgagagat cccgagtaca tctacagtca gccttacg                 108


<210> SEQ ID NO 7
<211> LENGTH: 1390
<212> TYPE: DNA
<213> ORGANISM: Homo sapiens

<400> SEQUENCE: 7

gggaagagac tcaagtagga gcgcctgccc gagctgagac tagatgtgaa cctttcacca     60

tgaaaatgtt aaaagatata aaggaaggag ttaaacaata tggrtccaac tcccccttata    120

taagaacakt attagattcc attgcycatg gaaatagact tactccttat gactgggaaa    180

ttttggccaa atcttccctt tcatcctctc agtatctaca gtttaaaacc tggtggattg    240

atggrgtaca rgaacaggta cgaaaaaatc aggctactaa gcccactgtt aatatagacg    300

cagaccaatt gttaggaaca ggtccaaatt ggagcaccat taaccaacaa tcagtgatgc    360

agaatgaggc tattgaacaa gtaagggcta tttgcctcag ggcctgggga aaaattcagg    420

acccaggaac agctttccct attaattcaa ttagacaagg ctctaaagag ccatatcctg    480
```

-continued

```
actttgtggc aagattacaa gatgctgctc aaaagtctat tacagatgac aatgcccgaa    540

aagttattgt agaattaatg gcctatgaaa atgcaaatcc agaatgtcag tcggccataa    600

agccattaaa aggaaaagtt ccagcaggag ttgatgtaat tacmgaatat gtgaaggctt    660

gtgatgggat tggaggagct atgcataagg caatgctaat ggctcaagca atgagggggc    720

tcactctagg aggacaagtt agaacatttg ggaaaaaatg ttataattgt ggtcaaatcg    780

gtcatckgaa aaggagttgc ccaggcttaa ayaarcagaa tataataaat caagctatta    840

cagcaaaaaa taaaaagcca tctggcctgt gtccaaaatg tggaaaagca aaacattggg    900

ccaatcaatg tcattctaaa tttgataaag atgggcaacc attgtctgga aacaggaaga    960

ggggccagcc tcaggccccc caacaaactg gggcattccc agttaaactg tttgttcctc   1020

agggttttca aggacaacaa cccctacaga aaataccacc acttcaggga gtcagccaat   1080

tacaacaatc caacagctgt cccgcgccac agcaggcagc accgcagtag atttatgttc   1140

cacccaaatg gtctttttac tccctggaaa gcccccacaa aagattccta gaggggtata   1200

tggcccgctg ccagaaggga gggtaggcct ttgagggaga tcaagtctaa atttgaaggg   1260

agtccaaatt catactgggg taatttactc agattataaa gggggaattc agttagtgat   1320

cagctccact gttccccgga gtgccaatcc aggtgataga attgctcaat tactgctttt   1380

gccttatgca                                                          1390
```

<210> SEQ ID NO 8
<211> LENGTH: 1416
<212> TYPE: DNA
<213> ORGANISM: Homo sapiens

<400> SEQUENCE: 8

```
acaacaatgg catgcagaga ttactatccc agcctcccta tacagcccca ggaatcaaaa     60

aatcatgact aaaatgggat agctccctaa aaagggacta ggaaagaaag aagtcccaat    120

tgaggctgaa aaaaatyaaa aaagaaaagg aatagggcat ccttttttagg agcggtcact    180

gtagagcctc caaaacccat tccattaact tgggaaaaaa amaactgtat ggtaaatcag    240

cagccgcttc caaaacaaaa rctggaggcy ttacayttat tagcaaagaa acmattagaa    300

aaaggacatt gagccttcat tttcgccttg gaattctgtt tgtrattcag aaaaaatccg    360

gcagatggcg tatgctaact gagccattaa tgccgtaatt caacccatgg gggctctccc    420

accccggttg ccctctccag ccatggtccc ctttaattat aattgatctg aaggattgct    480

tttttaccat tcctctggca aaacaggatt ttgaraaatt tgctttyacc acaccagcct    540

aaataataaa gaaccagcca ccaggtttca gtggaaagta ttgcctcagg gaatgcttaa    600

tagttcaact atttgtcagc tcaagctctg caaccagtta gagacaagtt ttcagactgt    660

tacatcgttc actatgttga tattttgtgt gctgcagaaa cgagagacaa attaattgac    720

cgttacacat ttctgcagac agaggttgcc aacgcgggrc tgacaataac atctgataag    780

attcaarcct ctactccttt ccgttacttg ggaatgcagg tagaggaaag gaaaattaaa    840

ccmcaaaaaa atagaaataa gaaaagacac attaaaagca ttaaatgagt ttcaaaagtt    900

gctaggagat actaattgga tttggagata ttaattggat ttggccaact ctaggcattc    960

ctacttatgc catgtcaaat ttgtwctctt tcttaagagg ggactcggaa ttaaatagtg   1020

aaagaacgtt aactccagag gcaactaaag aaattaaatt aattgaagaa aaaattcggt   1080

cagcacaagt aaatagaata gatcacttgg ccccactcca aattttgatt tttactactg   1140

cacattccct aacaggcatc attgttcaaa acacagatct tgtggagtgg tccttccttc   1200
```

-continued

```
ctcacagtac aattaagact tttacattgt acttggatca aatggctaca ttaattggtc   1260

agggaagatt atgaataata acattgtgtg gaaatgaccc agataaaatc actgttcctt   1320

tcaacaagca acaggttaga caagccttta tcaattctgg tgcatggcag attggtcttg   1380

ccgattttgt gggaattatt gacaatcgtt accaca                             1416
```

<210> SEQ ID NO 9
<211> LENGTH: 1420
<212> TYPE: DNA
<213> ORGANISM: Homo sapiens

<400> SEQUENCE: 9

```
acaacaatgg catgcagaga ttactatccc agcctcccta tacagcccca ggaatcaaaa     60

aatcatgact aaaatgggat agctccctaa aaagggacta ggaaagaaag aagtcccaat    120

tgaggctgaa aaaaatyaaa aaagaaaagg aatagggcat ccttttttagg agcggtcact    180

gtagagcctc caaaacccat tccattaact tgggggaaaa aaaaamaact gtatggtaaa    240

tcagcagccg cttccaaaac aaaarctgga ggcyttacay ttattagcaa agaaacmatt    300

agaaaaagga cattgagcct tcattttcgc cttggaattc tgtttgtrat tcagaaaaaa    360

tccggcagat ggcgtatgct aactgagcca ttaatgccgt aattcaaccc atgggggctc    420

tcccaccccg gttgccctct ccagccatgg tcccctttaa ttataattga tctgaaggat    480

tgcttttttta ccattcctct ggcaaaacag gatttgara aatttgcttt yaccacacca    540

gcctaaataa taaagaacca gccaccaggt ttcagtggaa agtattgcct cagggaatgc    600

ttaatagttc aactatttgt cagctcaagc tctgcaacca gttagagaca agttttcaga    660

ctgttacatc gttcactatg ttgatatttt gtgtgctgca gaaacgagag acaaattaat    720

tgaccgttac acatttctgc agacagaggt tgccaacgcg ggrctgacaa taacatctga    780

taagattcaa rcctctactc ctttccgtta cttgggaatg caggtagagg aaaggaaaat    840

taaaccmcaa aaaaatagaa ataagaaaag acacattaaa agcattaaat gagtttcaaa    900

agttgctagg agatactaat tggatttgga gatattaatt ggatttggcc aactctaggc    960

attcctactt atgccatgtc aaatttgtwc tctttcttaa gaggggactc ggaattaaat   1020

agtgaaagaa cgttaactcc agaggcaact aaagaaatta aattaattga agaaaaaatt   1080

cggtcagcac aagtaaatag aatagatcac ttggccccac tccaaatttt gatttttact   1140

actgcacatt ccctaacagg catcattgtt caaaacacag atcttgtgga gtggtccttc   1200

cttcctcaca gtacaattaa gacttttaca ttgtacttgg atcaaatggc tacattaatt   1260

ggtcagggaa gattatgaat aataacattg tgtggaaatg acccagataa aatcactgtt   1320

cctttcaaca agcaacaggt tagacaagcc tttatcaatt ctggtgcatg gcagattggt   1380

cttgccgatt ttgtgggaat tattgacaat cgttaccaca                         1420
```

<210> SEQ ID NO 10
<211> LENGTH: 837
<212> TYPE: DNA
<213> ORGANISM: Homo sapiens

<400> SEQUENCE: 10

```
ccaaaagaat gagtcatcaa aactcagtat cactygactc aaagagcaga gttggttgcc     60

gtcattacag tgttaacaag attttaatca gtctattaac attgtatcag attctgcata    120

tgtagtacag gctacaaagg atattgagag agccctaatc aaatacatta tggatgatca    180

gttaaacccg ctgtttaatt tgttacaaca aaatgtaaga aaawgaaatt tcccatttta    240
```

-continued

```
tattactcat attcgagcac acactaattt accagggcct ttaactaaag caaatgaaca    300

agctgacttg ctagtatcat ctgcattcat kgargcacaa gaacttcatg ccttgactca    360

tgtaaatgca ataggattaa aaaataratt tgatatcaca tggaaacaga caaaaaatat    420

tgtacaacat tgcrcccagt gtcagattct acacctggcc actcaggagg yaagagttaa    480

tcccagaggt ctatgtccta atgtgttatg gcaaatggat gtcatgcacg taccytcatt    540

tggaaaattg tcatttgtcc aygtgacagt tgatacttat tcacatttca tatgggcaac    600

ctgccagaca ggagaaagta cttcccatgt yaagagacat ttattatytt gttttcctgt    660

catgggagtt ccagaaaaag ttaaracaga caatgggcca ggttactgta gtaaagcagt    720

tcaaraattc ttaaatcagt ggaaaattac acatacaata ggaattctct ataattccca    780

aggacaggcc ataattgaaa gaactaatag aacactcaaa gctcaattgg ttaaaca       837
```

<210> SEQ ID NO 11
<211> LENGTH: 841
<212> TYPE: DNA
<213> ORGANISM: Homo sapiens
<220> FEATURE:
<221> NAME/KEY: misc_feature
<222> LOCATION: (1)..(841)
<223> OTHER INFORMATION: N=A,G,C,T

<400> SEQUENCE: 11

```
gggaagagac tcaagtagga gcgcctgccc gagctgagac tagatgtgaa cctttcacca     60

tgaaaatgtt aaaagatata aaggaaggag ttaaacaata tggatccaac tccccttata    120

taagaacagt attagattcc attgctcatg gaaatagact tactccttat gactgggaaa    180

ttttggccaa atcttccctt tcatcctctc agtatctaca gtttaaaacc tggtggattg    240

atggagtaca agaacaggta cgnaaaaaat caggctacta agcccactgt taatatagac    300

gcagaccaat tgttaggaac aggtccaaat tggagcacca ttaaccaaca atcagtgatg    360

cagaatgagg ctattgaaca agtaagggct atttgcctca gggcctgggg aaaaattcag    420

gacccaggaa cagctttccc tattaattca attagacaag gctctaaaga gccatatcct    480

gactttgtgg caagattaca agatgctgct caaaagtcta ttacagatga caatgcccga    540

aaagttattg tagaattaat ggcctatgaa aatgcaaatc cagaatgtca gtcggccata    600

aagccattaa aaggaaaagt tccagcagga gttgatgtaa ttacagaata tgtgaaggct    660

tgtgatggga ttggaggagc tatgcataag gcaatgctaa tggctcaagc aatgaggggg    720

ctcactctag gaggacaagt tagaacattt gggaaaaaat gttataattg tggtcaaatc    780

ggtcatctga aaaggagttg cccaggctta aataaacaga atataataaa tcaagctatt    840

a                                                                    841
```

<210> SEQ ID NO 12
<211> LENGTH: 924
<212> TYPE: DNA
<213> ORGANISM: Homo sapiens
<220> FEATURE:
<221> NAME/KEY: misc_feature
<222> LOCATION: (1)..(924)
<223> OTHER INFORMATION: N=A,G,C,T

<400> SEQUENCE: 12

```
nctgaaaaaa atnaaaaaag aaaaggaata gggcatcctt tttaggagcg gtcactgtag     60

agcctccaaa acccattcca ttaacttggg naaaaaaana actgtatggt aaatcagcag    120

ncgcttccaa aacaaaanct ggaggcntta canttattag caaagaaacc attagaaaaa    180
```

-continued

```
ggacattgag ccttcatttt cgccttggaa ttctgtttgt aattcagaaa aaatccggca    240

gatggcgtat gctaactgag ccattaatgc cgtaattcaa cccatggggg ctctcccacc    300

ccggttgccc tctccagcca tggtcccctt taattataat tgatctgaag gattgctttt    360

ttaccattcc tctggcaaaa caggattttg aaaaatttgc ttttaccaca ccagcctaaa    420

taataaagaa ccagccacca ggtttcagtg gaaagtattg cctcagggaa tgcttaatag    480

ttcaactatt tgtcagctca agctctgcaa ccagttagag acaagttttc agactgttac    540

atcgttcact atgttgatat tttgtgtgct gcagaaacga gagacaaatt aattgaccgt    600

tacacatttc tgcagacaga ggttgccaac gcgggactga caataacatc tgataagatt    660

caaacctcta ctcctttccg ttacttggga atgcaggtag aggaaaggaa aattaaacca    720

caaaaaaata gaaataagaa aagacacatt aaaagcatta aatgagtttc aaaagttgct    780

aggagatact aattggattt ggagatatta attggatttg gccaactcta ggcattccta    840

cttatgccat gtcaaatttg tnctctttct taagagggga ctcggaatta aatagtgaaa    900

gaacgttaac tccagaggca acta                                           924
```

<210> SEQ ID NO 13
<211> LENGTH: 833
<212> TYPE: DNA
<213> ORGANISM: Homo sapiens
<220> FEATURE:
<221> NAME/KEY: misc_feature
<222> LOCATION: (1)..(833)
<223> OTHER INFORMATION: N=A,G,C,T

<400> SEQUENCE: 13

```
ccaaaagaat gagtcatcaa aactcagtat cacttgactc aaagagcaga gttggttgcc     60

gtcattacag tgttaacaag attttaatca gtctattaac attgtatcag attctgcata    120

tgtagtacag gctacaaagg atattgagag agccctaatc aaatacatta tggatgatca    180

gttaaacccg ctgtttaatt tgttacaaca aaatgtaaga aaaagaaatt tcccatttta    240

tattactcat attcgagcac acactaattt accagggcct ttaactaaag caaatgaaca    300

agctgacttg ctagtatcat ctgcattcat ggaagcacaa gaacttcatg ccttgactca    360

tgtaaatgca ataggattaa aaaataaatt tgatatcaca tggaaacaga caaaaaaatat    420

tgtacaacat tgcacccagt gtcagattct acacctggcc actcaggagg caagagttaa    480

tcccagaggt ctatgtccta atgtgttatg gcaaatggat gtcatgcacg taccttcatt    540

tggaaaattg tcatttgtcc atgtgacagt tgatacttat tcacatttca tatgggcaac    600

ctgccagaca ggagaaagta cttcccatgt taagagacat ttattatctt gttttcctgt    660

catgggagtt ccagaaaaag ttaaaacaga caatgggcca ggttactgta gtaaagcagt    720

tcaaaaattc ttaaatcagt ggaaaattac acatacaata ggaattctct ataattccca    780

aggacaggcc ataattgaaa gaactaatag aacactcaaa gctcaattgg tta           833
```

<210> SEQ ID NO 14
<211> LENGTH: 868
<212> TYPE: DNA
<213> ORGANISM: Homo sapiens

<400> SEQUENCE: 14

```
gggaagagac tcaagtagga gcgcctgccc gagctgagac tagatgtgaa cctttcacca     60

tgaaaatgtt aaaagatata aaggaaggag ttaaacaata tggatccaac tcccccttata    120

taagaacagt attagattcc attgctcatg gaaatagact tactccttat gactgggaaa    180
```

-continued

```
ttttggccaa atcttccctt tcatcctctc agtatctaca gtttaaaacc tggtggattg    240

atggagtaca ggaacaggta cgaaaaaatc aggctactaa gcccactgtt aatatagacg    300

cagaccaatt gttaggaaca ggtccaaatt ggagcaccat taaccaacaa tcagtgatgc    360

agaatgaggc tattgaacaa gtaagggcta tttgcctcag ggcctgggga aaaattcagg    420

acccaggaac agctttccct attaattcaa ttagacaagg ctctaaagag ccatatcctg    480

actttgtggc aagattacaa gatgctgctc aaaagtctat tacagatgac aatgcccgaa    540

aagttattgt agaattaatg gcctatgaaa atgcaaatcc agaatgtcag tcggccataa    600

agccattaaa aggaaaagtt ccagcaggag ttgatgtaat tacagaatat gtgaaggctt    660

gtgatgggat tggaggagct atgcataagg caatgctaat ggctcaagca atgagggggc    720

tcactctagg aggacaagtt agaacatttg ggaaaaaatg ttataattgt ggtcaaatcg    780

gtcatctgaa aaggagttgc ccaggcttaa ataaacagaa tataataaat caagctatta    840

cagaaaaaaa aaaaaaaaaa aaaaaaaa                                        868
```

<210> SEQ ID NO 15
<211> LENGTH: 1417
<212> TYPE: DNA
<213> ORGANISM: Homo sapiens

<400> SEQUENCE: 15

```
gggaagagac tcaagtagga gcgcctgccc gagctgagac tagatgtgaa cctttcacca     60

tgaaaatgtt aaaagatata aaggaaggag ttaaacaata tgggtccaac tccccttata    120

taagaacatt attagattcc attgctcatg gaaatagact tactccttat gactgggaaa    180

ttttggccaa atcttccctt tcatcctctc agtatctaca gtttaaaacc tggtggattg    240

atggagtaca agaacaggta cgaaaaaatc aggctactaa gcccactgtt aatatagacg    300

cagaccaatt gttaggaaca ggtccaaatt ggagcaccat taaccaacaa tcagtgatgc    360

agaatgaggc tattgaacaa gtaagggcta tttgcctcag ggcctgggga aaaattcagg    420

acccaggaac agctttccct attaattcaa ttagacaagg ctctaaagag ccatatcctg    480

actttgtggc aagattacaa gatgctgctc aaaagtctat tacagatgac aatgcccgaa    540

aagttattgt agaattaatg gcctatgaaa atgcaaatcc agaatgtcag tcggccataa    600

agccattaaa aggaaaagtt ccagcaggag ttgatgtaat tacagaatat gtgaaggctt    660

gtgatgggat tggaggagct atgcataagg caatgctaat ggctcaagca atgagggggc    720

tcactctagg aggacaagtt agaacatttg ggaaaaaatg ttataattgt ggtcaaatcg    780

gtcatcggaa aaggagttgc ccaggcttaa ataaacagaa tataataaat caagctatta    840

cagcaaaaaa taaaaagcca tctggcctgt gtccaaaatg tggaaaagca aaacattggg    900

ccaatcaatg tcattctaaa tttgataaag atgggcaacc attgtctgga aacaggaaga    960

ggggccagcc tcaggccccc caacaaactg gggcattccc agttaaactg tttgttcctc   1020

agggttttca aggacaacaa cccctacaga aaataccacc acttcaggga gtcagccaat   1080

tacaacaatc caacagctgt cccgcgccac agcaggcagc accgcagtag atttatgttc   1140

cacccaaatg gtctttttac tccctggaaa gcccccacaa aagattccta gaggggtata   1200

tggcccgctg ccagaaggga gggtaggcct ttgagggaga tcaagtctaa atttgaaggg   1260

agtccaaatt catactgggg taatttactc agattataaa gggggaattc agttagtgat   1320

cagctccact gttccccgga gtgccaatcc aggtgataga attgctcaat tactgctttt   1380

gccttatgca aaaaaaaaaa aaaaaaaaaa aaaaaaa                            1417
```

-continued

<210> SEQ ID NO 16
<211> LENGTH: 841
<212> TYPE: DNA
<213> ORGANISM: Homo sapiens

<400> SEQUENCE: 16
aagagactca agtaggagcg cctgcccgag ctgagactag atgtgaacct ttcaccatga 60
aaatgttaaa agatataaag gaaggagtta aacaatatgg atccaactcc ccttatataa 120
gaacagtatt agattccatt gcccatggaa atagacttac tccttatgac tgggaaattt 180
tggccaaatc ttccctttca tcctctcagt atctacagtt taaaacctgg tggattgatg 240
gggtacaaga acaggtacga aaaaaatcag gctactaagc ccactgttaa tatagacgca 300
gaccaattgt taggaacagg tccaaattgg agcaccatta accaacaatc agtgatgcag 360
aatgaggcta ttgaacaagt aagggctatt tgcctcaggg cctggggaaa aattcaggac 420
ccaggaacag ctttccctat taattcaatt agacaaggct ctaaagagcc atatcctgac 480
tttgtggcaa gattacaaga tgctgctcaa aagtctatta cagatgacaa tgcccgaaaa 540
gttattgtag aattaatggc ctatgaaaat gcaaatccag aatgtcagtc ggccataaag 600
ccattaaaag gaaaagttcc agcaggagtt gatgtaatta ccgaatatgt gaaggcttgt 660
gatgggattg gaggagctat gcataaggca atgctaatgg ctcaagcaat gaggggggctc 720 actctaggag gacaagttag aacatttggg aaaaaatgtt ataattgtgg tcaaatcggt 780
catctgaaaa ggagttgccc aggcttaaac aagcaaaaaa aaaaaaaaaa aaaaaaaaaa 840
a 841

<210> SEQ ID NO 17
<211> LENGTH: 873
<212> TYPE: DNA
<213> ORGANISM: Homo sapiens

<400> SEQUENCE: 17
acaacaatgg catgcagaga ttactatccc agcctcccta tacagcccca ggaatcaaaa 60
aatcatgact aaaatgggat agctccctaa aaagggacta ggaaagaaag aagtcccaat 120
tgaggctgaa aaaaattaaa aaagaaaagg aatagggcat cctttttagg agcggtcact 180
gtagagcctc caaaacccat tccattaact tgggaaaaaa aaaactgtat ggtaaatcag 240
cagccgcttc caaaacaaaa gctggaggcc ttacacttat tagcaaagaa accattagaa 300
aaaggacatt gagccttcat tttcgccttg gaattctgtt tgtgattcag aaaaaatccg 360
gcagatggcg tatgctaact gagccattaa tgccgtaatt caacccatgg gggctctccc 420
accccggttg ccctctccag ccatggtccc ctttaattat aattgatctg aaggattgct 480
tttttaccat tcctctggca aaacaggatt ttgaaaaatt tgcttttacc acaccagcct 540
aaataataaa gaaccagcca ccaggtttca gtggaaagta ttgcctcagg gaatgcttaa 600
tagttcaact atttgtcagc tcaagctctg caaccagtta gagacaagtt ttcagactgt 660
tacatcgttc actatgttga tattttgtgt gctgcagaaa cgagagacaa attaattgac 720
cgttacacat ttctgcagac agaggttgcc aacgcggggc tgacaataac atctgataag 780
attcaaacct ctactccttt ccgttacttg ggaatgcagg tagaggaaag gaaaattaaa 840
ccccaaaaaa aaaaaaaaaa aaaaaaaaaa aaa 873

-continued

<210> SEQ ID NO 18
<211> LENGTH: 733
<212> TYPE: DNA
<213> ORGANISM: Homo sapiens

<400> SEQUENCE: 18
ctgaaaaaaa tcaaaaaaga aaaggaatag ggcatccttt ttaggagcgg tcactgtaga 60
gcctccaaaa cccattccat taacttgggg gaaaaaaaaa caactgtatg gtaaatcagc 120
agcgcttcca aaacaaaaac tggaggcttt acatttatta gcaaagaaac aattagaaaa 180
aggacattga gccttcattt tcgccttgga attctgtttg taattcagaa aaaatccggc 240
agatggcgta taatgccgta attcaaccca tgggggctct cccaccccgg ttgccctctc 300
cagccatggt ccccttttaat tataattgat ctgaaggatt gcttttttac cattcctctg 360
gcaaaacagg attttgagaa atttgctttt accacaccag cctaaataat aaagaaccag 420
ccaccaggtt tcagtggaaa gtattgcctc agggaatgct taatagttca actatttgtc 480
agctcaagct ctgcaaccag ttagagacaa gttttcagac tgttacatcg ttcactatgt 540
tgatattttg tgtgctgcag aaacgagaga caaattaatt gaccgttaca catttctgca 600
gacagaggtt gccaacgcgg gactgacaat aacatctgat aagattcaaa cctctactcc 660
tttccgttac ttgggaatgc aggtagagga aaggaaaatt aaaccacaaa aaaaaaaaaa 720
aaaaaaaaaa aaa 733

<210> SEQ ID NO 19
<211> LENGTH: 785
<212> TYPE: DNA
<213> ORGANISM: Homo sapiens

<400> SEQUENCE: 19
cattagaaaa aggacattga gccttcattt tcgccttgga attctgtttg taattcagaa 60
aaaatccggc agatggcgta tgctaactga gccattaatg ccgtaattca acccatgggg 120
gctctcccac cccggttgcc ctctccagcc atggtcccct ttaattataa ttgatctgaa 180
ggattgcttt tttaccattc ctctggcaaa acaggatttt gaaaaatttg cttttaccac 240
accagcctaa ataataaaga accagccacc aggtttcagt ggaaagtatt gcctcaggga 300
atgcttaata gttcaactat ttgtcagctc aagctctgca accagttaga gacaagtttt 360
cagactgtta catcgttcac tatgttgata ttttgtgtgc tgcagaaacg agagacaaat 420
taattgaccg ttacacattt ctgcagacag aggttgccaa cgcgggactg acaataacat 480
ctgataagat tcaaacctct actcctttcc gttacttggg aatgcaggta gaggaaagga 540
aaattaaacc acaaaaaaata gaaataagaa aagacacatt aaaagcatta aatgagtttc 600
aaaagttgct aggagatact aattggattt ggagatatta attggatttg gccaactcta 660
ggcattccta cttatgccat gtcaaatttg tactctttct taagagggga ctcggaatta 720
aatagtgaaa gaacgttaac tccagaggca actaaagaaa aaaaaaaaaa aaaaaaaaaa 780
aaaaa 785

<210> SEQ ID NO 20
<211> LENGTH: 1090
<212> TYPE: DNA
<213> ORGANISM: Homo sapiens -continued

<400> SEQUENCE: 20

```
atctttaccc tgtataaaca tctttctctt cccagtattt ctaagcatgt gacaatgaat     60
atgcaaagga agcgcagcag tccaccaggt gtgggatatg tgtggcacaa ttcaagacaa    120
tgattaaacc tccacttgat gttgcaaaag agattttgaa aaatttgctt tcaccacacc    180
agcctaaata ataaagaacc agccaccagg tttcagtgga aagtattgcc tcagggaatg    240
cttaatagtt caactatttg tcagctcaag ctctgcaacc agttagagac aagttttcag    300
actgttacat cgttcactat gttgatattt tgtgtgctgc agaaacgaga gacaaattaa    360
ttgaccgtta cacatttctg cagacagagg ttgccaacgc gggactgaca ataacatctg    420
ataagattca agcctctact cctttccgtt acttgggaat gcaggtagag gaaaggaaaa    480
ttaaaccaca aaaaaataga aataagaaaa gacacattaa aagcattaaa tgagtttcaa    540
aagttgctag gagatactaa ttggatttgg agatattaat tggatttggc caactctagg    600
cattcctact tatgccatgt caaatttgtt ctctttctta agaggggact cggaattaaa    660
tagtgaaaga acgttaactc cagaggcaac taaagaaatt aaattaattg aagaaaaaat    720
tcggtcagca caagtaaata gaatagatca cttggcccca ctccaaattt tgatttttac    780
tactgcacat tccctaacag gcatcattgt tcaaaacaca gatcttgtgg agtggtcctt    840
ccttcctcac agtacaatta agacttttac attgtacttg gatcaaatgg ctacattaat    900
tggtcaggga agattatgaa taataacatt gtgtggaaat gacccagata aaatcactgt    960
tcctttcaac aagcaacagg ttagacaagc ctttatcaat tctggtgcat ggcagattgg   1020
tcttgccgat tttgtgggaa ttattgacaa tcgttaccac aaaaaaaaaa aaaaaaaaaa   1080
aaaaaaaaaa                                                          1090
```

<210> SEQ ID NO 21
<211> LENGTH: 705
<212> TYPE: DNA
<213> ORGANISM: Homo sapiens

<400> SEQUENCE: 21

```
ccaaaagaat gagtcatcaa aactcagtat cacttgactc aaagagcaga gttggttgcc     60
gtcattacag tgttaacaag attttaatca gtctattaac attgtatcag attctgcata    120
tgtagtacag gctacaaagg atattgagag agccctaatc aaatacatta tggatgatca    180
gttaaacccg ctgtttaatt tgttacaaca aaatgtaaga aaaagaaatt tcccatttta    240
tattactcat attcgagcac acactaattt accagggcct ttaactaaag caaatgaaca    300
agctgacttg ctagtatcat ctgcattcat ggaagcacaa gaacttcatg ccttgactca    360
tgtaaatgca ataggattaa aaaataaatt tgatatcaca tggaaacaga caaaaaaatat    420
tgtacaacat tgcacccagt gtcagattct acacctggcc actcaggagg caagagttaa    480
tcccagaggt ctatgtccta atgtgttatg gcaaatggat gtcatgcacg taccttcatt    540
tggaaaattg tcatttgtcc atgtgacagt tgatacttat tcacatttca tatgggcaac    600
ctgccagaca ggagaaagta cttcccatgt caagagacat ttattatctt gttttcctgt    660
catgggagtt ccagaaaaaa aaaaaaaaaa aaaaaaaaaa aaaaa                    705
```

<210> SEQ ID NO 22
<211> LENGTH: 862
<212> TYPE: DNA
<213> ORGANISM: Homo sapiens -continued

<400> SEQUENCE: 22

```
ccaaaagaat gagtcatcaa aactcagtat cactcgactc aaagagcaga gttggttgcc     60
gtcattacag tgttaacaag attttaatca gtctattaac attgtatcag attctgcata    120
tgtagtacag gctacaaagg atattgagag agccctaatc aaatacatta tggatgatca    180
gttaaacccg ctgtttaatt tgttacaaca aaatgtaaga aaaagaaatt tcccatttta    240
tattactcat attcgagcac acactaattt accagggcct ttaactaaag caaatgaaca    300
agctgacttg ctagtatcat ctgcattcat ggaagcacaa gaacttcatg ccttgactca    360
tgtaaatgca ataggattaa aaaataaatt tgatatcaca tggaaacaga caaaaaaatat    420
tgtacaacat tgcgcccagt gtcagattct acacctggcc actcaggagg taagagttaa    480
tcccagaggt ctatgtccta atgtgttatg gcaaatggat gtcatgcacg taccctcatt    540
tggaaaattg tcatttgtcc atgtgacagt tgatacttat tcacatttca tatgggcaac    600
ctgccagaca ggagaaagta cttcccatgt taagagacat ttattatctt gttttcctgt    660
catgggagtt ccagaaaaag ttaaaacaga caatgggcca ggttactgta gtaaagcagt    720
tcaaaaattc ttaaatcagt ggaaaattac acatacaata ggaattctct ataattccca    780
aggacaggcc ataattgaaa gaactaatag aacactcaaa gctcaattgg ttaaacaaaa    840
aaaaaaaaaa aaaaaaaaaa aa                                             862
```

<210> SEQ ID NO 23
<211> LENGTH: 865
<212> TYPE: DNA
<213> ORGANISM: Homo sapiens

<400> SEQUENCE: 23

```
ccaaaagaat gagtcatcaa aactcagtat cacttgactc aaagagcaga gttggttgcc     60
gtcattacag tgttaacaag attttaatca gtctattaac attgtatcag attctgcata    120
tgtagtacag gctacaaagg atattgagag agccctaatc aaatacatta tggatgatca    180
gttaaacccg ctgtttaatt tgttacaaca aaatgtaaga aaaagaaatt tcccatttta    240
tattactcat attcgagcac acactaattt accagggcct ttaactaaag caaatgaaca    300
agctgacttg ctagtatcat ctgcattcat ggaggcacaa gaacttcatg ccttgactca    360
tgtaaatgca ataggattaa aaaatagatt tgatatcaca tggaaacaga caaaaaaatat    420
tgtacaacat tgcacccagt gtcagattct acacctggcc actcaggagg caagagttaa    480
tcccagaggt ctatgtccta atgtgttatg gcaaatggat gtcatgcacg taccttcatt    540
tggaaaattg tcatttgtcc atgtgacagt tgatacttat tcacatttca tatgggcaac    600
ctgccagaca ggagaaagta cttcccatgt taagagacat ttattatctt gttttcctgt    660
catgggagtt ccagaaaaag ttaaaacaga caatgggcca ggttactgta gtaaagcagt    720
tcaaaaattc ttaaatcagt ggaaaattac acatacaata ggaattctct ataattccca    780
aggacaggcc ataattgaaa gaactaatag aacactcaaa gctcaattgg ttaaacaaaa    840
aaaaaaaaaa aaaaaaaaaa aaaaa                                          865
```

<210> SEQ ID NO 24
<211> LENGTH: 866
<212> TYPE: DNA
<213> ORGANISM: Homo sapiens -continued

<400> SEQUENCE: 24

```
ccaaaagaat gagtcatcaa aactcagtat cacttgactc aaagagcaga gttggttgcc     60
gtcattacag tgttaacaag attttaatca gtctattaac attgtatcag attctgcata    120
tgtagtacag gctacaaagg atattgagag agccctaatc aaatacatta tggatgatca    180
gttaaacccg ctgtttaatt tgttacaaca aaatgtaaga aaatgaaatt tcccatttta    240
tattactcat attcgagcac acactaattt accagggcct ttaactaaag caaatgaaca    300
agctgacttg ctagtatcat ctgcattcat ggaagcacaa gaacttcatg ccttgactca    360
tgtaaatgca ataggattaa aaaataaatt tgatatcaca tggaaacaga caaaaaaatat    420
tgtacaacat tgcacccagt gtcagattct acacctggcc actcaggagg caagagttaa    480
tcccagaggt ctatgtccta atgtgttatg gcaaatggat gtcatgcacg taccttcatt    540
tggaaaattg tcatttgtcc atgtgacagt tgatacttat tcacatttca tatgggcaac    600
ctgccagaca ggagaaagta cttcccatgt taagagacat ttattatttt gttttcctgt    660
catgggagtt ccagaaaaag ttaaaacaga caatgggcca ggttactgta gtaaagcagt    720
tcaagaattc ttaaatcagt ggaaaattac acatacaata ggaattctct ataattccca    780
aggacaggcc ataattgaaa gaactaatag aacactcaaa gctcaattgg ttaaacaaaa    840
aaaaaaaaaa aaaaaaaaaa aaaaaa                                         866
```

<210> SEQ ID NO 25
<211> LENGTH: 882
<212> TYPE: DNA
<213> ORGANISM: Homo sapiens

<400> SEQUENCE: 25

```
ccaaaagaat gagtcatcaa aactcagtat cacttgactc aaagagcaga gttggttgcc     60
gtcattacag tgttaacaag attttaatca gtctattaac attgtatcag attctgcata    120
tgtagtacag gctacaaagg atattgagag agccctaatc aaatacatta tggatgatca    180
gttaaacccg ctgtttaatt tgttacaaca aaatgtaaga aaaagaaatt tcccatttta    240
tattactcat attcgagcac acactaattt accagggcct ttaactaaag caaatgaaca    300
agctgacttg ctagtatcat ctgcattcat tgaagcacaa gaacttcatg ccttgactca    360
tgtaaatgca ataggattaa aaaataaatt tgatatcaca tggaaacaga caaaaaaatat    420
tgtacaacat tgcacccagt gtcagattct acacctggcc actcaggagg caagagttaa    480
tcccagaggt ctatgtccta atgtgttatg gcaaatggat gtcatgcacg taccttcatt    540
tggaaaattg tcatttgtcc acgtgacagt tgatacttat tcacatttca tatgggcaac    600
ctgccagaca ggagaaagta cttcccatgt taagagacat ttattatctt gttttcctgt    660
catgggagtt ccagaaaaag ttaagacaga caatgggcca ggttactgta gtaaagcagt    720
tcaaaaattc ttaaatcagt ggaaaattac acatacaata ggaattctct ataattccca    780
aggacaggcc ataattgaaa gaactaatag aacactcaaa gctcaattgg ttaagcaaaa    840
aaaaaaaaaa aaaaaaaaaa aaacatgtcg gccgcctcgg cc                       882
```

<210> SEQ ID NO 26
<211> LENGTH: 860
<212> TYPE: DNA
<213> ORGANISM: Homo sapiens -continued

<400> SEQUENCE: 26

```
ccaaaagaat gagtcatcaa aactcagtat cacttgactc aaagagcaga gttggttgcc     60
gtcattacag tgttaacaag attttaatca gtctattaac attgtatcag attctgcata    120
tgtagtacag gctacaaagg atattgagag agccctaatc aaatacatta tggatgatca    180
gttaaacccg ctgtttaatt tgttacaaca aaatgtaaga aaaagaaatt tcccatttta    240
tattactcat attcgagcac acactaattt accagggcct ttaactaaag caaatgaaca    300
agctgacttg ctagtatcat ctgcattcat ggaagcacaa gaacttcatg ccttgactca    360
tgtaaatgca ataggattaa aaaataaatt tgatatcaca tggaaacaga caaaaaaatat    420
tgtacaacat tgcacccagt gtcagattct acacctggcc actcaggagg caagagttaa    480
tcccagaggt ctatgtccta atgtgttatg gcaaatggat gtcatgcacg taccttcatt    540
tggaaaattg tcatttgtcc atgtgacagt tgatacttat tcacatttca tatgggcaac    600
ctgccagaca ggagaaagta cttcccatgt taagagacat ttattatctt gttttcctgt    660
catgggagtt ccagaaaaag ttaaaacaga caatgggcca ggttactgta gtaaagcagt    720
tcaaaaattc ttaaatcagt ggaaaattac acatacaata ggaattctct ataattccca    780
aggacaggcc ataattgaaa gaactaatag aacactcaaa gctcaattgg ttaaacaaaa    840
agaaaaaaaa aaaaaaaaaa                                                860
```

<210> SEQ ID NO 27
<211> LENGTH: 778
<212> TYPE: DNA
<213> ORGANISM: Homo sapiens
<220> FEATURE:
<221> NAME/KEY: misc_feature
<222> LOCATION: (1)..(778)
<223> OTHER INFORMATION: N=A,G,C,T

<400> SEQUENCE: 27

```
accggcctta cggccgggga agagntcaag taggagcgcc tgcccgagct gagactagat     60
gtgaaccttt caccatgaaa atgttaaaag atataaagga aggagttaaa caatatggat    120
ccaactcccc ttatataaga acagtattag attccattgc tcatggaaat agacttactc    180
cttatgactg ggaaattttg gccaaatctt ccctttcatc ctctcagtat ctacagttta    240
aaacctggtg gattgatgga gtacaggaac aggtacgaaa aaatcaggct actaagccca    300
ctgttaatat agacgcagac caattgttag gaacaggtcc aaattggagc accattaacc    360
aacaatcagt gatgcagaat gaggctattg aacaagtaag ggctatttgc ctcagggcct    420
ggggaaaaat tcaggaccca ggaacagctt tccctattaa ttcaattaga caaggctcta    480
aagagccata tcctgacttt gtggcaagat tacaagatgc tgctcaaaag tctattacag    540
atgacaatgc ccgaaaagtt attgtagaat taatggccta tgaaaatgca aatccagaat    600
gtcagtcggc cataaagcca ttaaaaggaa aagttccagc aggagttgat gtaattacag    660
aatatgtgaa ggcttgtgat gggattggag gagctatgcn taaggcaatg ctaatggctc    720
aagcaatgag ggggctcact ctaggaggac aagttagaac atttgggaaa aaatgttt      778
```

<210> SEQ ID NO 28
<211> LENGTH: 668
<212> TYPE: DNA
<213> ORGANISM: Homo sapiens
<220> FEATURE:
<221> NAME/KEY: misc_feature
<222> LOCATION: (1)..(668)
<223> OTHER INFORMATION: N=A,G,C,T -continued

<400> SEQUENCE: 28
ttacggcctt acggccgggg aagnntntca agtaggagcg cctgcccgag ctgagactag 60
atgtgaacct ttcaccatga aaatgttaaa agatataaag gaaggagtta aacaatatgg 120
gtccaactcc ccttatataa gaacattatt agattccatt gctcatggaa atagacttac 180
tccttatgac tgggaaattt tggccaaatc ttccctttca tcctctcagt atctacagtt 240
taaaacctgg tggattgatg gagtacaaga acaggtacga aaaaatcagg ctactaagcc 300
cactgttaat atagacgcag accaattgtt aggaacaggt ccaaattgga gcaccattaa 360
ccaacaatca gtgatgcaga atgaggctat tgaacaagta agggctattt gcctcagggc 420
ctggggaaaa attcaggacc caggaacagc tttccctatt aattcaatta gacaaggctc 480
taaagagcca tatcctgact ttgtggcaag attacaagat gctgctcaaa agtctattac 540
agatgacaat gcccgaaaag ttattgtaga attaatggcc tatgaaaatg caaatccaga 600
atgtcagtcg gccataaagc cattaaaagg aaaagttcca gcaggagttg atgtaattac 660 agaatatn 668

<210> SEQ ID NO 29
<211> LENGTH: 659
<212> TYPE: DNA
<213> ORGANISM: Homo sapiens
<220> FEATURE:
<221> NAME/KEY: misc_feature
<222> LOCATION: (1)..(659)
<223> OTHER INFORMATION: N=A,G,C,T

<400> SEQUENCE: 29
cggccttacg gcccggggag anntcaagta ggagcgcctg cccgagctga gactagatgt 60
gaacctttca ccatgaaaat gttaaaagat ataaaggaag gagttaaaca atatggatcc 120
aactcccctt atataagaac agtattagat tccattgccc atggaaatag acttactcct 180
tatgactggg aaattttggc caaatcttcc ctttcatcct ctcagtatct acagtttaaa 240
acctggtgga ttgatggggt acaagaacag gtacgaaaaa aatcaggcta ctaagcccac 300
tgttaatata gacgcagacc aattgttagg aacaggtcca aattggagca ccattaacca 360
acaatcagtg atgcagaatg aggctattga acaagtaagg gctatttgcc tcagggcctg 420
gggaaaaatt caggacccag gaacagcttt ccctattaat tcaattagac aaggctctaa 480
agagccatat cctgactttg tggcaagatt acaagatgct gctcaaaagt ctattacaga 540
tgacaatgcc cgaaaagtta ttgtagaatt aatggcctat gaaaatgcaa atccagaatg 600
tcagtcggcc ataaagccat taaaaggaaa agttccagca ggagttgatg taattaccg 659

<210> SEQ ID NO 30
<211> LENGTH: 664
<212> TYPE: DNA
<213> ORGANISM: Homo sapiens
<220> FEATURE:
<221> NAME/KEY: misc_feature
<222> LOCATION: (1)..(664)
<223> OTHER INFORMATION: N=A,G,C,T

<400> SEQUENCE: 30
nccggcctta cggccgggnc aacaatggca tgcagagntt actatcccag cctccctata 60
cagccccagg aatcaaaaaa tcatgactaa aatgggatag ctccctaaaa agggactagg 120
aaagaaagaa gtcccaattg aggctgaaaa aaattaaaaa agaaaaggaa tagggcatcc 180
tttttaggag cggtcactgt agagcctcca aaacccattc cattaacttg ggaaaaaaaa 240

-continued

```
aactgtntgg taaatcagca gccgnttcca aaacaaaagc tggaggcctt acacttatta    300

ncaaagaanc cattanaaaa aggacattga gccttcattt tcgccttgga attctgtttg    360

tgattcaaaa aaaatccggc anatggcgta tgctaactga nccattaatg ccgtaattca    420

acccatgggg gctctcccac cccggttgcc ctntccagcc atggtcccct ttaattataa    480

ttgatctgaa ggattgcttt tttaccattc ctctggcaaa acaggatttt gaaaaatttg    540

cttttaccac accagcctaa ataataaana accanccacc aggtttcagt ggaaagtatt    600

gcctcaggga atgcttaata gttcaactat tngtcagctc aagctctgca accagttaga    660

gacn                                                                 664
```

<210> SEQ ID NO 31
<211> LENGTH: 743
<212> TYPE: DNA
<213> ORGANISM: Homo sapiens
<220> FEATURE:
<221> NAME/KEY: misc_feature
<222> LOCATION: (1)..(743)
<223> OTHER INFORMATION: N=A,G,C,T

<400> SEQUENCE: 31

```
ncctggcctt acggccgggg ctgaaaaaaa tcaaaaaaga aaaggaatag ggcatccttt     60

ttaggagcgg tcactgtaga gcctccaaaa cccattccat taacttgggg gaaaaaaaaa    120

caactgtatg gtaaatcagc agcgcttcca aaacaaaaac tggaggcttt acatttatta    180

gcaaagaaac aattagaaaa aggacattga gccttcattt tcgccttgga attctgtttg    240

taattcagaa aaaatccggc agatggcgta taatgccgta attcaaccca tgggggctct    300

cccaccccgg ttgccctctc cagccatggt cccctttaat tataattgat ctgaaggatt    360

gctttttac cattcctctg gcaaaacagg attttgagaa atttgctttt accacaccag    420

cctaaataat aaagaaccag ccaccaggtt tcagtggaaa gtattgcctc agggaatgct    480

taatagttca actatttgtc agctcaagct ctgcaaccag ttagagacaa gttttcagac    540

tgttacatcg ttcactatgt tgatattttg tgtgctgcag aaacgagaga caaattaatt    600

gaccgttaca catttctgca gacagaggtt gccaacgcgg gactgacaat aacatctgat    660

aagattcaaa cctctactcc tttccgttac ttgggaatgc aggtagagga aaggaaaatt    720

aaaccacaaa aaaaaaaaaa aan                                            743
```

<210> SEQ ID NO 32
<211> LENGTH: 679
<212> TYPE: DNA
<213> ORGANISM: Homo sapiens
<220> FEATURE:
<221> NAME/KEY: misc_feature
<222> LOCATION: (1)..(679)
<223> OTHER INFORMATION: N=A,G,C,T

<400> SEQUENCE: 32

```
nnnnncncgg gcattagaaa aaggacattg agccttcatt ttcgccttgg aattctgttt     60

gtaattcaga aaaaatccgg cagatggcgt atgctaactg agccattaat gccgtaattc    120

aacccatggg ggctctccca ccccggttgc cctctccagc catggtcccc tttaattata    180

attgatctga aggattgctt ttttaccatt cctctggcaa aacaggattt tgaaaaattt    240

gcttttacca caccagccta aataataaag aaccagccac caggtttcag tggaaagtat    300

tgcctcangg aatgcttaat agttcaacta tttgtcagct caaagctctg cacccagnta    360

gagacaagtt tcagactggt tcatcgtcct atgtgatatt ttgtgtgctg cagaacgaga    420
```

-continued

```
gacaaattat tggccgttca catttttgca gacagaggtt gccaacgcgg gactgacaat    480

aacatctgat aagattaaac ctctactcct tccgtacttg ggaatgcagg tggaggaaag    540

gaaaattaac ccccnnaaaa ttgaattang aaaagacccn ttaaagcctt aaatgagttc    600

aaaaagttgc taggagaaac taattggatt tggaganatt aattggattt ggcaactnta    660

ggcattccta cttatgccn                                                 679
```

<210> SEQ ID NO 33
<211> LENGTH: 656
<212> TYPE: DNA
<213> ORGANISM: Homo sapiens
<220> FEATURE:
<221> NAME/KEY: misc_feature
<222> LOCATION: (1)..(656)
<223> OTHER INFORMATION: N=A,G,C,T

<400> SEQUENCE: 33

```
tccggcctta cggccgggnt ctttaccctg tataaacatc tttctcttcc cagtatttct     60

aagcatgtga caatgaatat gcaaaggaag cgcagcagtc caccaggtgt gggatatgtg    120

tggcacaatt caagacaatg attaaacctc cacttgatgt tgcaaaagag attttgaaaa    180

atttgctttc accacaccag cctaaataat aaagaaccag ccaccaggtt tcagtggaaa    240

gtattgcctc agggaatgct taatagttca actatttgtc agctcaagct ctgcaaccag    300

ttagagacaa gttttcagac tgttacatcg ttcactatgt tgatattttg tgtgctgcag    360

aaacgagaga caaattaatt gaccgttaca catttctgca gacagaggtt gccaacgcgg    420

gactgacaat aacatctgat aagattcaag cctctactcc tttccgttac ttgggaatgc    480

aggtagagga aaggaaaatt aaaccacaaa aaaatagaaa taagaaaaga cacattaaaa    540

gcattaaatg agtttcaaaa gttgctagga gatactaatt ggatttggag atattaattg    600

gatttggcca actctaggca ttcctactta tgccatgtca aatttgttct ctttct        656
```

<210> SEQ ID NO 34
<211> LENGTH: 723
<212> TYPE: DNA
<213> ORGANISM: Homo sapiens
<220> FEATURE:
<221> NAME/KEY: misc_feature
<222> LOCATION: (1)..(723)
<223> OTHER INFORMATION: N=A,G,C,T

<400> SEQUENCE: 34

```
ttncggcctt acggccgggc caagatgagt catcaaaact cagtatcact tgactcaaag     60

agcagagttg gttgccgtca ttacagtgtt aacaagattt taatcagtct attaacattg    120

tatcagattc tgcatatgta gtacaggcta caaaggatat tgagagagcc ctaatcaaat    180

acattatgga tgatcagtta aacccgctgt ttaatttgtt acaacaaaat gtaagaaaaa    240

gaaatttccc attttatatt actcatattc gagcacacac taatttacca gggcctttaa    300

ctaaagcaaa tgaacaagct gacttgctag tatcatctgc attcatggaa gcacaagaac    360

ttcatgcctt gactcatgta aatgcaatag gattaaaaaa taaatttgat atcacatgga    420

aacagacaaa aaatattgta caacattgca cccagtgtca gattctacac ctggccactc    480

aggaggcaag agttaatccc agaggtctat gtcctaatgt gttatggcaa atggatgtca    540

ttgcacgtac cttcatttgg aaaattgtca tttgtccatg tgacagntga tacttattca    600

catttcatat gggcaacctg ccagacagga gaaagtactt nccatgtcaa gagacattta    660
```

-continued ttatcttggt ttcctggntg gggagntccc nnnnnnnann nnnnnnnaaa aaaaanannc 720 nnn 723

<210> SEQ ID NO 35
<211> LENGTH: 656
<212> TYPE: DNA
<213> ORGANISM: Homo sapiens

<400> SEQUENCE: 35
ttacggcctt acggccgggc caaagatgag tcatcaaaac tcagtatcac tcgactcaaa 60
gagcagagtt ggttgccgtc attacagtgt taacaagatt ttaatcagtc tattaacatt 120
gtatcagatt ctgcatatgt agtacaggct acaaaggata ttgagagagc cctaatcaaa 180
tacattatgg atgatcagtt aaacccgctg tttaatttgt tacaacaaaa tgtaagaaaa 240
agaaatttcc cattttatat tactcatatt cgagcacaca ctaatttacc agggccttta 300
actaaagcaa atgaacaagc tgacttgcta gtatcatctg cattcatgga agcacaagaa 360
cttcatgcct tgactcatgt aaatgcaata ggattaaaaa ataaatttga tatcacatgg 420
aaacagacaa aaaatattgt acaacattgc gcccagtgtc agattctaca cctggccact 480
caggaggtaa gagttaatcc cagaggtcta tgtcctaatg tgttatggca aatggatgtc 540
atgcacgtac cctcatttgg aaaattgtca tttgtccatg tgacagttga tacttattca 600
catttcatat gggcaacctg ccagacagga gaaagtactt cccatgttaa gagaca 656

<210> SEQ ID NO 36
<211> LENGTH: 773
<212> TYPE: DNA
<213> ORGANISM: Homo sapiens
<220> FEATURE:
<221> NAME/KEY: misc_feature
<222> LOCATION: (1)..(773)
<223> OTHER INFORMATION: N=A,G,C,T

<400> SEQUENCE: 36
atttgcctta cggccgggcc aaaagtatga gtcatcaaaa ctcagtatca cttgactcaa 60
agagcagagt tggttgccgt cattacagtg ttaacaagat tttaatcagt ctattaacat 120
tgtatcagat tctgcatatg tagtacaggc tacaaaggat attgagagag ccctaatcaa 180
atacattatg gatgatcagt taaacccgct gtttaatttg ttacaacaaa atgtaagaaa 240
aagaaatttc ccattttata ttactcatat tcgagcacac actaatttac cagggccttt 300
aactaaagca aatgaacaag ctgacttgct agtatcatct gcattcatgg aggcacaaga 360
acttcatgcc ttgactcatg taaatgcaat aggattaaaa aatagatttg atatcacatg 420
gaaacagaca aaaaatattg tacaacattg cacccagtgt cagattctac acctggccac 480
tcaggaggca agagttaatc ccagaggtct atgtcctaat gtgttatggc aaatggatgt 540
catgcacgta ccttcatttg gaaaattgtc atttgtccat gtgacagttg atacttattc 600
acatttcata tgggcaacct gccagacagg agaaagtact tcccatgtta agagacattt 660
attatcttgt tttcctgtca tgggagttcc agaaaaagtt aaaacagaca atgggccang 720
ttactgtagt aaagcagttc aaaaattctt aaatcagtgg aaaattacac atn 773

<210> SEQ ID NO 37
<211> LENGTH: 721
<212> TYPE: DNA
<213> ORGANISM: Homo sapiens -continued
<220> FEATURE:
<221> NAME/KEY: misc_feature
<222> LOCATION: (1)..(721)
<223> OTHER INFORMATION: N=A,G,C,T

<400> SEQUENCE: 37
cggccttacg gccgggccaa anatgaaggg nnnaangncg gttcccaggg acnnaggcgc 60
nttncatggt tgcngtngtt acacctgtta acaagattnt aatcagtcta ttaacattgt 120
atcaaattct gcatatgtag nacaggctac aaaggatatt gagagagccc taatcaaata 180
cattatggat gatcagttaa acccgctgtt taatttgtta caacaaaatg taagaaaatg 240
aaatttccca ttttatatta ctcatattcg agcacacact aatttaccag ggcctttnac 300
taaagcaaat gaacaagctg acttgctngt atcatctgca ttcatggaag cacaagaact 360
tcatgccttg actcatgtaa atgcaatagg attaaaaaat aaatttgata tcacatggaa 420
acagacaaaa aatattgtac aacattgcac ccagtgtcag attctacacc tggccactca 480
ggaggcaaga gttaatccca gaggtctatg tcctaatgtg ttatggcaaa tggatgtcat 540
gcacgtacct tcatttggaa aattgtcatt tgtccatgtg acagntgata cttattcaca 600
tttcatatgg gcaacctgcc agacangaga aagtncttcc catgttaaga gacatttatt 660
attttgntnt cctgncattg ggagttccan aaaaagtaaa acagacantg ggccaggtta 720
c 721

<210> SEQ ID NO 38
<211> LENGTH: 672
<212> TYPE: DNA
<213> ORGANISM: Homo sapiens
<220> FEATURE:
<221> NAME/KEY: misc_feature
<222> LOCATION: (1)..(672)
<223> OTHER INFORMATION: N=A,G,C,T

<400> SEQUENCE: 38
tacggcctta cggccgggcc aagatgagtc atcaaaactc agtatcactt gactcaaaga 60
gcagagttgg ttgccgtcnt tacagtgtta acaagatttt aatcagtcta ttaacattgt 120
atcagattct gcatatgtag tacaggctac aaaggatatt gagagagccc taatcaaata 180
cattatggat gatcagttaa acccgctgtt taatttgtta caacaaaatg taagaaaaag 240
aaatttccca ttttatatta ctcatattcg agcacacact aatttaccag ggcctttaac 300
taaagcaaat gaacaagctg acttgctagt atcatctgca ttcattgaag cacaagaact 360
tcatgccttg actcatgtaa atgcnatagg attaaaaaat aaatttgata tcacctggaa 420
acagacaaaa aatattgtac aacattgcac ccnnnngtcag attctacacc tggccnctcn 480
ngaggcaaga gttaatcccn canggctatg tcctnatgtg ttatggcaaa nggatgtnat 540
gcnccnncct tcctttngaa aannnnnntt tgtnccccnn acannngata cttattcacn 600
nttnntatng gnnacccccc ccacnngana aanaacctnc ccnntnnana naaantnntt 660
atttttnttt tn 672

<210> SEQ ID NO 39
<211> LENGTH: 757
<212> TYPE: DNA
<213> ORGANISM: Homo sapiens
<220> FEATURE:
<221> NAME/KEY: misc_feature
<222> LOCATION: (1)..(757)
<223> OTHER INFORMATION: N=A,G,C,T -continued
<400> SEQUENCE: 39
nccggcctta cggccgggcc aagatgagtc atcaaaactc agtatcactt gactcaaaga 60
gcagagttgg ttgccgtcat tacagtgtta acaagatttt aatcagtcta ttaacattgt 120
atcagattct gcatatgtag tacaggctac aaaggatatt gagagagccc taatcaaata 180
cattatggat gatcagttaa acccgctgtt taatttgtta caacaaaatg taagaaaaag 240
aaatttccca ttttatatta ctcatattcg agcacacact aatttaccag ggcctttaac 300
taaagcaaat gaacaagctg acttgctagt atcatctgca ttcatggaag cacaagaact 360
tcatgccttg actcatgtaa atgcaatagg attaaaaaat aaatttgata tcacatggaa 420
acagacaaaa aatattgtac aacattgcac ccagtgtcag attctacacc tggccactca 480
ggaggcaaga gttaatccca gaggtctatg tcctaatgtg ttatggcaaa tggatgtcat 540
gcacgtacct tcatttggaa aattgtcatt tgtccatgtg acagttgata cttattcaca 600
tttcatatgg gcaacctgcc agacaggaga aagtacttcc catgttaaga gacatttatt 660
atcttgtttt cctgtcatgg gagttccaga aaaagttaaa acagacaatg ggccaggtta 720
ctggagtaaa gcagttcaaa aattcttaaa tcagtgg 757

<210> SEQ ID NO 40
<211> LENGTH: 777
<212> TYPE: DNA
<213> ORGANISM: Homo sapiens
<400> SEQUENCE: 40
aaggcagtca agcaggagtt aaacaatatg gacctaactc tccttatatt agaatattat 60
taaattccat tgctcatgga aatagactta tttcttatga ttgggaaatt ctggctatat 120
cttccctttc accctctcag tatctccagt ttaaaacctg gtggattgat ggggtacaag 180
aacaggtacg aaaaaatcag gctactaatc ctgttgctta tatagatgaa gaccaattgc 240
taggaagagg tccaaactgg gacactatta accaacaatc agtaatgaaa atgaggctat 300
tgaacaacta taagggctat ttgcctcagg gcctgggaaa acattcagga cccaggaacc 360
tcatgccctt cttttagttc aatcagacaa ggctctaaag agccatatcc agactttgtg 420
gcaaggttgc aagatgcagc tcaaaaatcc attgcaggta acgcccgaaa agttattgta 480
gaaataatgg cttatcaaaa cgcaaattca gagtgtcaat cagccataaa gccattaaga 540
ggaaatgttt cagcaggagt tgatgtaatt acagaatatg tgaaggcttg tgatgggatt 600
ggaggagcta tgcataaggc aatgccattg gctcaagcaa ttacaggggt tgctatagga 660
ggacaagtta aaacatttgg gggaaaatgt tataattgtg gtcaaatcgg tcatctaaaa 720
aagaattgcc cgagcttaaa ttacccccca aaaaaaaaaa aaaaaaaaaa aaaaaaa 777

<210> SEQ ID NO 41
<211> LENGTH: 670
<212> TYPE: DNA
<213> ORGANISM: Homo sapiens
<220> FEATURE:
<221> NAME/KEY: misc_feature
<222> LOCATION: (1)..(670)
<223> OTHER INFORMATION: N=A,G,C,T
<400> SEQUENCE: 41
nccggcctta cggccgggaa aggcagtcaa gcaggagtta aacaatatgg acctaactct 60
ccttatatta gaatattatt aaattccatt gctcatggaa atagacttat ttcttatgat 120
tgggaaattc tggctatatc ttccctttca ccctctcagt atctccagtt taaaacctgg 180

-continued tggattgatg gggtacaaga acaggtaccg aaaaaatcag gctactaatc ctgttgctta 240
tatagatgaa gaccaattgc taggaagagg tccaaactgg gacactatta accaacaatc 300
agtaatgaaa atgaggctat tgaacaacta taagggctat ttgcctcagg gcctgggaaa 360
acattcagga cccaggaacc tcatgccctt cttttagttc aatcagacaa ggctctaaag 420
agccatatcc agactttgtg gcaaggttgc aagatgcagc tcaaaaatcc attgcaggta 480
acgcccgaaa agttattgta gaaataatgg cttatcaaaa cgcaaattca gagtgtcaat 540
cagccataaa gccattaaga ggaaatgttt cagcaggagt tgatgtaatt acagaatatg 600
tgaaggcttg tgatgggatt ggaggagcta tgcataaggc aatgccattg gctcaagcaa 660
ttacaggggt 670

<210> SEQ ID NO 42
<211> LENGTH: 397
<212> TYPE: DNA
<213> ORGANISM: Homo sapiens

<400> SEQUENCE: 42
aaaggcagtc aagcaggagt taaacaatat ggacctaact ctccttatat gagaacatta 60
ttaaattcca ttgctcatgg aaatagactt atttcttatg attgggaaat tctggctaaa 120
tcttcccttt caccctctca gtatctccag tttaaaacct ggtggattga tggggtacaa 180
gaacaggtac gaaaaaatca ggctactaat cctgttgctt atatagatga agaccaattg 240
ctaggaagag gtccaaactg ggacactatt aaccaacaat cagtaatgaa aatgaggcta 300
ttgaacaact ataagggcta tttgcctcag ggcctggga aaacattcag gacccaggga 360
acctcatgcc cttcttttag gttcaatcag acaaggt 397

<210> SEQ ID NO 43
<211> LENGTH: 413
<212> TYPE: DNA
<213> ORGANISM: Homo sapiens

<400> SEQUENCE: 43
gctgacttgc tagtatcatc tgcattcatt gaagcacaag aacttcatgc cttgactcat 60
gtaaatgcaa taggattaaa aaataaattt gatatcacat ggaaacagac aaaaaaatatt 120 gtacaacatt gcacccagtg tcagattcta cacctggcca ctcaggaagc aagagttaat 180
cccagaggtc tatgtcctaa tgtgttatgg caaatggatg tcatgcacgt accttcattt 240
ggaaaattgt catttgtcca tgtgacagtt gatacttatt cacatttcat atgggcaacc 300
tgccagacag gagaaagtct tcccatgtta aaagacattt attatcttgt tttcctgtca 360
tgggagttcc agaaaaagtt aaaacagaca atgggccagg ttctgtagta aag 413

<210> SEQ ID NO 44
<211> LENGTH: 11122
<212> TYPE: DNA
<213> ORGANISM: Homo sapiens

<400> SEQUENCE: 44
gccaaggtgg gaggattgct tgagcacagg agtttgaggc tgaagtgagc tatgatcgca 60
ccactgcaat caatcaatca ataaacttca gtcaaccctg ccaggagcta tggaacaatt 120
attgtttgtt ggagtgttct gtgttgggct aaatgtgaag cctctttata cttctacctt 180
actcagtcac catatggggg ctgccccaga gaggtcatga cctcaagtga ggaagtactc 240
agcagctgag ccaggcccta ctgatagctg gaggatgctg ctgcccatgc tgcccactgt 300

-continued

```
gaggcagcaa gcccttgctt gaagggggat ctggatagta tgtttctgtg tctaccaccc    360
ctagaaatgg tgcctagagt gagtcatcac aaaaagaatc aggatagctt ggtgtagtgg    420
caggtgccta taatcccagc tactcaggag actgtggcag gagaatgact taaaccaggg    480
agttggaggt tgcagtgagg tgaggtcaca caactgcact ccagactggg tgacagagtg    540
agactccatc tcaaaaaaaa aaaaaaaaag aaaagaaaag aaaaaagaaa aagaatcagg    600
aaatactaat atttaaagga taggtgaatg gaggaaaata atcaattgaa ggaggctgag    660
cagatgaggt caaagaagat agagatccat aacagtaacc tcatagaagc ttatggaagc    720
attttgacag tgctaaaagc cacataaagt tcaagtaaga cagtttcaga aatgtataaa    780
catgaatgcc tttgcagtga cttaagtgtg attctggtgt ttccttctaa aaatactgcc    840
ttctcaggtg tgggaaggat tctatctttt taggctttac caccatagtt ctctgcaggc    900
ttgcaatcct gaatcaggct tgacttcaga aagtgcttta aaagggaggc tgggcgcggt    960
ggctcatgcc tgtaatccca gcactctgag aggctgaggt tgtggggaaa agcaagagag   1020
atcagattgt tactgtgtct gtgtagaaag aagtagacat aggagactcc attttgttct   1080
gtactaagaa aaattcttct gccttgagat tctgttaatc tatgacctta cccccaaccc   1140
cgtgctctct gaaacaggtg ctgtgtcaaa ctcagggtta aatggattaa gggttgtgca   1200
agatgtgctt tgttaaacaa atgcttgaag gcagcatggt ccttaagagt catcaccact   1260
ccctaatctc aagtacccag ggacacaaac actgcggaag gccgcagaga cctctgccta   1320
ggaaagcaag gtattgtcca aggtttctcc ccatgtgata gtctgaaata tggcctcgtg   1380
ggaagggaaa gacctgaccg tccccccagcc tgacacccgt aaagggtctg tgctgaggag   1440
gattagtgta agaggaaggc atgcctcttg cagttgagac aagaggaagg catctgtctc   1500
ctgcccgtcc ctgggcaatg gaatgtctcg gtataaaacc cgattgattg tacgttccat   1560
ctactgagat aggaagaaaa cgccttaggg ctggaggtgt gggacaagcc ggcagcaata   1620
ctgctttgta aagcattgag atgtttatgt gtatgcatat ctaaaagcac agcacttgat   1680
tctttacctt gtctgtgatg caaagacctt tgttcacgtg tttgtctgct gaccctctcc   1740
ccactattgt cttgtgacca tgacacatcc ccctctcaga gaaacaccca cgaatgatca   1800
ataaatacta agggaactca gagacggcgc ggatcctcca tatgctgaac gctggttccc   1860
tgggtcccct tatttctttc tctatacttt gtgtcttttt cttttccaag tctctcgttc   1920
caccttacga gaaacaccca caggtgtgga ggggcaaccc accccttcat ctggtgccca   1980
acgtggaggc ttttctctag ggtgaaggta cgctcgagcg tggtcattga ggacaagttg   2040
acgagagatc ccgagtacat ctacagtcag ccttgcggta agtttgtgcg ctcggaagaa   2100
gctagggtga taatggggca aactaaaagt aaaactaaaa gtaaatatgc ctcttatctc   2160
agctttatta aaattctttt aaaaagaggg ggagttagag tatctacaaa aaatctaatc   2220
aagctatttc aaataataga acaattttgc ccatggtttc cagaacaagg aactttagat   2280
ctaaaagatt ggaaaagaat tggcgaggaa ctaaaacaag caggtagaaa gggtaatatc   2340
attccactta cagtatggaa tgattgggcc attattaaag cagctttaga accatttcaa   2400
acaaaagaag atagcgtttc agtttctgat gcccctggaa gctgtgtaat agattgtaat   2460
gaaaagacag ggagaaaatc ccagaaagaa acagaaagtt tacattgcga atatgtaaca   2520
gagccagtaa tggctcagtc aacgcaaaat gttgactata atcaattaca gggggtgata   2580
tatcctgaaa cgttaaaatt agaaggaaaa ggtccagaat tagtggggcc atcagagtct   2640
aaaccacgag ggccaagtcc tcttccagca ggtcaggtgc ccgtaacatt acaacctcaa   2700
```

-continued

```
acgcaggtta aagaaaataa gacccaaccg ccagtagctt atcaatactg gccgccggct   2760
gaacttcagt atctgccacc cccagaaagt cagtatggat atccaggaat gcccccagca   2820
ctacagggca gggcgccata tcctcagccg cccactgtga gacttaatcc tacagcatca   2880
cgtagtggac aaggtggtac actgcacgca gtcattgatg aagccagaaa acagggagat   2940
cttgaggcat ggcggttcct ggtaatttta caactggtac aggccgggga agagactcaa   3000
gtaggagcgc ctgcccgagc tgagactaga tgtgaacctt tcaccatgaa aatgttaaaa   3060
gatataaagg aaggagttaa acaatatgga tccaactccc cttatataag aacattatta   3120
gattccattg ctcatggaaa tagacttact ccttatgact gggaaagttt ggccaaatct   3180
tccctttcat cctctcagta tctacagttt aaaacctggt ggattgatgg agtacaagaa   3240
caggtacgaa aaaatcaggc tactaagccc actgttaata tagacgcaga ccaattgtta   3300
ggaacaggtc caaattggag caccattaac caacaatcag tgatgcagaa tgaggctatt   3360
gaacaagtaa gggctatttg cctcagggcc tggggaaaaa ttcaggaccc aggaacagct   3420
ttccctatta attcaattag acaaggctct aaagagccat atcctgactt tgtggcaaga   3480
ttacaagatg ctgctcaaaa gtctattaca gatgacaatg cccgaaaagt tattgtagaa   3540
ttaatggcct atgaaaatgc aaatccagaa tgtcagtcgg ccataaagcc attaaaagga   3600
aaagttccag caggagttga tgtaattaca gaatatgtga aggcttgtga tgggattgga   3660
ggagctatgc ataaggcaat gctaatggct caagcaatga gggggctcac tctaggagga   3720
caagttagaa catttgggaa aaaatgttat aattgtggtc aaatcggtca tctgaaaagg   3780
agttgcccag tcttaaataa acagaatata ataaatcaag ctattacagc aaaaaataaa   3840
aagccatctg gcctgtgtcc aaaatgtgga aaaggaaaac attgggccaa tcaatgtcat   3900
tctaaatttg ataaagatgg gcaaccattg tcgggaaaca ggaagagggg ccagcctcag   3960
gccccccaac aaactggggc attcccagtt caactgtttg ttcctcaggg ttttcaagga   4020
caacaacccc tacagaaaat accaccactt cagggagtca gccaattaca acaatccaac   4080
agctgtcccg cgccacagca ggcagcgcca cagtagattt atgttccacc caaatggtct   4140
ctttactccc tggagagccc ccacaaaaga ttcctagagg ggtatatggc ccgctgccag   4200
aagggagggt aggccttatt ttagggagat caagtctaaa tttgaaggga gtccaaattc   4260
atactggggt aatttattca gattataaag gggaattca gttagtgatc agctccactg   4320
ttccctggag tgccaatcca ggtgatagaa ttgctcaatt actgcttttg ccttatgtta   4380
aaattgggga aaacaaaacg gaaagaacag gagggtttgg aagtaccaac cctgcaggaa   4440
aagccactta ttgggctaat caggtctcag aggatagacc cgtgtgtaca gtcactattc   4500
agggaaagag tttgaaggat tagtggatac ccaggctgat gtttctatca tcggcatagg   4560
caccgcctca gaagtgtatc aaagtgccat gattttacat tgtctaggat ctgataatca   4620
agaaagtacg gttcagccta tgatcacttc tattccaatc aatttatggg gccgagactt   4680
gttacaacaa tggcatgcag agattactat cccagcctcc ctatacagcc ccaggaatca   4740
aaaaatcatg actaaaatgg gatagctccc taaaaaggga ctaggaaaga atgaagatgg   4800
cattaaagtc ccaactgagg ctgaaaaaaa tcaaaaaaag aaaaggaata gggcatcctt   4860
tttagaagcg gtcactgtag agcctccaaa acccattcca ttaatttggg gggaaaaaaa   4920
aaactgtatg gtaaatcagt agccgcttcc aaaacaaaaa ctggaggctt tacacttatt   4980
agcaaagaaa cagttagaaa aaggacatat tgagccttca ttttcgcctt ggaattctcc   5040
tgtttgtaat tcagaaaaaa tccggcagat ggcgtatgct aactgactta agagccatta   5100
```

-continued

```
atgccataat tcaacccatg ggggctctcc catcccggtt gccctctcca gccatggtcc   5160
cctttaatta taattgatct gaaggattgc ttttttacca ttcctctggc aaaagaggat   5220
tttgaaaaat ttgcttttac tataccagcc taaataataa agaaccagcc accaggtttc   5280
agtggaaagt attgcctcag ggaatgctta ataattcaac tatttgtcag actttcatag   5340
ctcaagctct gcaaccagtt agagacaagt tttcagactg ttatatcgtt cattatgttg   5400
atattttgtg tgctgcagaa acgagagaca aattaattga ccgttacaca tttctcagac   5460
agaggttgcc aacgcgggac tgacaatagc atctgataag attcaaacct ctcctccttt   5520
ccattacttg ggaatgcagg tagaggaaag gaaaattaaa ccacaaaaaa tagaaataag   5580
aaaagacaca ttaaaaacat taaatgagtt tcaaaagttg gtaggagata ctaattggat   5640
tcggagatat taattggatt tggccaactc taggcattcc tacttatgcc atgtcaattt   5700
tgttctcttt cttaagaggg gacttggaat taaatagtga aagaatgtta cctccagagg   5760
caactaaaga aattaaatta attgaagaaa aaaattcggt cagcacaagt aaataggatc   5820
acttggcccc actccaaatt ttgatttttg gtactgcaca ttctctaaca gccatcattg   5880
ttcaaaacac agatcttgtg gattggtcct tccttcctca tagtacaatt aagactttta   5940
cattgtactt ggatcaaatg gctacattaa ttggtcaggg aagattacga ataataacat   6000
tgtgtggaaa tgacccagat aaaatcactg ttcctttcaa caagcaacaa gttagacaag   6060
cctttatcag ttctggtgca tggcagattg gtcttgctaa ttttctggga attattgata   6120
atcattaccc aaaaacaaaa atcttccagt tcttaaaatt gactacttgg attctaccta   6180
aaattaccag acgtgaacct ttagaaaatg ctctaacagt atttactgat ggttccagca   6240
atggaaaagc ggcttacaca gggccgaaag aacgagtaat caaaactccg tatcaatcag   6300
ctcaaagagc agagttggtt gcagtcatta cagtgttaca agattttgac caacctatca   6360
atattatatc agattctgca tatgtagtac aggctacaag ggatgttgag acagctctaa   6420
ttaaatatag cacggacgat catttaaacc agctattcaa tttattacaa caaactgtaa   6480
gaaaaagaaa tttcccattt tatattactc atattcgagc acacactaat ttaccagggc   6540
ctttgactaa agcaaatgaa caagctgact tactggtatc atctgcattc ataaaagcac   6600
aagaacttct tgctttgact catgtaaatg cagcaggatt aaaaaacaaa tttgatgtca   6660
catggaaaca ggcaaaagat attgtacaac attgcaccca gtgtcaagtc ttacacctgt   6720
ccactcaaga ggcaggagtt aatcccagag gtctgtgtcc taatgcgtta tggcaaatgg   6780
atggcacgca tgttccttca tttggaagat tatcatatgt tcatgtaaca gttgatactt   6840
attcacattt catatgggca acttgccaaa caggagaaag tacttcccat gttaaaaaac   6900
atttattatc ttgttttgct gtaatgggag ttccagaaaa aatcaaaact gacaatggac   6960
caggatattg tagtaaagct ttccaaaaat tcttaagtca gtggaaaatt tcacatacaa   7020
caggaattcc ttataattcc caaggacagg ccatagttga aagaactaat agaacactca   7080
aaactcaatt agttaaacaa aaagaagggg gagacagtaa ggagtgtacc actcctcaga   7140
tgcaacttaa tctagcactc tatactttaa atttttaaa catttataga aatcagacta   7200
ctacttctgc aaaacaacat cttactggta aaaagcacag cccacatgaa ggaaaactaa   7260
tttggtggaa agataataaa aataagacat gggaaatagg gaaggtgata acgtggggga   7320
gaggttttgc ttgtgtttca ccaggagaaa atcagcttcc tgtttggata cccactagac   7380
atttgaagtt ctacaatgaa cccatcggag atgcaaagaa aagggcctcc acagagatgg   7440
taaccccagt cacatggatg gataatccta tagaagtata tgttaatgat agtgtatggg   7500
```

-continued

```
tacctggccc cacagatgat cgctgccctg ccaaacctga ggaagaaggg atgatgataa   7560
atatttccat tgtgtatcgt tatcctccta tttgcctagg gagagcacca ggatgtttaa   7620
tgcctgcagt ccaaaattgg ttggtagaag tacctactgt cagtcctaac agtagattca   7680
cttatcacat ggtaagcggg atgtcactca ggccacgggt aaattattta caagactttt   7740
cttatcaaag atcattaaaa tttagaccta aagggaaacc ttgccccaag gaaattccca   7800
aagaatcaaa aaatacagaa gttttagttt gggaagaatg tgtggccaat agtgcggtga   7860
tattacaaaa caatgaattc ggaactatta tagattgggc acctcgaggt caattctacc   7920
acaattgctc aggacaaact cagtcgtgtc caagtgcaca agtgagtcca gctgttgata   7980
gcgacttaac agaaagtcta gacaaacata agcataaaaa attacagtct ttctaccctt   8040
gggaatgggg agaaaaagga atctctaccc caagaccaga aataataagt cctgtttctg   8100
gtcctgaaca tccagaatta tggaggcttt ggcctgacac cacattagaa tttggtctgg   8160
aaatcaaact ttagaaacaa gagatcgtaa gccattttat actatcgacc taaattccag   8220
tctaacggtt cctttacaaa gttgcgtaaa gccctcttat atgctagttg taggaaatat   8280
agttattaaa ccagactccc aaactataac ctgtgaaaat tgtagattgt ttacttgcat   8340
tgattcaact tttaattggc ggcaccgtat tctgctggtg agagcaagag agggcgtgtg   8400
gatctctgtg tccgtggact gaccgtggga ggcctcgcca tccatccata ttttgactga   8460
agtattaaaa gacattttaa atagatccaa aagattcatt tttaccttaa ttgcagtgat   8520
tatgggatta attgcagtca cagctacggc tgctgtggca ggagttgcat tgcactcttc   8580
tgttcagtcg gtaaactttg ttaatgattg gcaaaagaat tctacaagat tgtggaattc   8640
acaatctagt attgatcaaa aattggcaaa tcaaattaat gatcttagac aaactgtcat   8700
ttggatggga gacagactca tgagcttaga acattgtttc cagttacagt gtgactggaa   8760
tacgtcagat tttgtatta  caccccaaat ttataatgag tctgagcatc actgggacat   8820
ggttagacgc catctacagg gaagagaaga taatctcact ttagacattt ccaaattaaa   8880
ataacaaatt ttcgaagcat caaaagccca tttaaatttg atgccaggaa ctgaggcaat   8940
tgcaggagtt gctgatggcc tcgcaaatct taaccctgtc acttgggtta agaccatcgg   9000
aagtactatg attataaatc tcatattaat ccttgtgtgc ctgttttgtc tgttgttagt   9060
ctgcaggtgt acccaacagc tccgaagaga cagcgaccat cgagaacggg ccatgatgac   9120
gatggcggtt ttgtcgaaaa gaaaagggg  aaatgtgggg aaaagcaaga gagatcagat   9180
tgttactgtg tctgtgtaga aagaagtaga cataggagac tccattttgt tctgtactaa   9240
gaaaaattct tctgccttga gattctgtta atctatgacc ttacccccaa ccccgtgctc   9300
tctgaaacag gtgctgtgtc aaactcaggg ttaaatggat taagggttgt gcaagatgtg   9360
ctttgttaaa caaatgcttg aaggcagcat gctccttaag agtcatcacc actccctaat   9420
ctcaagtacc cagggacaca aaaactgcgg aaggccgcag ggacctctgc ctaggaaagc   9480
caggtattgt ccaaggtttc tccccatgtg atagtctgaa atatggcctc atgggaaggg   9540
aaagacctga ccgtccccca gcccgacacc cgtaaagggt ctgtgctgag gaggattagt   9600
ataagaggaa ggcattcctc ttgcagttga gacaagagga aggcatctgt ctcctgcccg   9660
tccctgggca atggaatgtc tcggtataaa acccgattgt acgttccatc tactgagata   9720
ggaagaaaac gccttagggc tggaggtggg acatgcaggc agcaatactg ctttgtaaag   9780
cattgagatg tttatgtgta tgcatatcta aaagcacagc acttgattct ttaccttgtc   9840
tatgatgcaa agacctttgt tcacctgttt gtctgctgac cctctcccca ctattgtctt   9900
```

-continued

```
gtgaccatga cacatccccc tctcagagaa acacccacga atgatcaata aatactaagg   9960

gaactcagag acggcgcgga tcctccatat gctgaacgct ggttccctgg gtccccttat  10020

ttctttctct atactttgtc tctgtgtctt tttcttttcc aagtctctca ttccacctta  10080

agagaaacac tcacaggtgt ggaggggcaa cccatccctt cagaggtggg tggatcacct  10140

gaggtcagga gttcaagaca agcctggcca acatggtgaa accccatctc tactaaaaat  10200

acaaaattag ccaggtgtgg tggcaggtgt ctgtagtccc agctacttgg gaggctgacg  10260

agaatcgctt gaacctggga gggggaggtt tcagtgagcc gagattgcac cactgcactc  10320

cagcctgggg gacagagtga aactctgtct caaaaaaaca acaaaaaacc ccacctatag  10380

acaggactag ctacataaat aacttgcagg gctcagtgta aaatgaaagt gtgaggtccc  10440

tttttcaaag acgtagaagg ccgggtgcgg tggctcatgc ctgtaatccc agcactttgg  10500

gaggctgagg caggcaggtt atgaggtcag gagttcgaga cagcctgacc aatatggtga  10560

aaccccatct ctactaaaaa tacaaaaatt agctgggtgt ggtagcgggc gcctgtagtc  10620

ccagctactc aggaggctga ggcagaagaa ttacttgaac ccaggagacg gaggttgcag  10680

tgagctgaga tcgtgccact gcactctcca gcctcctcgg tgacagagcg agactctgtc  10740

tcaaaaaaaa aaaaaaaaac agaaaaaggt gctattaaag ataccaaaat ataaggcact  10800

ttcctttatt ctgcaatctg tctctccact tttcatagta ttttttcatt tgttatttaa  10860

catcatgttt tgtcaggtga ggacatttac tcagccagtg cagcactcac tggtatccag  10920

gggccatagg tgatttgacg cacccacatg gcccaccagc tgttgagttc cacctccagc  10980

cagccactgg accaacatgc agtgccctgg ctgggggcag gaaagtctaa caaaccattt  11040

cattccactg tcctcctggc caaacccaca gaggacaggt aaaccccctt gtatgtgttt  11100

tgtacttgga tctggggtgg gc                                            11122
```

```
<210> SEQ ID NO 45
<211> LENGTH: 9179
<212> TYPE: DNA
<213> ORGANISM: Homo sapiens

<400> SEQUENCE: 45

tgtggggaaa agcaagagag atcaaattgt tactgtgtct gtgtagaaag aagtagacat     60

aggagactcc attttgttat gtgctaagaa aaattcttct gccttgagat tctgttaatc    120

tatgacctta cccccaaccc cgtgctctct gaaacgtgtg ctgtgtcaac tcagggttga    180

atggattaag ggcggtgcag gatgtgcttt gttaaacaga tgcttgaagg cagcatgctc    240

cttaagagtc atcaccactc cctaatctca agtacccagg gacacaaaaa ctgcggaagg    300

ccgcagggac ctctgcctag gaaagccagg tattgtccaa ggtttctccc catgtgatag    360

tctgaaatat ggcctcgtgg gaagggaaag acctgaccgt cccccagccc gacacctgta    420

aagggtctgt gctgaggagg attagtaaaa gaggaaggaa tgcctcttgc agttgagaca    480

agaggaaggc atctgtctcc tgcctgtccc tgggcaatgg aatgtctcgg tataaaaccc    540

gattgtatgc tccatctact gagataggga aaaaccgcct tagggctgga ggtgggacct    600

gcgggcagca atactgcttt gtaaagcatt gagatgttta tgtgtatgca tatccaaaag    660

cacagcactt aatcctttac attgtctatg atgccaagac ctttgttcac gtgtttgtct    720

gctgaccctc tccccacaat tgtcttgtga ccctgacaca tccccctctt tgagaaacac    780

ccacagatga tcaataaata ctaagggaac tcagaggctg gcgggatcct ccatatgctg    840

aacgctggtt ccccgggtcc ccttatttct ttctctatac tttgtctctg tgtctttttc    900
```

-continued

```
ttttccaaat ctctcgtccc accttacgag aaacacccac aggtgtgtag gggcaaccca    960
cccctacatc tggtgcccaa cgtggaggct tttctctagg gtgaaggtac gctcgagcgt   1020
aatcattgag gacaagtcga cgagagatcc cgagtacatc tacagtcagc cttacggtaa   1080
gcttgcgcgc tcggaagaag ctagggtgat aatggggcaa actaaaagta aaattaaaag   1140
taaatatgcc tcttatctca gctttattaa aattctttta aaaagagggg gagttaaagt   1200
atctacaaaa aatctaatca agctatttca aataatagaa caattttgcc catggtttcc   1260
agaacaagga acttcagatc taaaagattg gaaaagaatt ggtaaggaac taaaacaagc   1320
aggtaggaag ggtaatatca ttccacttac agtatggaat gattgggcca ttattaaagc   1380
agctttagaa ccatttcaaa cagaagaaga tagcatttca gtttctgatg cccctggaag   1440
ctgtttaata gattgtaatg aaaacacaag gaaaaaatcc cagaaagaaa ccgaaagttt   1500
acattgcgaa tatgtagcag agccggtaat ggctcagtca acgcaaaatg ttgactataa   1560
tcaattacag gaggtgatat atcctgaaac gttaaaatta gaaggaaaag gtccagaatt   1620
aatggggcca tcagagtcta aaccacgagg cacaagtcct cttccagcag gtcaggtgct   1680
cgtaagatta caacctcaaa agcaggttaa agaaaataag acccaaccgc aagtagccta   1740
tcaatactgc cgctggctga acttcagtat cggccacccc cagaaagtca gtatggatat   1800
ccaggaatgc cccagcacc acagggcagg gcgccatacc atcagccgcc cactaggaga   1860
cttaatccta tggcaccacc tagtagacag ggtagtgaat tacatgaaat tattgataaa   1920
tcaagaaagg aaggagatac tgaggcatgg caattcccag taacgttaga accgatgcca   1980
cctggagaag gagcccaaga gggagagcct cccacagttg aggccagata caagtctttt   2040
tcgataaaaa tgctaaaaga tatgaaagag ggagtaaaac agtatggacc caactcccct   2100
tatatgagga cattattaga ttccattgct tatggacata gactcattcc ttatgattgg   2160
gagattctgg caaaatcgtc tctctcaccc tctcaatttt tacaatttaa gacttggtgg   2220
attgatgggg tacaagaaca ggtccgaaga aatagggctg ccaatcctcc agttaacata   2280
gatgcagatc aactattagg aataggtcaa aattggagta ctattagtca acaagcatta   2340
atgcaaaatg aggccattga gcaagttaga gctatctgcc ttagagcttg ggaaaaaatc   2400
caagacccag gaagtacctg cccctcattt aatacagtaa gacaaggttc aaaagagccc   2460
taccctgatt ttgtggcaag gctccaagat gttgctcaaa agtcaattgc cgatgaaaaa   2520
gccggtaagg tcatagtgga gttgatggca tatgaaaacg ccaatcctga gtgtcaatca   2580
gccattaagc cattaaaagg aaaggttcct gcaggatcag atgtaatctc agaatatgta   2640
aaagcctgtg atggaatcgg aggagctatg cataaagcta tgcttatggc tcaagcaata   2700
acaggagttg ttttaggagg acaagttaga acatttggag gaaaatgtta taattgtggt   2760
caaattggtc acttaaaaaa gaattgccca gtcttaaaca aacagaatat aactattcaa   2820
gcaactacaa caggtagaga gccacctgac ttatgtccaa gatgtaaaaa aggaaaacat   2880
tgggctagtc aatgtcgttc taaatttgat aaaaatgggc aaccattgtc gggaaacgag   2940
caaaggggcc agcctcaggc cccacaacaa actggggcat tcccaattca gccatttgtt   3000
cctcagggtt ttcagggaca acaaccccca ctgtcccaag tgtttcaggg aataagccag   3060
ttaccacaat acaacaattg tccctcacca caagcggcag tgcagcagta gatttatgta   3120
ctatacaagc agtctctctg cttccagggg agcccccaca aaaaatccct acaggggtat   3180
atggcccact gcctgagggg actgtaggac taatcttggg aagatcaagt ctaaatctaa   3240
aaggagttca aattcatact agtgtggttg attcagacta taaaggcgaa attcaattgg   3300
```

-continued

```
ttattagctc ttcaattcct tggagtgcca gtccaagaga caggattgct caattattac   3360
tcctgccata tattaagggt ggaaatagtg aaataaaaag aataggaggg cttgtaagca   3420
ctgatccaac aggaaaggct gcatattggg caagtcaggt ctcagagaac agacctgtgt   3480
gtaaggccat tattcaagga aaacagtttg aagggttggt agacactgga gcagatgtct   3540
ctattattgc tttaaatcag tggccaaaaa actggcctaa acaaaaggct gttacaggac   3600
ttgtcggcat aggcacagcc tcagaagtgt atcaaagtat ggagatttta cattgcttag   3660
ggccagataa tcaagaaagt actgttcagc caatgattac ttcaattcct cttaatctgt   3720
ggggtcgaga tttattacaa caatggggtg cggaaatcac catgcccgct ccattatata   3780
gccccacgag tcaaaaaatc atgaccaaga tgggatatat accaggaaag ggactaggga   3840
aaaatgaaga tggcattaaa gttccagttg aggctaaaat aaatcaagaa agagaaggaa   3900
tagggtatcc tttttagggg cggtcactgt agagcctcct aaacccatac cactaacttg   3960
gaaaacagaa aaaccggtgt gggtaaatca gtggccgcta ccaaaacaaa aactggaggc   4020
tttacattta ttagcaaatg aacagttaga aaagggtcac attgagcctt cgttctcacc   4080
ttggaattct cctgtgtttg taattcagaa gaaatcaggc aaatggcata cgttaactga   4140
cttaagggct gtaaacgccg taattcaacc catggggcct ctccaacccg ggttgccctc   4200
tccggccatg atcccaaaag attggccttt aattataatt gatctaaagg attgcttttt   4260
taccatccct ctggcagagc aggattgtga aaaatttgcc tttactatac cagccataaa   4320
taataaagaa ccagccacca ggtttcagtg gaaagtgtta cctcagggaa tgcttaatag   4380
tccaactatt tgtcagactt ttgtaggtcg agctcttcaa ccagtgagag aaaagttttc   4440
agactgttat attattcatt atattgatga tattttatgt gctgcagaaa cgaaagataa   4500
attaattgac tgttatacat ttctgcaagc agaggttgcc aatgctggac tggcaatagc   4560
atccgataag atccaaacct ctactccttt tcattattta gggatgcaga tagaaaatag   4620
aaaaattaag ccacaaaaaa tagaaataag aaaagacaca ttaaaaacac taaatgattt   4680
tcaaaaatta ctaggagata ttaattggat tcggccaact ctaggcattc ctacttatgc   4740
catgtcaaat ttgttctcta tcttaagagg agactcagac ttaaatagtc aaagaatatt   4800
aaccccagag gcaacaaaag aaattaaatt agtggaagaa aaaattcagt cagcgcaaat   4860
aaatagaata gatcccttag ccccactcca acttttgatt tttgccactg cacattctcc   4920
aacaggcatc attattcaaa atactgatct tgtggagtgg tcattccttc ctcacagtac   4980
agttaagact tttacattgt acttggatca aatagctaca ttaatcggtc agacaagatt   5040
acgaataaca aaattatgtg gaaatgaccc agacaaaata gttgtccctt taaccaagga   5100
acaagttaga caagccttta tcaattctgg tgcatggcag attggtcttg ctaattttgt   5160
gggacttatt gataatcatt acccaaaaac aaagatcttc cagttcttaa aattgactac   5220
ttggattcta cctaaaatta ccagacgtga acctttagaa aatgctctaa cagtatttac   5280
tgatggttcc agcaatggaa aagcagctta cacagggccg aaagaacgag taatcaaaac   5340
tccatatcaa tcggctcaaa gagacgagtt ggttgcagtc attacagtgt tacaagattt   5400
tgaccaacct atcaatatta tatcagattc tgcatatgta gtacaggcta caagggatgt   5460
tgagacagct ctaattaaat atagcatgga tgatcagtta aaccagctat tcaatttatt   5520
acaacaaact gtaagaaaaa gaaatttccc attttatatt acttatattc gagcacacac   5580
taatttacca gggcctttga ctaaagcaaa tgaacaagct gacttactgg tatcatctgc   5640
actcataaaa gcacaagaac ttcatgcttt gactcatgta aatgcagcag gattaaaaaa   5700
```

-continued

```
caaatttgat gtcacatgga aacaggcaaa agatattgta caacattgca cccagtgtca   5760
agtcttacac ctgcccactc aagaggcagg agttaatccc agaggtctgt gtcctaatgc   5820
attatggcaa atggatgtca cgcatgtacc ttcatttgga agattatcat atgttcatgt   5880
aacagttgat acttattcac atttcatatg ggcaacttgc caaacaggag aaagtacttc   5940
ccatgttaaa aaacatttat tgtcttgttt tgctgtaatg ggagttccag aaaaaatcaa   6000
aactgacaat ggaccaggat attgtagtaa agctttccaa aaattcttaa gtcagtggaa   6060
aatttcacat acaacaggaa ttccttataa ttcccaagga caggccatag ttgaaagaac   6120
taatagaaca ctcaaaactc aattagttaa acaaaaagaa gggggagaca gtaaggagtg   6180
taccactcct cagatgcaac ttaatctagc actctatact ttaaattttt taaacattta   6240
tagaaatcag actactactt ctgcagaaca acatcttact ggtaaaaaga acagcccaca   6300
tgaaggaaaa ctaatttggt ggaaagataa taaaaataag acatgggaaa tagggaaggt   6360
gataacgtgg gggagaggtt ttgcttgtgt ttcaccagga gaaaatcagc ttcctgtttg   6420
gttacccact agacatttga agttctacaa tgaacccatc ggagatgcaa agaaaagggc   6480
ctccacggag atggtaacac cagtcacatg gatggataat cctatagaag tatatgttaa   6540
tgatagtata tgggtacctg gccccataga tgatcgctgc cctgccaaac ctgaggaaga   6600
agggatgatg ataaatattt ccattgggta tcgttatcct cctatttgcc tagggagagc   6660
accaggatgt ttaatgcctg cagtccaaaa ttggttggta gaagtaccta ctgtcagtcc   6720
catcagtaga ttcacttatc acatggtaag cgggatgtca ctcaggccac gggtaaatta   6780
tttacaagac ttttcttatc aaagatcatt aaaatttaga cctaaaggga aaccttgccc   6840
caaggaaatt cccaaagaat caaaaaatac agaagtttta gtttgggaag aatgtgtggc   6900
caatagtgcg gtgatattat aaaacaatga atttggaact attatagatt gggcacctcg   6960
aggtcaattc taccacaatt gctcaggaca aactcagtcg tgtccaagtg cacaagtgag   7020
tccagctgtt gatagcgact taacagaaag tttagacaaa cataagcata aaaaattgca   7080
gtctttctac ccttgggaat ggggagaaaa aggaatctct accccaagac caaaaaatagt   7140
aagtcctgtt tctggtcctg aacatccaga attatggagg cttactgtgg cctcacacca   7200
cattagaatt tggtctggaa atcaaacttt agaaacaaga gattgtaagc cattttatac   7260
tgtcgaccta aattccagtc taacagttcc tttacaaagt tgcgtaaagc cccccttatat   7320
gctagttgta ggaaatatag ttattaaacc agactcccag actataacct gtgaaaattg   7380
tagattgctt acttgcattg attcaacttt taattggcaa caccgtattc tgctggtgag   7440
agcaagagag ggcgtgtgga tccctgtgtc catggaccga ccgtgggagg cctcaccatc   7500
cgtccatatt ttgactgaag tattaaaagg tgttttaaat agatccaaaa gattcatttt   7560
tactttaatt gcagtgatta tgggattaat tgcagtcaca gctacggctg ctgtagcagg   7620
agttgcattg cactcttctg ttcagtcagt aaactttgtt aatgattggc aaaagaattc   7680
tacaagattg tggaattcac aatctagtat tgatcaaaaa ttggcaaatc aaattaatga   7740
tcttagacaa actgtcattt ggatgggaga cagactcatg agcttagaac atcgtttcca   7800
gttacaatgt gactggaata cgtcagattt ttgtattaca ccccaaattt ataatgagtc   7860
tgagcatcac tgggacatgg ttagacgcca tctacaggga agagaagata atctcacttt   7920
agacatttcc aaattaaaag aacaaatttt cgaagcatca aaagcccatt taaatttggt   7980
gccaggaact gaggcaattg caggagttgc tgatggcctc gcaaatctta accctgtcac   8040
ttgggttaag accattggaa gtacatcgat tataaatctc atattaatcc ttgtgtgcct   8100
```

-continued

```
gttttgtctg ttgttagtct gcaggtgtac ccaacagctc cgaagagaca gcgaccatcg   8160

agaacgggcc atgatgacga tggcggtttt gtcgaaaaga aaagggggaa atgtggggaa   8220

aagcaagaga gatcaaattg ttactgtgtc tgtgtagaaa gaagtagaca taggagactc   8280

cattttgtta tgtgctaaga aaaattcttc tgccttgaga ttctgttaat ctatgacctt   8340

acccccaacc ccgtgctctc tgaaacatgt gctgtgtcaa ctcagggttg aatggattaa   8400

gggcggtgca ggatgtgctt tgttaaacag atgcttgaag gcagcatgct ccttaagagt   8460

catcaccact ccctaatctc aagtacccag ggacacaaaa actgcagaag gccgcaggga   8520

cctctgccta ggaaagccag gtattgtcca aggtttctcc ccatgtgata gtctgaaata   8580

tggcctcgtg ggaagggaaa gacctgaccg tcccccagcc cgacacctgt aaagggtctg   8640

tgctgaggag gattagtaaa agaggaagga atgcctcttg cagttgagac aagaggaagg   8700

catctgtctc ctgcctgtcc ctgggcaatg gaatgtctcg gtataaaacc cgattgtatg   8760

ctccatctac tgagataggg aaaaaccgcc ttagggctgg aggtgggacc tgcgggcagc   8820

aatactgctt tgtaaagcat tgagatgttt atgtgtatgc atatccaaaa gcacagcact   8880

taatccttta cattgtctat gatgccaaga cctttgttca cgtgtttgtc tgctgaccct   8940

ctccccacaa ttgtcttgtg accctgacac atccccctct ttgagaaaca cccacagatg   9000

atcaataaat actaagggaa ctcagaggct ggcgggatcc tccatatgct gaacgctggt   9060

tccccgggtc cccttatttc tttctctata ctttgtctct gtgtcttttt cttttccaaa   9120

tctctcgtcc caccttacga gaaacaccca caggtgtgta ggggcaaccc acccctaca    9179
```

<210> SEQ ID NO 46
<211> LENGTH: 279
<212> TYPE: PRT
<213> ORGANISM: Homo sapiens
<220> FEATURE:
<221> NAME/KEY: MISC_FEATURE
<222> LOCATION: (1)..(279)
<223> OTHER INFORMATION: Xaa=Any amino acid

<400> SEQUENCE: 46

```
Glu Thr Gln Val Gly Ala Pro Ala Arg Ala Glu Thr Arg Cys Glu Pro
1               5                   10                  15

Phe Thr Met Lys Met Leu Lys Asp Ile Lys Glu Gly Val Lys Gln Tyr
            20                  25                  30

Gly Ser Asn Ser Pro Tyr Ile Arg Thr Val Leu Asp Ser Ile Ala His
        35                  40                  45

Gly Asn Arg Leu Thr Pro Tyr Asp Trp Glu Ile Leu Ala Lys Ser Ser
    50                  55                  60

Leu Ser Ser Ser Gln Tyr Leu Gln Phe Lys Thr Trp Trp Ile Asp Gly
65                  70                  75                  80

Val Gln Glu Gln Val Arg Lys Lys Ser Gly Tyr Xaa Ala His Cys Xaa
                85                  90                  95

Tyr Arg Arg Arg Pro Ile Val Arg Asn Arg Ser Lys Leu Glu His His
            100                 105                 110

Xaa Pro Thr Ile Ser Asp Ala Glu Xaa Gly Tyr Xaa Thr Ser Lys Gly
        115                 120                 125

Tyr Leu Pro Gln Gly Leu Gly Lys Asn Ser Gly Pro Arg Asn Ser Phe
    130                 135                 140

Pro Tyr Xaa Phe Asn Xaa Thr Arg Leu Xaa Arg Ala Ile Ser Xaa Leu
145                 150                 155                 160
```

-continued

```
Cys Gly Lys Ile Thr Arg Cys Cys Ser Lys Val Tyr Tyr Arg Xaa Gln
                165                 170                 175

Cys Pro Lys Ser Tyr Cys Arg Ile Asn Gly Leu Xaa Lys Cys Lys Ser
            180                 185                 190

Arg Met Ser Val Gly His Lys Ala Ile Lys Arg Lys Ser Ser Ser Arg
        195                 200                 205

Ser Xaa Cys Asn Tyr Arg Ile Cys Glu Gly Leu Xaa Trp Asp Trp Arg
    210                 215                 220

Ser Tyr Ala Xaa Gly Asn Ala Asn Gly Ser Ser Asn Glu Gly Ala His
225                 230                 235                 240

Ser Arg Arg Thr Ser Xaa Asn Ile Trp Glu Lys Met Leu Xaa Leu Trp
                245                 250                 255

Ser Asn Arg Ser Ser Glu Lys Glu Leu Pro Arg Leu Lys Gln Ala Lys
            260                 265                 270

Lys Lys Lys Lys Lys Lys Lys
        275


<210> SEQ ID NO 47
<211> LENGTH: 288
<212> TYPE: PRT
<213> ORGANISM: Homo sapiens

<400> SEQUENCE: 47

Glu Glu Thr Gln Val Gly Ala Pro Ala Arg Ala Glu Thr Arg Cys Glu
1               5                   10                  15

Pro Phe Thr Met Lys Met Leu Lys Asp Ile Lys Glu Gly Val Lys Gln
            20                  25                  30

Tyr Gly Ser Asn Ser Pro Tyr Ile Arg Thr Val Leu Asp Ser Ile Ala
        35                  40                  45

His Gly Asn Arg Leu Thr Pro Tyr Asp Trp Glu Ile Leu Ala Lys Ser
    50                  55                  60

Ser Leu Ser Ser Ser Gln Tyr Leu Gln Phe Lys Thr Trp Trp Ile Asp
65                  70                  75                  80

Gly Val Gln Glu Gln Val Arg Lys Asn Gln Ala Thr Lys Pro Thr Val
                85                  90                  95

Asn Ile Asp Ala Asp Gln Leu Leu Gly Thr Gly Pro Asn Trp Ser Thr
            100                 105                 110

Ile Asn Gln Gln Ser Val Met Gln Asn Glu Ala Ile Glu Gln Val Arg
        115                 120                 125

Ala Ile Cys Leu Arg Ala Trp Gly Lys Ile Gln Asp Pro Gly Thr Ala
    130                 135                 140

Phe Pro Ile Asn Ser Ile Arg Gln Gly Ser Lys Glu Pro Tyr Pro Asp
145                 150                 155                 160

Phe Val Ala Arg Leu Gln Asp Ala Ala Gln Lys Ser Ile Thr Asp Asp
                165                 170                 175

Asn Ala Arg Lys Val Ile Val Glu Leu Met Ala Tyr Glu Asn Ala Asn
            180                 185                 190

Pro Glu Cys Gln Ser Ala Ile Lys Pro Leu Lys Gly Lys Val Pro Ala
        195                 200                 205

Gly Val Asp Val Ile Thr Glu Tyr Val Lys Ala Cys Asp Gly Ile Gly
    210                 215                 220

Gly Ala Met His Lys Ala Met Leu Met Ala Gln Ala Met Arg Gly Leu
225                 230                 235                 240

Thr Leu Gly Gly Gln Val Arg Thr Phe Gly Lys Lys Cys Tyr Asn Cys
                245                 250                 255
```

-continued

Gly Gln Ile Gly His Leu Lys Arg Ser Cys Pro Gly Leu Asn Lys Gln
260 265 270

Asn Ile Ile Asn Gln Ala Ile Thr Glu Lys Lys Lys Lys Lys Lys Lys
275 280 285

<210> SEQ ID NO 48
<211> LENGTH: 471
<212> TYPE: PRT
<213> ORGANISM: Homo sapiens
<220> FEATURE:
<221> NAME/KEY: MISC_FEATURE
<222> LOCATION: (1)..(471)
<223> OTHER INFORMATION: Xaa=Any amino acid

<400> SEQUENCE: 48

Glu Glu Thr Gln Val Gly Ala Pro Ala Arg Ala Glu Thr Arg Cys Glu
1 5 10 15

Pro Phe Thr Met Lys Met Leu Lys Asp Ile Lys Glu Gly Val Lys Gln
20 25 30

Tyr Gly Ser Asn Ser Pro Tyr Ile Arg Thr Leu Leu Asp Ser Ile Ala
35 40 45

His Gly Asn Arg Leu Thr Pro Tyr Asp Trp Glu Ile Leu Ala Lys Ser
50 55 60

Ser Leu Ser Ser Ser Gln Tyr Leu Gln Phe Lys Thr Trp Trp Ile Asp
65 70 75 80

Gly Val Gln Glu Gln Val Arg Lys Asn Gln Ala Thr Lys Pro Thr Val
85 90 95

Asn Ile Asp Ala Asp Gln Leu Leu Gly Thr Gly Pro Asn Trp Ser Thr
100 105 110

Ile Asn Gln Gln Ser Val Met Gln Asn Glu Ala Ile Glu Gln Val Arg
115 120 125

Ala Ile Cys Leu Arg Ala Trp Gly Lys Ile Gln Asp Pro Gly Thr Ala
130 135 140

Phe Pro Ile Asn Ser Ile Arg Gln Gly Ser Lys Glu Pro Tyr Pro Asp
145 150 155 160

Phe Val Ala Arg Leu Gln Asp Ala Ala Gln Lys Ser Ile Thr Asp Asp
165 170 175

Asn Ala Arg Lys Val Ile Val Glu Leu Met Ala Tyr Glu Asn Ala Asn
180 185 190

Pro Glu Cys Gln Ser Ala Ile Lys Pro Leu Lys Gly Lys Val Pro Ala
195 200 205

Gly Val Asp Val Ile Thr Glu Tyr Val Lys Ala Cys Asp Gly Ile Gly
210 215 220

Gly Ala Met His Lys Ala Met Leu Met Ala Gln Ala Met Arg Gly Leu
225 230 235 240

Thr Leu Gly Gly Gln Val Arg Thr Phe Gly Lys Lys Cys Tyr Asn Cys
245 250 255

Gly Gln Ile Gly His Arg Lys Arg Ser Cys Pro Gly Leu Asn Lys Gln
260 265 270

Asn Ile Ile Asn Gln Ala Ile Thr Ala Lys Asn Lys Lys Pro Ser Gly
275 280 285

Leu Cys Pro Lys Cys Gly Lys Ala Lys His Trp Ala Asn Gln Cys His
290 295 300

Ser Lys Phe Asp Lys Asp Gly Gln Pro Leu Ser Gly Asn Arg Lys Arg
305 310 315 320

-continued

```
Gly Gln Pro Gln Ala Pro Gln Gln Thr Gly Ala Phe Pro Val Lys Leu
                325                 330                 335

Phe Val Pro Gln Gly Phe Gln Gly Gln Gln Pro Leu Gln Lys Ile Pro
            340                 345                 350

Pro Leu Gln Gly Val Ser Gln Leu Gln Gln Ser Asn Ser Cys Pro Ala
        355                 360                 365

Pro Gln Gln Ala Ala Pro Gln Xaa Ile Tyr Val Pro Pro Lys Trp Ser
    370                 375                 380

Phe Tyr Ser Leu Glu Ser Pro His Lys Arg Phe Leu Glu Gly Tyr Met
385                 390                 395                 400

Ala Arg Cys Gln Lys Gly Gly Xaa Ala Phe Glu Gly Asp Gln Val Xaa
                405                 410                 415

Ile Xaa Arg Glu Ser Lys Phe Ile Leu Gly Xaa Phe Thr Gln Ile Ile
            420                 425                 430

Lys Gly Glu Phe Ser Xaa Xaa Ser Ala Pro Leu Phe Pro Gly Val Pro
        435                 440                 445

Ile Gln Val Ile Glu Leu Leu Asn Tyr Cys Phe Cys Leu Met Gln Lys
    450                 455                 460

Lys Lys Lys Lys Lys Lys Lys
465                 470
```

<210> SEQ ID NO 49
<211> LENGTH: 258
<212> TYPE: PRT
<213> ORGANISM: Homo sapiens
<220> FEATURE:
<221> NAME/KEY: MISC_FEATURE
<222> LOCATION: (1)..(258)
<223> OTHER INFORMATION: Xaa=Any amino acid

<400> SEQUENCE: 49

```
Gly Ser Gln Ala Gly Val Lys Gln Tyr Gly Pro Asn Ser Pro Tyr Ile
1               5                   10                  15

Arg Ile Leu Leu Asn Ser Ile Ala His Gly Asn Arg Leu Ile Ser Tyr
            20                  25                  30

Asp Trp Glu Ile Leu Ala Ile Ser Ser Leu Ser Pro Ser Gln Tyr Leu
        35                  40                  45

Gln Phe Lys Thr Trp Trp Ile Asp Gly Val Gln Glu Gln Val Arg Lys
    50                  55                  60

Asn Gln Ala Thr Asn Pro Val Ala Tyr Ile Asp Glu Asp Gln Leu Leu
65                  70                  75                  80

Gly Arg Gly Pro Asn Trp Asp Thr Ile Asn Gln Gln Ser Val Met Lys
                85                  90                  95

Met Arg Leu Leu Asn Asn Tyr Lys Gly Tyr Leu Pro Gln Gly Leu Gly
            100                 105                 110

Lys His Ser Gly Pro Arg Asn Leu Met Pro Phe Phe Xaa Phe Asn Gln
        115                 120                 125

Thr Arg Leu Xaa Arg Ala Ile Ser Arg Leu Cys Gly Lys Val Ala Arg
    130                 135                 140

Cys Ser Ser Lys Ile His Cys Arg Xaa Arg Pro Lys Ser Tyr Cys Arg
145                 150                 155                 160

Asn Asn Gly Leu Ser Lys Arg Lys Phe Arg Val Ser Ile Ser His Lys
                165                 170                 175

Ala Ile Lys Arg Lys Cys Phe Ser Arg Ser Xaa Cys Asn Tyr Arg Ile
            180                 185                 190
```

-continued

```
Cys Glu Gly Leu Xaa Trp Asp Trp Arg Ser Tyr Ala Xaa Gly Asn Ala
        195                 200                 205

Ile Gly Ser Ser Asn Tyr Arg Gly Cys Tyr Arg Arg Thr Ser Xaa Asn
    210                 215                 220

Ile Trp Gly Lys Met Leu Xaa Leu Trp Ser Asn Arg Ser Ser Lys Lys
225                 230                 235                 240

Glu Leu Pro Glu Leu Lys Leu Pro Pro Lys Lys Lys Lys Lys Lys Lys
                245                 250                 255

Lys Lys
```

<210> SEQ ID NO 50
<211> LENGTH: 288
<212> TYPE: PRT
<213> ORGANISM: Homo sapiens
<220> FEATURE:
<221> NAME/KEY: MISC_FEATURE
<222> LOCATION: (1)..(288)
<223> OTHER INFORMATION: Xaa=Any amino acid

<400> SEQUENCE: 50

```
Gln Lys Asn Glu Ser Ser Lys Leu Ser Ile Thr Xaa Leu Lys Glu Gln
1               5                   10                  15

Ser Trp Leu Pro Ser Leu Gln Cys Xaa Gln Asp Phe Asn Gln Ser Ile
            20                  25                  30

Asn Ile Val Ser Asp Ser Ala Tyr Val Val Gln Ala Thr Lys Asp Ile
        35                  40                  45

Glu Arg Ala Leu Ile Lys Tyr Ile Met Asp Asp Gln Leu Asn Pro Leu
    50                  55                  60

Phe Asn Leu Leu Gln Gln Asn Val Arg Lys Arg Asn Phe Pro Phe Tyr
65                  70                  75                  80

Ile Thr His Ile Arg Ala His Thr Asn Leu Pro Gly Pro Leu Thr Lys
                85                  90                  95

Ala Asn Glu Gln Ala Asp Leu Leu Val Ser Ser Ala Phe Met Glu Ala
            100                 105                 110

Gln Glu Leu His Ala Leu Thr His Val Asn Ala Ile Gly Leu Lys Asn
        115                 120                 125

Arg Phe Asp Ile Thr Trp Lys Gln Thr Lys Asn Ile Val Gln His Cys
    130                 135                 140

Thr Gln Cys Gln Ile Leu His Leu Ala Thr Gln Glu Ala Arg Val Asn
145                 150                 155                 160

Pro Arg Gly Leu Cys Pro Asn Val Leu Trp Gln Met Asp Val Met His
                165                 170                 175

Val Pro Ser Phe Gly Lys Leu Ser Phe Val His Val Thr Val Asp Thr
            180                 185                 190

Tyr Ser His Phe Ile Trp Ala Thr Cys Gln Thr Gly Glu Ser Thr Ser
        195                 200                 205

His Val Lys Arg His Leu Leu Ser Cys Phe Pro Val Met Gly Val Pro
    210                 215                 220

Glu Lys Val Lys Thr Asp Asn Gly Pro Gly Tyr Cys Ser Lys Ala Val
225                 230                 235                 240

Gln Lys Phe Leu Asn Gln Trp Lys Ile Thr His Thr Ile Gly Ile Leu
                245                 250                 255
```

-continued

```
Tyr Asn Ser Gln Gly Gln Ala Ile Ile Glu Arg Thr Asn Arg Thr Leu
            260                 265                 270

Lys Ala Gln Leu Val Lys Gln Lys Lys Lys Lys Lys Lys Lys Lys Lys
        275                 280                 285


<210> SEQ ID NO 51
<211> LENGTH: 286
<212> TYPE: PRT
<213> ORGANISM: Homo sapiens
<220> FEATURE:
<221> NAME/KEY: MISC_FEATURE
<222> LOCATION: (1)..(286)
<223> OTHER INFORMATION: Xaa=Any amino acid

<400> SEQUENCE: 51

Gln Lys Asn Glu Ser Ser Lys Leu Ser Ile Thr Xaa Leu Lys Glu Gln
1               5                   10                  15

Ser Trp Leu Pro Ser Leu Gln Cys Xaa Gln Asp Phe Asn Gln Ser Ile
            20                  25                  30

Asn Ile Val Ser Asp Ser Ala Tyr Val Val Gln Ala Thr Lys Asp Ile
        35                  40                  45

Glu Arg Ala Leu Ile Lys Tyr Ile Met Asp Asp Gln Leu Asn Pro Leu
    50                  55                  60

Phe Asn Leu Leu Gln Gln Asn Val Arg Lys Arg Asn Phe Pro Phe Tyr
65                  70                  75                  80

Ile Thr His Ile Arg Ala His Thr Asn Leu Pro Gly Pro Leu Thr Lys
                85                  90                  95

Ala Asn Glu Gln Ala Asp Leu Leu Val Ser Ser Ala Phe Met Glu Ala
            100                 105                 110

Gln Glu Leu His Ala Leu Thr His Val Asn Ala Ile Gly Leu Lys Asn
        115                 120                 125

Lys Phe Asp Ile Thr Trp Lys Gln Thr Lys Asn Ile Val Gln His Cys
    130                 135                 140

Thr Gln Cys Gln Ile Leu His Leu Ala Thr Gln Glu Ala Arg Val Asn
145                 150                 155                 160

Pro Arg Gly Leu Cys Pro Asn Val Leu Trp Gln Met Asp Val Met His
                165                 170                 175

Val Pro Ser Phe Gly Lys Leu Ser Phe Val His Val Thr Val Asp Thr
            180                 185                 190

Tyr Ser His Phe Ile Trp Ala Thr Cys Gln Thr Gly Glu Ser Thr Ser
        195                 200                 205

His Val Lys Arg His Leu Leu Ser Cys Phe Pro Val Met Gly Val Pro
    210                 215                 220

Glu Lys Val Lys Thr Asp Asn Gly Pro Gly Tyr Cys Ser Lys Ala Val
225                 230                 235                 240

Gln Lys Phe Leu Asn Gln Trp Lys Ile Thr His Thr Ile Gly Ile Leu
                245                 250                 255

Tyr Asn Ser Gln Gly Gln Ala Ile Ile Glu Arg Thr Asn Arg Thr Leu
            260                 265                 270

Lys Ala Gln Leu Val Lys Gln Lys Glu Lys Lys Lys Lys Lys
        275                 280                 285


<210> SEQ ID NO 52
<211> LENGTH: 287
<212> TYPE: PRT
<213> ORGANISM: Homo sapiens
```

-continued

<220> FEATURE:
<221> NAME/KEY: MISC_FEATURE
<222> LOCATION: (1)..(287)
<223> OTHER INFORMATION: Xaa=Any amino acid

<400> SEQUENCE: 52

```
Gln Lys Asn Glu Ser Ser Lys Leu Ser Ile Thr Arg Leu Lys Glu Gln
1               5                   10                  15

Ser Trp Leu Pro Ser Leu Gln Cys Xaa Gln Asp Phe Asn Gln Ser Ile
            20                  25                  30

Asn Ile Val Ser Asp Ser Ala Tyr Val Val Gln Ala Thr Lys Asp Ile
        35                  40                  45

Glu Arg Ala Leu Ile Lys Tyr Ile Met Asp Asp Gln Leu Asn Pro Leu
    50                  55                  60

Phe Asn Leu Leu Gln Gln Asn Val Arg Lys Arg Asn Phe Pro Phe Tyr
65                  70                  75                  80

Ile Thr His Ile Arg Ala His Thr Asn Leu Pro Gly Pro Leu Thr Lys
                85                  90                  95

Ala Asn Glu Gln Ala Asp Leu Leu Val Ser Ser Ala Phe Met Glu Ala
            100                 105                 110

Gln Glu Leu His Ala Leu Thr His Val Asn Ala Ile Gly Leu Lys Asn
        115                 120                 125

Lys Phe Asp Ile Thr Trp Lys Gln Thr Lys Asn Ile Val Gln His Cys
    130                 135                 140

Ala Gln Cys Gln Ile Leu His Leu Ala Thr Gln Glu Val Arg Val Asn
145                 150                 155                 160

Pro Arg Gly Leu Cys Pro Asn Val Leu Trp Gln Met Asp Val Met His
                165                 170                 175

Val Pro Ser Phe Gly Lys Leu Ser Phe Val His Val Thr Val Asp Thr
            180                 185                 190

Tyr Ser His Phe Ile Trp Ala Thr Cys Gln Thr Gly Glu Ser Thr Ser
        195                 200                 205

His Val Lys Arg His Leu Leu Ser Cys Phe Pro Val Met Gly Val Pro
    210                 215                 220

Glu Lys Val Lys Thr Asp Asn Gly Pro Gly Tyr Cys Ser Lys Ala Val
225                 230                 235                 240

Gln Lys Phe Leu Asn Gln Trp Lys Ile Thr His Thr Ile Gly Ile Leu
                245                 250                 255

Tyr Asn Ser Gln Gly Gln Ala Ile Ile Glu Arg Thr Asn Arg Thr Leu
            260                 265                 270

Lys Ala Gln Leu Val Lys Gln Lys Lys Lys Lys Lys Lys Lys Lys
        275                 280                 285
```

<210> SEQ ID NO 53
<211> LENGTH: 288
<212> TYPE: PRT
<213> ORGANISM: Homo sapiens
<220> FEATURE:
<221> NAME/KEY: MISC_FEATURE
<222> LOCATION: (1)..(288)
<223> OTHER INFORMATION: Xaa=Any amino acid

<400> SEQUENCE: 53

```
Gln Lys Asn Glu Ser Ser Lys Leu Ser Ile Thr Xaa Leu Lys Glu Gln
1               5                   10                  15

Ser Trp Leu Pro Ser Leu Gln Cys Xaa Gln Asp Phe Asn Gln Ser Ile
            20                  25                  30
```

-continued

```
Asn Ile Val Ser Asp Ser Ala Tyr Val Val Gln Ala Thr Lys Asp Ile
        35                  40                  45

Glu Arg Ala Leu Ile Lys Tyr Ile Met Asp Asp Gln Leu Asn Pro Leu
    50                  55                  60

Phe Asn Leu Leu Gln Gln Asn Val Arg Lys Xaa Asn Phe Pro Phe Tyr
65                  70                  75                  80

Ile Thr His Ile Arg Ala His Thr Asn Leu Pro Gly Pro Leu Thr Lys
                85                  90                  95

Ala Asn Glu Gln Ala Asp Leu Leu Val Ser Ser Ala Phe Met Glu Ala
            100                 105                 110

Gln Glu Leu His Ala Leu Thr His Val Asn Ala Ile Gly Leu Lys Asn
        115                 120                 125

Lys Phe Asp Ile Thr Trp Lys Gln Thr Lys Asn Ile Val Gln His Cys
    130                 135                 140

Thr Gln Cys Gln Ile Leu His Leu Ala Thr Gln Glu Ala Arg Val Asn
145                 150                 155                 160

Pro Arg Gly Leu Cys Pro Asn Val Leu Trp Gln Met Asp Val Met His
                165                 170                 175

Val Pro Ser Phe Gly Lys Leu Ser Phe Val His Val Thr Val Asp Thr
            180                 185                 190

Tyr Ser His Phe Ile Trp Ala Thr Cys Gln Thr Gly Glu Ser Thr Ser
        195                 200                 205

His Val Lys Arg His Leu Leu Phe Cys Phe Pro Val Met Gly Val Pro
    210                 215                 220

Glu Lys Val Lys Thr Asp Asn Gly Pro Gly Tyr Cys Ser Lys Ala Val
225                 230                 235                 240

Gln Glu Phe Leu Asn Gln Trp Lys Ile Thr His Thr Ile Gly Ile Leu
                245                 250                 255

Tyr Asn Ser Gln Gly Gln Ala Ile Ile Glu Arg Thr Asn Arg Thr Leu
            260                 265                 270

Lys Ala Gln Leu Val Lys Gln Lys Lys Lys Lys Lys Lys Lys Lys Lys
        275                 280                 285


<210> SEQ ID NO 54
<211> LENGTH: 234
<212> TYPE: PRT
<213> ORGANISM: Homo sapiens
<220> FEATURE:
<221> NAME/KEY: MISC_FEATURE
<222> LOCATION: (1)..(234)
<223> OTHER INFORMATION: Xaa=Any amino acid

<400> SEQUENCE: 54

Gln Lys Asn Glu Ser Ser Lys Leu Ser Ile Thr Xaa Leu Lys Glu Gln
1               5                   10                  15

Ser Trp Leu Pro Ser Leu Gln Cys Xaa Gln Asp Phe Asn Gln Ser Ile
            20                  25                  30

Asn Ile Val Ser Asp Ser Ala Tyr Val Val Gln Ala Thr Lys Asp Ile
        35                  40                  45

Glu Arg Ala Leu Ile Lys Tyr Ile Met Asp Asp Gln Leu Asn Pro Leu
    50                  55                  60

Phe Asn Leu Leu Gln Gln Asn Val Arg Lys Arg Asn Phe Pro Phe Tyr
65                  70                  75                  80

Ile Thr His Ile Arg Ala His Thr Asn Leu Pro Gly Pro Leu Thr Lys
                85                  90                  95
```

-continued

```
Ala Asn Glu Gln Ala Asp Leu Leu Val Ser Ser Ala Phe Met Glu Ala
            100                 105                 110

Gln Glu Leu His Ala Leu Thr His Val Asn Ala Ile Gly Leu Lys Asn
        115                 120                 125

Lys Phe Asp Ile Thr Trp Lys Gln Thr Lys Asn Ile Val Gln His Cys
    130                 135                 140

Thr Gln Cys Gln Ile Leu His Leu Ala Thr Gln Glu Ala Arg Val Asn
145                 150                 155                 160

Pro Arg Gly Leu Cys Pro Asn Val Leu Trp Gln Met Asp Val Met His
                165                 170                 175

Val Pro Ser Phe Gly Lys Leu Ser Phe Val His Val Thr Val Asp Thr
            180                 185                 190

Tyr Ser His Phe Ile Trp Ala Thr Cys Gln Thr Gly Glu Ser Thr Ser
        195                 200                 205

His Val Lys Arg His Leu Leu Ser Cys Phe Pro Val Met Gly Val Pro
    210                 215                 220

Glu Lys Lys Lys Lys Lys Lys Lys Lys Lys
225                 230


<210> SEQ ID NO 55
<211> LENGTH: 293
<212> TYPE: PRT
<213> ORGANISM: Homo sapiens
<220> FEATURE:
<221> NAME/KEY: MISC_FEATURE
<222> LOCATION: (1)..(293)
<223> OTHER INFORMATION: Xaa=Any amino acid

<400> SEQUENCE: 55

Gln Lys Asn Glu Ser Ser Lys Leu Ser Ile Thr Xaa Leu Lys Glu Gln
1               5                   10                  15

Ser Trp Leu Pro Ser Leu Gln Cys Xaa Gln Asp Phe Asn Gln Ser Ile
            20                  25                  30

Asn Ile Val Ser Asp Ser Ala Tyr Val Val Gln Ala Thr Lys Asp Ile
        35                  40                  45

Glu Arg Ala Leu Ile Lys Tyr Ile Met Asp Asp Gln Leu Asn Pro Leu
    50                  55                  60

Phe Asn Leu Leu Gln Gln Asn Val Arg Lys Arg Asn Phe Pro Phe Tyr
65                  70                  75                  80

Ile Thr His Ile Arg Ala His Thr Asn Leu Pro Gly Pro Leu Thr Lys
                85                  90                  95

Ala Asn Glu Gln Ala Asp Leu Leu Val Ser Ser Ala Phe Ile Glu Ala
            100                 105                 110

Gln Glu Leu His Ala Leu Thr His Val Asn Ala Ile Gly Leu Lys Asn
        115                 120                 125

Lys Phe Asp Ile Thr Trp Lys Gln Thr Lys Asn Ile Val Gln His Cys
    130                 135                 140

Thr Gln Cys Gln Ile Leu His Leu Ala Thr Gln Glu Ala Arg Val Asn
145                 150                 155                 160

Pro Arg Gly Leu Cys Pro Asn Val Leu Trp Gln Met Asp Val Met His
                165                 170                 175

Val Pro Ser Phe Gly Lys Leu Ser Phe Val His Val Thr Val Asp Thr
            180                 185                 190

Tyr Ser His Phe Ile Trp Ala Thr Cys Gln Thr Gly Glu Ser Thr Ser
        195                 200                 205
```

-continued

```
His Val Lys Arg His Leu Leu Ser Cys Phe Pro Val Met Gly Val Pro
    210                 215                 220

Glu Lys Val Lys Thr Asp Asn Gly Pro Gly Tyr Cys Ser Lys Ala Val
225                 230                 235                 240

Gln Lys Phe Leu Asn Gln Trp Lys Ile Thr His Thr Ile Gly Ile Leu
                245                 250                 255

Tyr Asn Ser Gln Gly Gln Ala Ile Ile Glu Arg Thr Asn Arg Thr Leu
            260                 265                 270

Lys Ala Gln Leu Val Lys Gln Lys Lys Lys Lys Lys Lys Lys Lys Thr
        275                 280                 285

Cys Arg Pro Pro Arg
    290


<210> SEQ ID NO 56
<211> LENGTH: 375
<212> TYPE: PRT
<213> ORGANISM: Homo sapiens

<400> SEQUENCE: 56

Glu Glu Thr Gln Val Gly Ala Pro Ala Arg Ala Glu Thr Arg Cys Glu
1               5                   10                  15

Pro Phe Thr Met Lys Met Leu Lys Asp Ile Lys Glu Gly Val Lys Gln
            20                  25                  30

Tyr Gly Ser Asn Ser Pro Tyr Ile Arg Thr Leu Leu Asp Ser Ile Ala
        35                  40                  45

His Gly Asn Arg Leu Thr Pro Tyr Asp Trp Glu Ile Leu Ala Lys Ser
    50                  55                  60

Ser Leu Ser Ser Ser Gln Tyr Leu Gln Phe Lys Thr Trp Trp Ile Asp
65                  70                  75                  80

Gly Val Gln Glu Gln Val Arg Lys Asn Gln Ala Thr Lys Pro Thr Val
                85                  90                  95

Asn Ile Asp Ala Asp Gln Leu Leu Gly Thr Gly Pro Asn Trp Ser Thr
            100                 105                 110

Ile Asn Gln Gln Ser Val Met Gln Asn Glu Ala Ile Glu Gln Val Arg
        115                 120                 125

Ala Ile Cys Leu Arg Ala Trp Gly Lys Ile Gln Asp Pro Gly Thr Ala
    130                 135                 140

Phe Pro Ile Asn Ser Ile Arg Gln Gly Ser Lys Glu Pro Tyr Pro Asp
145                 150                 155                 160

Phe Val Ala Arg Leu Gln Asp Ala Ala Gln Lys Ser Ile Thr Asp Asp
                165                 170                 175

Asn Ala Arg Lys Val Ile Val Glu Leu Met Ala Tyr Glu Asn Ala Asn
            180                 185                 190

Pro Glu Cys Gln Ser Ala Ile Lys Pro Leu Lys Gly Lys Val Pro Ala
        195                 200                 205

Gly Val Asp Val Ile Thr Glu Tyr Val Lys Ala Cys Asp Gly Ile Gly
    210                 215                 220

Gly Ala Met His Lys Ala Met Leu Met Ala Gln Ala Met Arg Gly Leu
225                 230                 235                 240

Thr Leu Gly Gly Gln Val Arg Thr Phe Gly Lys Lys Cys Tyr Asn Cys
                245                 250                 255

Gly Gln Ile Gly His Arg Lys Arg Ser Cys Pro Gly Leu Asn Lys Gln
            260                 265                 270

Asn Ile Ile Asn Gln Ala Ile Thr Ala Lys Asn Lys Lys Pro Ser Gly
        275                 280                 285
```

-continued

```
Leu Cys Pro Lys Cys Gly Lys Ala Lys His Trp Ala Asn Gln Cys His
    290                 295                 300

Ser Lys Phe Asp Lys Asp Gly Gln Pro Leu Ser Gly Asn Arg Lys Arg
305                 310                 315                 320

Gly Gln Pro Gln Ala Pro Gln Gln Thr Gly Ala Phe Pro Val Lys Leu
                325                 330                 335

Phe Val Pro Gln Gly Phe Gln Gly Gln Gln Pro Leu Gln Lys Ile Pro
            340                 345                 350

Pro Leu Gln Gly Val Ser Gln Leu Gln Gln Ser Asn Ser Cys Pro Ala
        355                 360                 365

Pro Gln Gln Ala Ala Pro Gln
    370                 375


<210> SEQ ID NO 57
<211> LENGTH: 288
<212> TYPE: PRT
<213> ORGANISM: Homo sapiens

<400> SEQUENCE: 57

Glu Glu Thr Gln Val Gly Ala Pro Ala Arg Ala Glu Thr Arg Cys Glu
1               5                   10                  15

Pro Phe Thr Met Lys Met Leu Lys Asp Ile Lys Glu Gly Val Lys Gln
            20                  25                  30

Tyr Gly Ser Asn Ser Pro Tyr Ile Arg Thr Val Leu Asp Ser Ile Ala
        35                  40                  45

His Gly Asn Arg Leu Thr Pro Tyr Asp Trp Glu Ile Leu Ala Lys Ser
    50                  55                  60

Ser Leu Ser Ser Ser Gln Tyr Leu Gln Phe Lys Thr Trp Trp Ile Asp
65                  70                  75                  80

Gly Val Gln Glu Gln Val Arg Lys Asn Gln Ala Thr Lys Pro Thr Val
                85                  90                  95

Asn Ile Asp Ala Asp Gln Leu Leu Gly Thr Gly Pro Asn Trp Ser Thr
            100                 105                 110

Ile Asn Gln Gln Ser Val Met Gln Asn Glu Ala Ile Glu Gln Val Arg
        115                 120                 125

Ala Ile Cys Leu Arg Ala Trp Gly Lys Ile Gln Asp Pro Gly Thr Ala
    130                 135                 140

Phe Pro Ile Asn Ser Ile Arg Gln Gly Ser Lys Glu Pro Tyr Pro Asp
145                 150                 155                 160

Phe Val Ala Arg Leu Gln Asp Ala Ala Gln Lys Ser Ile Thr Asp Asp
                165                 170                 175

Asn Ala Arg Lys Val Ile Val Glu Leu Met Ala Tyr Glu Asn Ala Asn
            180                 185                 190

Pro Glu Cys Gln Ser Ala Ile Lys Pro Leu Lys Gly Lys Val Pro Ala
        195                 200                 205

Gly Val Asp Val Ile Thr Glu Tyr Val Lys Ala Cys Asp Gly Ile Gly
    210                 215                 220

Gly Ala Met His Lys Ala Met Leu Met Ala Gln Ala Met Arg Gly Leu
225                 230                 235                 240

Thr Leu Gly Gly Gln Val Arg Thr Phe Gly Lys Lys Cys Tyr Asn Cys
                245                 250                 255

Gly Gln Ile Gly His Leu Lys Arg Ser Cys Pro Gly Leu Asn Lys Gln
            260                 265                 270

Asn Ile Ile Asn Gln Ala Ile Thr Glu Lys Lys Lys Lys Lys Lys Lys
        275                 280                 285
```

-continued

<210> SEQ ID NO 58
<211> LENGTH: 268
<212> TYPE: PRT
<213> ORGANISM: Homo sapiens

<400> SEQUENCE: 58

```
Gln Asp Phe Asn Gln Ser Ile Asn Ile Val Ser Asp Ser Ala Tyr Val
1               5                   10                  15

Val Gln Ala Thr Lys Asp Ile Glu Arg Ala Leu Ile Lys Tyr Ile Met
            20                  25                  30

Asp Asp Gln Leu Asn Pro Leu Phe Asn Leu Leu Gln Gln Asn Val Arg
        35                  40                  45

Lys Arg Asn Phe Pro Phe Tyr Ile Thr His Ile Arg Ala His Thr Asn
    50                  55                  60

Leu Pro Gly Pro Leu Thr Lys Ala Asn Glu Gln Ala Asp Leu Leu Val
65                  70                  75                  80

Ser Ser Ala Phe Met Glu Ala Gln Glu Leu His Ala Leu Thr His Val
                85                  90                  95

Asn Ala Ile Gly Leu Lys Asn Lys Phe Asp Ile Thr Trp Lys Gln Thr
            100                 105                 110

Lys Asn Ile Val Gln His Cys Thr Gln Cys Gln Ile Leu His Leu Ala
        115                 120                 125

Thr Gln Glu Ala Arg Val Asn Pro Arg Gly Leu Cys Pro Asn Val Leu
    130                 135                 140

Trp Gln Met Asp Val Met His Val Pro Ser Phe Gly Lys Leu Ser Phe
145                 150                 155                 160

Val His Val Thr Val Asp Thr Tyr Ser His Phe Ile Trp Ala Thr Cys
                165                 170                 175

Gln Thr Gly Glu Ser Thr Ser His Val Lys Arg His Leu Leu Ser Cys
            180                 185                 190

Phe Pro Val Met Gly Val Pro Glu Lys Val Lys Thr Asp Asn Gly Pro
        195                 200                 205

Gly Tyr Cys Ser Lys Ala Val Gln Lys Phe Leu Asn Gln Trp Lys Ile
    210                 215                 220

Thr His Thr Ile Gly Ile Leu Tyr Asn Ser Gln Gly Gln Ala Ile Ile
225                 230                 235                 240

Glu Arg Thr Asn Arg Thr Leu Lys Ala Gln Leu Val Lys Gln Lys Lys
                245                 250                 255

Lys Lys Lys Lys Lys Lys Thr Cys Arg Pro Pro Arg
            260                 265
```

<210> SEQ ID NO 59
<211> LENGTH: 15
<212> TYPE: DNA
<213> ORGANISM: Homo sapiens

<400> SEQUENCE: 59
taggcctttg aggga 15

<210> SEQ ID NO 60
<211> LENGTH: 19
<212> TYPE: DNA
<213> ORGANISM: Homo sapiens

<400> SEQUENCE: 60
cattagaaaa aggacattg 19

-continued

<210> SEQ ID NO 61
<211> LENGTH: 17
<212> TYPE: DNA
<213> ORGANISM: Homo sapiens

<400> SEQUENCE: 61
ttggaattct gtttgta 17

<210> SEQ ID NO 62
<211> LENGTH: 16
<212> TYPE: DNA
<213> ORGANISM: Homo sapiens

<400> SEQUENCE: 62
taactgagcc attaat 16

<210> SEQ ID NO 63
<211> LENGTH: 21
<212> TYPE: DNA
<213> ORGANISM: Homo sapiens

<400> SEQUENCE: 63
agccatggtc ccctttaatt a 21

<210> SEQ ID NO 64
<211> LENGTH: 17
<212> TYPE: DNA
<213> ORGANISM: Homo sapiens

<400> SEQUENCE: 64
ttttaccaca ccagcct 17

<210> SEQ ID NO 65
<211> LENGTH: 15
<212> TYPE: DNA
<213> ORGANISM: Homo sapiens

<400> SEQUENCE: 65
ttgtcagctc aagct 15

<210> SEQ ID NO 66
<211> LENGTH: 15
<212> TYPE: DNA
<213> ORGANISM: Homo sapiens

<400> SEQUENCE: 66
tacatcgttc actat 15

<210> SEQ ID NO 67
<211> LENGTH: 15
<212> TYPE: DNA
<213> ORGANISM: Homo sapiens

<400> SEQUENCE: 67
ttaaaagcat taaat 15

<210> SEQ ID NO 68
<211> LENGTH: 17
<212> TYPE: DNA
<213> ORGANISM: Homo sapiens

<400> SEQUENCE: 68
agaagtccca attgagg 17

-continued

<210> SEQ ID NO 69
<211> LENGTH: 15
<212> TYPE: DNA
<213> ORGANISM: Homo sapiens

<400> SEQUENCE: 69
ggtcttgccg atttt 15

<210> SEQ ID NO 70
<211> LENGTH: 15
<212> TYPE: DNA
<213> ORGANISM: Homo sapiens

<400> SEQUENCE: 70
acaatcgtta ccaca 15

<210> SEQ ID NO 71
<211> LENGTH: 15
<212> TYPE: DNA
<213> ORGANISM: Homo sapiens

<400> SEQUENCE: 71
aaaagaatga gtcat 15

<210> SEQ ID NO 72
<211> LENGTH: 15
<212> TYPE: DNA
<213> ORGANISM: Homo sapiens

<400> SEQUENCE: 72
cagtatcact tgact 15

<210> SEQ ID NO 73
<211> LENGTH: 23
<212> TYPE: DNA
<213> ORGANISM: Homo sapiens

<400> SEQUENCE: 73
ttttaatcag tctattaaca ttg 23

<210> SEQ ID NO 74
<211> LENGTH: 16
<212> TYPE: DNA
<213> ORGANISM: Homo sapiens

<400> SEQUENCE: 74
aaaggatatt gagaga 16

<210> SEQ ID NO 75
<211> LENGTH: 16
<212> TYPE: DNA
<213> ORGANISM: Homo sapiens

<400> SEQUENCE: 75
cctaatcaaa tacatt 16

<210> SEQ ID NO 76
<211> LENGTH: 15
<212> TYPE: DNA
<213> ORGANISM: Homo sapiens

<400> SEQUENCE: 76
cgctgtttaa tttgt 15

-continued

<210> SEQ ID NO 77
<211> LENGTH: 16
<212> TYPE: DNA
<213> ORGANISM: Homo sapiens

<400> SEQUENCE: 77
tgcattcatg gaagca 16

<210> SEQ ID NO 78
<211> LENGTH: 15
<212> TYPE: DNA
<213> ORGANISM: Homo sapiens

<400> SEQUENCE: 78
actcaggagg caaga 15

<210> SEQ ID NO 79
<211> LENGTH: 16
<212> TYPE: DNA
<213> ORGANISM: Homo sapiens

<400> SEQUENCE: 79
ttaagagaca tttatt 16

<210> SEQ ID NO 80
<211> LENGTH: 16
<212> TYPE: DNA
<213> ORGANISM: Homo sapiens

<400> SEQUENCE: 80
taaagcagtt caaaaa 16

<210> SEQ ID NO 81
<211> LENGTH: 15
<212> TYPE: DNA
<213> ORGANISM: Homo sapiens

<400> SEQUENCE: 81
aataggaatt ctcta 15

<210> SEQ ID NO 82
<211> LENGTH: 16
<212> TYPE: DNA
<213> ORGANISM: Homo sapiens

<400> SEQUENCE: 82
aaagctcaat tggtta 16

<210> SEQ ID NO 83
<211> LENGTH: 25
<212> TYPE: DNA
<213> ORGANISM: Homo sapiens

<400> SEQUENCE: 83
taggaggaca agttagaaca tttgg 25

<210> SEQ ID NO 84
<211> LENGTH: 24
<212> TYPE: DNA
<213> ORGANISM: Homo sapiens

<400> SEQUENCE: 84
aaaatgttat aattgtggtc aaat 24

-continued

<210> SEQ ID NO 85
<211> LENGTH: 1998
<212> TYPE: DNA
<213> ORGANISM: Homo sapiens

<400> SEQUENCE: 85
atggggcaaa ctaaaagtaa aattaaaagt aaatatgcct cttatctcag ctttattaaa 60
attcttttaa aaagaggggg agttaaagta tctacaaaaa atctaatcaa gctatttcaa 120
ataatagaac aattttgccc atggtttcca gaacaaggaa ctttagatct aaaagattgg 180
aaaagaattg gtaaggaact aaaacaagca ggtaggaagg gtaatatcat tccacttaca 240
gtatggaatg attgggccat tattaaagca gctttagaac catttcaaac agaagaagat 300
agcgtttcag tttctgatgc ccctggaagc tgtataatag attgtaatga aaacacaagg 360
aaaaaatccc agaaagaaac ggaaggttta cattgcgaat atgtagcaga gccggtaatg 420
gctcagtcaa cgcaaaatgt tgactataat caattacagg aggtgatata tcctgaaacg 480
ttaaaattag aaggaaaagg tccagaatta gtggggccat cagagtctaa accacgaggc 540
acaagtcctc ttccagcagg tcaggtgcct gtaacattac aacctcaaaa gcaggttaaa 600
gaaaataaga cccaaccgcc agtagcctat caatactggc ctccggctga acttcagtat 660
cggccacccc cagaaagtca gtatggatat ccaggaatgc cccagcacc acagggcagg 720 gcgccatacc ctcagccgcc cactaggaga cttaatccta cggcaccacc tagtagacag 780
ggtagtaaat tacatgaaat tattgataaa tcaagaaagg aaggagatac tgaggcatgg 840
caattcccag taacgttaga accgatgcca cctggagaag gagcccaaga gggagagcct 900
cccacagttg aggccagata caagtctttt tcgataaaaa agctaaaaga tatgaaagag 960
ggagtaaaac agtatggacc caactcccct tatatgagga cattattaga ttccattgct 1020
catggacata gactcattcc ttatgattgg gagattctgg caaaatcgtc tctctcaccc 1080
tctcaatttt tacaatttaa gacttggtgg attgatgggg tacaagaaca ggtccgaaga 1140
aatagggctg ccaatcctcc agttaacata gatgcagatc aactattagg aataggtcaa 1200
aattggagta ctattagtca acaagcatta atgcaaaatg aggccattga gcaagttaga 1260
gctatctgcc ttagagcctg ggaaaaaatc caagacccag gaagtacctg cccctcattt 1320
aatacagtaa gacaaggttc aaaagagccc tatcctgatt ttgtggcaag gctccaagat 1380
gttgctcaaa agtcaattgc tgatgaaaaa gcccgtaagg tcatagtgga gttgatggca 1440
tatgaaaacg ccaatcctga gtgtcaatca gccattaagc cattaaaagg aaaggttcct 1500
gcaggatcag atgtaatctc agaatatgta aaagcctgtg atggaatcgg aggagctatg 1560
cataaagcta tgcttatggc tcaagcaata acaggagttg ttttaggagg acaagttaga 1620
acatttggaa gaaaatgtta taattgtggt caaattggtc acttaaaaaa gaattgccca 1680
gtcttaaata aacagaatat aactattcaa gcaactacaa caggtagaga gccacctgac 1740
ttatgtccaa gatgtaaaaa aggaaaacat tgggctagtc aatgtcgttc taaatttgat 1800
aaaaatgggc aaccattgtc gggaaacgag caaaggggcc agcctcaggc cccacaacaa 1860
actggggcat tcccaattca gccatttgtt cctcagggtt ttcagggaca acaaccccca 1920
ctgtcccaag tgtttcaggg aataagccag ttaccacaat acaacaattg tcccccgcca 1980
caagcggcag tgcagcag 1998

<210> SEQ ID NO 86
<211> LENGTH: 1000
<212> TYPE: DNA
<213> ORGANISM: Homo sapiens

<400> SEQUENCE: 86
atgggcaacc attgtcggga aacgagcaaa ggggccagcc tcaggcccca caacaaactg 60
gggcattccc aattcagcca tttgttcctc agggttttca gggacaacaa cccccactgt 120
cccaagtgtt tcagggaata agccagttac cacaatacaa caattgtccc ccgccacaag 180
cggcagtgca gcagtagatt tatgtactat acaagcagtc tctctgcttc caggggagcc 240
cccacaaaaa acccccacag gggtatatgg acccctgcct aaggggactg taggactaat 300
cttgggacga tcaagtctaa atctaaaagg agttcaaatt catactagtg tggttgattc 360
agactataaa ggcgaaattc aattggttat tagctcttca attccttgga gtgccagtcc 420
aagagacagg attgctcaat tattactcct gccatacatt aagggtggaa atagtgaaat 480
aaaaagaata ggagggcttg gaagcactga tccaacagga aaggctgcat attgggcaag 540
tcaggtctca gagaacagac ctgtgtgtaa ggccattatt caaggaaaac agtttgaagg 600
gttggtagac actggagcag atgtctctat cattgcttta aatcagtggc caaaaaattg 660
gcctaaacaa aaggctgtta caggacttgt cggcataggc acagcctcag aagtgtatca 720
aagtacggag attttacatt gcttagggcc agataatcaa gaaagtactg ttcagccaat 780
gattacttca attcctctta atctgtgggg tcgagattta ttacaacaat ggggtgcgga 840
aatcaccatg cccgctccat catatagccc cacgagtcaa aaaatcatga ccaagatggg 900
atatatacca ggaaagggac tagggaaaaa tgaagatggc attaaaattc cagttgaggc 960
taaaataaat caagaaagag aaggaatagg gaatccttgc 1000

<210> SEQ ID NO 87
<211> LENGTH: 2896
<212> TYPE: DNA
<213> ORGANISM: Homo sapiens

<400> SEQUENCE: 87
atggcattaa aattccagtt gaggctaaaa taaatcaaga aagagaagga atagggaatc 60
cttgctaggg gcggccactg tagagcctcc taaacccata ccattaactt ggaaaacaga 120
aaaaccagtg tgggtaaatc agtggccgct accaaaacaa aaactggagg ctttacattt 180
attagcaaat gaacagttag aaaagggtca tattgagcct tcgttctcac cttggaattc 240
tcctgtgttt gtaattcaga agaaatcagg caaatggcgt atgttaactg acttaagggc 300
tgtaaacgcc gtaattcaac ccatggggcc tctccaaccc gggttgccct ctccggccat 360
gatcccaaaa gattggcctt taattataat tgatctaaag gattgctttt ttaccatccc 420
tctggcagag caggattgcg aaaaatttgc ctttactata ccagccataa ataataaaga 480
accagccacc aggtttcagt ggaaagtgtt acctcaggga atgcttaata gtccaactat 540
ttgtcagact tttgtaggtc gagctcttca accagttaga gaaaagtttt cagactgtta 600
tattattcat tgtattgatg atattttatg tgctgcagaa acgaaagata aattaattga 660
ctgttataca tttctgcaag cagaggttgc caatgctgga ctggcaatag catctgataa 720
gatccaaacc tctactcctt ttcattattt agggatgcag atagaaaata gaaaaattaa 780
gccacaaaaa atagaaataa gaaaagacac attaaaaaca ctaaatgatt ttcaaaaatt 840
actaggagat attaattgga ttcggccaac tctaggcatt cctacttatg ccatgtcaaa 900

-continued

```
tttgttctct atcttaagag gagactcaga cttaaatagt aaaagaatgt taaccccaga    960

ggcaacaaaa gaaattaaat tagtggaaga aaaaattcag tcagcgcaaa taaatagaat   1020

agatccctta gccccactcc aacttttgat ttttgccact gcacattctc caacaggcat   1080

cattattcaa aatactgatc ttgtggagtg gtcattcctt cctcacagta cagttaagac   1140

ttttacattg tacttggatc aaatagctac attaatcggt cagacaagat tacgaataat   1200

aaaattatgt gggaatgacc cagacaaaat agttgtccct ttaaccaagg aacaagttag   1260

acaagccttt atcaattctg gtgcatggaa gattggtctt gctaattttg tgggaattat   1320

tgataatcat tacccaaaaa caaagatctt ccagttctta aaattgacta cttggattct   1380

acctaaaatt accagacgtg aacctttaga aaatgctcta acagtattta ctgatggttc   1440

cagcaatgga aaagcagctt acacaggacc gaaagaacga gtaatcaaaa ctccatatca   1500

atcggctcaa agagcagagt tggttgcagt cattacagtg ttacaagatt ttgaccaacc   1560

tatcaatatt atatcagatt ctgcatatgt agtacaggct acaagggatg ttgagacagc   1620

tctaattaaa tatagcatgg atgatcagtt aaaccagcta ttcaatttat tacaacaaac   1680

tgtaagaaaa agaaatttcc cattttatat tacacatatt cgagcacaca ctaatttacc   1740

agggcctttg actaaagcaa atgaacaagc tgacttactg gtatcatctg cactcataaa   1800

agcacaagaa cttcatgctt tgactcatgt aaatgcagca ggattaaaaa acaaatttga   1860

tgtcacatgg aaacaggcaa aagatattgt acaacattgc acccagtgtc aagtcttaca   1920

cctgcccact caagaggcag gagttaatcc cagaggtctg tgtcctaatg cattatggca   1980

aatggatgtc acgcatgtac cttcatttgg aagattatca tatgttcacg taacagttga   2040

tacttattca catttcatat gggcaacttg ccaaacagga gaaagtactt cccatgttaa   2100

aaaacattta ttgtcttgtt ttgctgtaat gggagttcca gaaaaaatca aaactgacaa   2160

tggaccagga tattgtagta aagctttcca aaaattctta agtcagtgga aaatttcaca   2220

tacaacagga attccttata attcccaagg acaggccata gttgaaagaa ctaatagaac   2280

actcaaaact caattagtta aacaaaaaga agggggagac agtaaggagt gtaccactcc   2340

tcagatgcaa cttaatctag cactctatac tttaaatttt ttaaacattt atagaaatca   2400

gactactact tctgcagaac aacatcttac tggtaaaaag aacagcccac atgaaggaaa   2460

actaatttgg tggaaagata ataaaaataa gacatgggaa atagggaagg tgataacgtg   2520

ggggagaggt tttgcttgtg tttcaccagg agaaaatcag cttcctgttt ggatacccac   2580

tagacatttg aagttctaca atgaacccat cagagatgca aagaaaagca cctccgcgga   2640

gacggagaca tcgcaatcga gcaccgttga ctcacaagat gaacaaaatg gtgacgtcag   2700

aagaacagat gaagttgcca tccaccaaga aggcagagcc gccaacttgg gcacaactaa   2760

agaagctgac gcagttagct acaaaatatc tagagaacac aaaggtgaca caaaccccag   2820

agagtatgct gcttgcagcc ttgatgattg tatcaatggt ggtaagtctc cctatgcctg   2880

caggagcagc tgcagc                                                   2896
```

<210> SEQ ID NO 88
<211> LENGTH: 2000
<212> TYPE: DNA
<213> ORGANISM: Homo sapiens

<400> SEQUENCE: 88

```
atgaacccat cagagatgca aagaaaagca cctccgcgga gacggagaca tcgcaatcga     60

gcaccgttga ctcacaagat gaacaaaatg gtgacgtcag aagaacagat gaagttgcca    120
```

-continued

```
tccaccaaga aggcagagcc gccaacttgg gcacaactaa agaagctgac gcagttagct    180

acaaaatatc tagagaacac aaaggtgaca caaaccccag agagtatgct gcttgcagcc    240

ttgatgattg tatcaatggt ggtaagtctc cctatgcctg caggagcagc tgcagctaac    300

tatacctact gggcctatgt gcctttcccg cccttaattc gggcagtcac atggatggat    360

aatcctacag aagtatatgt taatgatagt gtatgggtac ctggccccat agatgatcgc    420

tgccctgcca aacctgagga agaagggatg atgataaata tttccattgg gtatcattat    480

cctcctattt gcctagggag agcaccagga tgtttaatgc ctgcagtcca aaattggttg    540

gtagaagtac ctactgtcag tcccatctgt agattcactt atcacatggt aagcgggatg    600

tcactcaggc cacgggtaaa ttatttacaa gacttttctt atcaaagatc attaaaattt    660

agacctaaag ggaaaccttg ccccaaggaa attcccaaag aatcaaaaaa tacagaagtt    720

ttagtttggg aagaatgtgt ggccaatagt gcggtgatat tacaaaacaa tgaattcgga    780

actattatag attgggcacc tcgaggtcaa ttctaccaca attgctcagg acaaactcag    840

tcgtgtccaa gtgcacaagt gagtccagct gttgatagcg acttaacaga aagtttagac    900

aaacataagc ataaaaaatt gcagtctttc taccettggg aatggggaga aaaaggaatc    960

tctaccccaa gaccaaaaat agtaagtcct gtttctggtc ctgaacatcc agaattatgg   1020

aggcttactg tggcctcaca ccacattaga atttggtctg gaaatcaaac tttagaaaca   1080

agagatcgta agccatttta tactattgac ctgaattcca gtctaacagt tcctttacaa   1140

agttgcgtaa agcccectta tatgctagtt gtaggaaata tagttattaa accagactcc   1200

cagactataa cctgtgaaaa ttgtagattg cttacttgca ttgattcaac ttttaattgg   1260

caacaccgta ttctgctggt gagagcaaga gagggcgtgt ggatccctgt gtccatggac   1320

cgaccgtggg aggcctcgcc atccgtccat attttgactg aagtattaaa aggtgtttta   1380

aatagatcca aaagattcat ttttacttta attgcagtga ttatgggatt aattgcagtc   1440

acagctacgg ctgctgtagc aggagttgca ttgcactctt ctgttcagtc agtaaacttt   1500

gttaatgatt ggcaaaaaaa ttctacaaga ttgtggaatt cacaatctag tattgatcaa   1560

aaattggcaa atcaaattaa tgatcttaga caaactgtca tttggatggg agacagactc   1620

atgagcttag aacatcgttt ccagttacaa tgtgactgga atacgtcaga tttttgtatt   1680

acaccccaaa tttataatga gtctgagcat cactgggaca tggttagacg ccatctacag   1740

ggaagagaag ataatctcac tttagacatt tccaaattaa aagaacaaat tttcgaagca   1800

tcaaaagccc atttaaattt ggtgccagga actgaggcaa ttgcaggagt tgctgatggc   1860

ctcgcaaatc ttaaccctgt cacttgggtt aagaccattg gaagtactac gattataaat   1920

ctcatattaa tccttgtgtg cctgttttgt ctgttgttag tctgcaggtg tacccaacag   1980

ctccgaagag acagcgacca                                                2000
```

<210> SEQ ID NO 89
<211> LENGTH: 294
<212> TYPE: DNA
<213> ORGANISM: Homo sapiens

<400> SEQUENCE: 89

```
agttctacaa tgaacccatc agagatgcaa agaaaagcac ctccgcggag acggagacat     60

cgcaatcgag caccgttgac tcacaagatg aacaaaatgg tgacgtcaga agaacagatg    120

aagttgccat ccaccaagaa ggcagagccg ccaacttggg cacaactaaa gaagctgacg    180
```

-continued

```
cagttagcta caaaatatct agagaacaca aaggtgacac aaaccccaga gagtatgctg    240

cttgcagcct tgatgattgt atcaatggtg gtaagtctcc ctatgcctgc agga          294
```

<210> SEQ ID NO 90
<211> LENGTH: 57
<212> TYPE: DNA
<213> ORGANISM: Homo sapiens

<400> SEQUENCE: 90

```
tctgcaggtg tacccaacag ctccgaagag acagcgacca tcgagaacgg gccatga        57
```

<210> SEQ ID NO 91
<211> LENGTH: 2001
<212> TYPE: DNA
<213> ORGANISM: Homo sapiens

<400> SEQUENCE: 91

```
atggggcaaa ctaaaagtaa aattaaaagt aaatatgcct cttatctcag ctttattaaa     60

attcttttaa aaagaggggg agttaaagta tctacaaaaa atctaatcaa gctatttcaa    120

ataatagaac aattttgccc atggtttcca gaacaaggaa ctttagatct aaaagattgg    180

aaaagaattg gtaaggaact aaaacaagca ggtaggaagg gtaatatcat tccacttaca    240

gtatggaatg attgggccat tattaaagca gctttagaac catttcaaac agaagaagat    300

agcgtttcag tttctgatgc ccctggaagc tgtataatag attgtaatga aaacacaagg    360

aaaaaatccc agaaagaaac ggaaggttta cattgcgaat atgtagcaga gccggtaatg    420

gctcagtcaa cgcaaaatgt tgactataat caattacagg aggtgatata tcctgaaacg    480

ttaaaattag aaggaaaagg tccagaatta gtggggccat cagagtctaa accacgaggc    540

acaagtcctc ttccagcagg tcaggtgcct gtaacattac aacctcaaaa gcaggttaaa    600

gaaaataaga cccaaccgcc agtagcctat caatactggc ctccggctga acttcagtat    660

cggccacccc cagaaagtca gtatggatat ccaggaatgc cccagcacc acagggcagg     720

gcgccatacc ctcagccgcc cactaggaga cttaatccta cggcaccacc tagtagacag    780

ggtagtaaat tacatgaaat tattgataaa tcaagaaagg aaggagatac tgaggcatgg    840

caattcccag taacgttaga accgatgcca cctggagaag gagcccaaga gggagagcct    900

cccacagttg aggccagata caagtctttt tcgataaaaa agctgaaaga tatgaaagag    960

ggagtaaaac agtatggacc caactcccct tatatgagga cattattaga ttccattgct   1020

catggacata gactcattcc ttatgattgg gagattctgg caaaatcgtc tctctcaccc   1080

tctcaatttt tacaatttaa gacttggtgg attgatgggg tacaagaaca ggtccgaaga   1140

aatagggctg ccaatcctcc agttaacata gatgcagatc aactattagg aataggtcaa   1200

aattggagta ctattagtca acaagcatta atgcaaaatg aggccattga gcaagttaga   1260

gctatctgcc ttagagcctg ggaaaaaatc caagacccag gaagtacctg cccctcattt   1320

aatacagtaa gacaaggttc aaaagagccc tatcctgatt ttgtggcaag gctccaagat   1380

gttgctcaaa agtcaattgc tgatgaaaaa gcccgtaagg tcatagtgga gttgatggca   1440

tatgaaaacg ccaatcctga gtgtcaatca gccattaagc cattaaaagg aaaggttcct   1500

gcaggatcag atgtaatctc agaatatgta aaagcctgtg atggaatcgg aggagctatg   1560

tataaagcta tgcttatggc tcaagcaata acaggagttg ttttaggagg acaagttaga   1620

acatttggaa gaaaatgtta taattgtggt caaattggtc acttaaaaaa gaattgccca   1680

gtcttaaata aacagaatat aactattcaa gcaactacaa caggtagaga gccacctgac   1740
```

-continued

```
ttatgtccaa gatgtaaaaa aggaaaacat tgggctagtc aatgtcgttc taaatttgat   1800

aaaaatgggc aaccattgtc gggaaacgag caaaggggcc agcctcaggc cccacaacaa   1860

actggggcat tcccaattca gccatttgtt cctcagggtt ttcagggaca acaaccccca   1920

ctgtcccaag tgtttcaggg aataagccag ttaccacaat acaacaattg tcccccgcca   1980

caagcggcag tgcagcagta g                                             2001


<210> SEQ ID NO 92
<211> LENGTH: 666
<212> TYPE: PRT
<213> ORGANISM: Homo sapiens

<400> SEQUENCE: 92

Met Gly Gln Thr Lys Ser Lys Ile Lys Ser Lys Tyr Ala Ser Tyr Leu
1               5                   10                  15

Ser Phe Ile Lys Ile Leu Leu Lys Arg Gly Gly Val Lys Val Ser Thr
            20                  25                  30

Lys Asn Leu Ile Lys Leu Phe Gln Ile Ile Glu Gln Phe Cys Pro Trp
        35                  40                  45

Phe Pro Glu Gln Gly Thr Leu Asp Leu Lys Asp Trp Lys Arg Ile Gly
    50                  55                  60

Lys Glu Leu Lys Gln Ala Gly Arg Lys Gly Asn Ile Ile Pro Leu Thr
65                  70                  75                  80

Val Trp Asn Asp Trp Ala Ile Ile Lys Ala Ala Leu Glu Pro Phe Gln
                85                  90                  95

Thr Glu Glu Asp Ser Val Ser Val Ser Asp Ala Pro Gly Ser Cys Ile
            100                 105                 110

Ile Asp Cys Asn Glu Asn Thr Arg Lys Lys Ser Gln Lys Glu Thr Glu
        115                 120                 125

Gly Leu His Cys Glu Tyr Val Ala Glu Pro Val Met Ala Gln Ser Thr
    130                 135                 140

Gln Asn Val Asp Tyr Asn Gln Leu Gln Glu Val Ile Tyr Pro Glu Thr
145                 150                 155                 160

Leu Lys Leu Glu Gly Lys Gly Pro Glu Leu Val Gly Pro Ser Glu Ser
                165                 170                 175

Lys Pro Arg Gly Thr Ser Pro Leu Pro Ala Gly Gln Val Pro Val Thr
            180                 185                 190

Leu Gln Pro Gln Lys Gln Val Lys Glu Asn Lys Thr Gln Pro Pro Val
        195                 200                 205

Ala Tyr Gln Tyr Trp Pro Pro Ala Glu Leu Gln Tyr Arg Pro Pro Pro
    210                 215                 220

Glu Ser Gln Tyr Gly Tyr Pro Gly Met Pro Pro Ala Pro Gln Gly Arg
225                 230                 235                 240

Ala Pro Tyr Pro Gln Pro Pro Thr Arg Arg Leu Asn Pro Thr Ala Pro
                245                 250                 255

Pro Ser Arg Gln Gly Ser Lys Leu His Glu Ile Ile Asp Lys Ser Arg
            260                 265                 270

Lys Glu Gly Asp Thr Glu Ala Trp Gln Phe Pro Val Thr Leu Glu Pro
        275                 280                 285

Met Pro Pro Gly Glu Gly Ala Gln Glu Gly Glu Pro Pro Thr Val Glu
    290                 295                 300

Ala Arg Tyr Lys Ser Phe Ser Ile Lys Lys Leu Lys Asp Met Lys Glu
305                 310                 315                 320
```

-continued

```
Gly Val Lys Gln Tyr Gly Pro Asn Ser Pro Tyr Met Arg Thr Leu Leu
                325                 330                 335

Asp Ser Ile Ala His Gly His Arg Leu Ile Pro Tyr Asp Trp Glu Ile
            340                 345                 350

Leu Ala Lys Ser Ser Leu Ser Pro Ser Gln Phe Leu Gln Phe Lys Thr
        355                 360                 365

Trp Trp Ile Asp Gly Val Gln Glu Gln Val Arg Arg Asn Arg Ala Ala
    370                 375                 380

Asn Pro Pro Val Asn Ile Asp Ala Asp Gln Leu Leu Gly Ile Gly Gln
385                 390                 395                 400

Asn Trp Ser Thr Ile Ser Gln Gln Ala Leu Met Gln Asn Glu Ala Ile
                405                 410                 415

Glu Gln Val Arg Ala Ile Cys Leu Arg Ala Trp Glu Lys Ile Gln Asp
            420                 425                 430

Pro Gly Ser Thr Cys Pro Ser Phe Asn Thr Val Arg Gln Gly Ser Lys
        435                 440                 445

Glu Pro Tyr Pro Asp Phe Val Ala Arg Leu Gln Asp Val Ala Gln Lys
    450                 455                 460

Ser Ile Ala Asp Glu Lys Ala Arg Lys Val Ile Val Glu Leu Met Ala
465                 470                 475                 480

Tyr Glu Asn Ala Asn Pro Glu Cys Gln Ser Ala Ile Lys Pro Leu Lys
                485                 490                 495

Gly Lys Val Pro Ala Gly Ser Asp Val Ile Ser Glu Tyr Val Lys Ala
            500                 505                 510

Cys Asp Gly Ile Gly Gly Ala Met Tyr Lys Ala Met Leu Met Ala Gln
        515                 520                 525

Ala Ile Thr Gly Val Val Leu Gly Gly Gln Val Arg Thr Phe Gly Arg
    530                 535                 540

Lys Cys Tyr Asn Cys Gly Gln Ile Gly His Leu Lys Lys Asn Cys Pro
545                 550                 555                 560

Val Leu Asn Lys Gln Asn Ile Thr Ile Gln Ala Thr Thr Thr Gly Arg
                565                 570                 575

Glu Pro Pro Asp Leu Cys Pro Arg Cys Lys Lys Gly Lys His Trp Ala
            580                 585                 590

Ser Gln Cys Arg Ser Lys Phe Asp Lys Asn Gly Gln Pro Leu Ser Gly
        595                 600                 605

Asn Glu Gln Arg Gly Gln Pro Gln Ala Pro Gln Gln Thr Gly Ala Phe
    610                 615                 620

Pro Ile Gln Pro Phe Val Pro Gln Gly Phe Gln Gly Gln Gln Pro Pro
625                 630                 635                 640

Leu Ser Gln Val Phe Gln Gly Ile Ser Gln Leu Pro Gln Tyr Asn Asn
                645                 650                 655

Cys Pro Pro Pro Gln Ala Ala Val Gln Gln
            660                 665
```

<210> SEQ ID NO 93
<211> LENGTH: 2619
<212> TYPE: DNA
<213> ORGANISM: Homo sapiens

<400> SEQUENCE: 93

```
atgttaactg acttaagggc tgtaaacgcc gtaattcaac ccatggggcc tctccaaccc      60

gggttgccct ctccggccat gatcccaaaa gattggcctt taattataat tgatctaaag     120

gattgctttt ttaccatccc tctggcagag caggattgcg aaaaatttgc ctttactata     180
```

-continued

```
ccagccataa ataataaaga accagccacc aggtttcagt ggaaagtgtt acctcaggga    240
atgcttaata gtccaactat ttgtcagact tttgtaggtc gagctcttca accagttaga    300
gaaaagtttt cagactgtta tattattcat tgtattgatg atattttatg tgctgcagaa    360
acgaaagata aattaattga ctgttataca tttctgcaag cagaggttgc caatgctgga    420
ctggcaatag catctgataa gatccaaacc tctactcctt ttcattattt agggatgcag    480
atagaaaata gaaaaattaa gccacaaaaa atagaaataa gaaaagacac attaaaaaca    540
ctaaatgatt ttcaaaaatt actaggagat attaattgga ttcggccaac tctaggcatt    600
cctacttatg ccatgtcaaa tttgttctct atcttaagag gagactcaga cttaaatagt    660
aaaagaatgt taaccccaga ggcaacaaaa gaaattaaat tagtggaaga aaaaattcag    720
tcagcgcaaa taaatagaat agatccctta gccccactcc aactttttgat ttttgccact    780
gcacattctc caacaggcat cattattcaa aatactgatc ttgtggagtg gtcattcctt    840
cctcacagta cagttaagac ttttacattg tacttggatc aaatagctac attaatcggt    900
cagacaagat tacgaataat aaaattatgt gggaatgacc cagacaaaat agttgtccct    960
ttaaccaagg aacaagttag acaagccttt atcaattctg gtgcatggaa gattggtctt   1020
gctaattttg tgggaattat tgataatcat tacccaaaaa caaagatctt ccagttctta   1080
aaattgacta cttggattct acctaaaatt accagacgtg aacctttaga aaatgctcta   1140
acagtattta ctgatggttc cagcaatgga aaagcagctt acacaggacc gaaagaacga   1200
gtaatcaaaa ctccatatca atcggctcaa agagcagagt tggttgcagt cattacagtg   1260
ttacaagatt ttgaccaacc tatcaatatt atatcagatt ctgcatatgt agtacaggct   1320
acaagggatg ttgagacagc tctaattaaa tatagcatgg atgatcagtt aaaccagcta   1380
ttcaatttat tacaacaaac tgtaagaaaa agaaatttcc cattttatat tacacatatt   1440
cgagcacaca ctaatttacc agggcctttg actaaagcaa atgaacaagc tgacttactg   1500
gtatcatctg cactcataaa agcacaagaa cttcatgctt tgactcatgt aaatgcagca   1560
ggattaaaaa acaaatttga tgtcacatgg aaacaggcaa aagatattgt acaacattgc   1620
acccagtgtc aagtcttaca cctgcccact caagaggcag gagttaatcc cagaggtctg   1680
tgtcctaatg cattatggca aatggatgtc acgcatgtac cttcatttgg aagattatca   1740
tatgttcacg taacagttga tacttattca catttcatat gggcaacttg ccaaacagga   1800
gaaagtactt cccatgttaa aaaacattta ttgtcttgtt ttgctgtaat gggagttcca   1860
gaaaaaatca aaactgacaa tggaccagga tattgtagta aagctttcca aaaattctta   1920
agtcagtgga aaatttcaca tacaacagga attccttata attcccaagg acaggccata   1980
gttgaaagaa ctaatagaac actcaaaact caattagtta aacaaaaaga agggggagac   2040
agtaaggagt gtaccactcc tcagatgcaa cttaatctag cactctatac tttaaatttt   2100
ttaaacattt atagaaatca gactactact tctgcagaac aacatcttac tggtaaaaag   2160
aacagcccac atgaaggaaa actaatttgg tggaaagata gtaaaaataa gacatgggaa   2220
atagggaagg tgataacgtg gggggagaggt tttgcttgtg tttcaccagg agaaaatcag   2280
cttcctgttt ggatacccac tagacatttg aagttctaca atgaacccat cagagatgca   2340
aagaaaagca cctccgcgga gacggagaca tcgcaatcga gcaccgttga ctcacaagat   2400
gaacaaaatg gtgacgtcag aagaacagat gaagttgcca tccaccaaga aggcagagcc   2460
gccaacttgg gcacaactaa agaagctgac gcagttagct acaaaatatc tagagaacac   2520
```

-continued

```
aaaggtgaca caaaccccag agagtatgct gcttgcagcc ttgatgattg tatcaatggt   2580

ggtaagtctc cctatgcctg caggagcagc tgcagctaa                          2619


<210> SEQ ID NO 94
<211> LENGTH: 872
<212> TYPE: PRT
<213> ORGANISM: Homo sapiens

<400> SEQUENCE: 94

Met Leu Thr Asp Leu Arg Ala Val Asn Ala Val Ile Gln Pro Met Gly
1               5                   10                  15

Pro Leu Gln Pro Gly Leu Pro Ser Pro Ala Met Ile Pro Lys Asp Trp
            20                  25                  30

Pro Leu Ile Ile Ile Asp Leu Lys Asp Cys Phe Phe Thr Ile Pro Leu
        35                  40                  45

Ala Glu Gln Asp Cys Glu Lys Phe Ala Phe Thr Ile Pro Ala Ile Asn
    50                  55                  60

Asn Lys Glu Pro Ala Thr Arg Phe Gln Trp Lys Val Leu Pro Gln Gly
65                  70                  75                  80

Met Leu Asn Ser Pro Thr Ile Cys Gln Thr Phe Val Gly Arg Ala Leu
                85                  90                  95

Gln Pro Val Arg Glu Lys Phe Ser Asp Cys Tyr Ile Ile His Cys Ile
            100                 105                 110

Asp Asp Ile Leu Cys Ala Ala Glu Thr Lys Asp Lys Leu Ile Asp Cys
        115                 120                 125

Tyr Thr Phe Leu Gln Ala Glu Val Ala Asn Ala Gly Leu Ala Ile Ala
    130                 135                 140

Ser Asp Lys Ile Gln Thr Ser Thr Pro Phe His Tyr Leu Gly Met Gln
145                 150                 155                 160

Ile Glu Asn Arg Lys Ile Lys Pro Gln Lys Ile Glu Ile Arg Lys Asp
                165                 170                 175

Thr Leu Lys Thr Leu Asn Asp Phe Gln Lys Leu Leu Gly Asp Ile Asn
            180                 185                 190

Trp Ile Arg Pro Thr Leu Gly Ile Pro Thr Tyr Ala Met Ser Asn Leu
        195                 200                 205

Phe Ser Ile Leu Arg Gly Asp Ser Asp Leu Asn Ser Lys Arg Met Leu
    210                 215                 220

Thr Pro Glu Ala Thr Lys Glu Ile Lys Leu Val Glu Glu Lys Ile Gln
225                 230                 235                 240

Ser Ala Gln Ile Asn Arg Ile Asp Pro Leu Ala Pro Leu Gln Leu Leu
                245                 250                 255

Ile Phe Ala Thr Ala His Ser Pro Thr Gly Ile Ile Ile Gln Asn Thr
            260                 265                 270

Asp Leu Val Glu Trp Ser Phe Leu Pro His Ser Thr Val Lys Thr Phe
        275                 280                 285

Thr Leu Tyr Leu Asp Gln Ile Ala Thr Leu Ile Gly Gln Thr Arg Leu
    290                 295                 300

Arg Ile Ile Lys Leu Cys Gly Asn Asp Pro Asp Lys Ile Val Val Pro
305                 310                 315                 320

Leu Thr Lys Glu Gln Val Arg Gln Ala Phe Ile Asn Ser Gly Ala Trp
                325                 330                 335

Lys Ile Gly Leu Ala Asn Phe Val Gly Ile Ile Asp Asn His Tyr Pro
            340                 345                 350
```

-continued

```
Lys Thr Lys Ile Phe Gln Phe Leu Lys Leu Thr Thr Trp Ile Leu Pro
        355                 360                 365

Lys Ile Thr Arg Arg Glu Pro Leu Glu Asn Ala Leu Thr Val Phe Thr
    370                 375                 380

Asp Gly Ser Ser Asn Gly Lys Ala Ala Tyr Thr Gly Pro Lys Glu Arg
385                 390                 395                 400

Val Ile Lys Thr Pro Tyr Gln Ser Ala Gln Arg Ala Glu Leu Val Ala
                405                 410                 415

Val Ile Thr Val Leu Gln Asp Phe Asp Gln Pro Ile Asn Ile Ile Ser
            420                 425                 430

Asp Ser Ala Tyr Val Val Gln Ala Thr Arg Asp Val Glu Thr Ala Leu
        435                 440                 445

Ile Lys Tyr Ser Met Asp Asp Gln Leu Asn Gln Leu Phe Asn Leu Leu
    450                 455                 460

Gln Gln Thr Val Arg Lys Arg Asn Phe Pro Phe Tyr Ile Thr His Ile
465                 470                 475                 480

Arg Ala His Thr Asn Leu Pro Gly Pro Leu Thr Lys Ala Asn Glu Gln
                485                 490                 495

Ala Asp Leu Leu Val Ser Ser Ala Leu Ile Lys Ala Gln Glu Leu His
            500                 505                 510

Ala Leu Thr His Val Asn Ala Ala Gly Leu Lys Asn Lys Phe Asp Val
        515                 520                 525

Thr Trp Lys Gln Ala Lys Asp Ile Val Gln His Cys Thr Gln Cys Gln
    530                 535                 540

Val Leu His Leu Pro Thr Gln Glu Ala Gly Val Asn Pro Arg Gly Leu
545                 550                 555                 560

Cys Pro Asn Ala Leu Trp Gln Met Asp Val Thr His Val Pro Ser Phe
                565                 570                 575

Gly Arg Leu Ser Tyr Val His Val Thr Val Asp Thr Tyr Ser His Phe
            580                 585                 590

Ile Trp Ala Thr Cys Gln Thr Gly Glu Ser Thr Ser His Val Lys Lys
        595                 600                 605

His Leu Leu Ser Cys Phe Ala Val Met Gly Val Pro Glu Lys Ile Lys
    610                 615                 620

Thr Asp Asn Gly Pro Gly Tyr Cys Ser Lys Ala Phe Gln Lys Phe Leu
625                 630                 635                 640

Ser Gln Trp Lys Ile Ser His Thr Thr Gly Ile Pro Tyr Asn Ser Gln
                645                 650                 655

Gly Gln Ala Ile Val Glu Arg Thr Asn Arg Thr Leu Lys Thr Gln Leu
            660                 665                 670

Val Lys Gln Lys Glu Gly Gly Asp Ser Lys Glu Cys Thr Thr Pro Gln
        675                 680                 685

Met Gln Leu Asn Leu Ala Leu Tyr Thr Leu Asn Phe Leu Asn Ile Tyr
    690                 695                 700

Arg Asn Gln Thr Thr Thr Ser Ala Glu Gln His Leu Thr Gly Lys Lys
705                 710                 715                 720

Asn Ser Pro His Glu Gly Lys Leu Ile Trp Trp Lys Asp Ser Lys Asn
                725                 730                 735

Lys Thr Trp Glu Ile Gly Lys Val Ile Thr Trp Gly Arg Gly Phe Ala
            740                 745                 750

Cys Val Ser Pro Gly Glu Asn Gln Leu Pro Val Trp Ile Pro Thr Arg
        755                 760                 765
```

-continued

```
His Leu Lys Phe Tyr Asn Glu Pro Ile Arg Asp Ala Lys Lys Ser Thr
    770                 775                 780

Ser Ala Glu Thr Glu Thr Ser Gln Ser Ser Thr Val Asp Ser Gln Asp
785                 790                 795                 800

Glu Gln Asn Gly Asp Val Arg Arg Thr Asp Glu Val Ala Ile His Gln
                805                 810                 815

Glu Gly Arg Ala Ala Asn Leu Gly Thr Thr Lys Glu Ala Asp Ala Val
            820                 825                 830

Ser Tyr Lys Ile Ser Arg Glu His Lys Gly Asp Thr Asn Pro Arg Glu
        835                 840                 845

Tyr Ala Ala Cys Ser Leu Asp Asp Cys Ile Asn Gly Gly Lys Ser Pro
    850                 855                 860

Tyr Ala Cys Arg Ser Ser Cys Ser
865                 870


<210> SEQ ID NO 95
<211> LENGTH: 2085
<212> TYPE: DNA
<213> ORGANISM: Homo sapiens

<400> SEQUENCE: 95

atgcaaagaa aagcacctcc gcggagacgg agacatcgca atcgagcacc gttgactcac      60

aagatgaaca aaatggtgac gtcagaagaa cagatgaagt tgccatccac caagaaggca     120

gagccgccaa cttgggcaca actaaagaag ctgacgcagt tagctacaaa atatctagag     180

aacacaaagg tgacacaaac cccagagagt atgctgcttg cagccttgat gattgtatca     240

atggtggtaa gtctccctat gcctgcagga gcagctgcag ctaactatac ctactgggcc     300

tatgtgcctt tcccgccctt aattcgggca gtcacatgga tggataatcc tacagaagta     360

tatgttaatg atagtgtatg ggtacctggc cccatagatg atcgctgccc tgccaaacct     420

gaggaagaag ggatgatgat aaatatttcc attgggtatc attatcctcc tatttgccta     480

gggagagcac caggatgttt aatgcctgca gtccaaaatt ggttggtaga agtacctact     540

gtcagtccca tctgtagatt cacttatcac atggtaagcg ggatgtcact caggccacgg     600

gtaaattatt tacaagactt ttcttatcaa agatcattaa aatttagacc taaagggaaa     660

ccttgcccca aggaaattcc caaagaatca aaaaatacag aagttttagt ttgggaagaa     720

tgtgtggcca atagtgcggt gatattacaa aacaatgaat tcggaactat tatagattgg     780

gcacctcgag gtcaattcta ccacaattgc tcaggacaaa ctcagtcgtg tcaaagtgca     840

caagtgagtc cagctgttga tagcgactta acagaaagtt tagacaaaca taagcataaa     900

aaattgcagt ctttctaccc ttgggaatgg ggagaaaaag gaatctctac cccaagacca     960

aaaatagtaa gtcctgtttc tggtcctgaa catccagaat tatggaggct tactgtggcc    1020

tcacaccaca ttagaatttg gtctggaaat caaactttag aaacaagaga tcgtaagcca    1080

ttttatacta ttgacctgaa ttccagtcta acagttcctt tacaaagttg cgtaaagccc    1140

ccttatatgc tagttgtagg aaatatagtt attaaaccag actcccagac tataacctgt    1200

gaaaattgta gattgcttac ttgcattgat tcaactttta attggcaaca ccgtattctg    1260

ctggtgagag caagagaggg cgtgtggatc cctgtgtcca tggaccgacc gtgggaggcc    1320

tcgccatccg tccatatttt gactgaagta ttaaaaggtg ttttaaatag atccaaaaga    1380

ttcattttta ctttaattgc agtgattatg ggattaattg cagtcacagc tacggctgct    1440

gtagcaggag ttgcattgca ctcttctgtt cagtcagtaa actttgttaa tgattggcaa    1500
```

-continued

```
aaaaattcta caagattgtg gaattcacaa tctagtattg atcaaaaatt ggcaaatcaa   1560

attaatgatc ttagacaaac tgtcatttgg atgggagaca gactcatgag cttagaacat   1620

cgtttccagt tacaatgtga ctggaatacg tcagattttt gtattacacc ccaaatttat   1680

aatgagtctg agcatcactg ggacatggtt agacgccatc tacagggaag agaagataat   1740

ctcactttag acatttccaa attaaaagaa caaatttcg aagcatcaaa agcccattta    1800

aatttggtgc caggaactga ggcaattgca ggagttgctg atggcctcgc aaatcttaac   1860

cctgtcactt gggttaagac cattggaagt actacgatta taaatctcat attaatcctt   1920

gtgtgcctgt tttgtctgtt gttagtctgc aggtgtaccc aacagctccg aagagacagc   1980

gaccatcgag aacgggccat gatgacgatg gcggttttgt cgaaaagaaa agggggaaat   2040

gtggggaaaa gcaagagaga tcagattgtt actgtgtctg tgtag                   2085
```

<210> SEQ ID NO 96
<211> LENGTH: 694
<212> TYPE: PRT
<213> ORGANISM: Homo sapiens

<400> SEQUENCE: 96

```
Met Gln Arg Lys Ala Pro Pro Arg Arg Arg Arg His Arg Asn Arg Ala
1               5                   10                  15

Pro Leu Thr His Lys Met Asn Lys Met Val Thr Ser Glu Glu Gln Met
            20                  25                  30

Lys Leu Pro Ser Thr Lys Lys Ala Glu Pro Pro Thr Trp Ala Gln Leu
        35                  40                  45

Lys Lys Leu Thr Gln Leu Ala Thr Lys Tyr Leu Glu Asn Thr Lys Val
    50                  55                  60

Thr Gln Thr Pro Glu Ser Met Leu Leu Ala Ala Leu Met Ile Val Ser
65                  70                  75                  80

Met Val Val Ser Leu Pro Met Pro Ala Gly Ala Ala Ala Ala Asn Tyr
                85                  90                  95

Thr Tyr Trp Ala Tyr Val Pro Phe Pro Pro Leu Ile Arg Ala Val Thr
            100                 105                 110

Trp Met Asp Asn Pro Thr Glu Val Tyr Val Asn Asp Ser Val Trp Val
        115                 120                 125

Pro Gly Pro Ile Asp Asp Arg Cys Pro Ala Lys Pro Glu Glu Glu Gly
    130                 135                 140

Met Met Ile Asn Ile Ser Ile Gly Tyr His Tyr Pro Pro Ile Cys Leu
145                 150                 155                 160

Gly Arg Ala Pro Gly Cys Leu Met Pro Ala Val Gln Asn Trp Leu Val
                165                 170                 175

Glu Val Pro Thr Val Ser Pro Ile Cys Arg Phe Thr Tyr His Met Val
            180                 185                 190

Ser Gly Met Ser Leu Arg Pro Arg Val Asn Tyr Leu Gln Asp Phe Ser
        195                 200                 205

Tyr Gln Arg Ser Leu Lys Phe Arg Pro Lys Gly Lys Pro Cys Pro Lys
    210                 215                 220

Glu Ile Pro Lys Glu Ser Lys Asn Thr Glu Val Leu Val Trp Glu Glu
225                 230                 235                 240

Cys Val Ala Asn Ser Ala Val Ile Leu Gln Asn Asn Glu Phe Gly Thr
                245                 250                 255

Ile Ile Asp Trp Ala Pro Arg Gly Gln Phe Tyr His Asn Cys Ser Gly
            260                 265                 270
```

-continued

```
Gln Thr Gln Ser Cys Gln Ser Ala Gln Val Ser Pro Ala Val Asp Ser
        275                 280                 285

Asp Leu Thr Glu Ser Leu Asp Lys His Lys His Lys Lys Leu Gln Ser
    290                 295                 300

Phe Tyr Pro Trp Glu Trp Gly Glu Lys Gly Ile Ser Thr Pro Arg Pro
305                 310                 315                 320

Lys Ile Val Ser Pro Val Ser Gly Pro Glu His Pro Glu Leu Trp Arg
                325                 330                 335

Leu Thr Val Ala Ser His His Ile Arg Ile Trp Ser Gly Asn Gln Thr
            340                 345                 350

Leu Glu Thr Arg Asp Arg Lys Pro Phe Tyr Thr Ile Asp Leu Asn Ser
        355                 360                 365

Ser Leu Thr Val Pro Leu Gln Ser Cys Val Lys Pro Pro Tyr Met Leu
    370                 375                 380

Val Val Gly Asn Ile Val Ile Lys Pro Asp Ser Gln Thr Ile Thr Cys
385                 390                 395                 400

Glu Asn Cys Arg Leu Leu Thr Cys Ile Asp Ser Thr Phe Asn Trp Gln
                405                 410                 415

His Arg Ile Leu Leu Val Arg Ala Arg Glu Gly Val Trp Ile Pro Val
            420                 425                 430

Ser Met Asp Arg Pro Trp Glu Ala Ser Pro Ser Val His Ile Leu Thr
        435                 440                 445

Glu Val Leu Lys Gly Val Leu Asn Arg Ser Lys Arg Phe Ile Phe Thr
    450                 455                 460

Leu Ile Ala Val Ile Met Gly Leu Ile Ala Val Thr Ala Thr Ala Ala
465                 470                 475                 480

Val Ala Gly Val Ala Leu His Ser Ser Val Gln Ser Val Asn Phe Val
                485                 490                 495

Asn Asp Trp Gln Lys Asn Ser Thr Arg Leu Trp Asn Ser Gln Ser Ser
            500                 505                 510

Ile Asp Gln Lys Leu Ala Asn Gln Ile Asn Asp Leu Arg Gln Thr Val
        515                 520                 525

Ile Trp Met Gly Asp Arg Leu Met Ser Leu Glu His Arg Phe Gln Leu
    530                 535                 540

Gln Cys Asp Trp Asn Thr Ser Asp Phe Cys Ile Thr Pro Gln Ile Tyr
545                 550                 555                 560

Asn Glu Ser Glu His His Trp Asp Met Val Arg Arg His Leu Gln Gly
                565                 570                 575

Arg Glu Asp Asn Leu Thr Leu Asp Ile Ser Lys Leu Lys Glu Gln Ile
            580                 585                 590

Phe Glu Ala Ser Lys Ala His Leu Asn Leu Val Pro Gly Thr Glu Ala
        595                 600                 605

Ile Ala Gly Val Ala Asp Gly Leu Ala Asn Leu Asn Pro Val Thr Trp
    610                 615                 620

Val Lys Thr Ile Gly Ser Thr Thr Ile Ile Asn Leu Ile Leu Ile Leu
625                 630                 635                 640

Val Cys Leu Phe Cys Leu Leu Leu Val Cys Arg Cys Thr Gln Gln Leu
                645                 650                 655

Arg Arg Asp Ser Asp His Arg Glu Arg Ala Met Met Thr Met Ala Val
            660                 665                 670
```

-continued

```
Leu Ser Lys Arg Lys Gly Gly Asn Val Gly Lys Ser Lys Arg Asp Gln
        675                 680                 685

Ile Val Thr Val Ser Val
    690


<210> SEQ ID NO 97
<211> LENGTH: 2004
<212> TYPE: DNA
<213> ORGANISM: Homo sapiens

<400> SEQUENCE: 97

atggggcaaa ctaaaagtaa aactaaaagt aaatatgcct cttatctcag ctttattaaa     60

attcttttaa aaagaggggg agttagagta tctacaaaaa atctaatcaa gctatttcaa    120

ataatagaac aattttgccc atggtttcca gaacaaggaa ctttagatct aaaagattgg    180

aaaagaattg gcgaggaact aaaacaagca ggtagaaagg gtaatatcat tccacttaca    240

gtatggaatg attgggccat tattaaagca gctttagaac catttcaaac aaaagaagat    300

agcgtttcag tttctgatgc ccctggaagc tgtgtaatag attgtaatga aaagacaggg    360

agaaaatccc agaaagaaac agaaagttta cattgcgaat atgtaacaga gccagtaatg    420

gctcagtcaa cgcaaaatgt tgactataat caattacagg gggtgatata tcctgaaacg    480

ttaaaattag aaggaaaagg tccagaatta gtggggccat cagagtctaa accacgaggg    540

ccaagtcctc ttccagcagg tcaggtgccc gtaacattac aacctcaaac gcaggttaaa    600

gaaaataaga cccaaccgcc agtagcttat caatactggc cgccggctga acttcagtat    660

ctgccacccc cagaaagtca gtatggatat ccaggaatgc cccagcact acagggcagg    720

gcgccatatc ctcagccgcc cactgtgaga cttaatccta cagcatcacg tagtggacaa    780

ggtggtacac tgcacgcagt cattgatgaa gccagaaaac agggagatct tgaggcatgg    840

cggttcctgg taattttaca actggtacag gccggggaag agactcaagt aggagcgcct    900

gcccgagctg agactagatg tgaacctttc accatgaaaa tgttaaaaga tataaaggaa    960

ggagttaaac aatatggatc caactcccct tatataagaa cattattaga ttccattgct   1020

catggaaata gacttactcc ttatgactgg gaaagtttgg ccaaatcttc cctttcatcc   1080

tctcagtatc tacagtttaa aacctggtgg attgatggag tacaagaaca ggtacgaaaa   1140

aatcaggcta ctaagcccac tgttaatata gacgcagacc aattgttagg aacaggtcca   1200

aattggagca ccattaacca acaatcagtg atgcagaatg aggctattga acaagtaagg   1260

gctatttgcc tcagggcctg ggaaaaaatt caggacccag gaacagcttt ccctattaat   1320

tcaattagac aaggctctaa agagccatat cctgactttg tggcaagatt acaagatgct   1380

gctcaaaagt ctattacaga tgacaatgcc cgaaaagtta ttgtagaatt aatggcctat   1440

gaaaatgcaa atccagaatg tcagtcggcc ataaagccat taaaaggaaa agttccagca   1500

ggagttgatg taattacaga atatgtgaag gcttgtgatg ggattggagg agctatgcat   1560

aaggcaatgc taatggctca agcaatgagg gggctcactc taggaggaca agttagaaca   1620

tttgggaaaa aatgttataa ttgtggtcaa atcggtcatc tgaaaaggag ttgcccagtc   1680

ttaaataaac agaatataat aaatcaagct attacagcaa aaaataaaaa gccatctggc   1740

ctgtgtccaa aatgtggaaa aggaaaacat tgggccaatc aatgtcattc taaatttgat   1800

aaagatgggc aaccattgtc gggaaacagg aagaggggcc agcctcaggc cccccaacaa   1860

actggggcat tcccagttca actgtttgtt cctcagggtt ttcaaggaca acaaccccta   1920
```

-continued

```
cagaaaatac caccacttca gggagtcagc caattacaac aatccaacag ctgtcccgcg   1980

ccacagcagg cagcgccaca gtag                                          2004


<210> SEQ ID NO 98
<211> LENGTH: 667
<212> TYPE: PRT
<213> ORGANISM: Homo sapiens

<400> SEQUENCE: 98

Met Gly Gln Thr Lys Ser Lys Thr Lys Ser Lys Tyr Ala Ser Tyr Leu
1               5                   10                  15

Ser Phe Ile Lys Ile Leu Leu Lys Arg Gly Gly Val Arg Val Ser Thr
            20                  25                  30

Lys Asn Leu Ile Lys Leu Phe Gln Ile Ile Glu Gln Phe Cys Pro Trp
        35                  40                  45

Phe Pro Glu Gln Gly Thr Leu Asp Leu Lys Asp Trp Lys Arg Ile Gly
    50                  55                  60

Glu Glu Leu Lys Gln Ala Gly Arg Lys Gly Asn Ile Ile Pro Leu Thr
65                  70                  75                  80

Val Trp Asn Asp Trp Ala Ile Ile Lys Ala Ala Leu Glu Pro Phe Gln
                85                  90                  95

Thr Lys Glu Asp Ser Val Ser Val Ser Asp Ala Pro Gly Ser Cys Val
            100                 105                 110

Ile Asp Cys Asn Glu Lys Thr Gly Arg Lys Ser Gln Lys Glu Thr Glu
        115                 120                 125

Ser Leu His Cys Glu Tyr Val Thr Glu Pro Val Met Ala Gln Ser Thr
    130                 135                 140

Gln Asn Val Asp Tyr Asn Gln Leu Gln Gly Val Ile Tyr Pro Glu Thr
145                 150                 155                 160

Leu Lys Leu Glu Gly Lys Gly Pro Glu Leu Val Gly Pro Ser Glu Ser
                165                 170                 175

Lys Pro Arg Gly Pro Ser Pro Leu Pro Ala Gly Gln Val Pro Val Thr
            180                 185                 190

Leu Gln Pro Gln Thr Gln Val Lys Glu Asn Lys Thr Gln Pro Pro Val
        195                 200                 205

Ala Tyr Gln Tyr Trp Pro Pro Ala Glu Leu Gln Tyr Leu Pro Pro Pro
    210                 215                 220

Glu Ser Gln Tyr Gly Tyr Pro Gly Met Pro Pro Ala Leu Gln Gly Arg
225                 230                 235                 240

Ala Pro Tyr Pro Gln Pro Pro Thr Val Arg Leu Asn Pro Thr Ala Ser
                245                 250                 255

Arg Ser Gly Gln Gly Gly Thr Leu His Ala Val Ile Asp Glu Ala Arg
            260                 265                 270

Lys Gln Gly Asp Leu Glu Ala Trp Arg Phe Leu Val Ile Leu Gln Leu
        275                 280                 285

Val Gln Ala Gly Glu Glu Thr Gln Val Gly Ala Pro Ala Arg Ala Glu
    290                 295                 300

Thr Arg Cys Glu Pro Phe Thr Met Lys Met Leu Lys Asp Ile Lys Glu
305                 310                 315                 320

Gly Val Lys Gln Tyr Gly Ser Asn Ser Pro Tyr Ile Arg Thr Leu Leu
                325                 330                 335

Asp Ser Ile Ala His Gly Asn Arg Leu Thr Pro Tyr Asp Trp Glu Ser
            340                 345                 350
```

-continued

```
Leu Ala Lys Ser Ser Leu Ser Ser Ser Gln Tyr Leu Gln Phe Lys Thr
        355                 360                 365

Trp Trp Ile Asp Gly Val Gln Glu Gln Val Arg Lys Asn Gln Ala Thr
    370                 375                 380

Lys Pro Thr Val Asn Ile Asp Ala Asp Gln Leu Leu Gly Thr Gly Pro
385                 390                 395                 400

Asn Trp Ser Thr Ile Asn Gln Gln Ser Val Met Gln Asn Glu Ala Ile
                405                 410                 415

Glu Gln Val Arg Ala Ile Cys Leu Arg Ala Trp Gly Lys Ile Gln Asp
            420                 425                 430

Pro Gly Thr Ala Phe Pro Ile Asn Ser Ile Arg Gln Gly Ser Lys Glu
        435                 440                 445

Pro Tyr Pro Asp Phe Val Ala Arg Leu Gln Asp Ala Ala Gln Lys Ser
    450                 455                 460

Ile Thr Asp Asp Asn Ala Arg Lys Val Ile Val Glu Leu Met Ala Tyr
465                 470                 475                 480

Glu Asn Ala Asn Pro Glu Cys Gln Ser Ala Ile Lys Pro Leu Lys Gly
                485                 490                 495

Lys Val Pro Ala Gly Val Asp Val Ile Thr Glu Tyr Val Lys Ala Cys
            500                 505                 510

Asp Gly Ile Gly Gly Ala Met His Lys Ala Met Leu Met Ala Gln Ala
        515                 520                 525

Met Arg Gly Leu Thr Leu Gly Gly Gln Val Arg Thr Phe Gly Lys Lys
    530                 535                 540

Cys Tyr Asn Cys Gly Gln Ile Gly His Leu Lys Arg Ser Cys Pro Val
545                 550                 555                 560

Leu Asn Lys Gln Asn Ile Ile Asn Gln Ala Ile Thr Ala Lys Asn Lys
                565                 570                 575

Lys Pro Ser Gly Leu Cys Pro Lys Cys Gly Lys Gly Lys His Trp Ala
            580                 585                 590

Asn Gln Cys His Ser Lys Phe Asp Lys Asp Gly Gln Pro Leu Ser Gly
        595                 600                 605

Asn Arg Lys Arg Gly Gln Pro Gln Ala Pro Gln Gln Thr Gly Ala Phe
    610                 615                 620

Pro Val Gln Leu Phe Val Pro Gln Gly Phe Gln Gly Gln Gln Pro Leu
625                 630                 635                 640

Gln Lys Ile Pro Pro Leu Gln Gly Val Ser Gln Leu Gln Gln Ser Asn
                645                 650                 655

Ser Cys Pro Ala Pro Gln Gln Ala Ala Pro Gln
            660                 665
```

```
<210> SEQ ID NO 99
<211> LENGTH: 1004
<212> TYPE: DNA
<213> ORGANISM: Homo sapiens

<400> SEQUENCE: 99

atgggcaacc attgtcggga aacaggaaga ggggccagcc tcaggccccc caacaaactg      60

gggcattccc agttcaactg tttgttcctc agggttttca aggacaacaa cccctacaga     120

aaataccacc acttcaggga gtcagccaat tacaacaatc caacagctgt cccgcgccac     180

agcaggcagc gccacagtag atttatgttc cacccaaatg gtctctttac tccctggaga     240

gcccccacaa aagattccta gaggggtata tggcccgctg ccagaaggga gggtaggcct     300

tattttaggg agatcaagtc taaatttgaa gggagtccaa attcatactg ggtaatttta     360
```

-continued

```
ttcagattat aaagggggaa ttcagttagt gatcagctcc actgttccct ggagtgccaa    420

tccaggtgat agaattgctc aattactgct tttgccttat gttaaaattg gggaaaacaa    480

aacggaaaga acaggagggt ttggaagtac caaccctgca ggaaaagcca cttattgggc    540

taatcaggtc tcagaggata gacccgtgtg tacagtcact attcagggaa agagtttgaa    600

ggattagtgg atacccaggc tgatgtttct atcatcggca taggcaccgc ctcagaagtg    660

tatcaaagtg ccatgatttt acattgtcta ggatctgata atcaagaaag tacggttcag    720

cctatgatca cttctattcc aatcaattta tggggccgag acttgttaca acaatggcat    780

gcagagatta ctatcccagc ctccctatac agccccagga atcaaaaaat catgactaaa    840

atgggatagc tccctaaaaa gggactagga aagaatgaag atggcattaa agtcccaact    900

gaggctgaaa aaaatcaaaa aaagaaaagg aatagggcat cctttttaga agcggtcact    960

gtagagcctc caaaacccat tccattaatt tggggggaaa aaaa                    1004
```

<210> SEQ ID NO 100
<211> LENGTH: 2671
<212> TYPE: DNA
<213> ORGANISM: Homo sapiens

<400> SEQUENCE: 100

```
atggcattaa agtcccaact gaggctgaaa aaaatcaaaa aaagaaaagg aatagggcat     60

cctttttaga agcggtcact gtagagcctc caaaacccat tccattaatt tggggggaaa    120

aaaaaaactg tatggtaaat cagtagccgc ttccaaaaca aaaactggag gctttacact    180

tattagcaaa gaaacagtta gaaaaaggac atattgagcc ttcattttcg ccttggaatt    240

ctcctgtttg taattcagaa aaaatccggc agatggcgta tgctaactga cttaagagcc    300

attaatgcca taattcaacc catgggggct ctcccatccc ggttgccctc tccagccatg    360

gtccccttta attataattg atctgaagga ttgctttttt accattcctc tggcaaaaga    420

ggattttgaa aaatttgctt ttactatacc agcctaaata ataaagaacc agccaccagg    480

tttcagtgga aagtattgcc tcagggaatg cttaataatt caactatttg tcagactttc    540

atagctcaag ctctgcaacc agttagagac aagttttcag actgttatat cgttcattat    600

gttgatattt tgtgtgctgc agaaacgaga gacaaattaa ttgaccgtta cacatttctc    660

agacagaggt tgccaacgcg ggactgacaa tagcatctga taagattcaa acctctcctc    720

ctttccatta cttgggaatg caggtagagg aaaggaaaat taaaccacaa aaaatagaaa    780

taagaaaaga cacattaaaa acattaaatg agtttcaaaa gttggtagga gatactaatt    840

ggattcggag atattaattg gatttggcca actctaggca ttcctactta tgccatgtca    900

attttgttct ctttcttaag aggggacttg gaattaaata gtgaaagaat gttacctcca    960

gaggcaacta aagaaattaa attaattgaa gaaaaaaatt cggtcagcac aagtaaatag   1020

gatcacttgg ccccactcca aattttgatt tttggtactg cacattctct aacagccatc   1080

attgttcaaa acacagatct tgtggattgg tccttccttc ctcatagtac aattaagact   1140

tttacattgt acttggatca aatggctaca ttaattggtc agggaagatt acgaataata   1200

acattgtgtg gaaatgaccc agataaaatc actgttcctt tcaacaagca acaagttaga   1260

caagccttta tcagttctgg tgcatggcag attggtcttg ctaattttct gggaattatt   1320

gataatcatt acccaaaaac aaaaatcttc cagttcttaa aattgactac ttggattcta   1380

cctaaaatta ccagacgtga acctttagaa aatgctctaa cagtatttac tgatggttcc   1440

agcaatggaa aagcggctta cacagggccg aaagaacgag taatcaaaac tccgtatcaa   1500
```

-continued

```
tcagctcaaa gagcagagtt ggttgcagtc attacagtgt tacaagattt tgaccaacct   1560

atcaatatta tatcagattc tgcatatgta gtacaggcta caagggatgt tgagacagct   1620

ctaattaaat atagcacgga cgatcattta aaccagctat tcaatttatt acaacaaact   1680

gtaagaaaaa gaaatttccc attttatatt actcatattc gagcacacac taatttacca   1740

gggcctttga ctaaagcaaa tgaacaagct gacttactgg tatcatctgc attcataaaa   1800

gcacaagaac ttcttgcttt gactcatgta aatgcagcag gattaaaaaa caaatttgat   1860

gtcacatgga aacaggcaaa agatattgta caacattgca cccagtgtca agtcttacac   1920

ctgtccactc aagaggcagg agttaatccc agaggtctgt gtcctaatgc gttatggcaa   1980

atggatggca cgcatgttcc ttcatttgga agattatcat atgttcatgt aacagttgat   2040

acttattcac atttcatatg ggcaacttgc caaacaggag aaagtacttc ccatgttaaa   2100

aaacatttat tatcttgttt tgctgtaatg ggagttccag aaaaaatcaa aactgacaat   2160

ggaccaggat attgtagtaa agctttccaa aaattcttaa gtcagtggaa aatttcacat   2220

acaacaggaa ttccttataa ttcccaagga caggccatag ttgaaagaac taatagaaca   2280

ctcaaaactc aattagttaa acaaaaagaa gggggagaca gtaaggagtg taccactcct   2340

cagatgcaac ttaatctagc actctatact ttaaattttt taaacattta tagaaatcag   2400

actactactt ctgcaaaaca acatcttact ggtaaaaagc acagcccaca tgaaggaaaa   2460

ctaatttggt ggaaagataa taaaaataag acatgggaaa tagggaaggt gataacgtgg   2520

gggagaggtt ttgcttgtgt ttcaccagga gaaaatcagc ttcctgtttg gatacccact   2580

agacatttga agttctacaa tgaacccatc ggagatgcaa agaaaagggc ctccacagag   2640

atggtaaccc cagtcacatg gatggataat c                                  2671
```

<210> SEQ ID NO 101
<211> LENGTH: 1665
<212> TYPE: DNA
<213> ORGANISM: Homo sapiens

<400> SEQUENCE: 101

```
gtcacatgga tggataatcc tatagaagta tatgttaatg atagtgtatg ggtacctggc     60

cccacagatg atcgctgccc tgccaaacct gaggaagaag ggatgatgat aaatatttcc    120

attgtgtatc gttatcctcc tatttgccta gggagagcac caggatgttt aatgcctgca    180

gtccaaaatt ggttggtaga agtacctact gtcagtccta acagtagatt cacttatcac    240

atggtaagcg ggatgtcact caggccacgg gtaaattatt tacaagactt ttcttatcaa    300

agatcattaa aatttagacc taaagggaaa ccttgcccca aggaaattcc caaagaatca    360

aaaaatacag aagttttagt ttgggaagaa tgtgtggcca atagtgcggt gatattacaa    420

aacaatgaat tcggaactat tatagattgg gcacctcgag gtcaattcta ccacaattgc    480

tcaggacaaa ctcagtcgtg tccaagtgca caagtgagtc cagctgttga tagcgactta    540

acagaaagtc tagacaaaca taagcataaa aaattacagt ctttctaccc ttgggaatgg    600

ggagaaaaag gaatctctac cccaagacca gaaataataa gtcctgtttc tggtcctgaa    660

catccagaat tatggaggct ttggcctgac accacattag aatttggtct ggaaatcaaa    720

ctttagaaac aagagatcgt aagccatttt atactatcga cctaaattcc agtctaacgg    780

ttcctttaca aagttgcgta aagccctctt atatgctagt tgtaggaaat atagttatta    840

aaccagactc ccaaactata acctgtgaaa attgtagatt gtttacttgc attgattcaa    900

cttttaattg gcggcaccgt attctgctgg tgagagcaag agagggcgtg tggatctctg    960
```

-continued

```
tgtccgtgga ctgaccgtgg gaggcctcgc catccatcca tattttgact gaagtattaa   1020

aagacatttt aaatagatcc aaaagattca tttttacctt aattgcagtg attatgggat   1080

taattgcagt cacagctacg gctgctgtgg caggagttgc attgcactct tctgttcagt   1140

cggtaaactt tgttaatgat tggcaaaaga attctacaag attgtggaat tcacaatcta   1200

gtattgatca aaaattggca aatcaaatta atgatcttag acaaactgtc atttggatgg   1260

gagacagact catgagctta gaacattgtt tccagttaca gtgtgactgg aatacgtcag   1320

atttttgtat tacaccccaa atttataatg agtctgagca tcactgggac atggttagac   1380

gccatctaca gggaagagaa gataatctca ctttagacat ttccaaatta aaataacaaa   1440

ttttcgaagc atcaaaagcc catttaaatt tgatgccagg aactgaggca attgcaggag   1500

ttgctgatgg cctcgcaaat cttaaccctg tcacttgggt taagaccatc ggaagtacta   1560

tgattataaa tctcatatta atccttgtgt gcctgttttg tctgttgtta gtctgcaggt   1620

gtacccaaca gctccgaaga gacagcgacc atcgagaacg ggcca                   1665
```

<210> SEQ ID NO 102
<211> LENGTH: 852
<212> TYPE: DNA
<213> ORGANISM: Homo sapiens

<400> SEQUENCE: 102

```
atggggcaaa ctaaaagtaa aattaaaagt aaatatgcct cttatctcag ctttattaaa     60

attcttttaa aaagaggggg agttaaagta tctacaaaaa atctaatcaa gctatttcaa    120

ataatagaac aattttgccc atggtttcca gaacaaggaa cttcagatct aaaagattgg    180

aaaagaattg gtaaggaact aaaacaagca ggtaggaagg gtaatatcat tccacttaca    240

gtatggaatg attgggccat tattaaagca gctttagaac catttcaaac agaagaagat    300

agcatttcag tttctgatgc ccctggaagc tgtttaatag attgtaatga aaacacaagg    360

aaaaaatccc agaaagaaac cgaaagttta cattgcgaat atgtagcaga gccggtaatg    420

gctcagtcaa cgcaaaatgt tgactataat caattacagg aggtgatata tcctgaaacg    480

ttaaaattag aaggaaaagg tccagaatta atggggccat cagagtctaa accacgaggc    540

acaagtcctc ttccagcagg tcaggtgctc gtaagattac aacctcaaaa gcaggttaaa    600

gaaaataaga cccaaccgca agtagcctat caatactgcc gctggctgaa cttcagtatc    660

ggccaccccc agaaagtcag tatggatatc caggaatgcc cccagcacca cagggcaggg    720

cgccatacca tcagccgccc actaggagac ttaatcctat ggcaccacct agtagacagg    780

gtagtgaatt acatgaaatt attgataaat caagaaagga aggagatact gaggcatggc    840

aattcccagt aa                                                        852
```

<210> SEQ ID NO 103
<211> LENGTH: 283
<212> TYPE: PRT
<213> ORGANISM: Homo sapiens

<400> SEQUENCE: 103

```
Met Gly Gln Thr Lys Ser Lys Ile Lys Ser Lys Tyr Ala Ser Tyr Leu
1               5                   10                  15

Ser Phe Ile Lys Ile Leu Leu Lys Arg Gly Gly Val Lys Val Ser Thr
            20                  25                  30

Lys Asn Leu Ile Lys Leu Phe Gln Ile Ile Glu Gln Phe Cys Pro Trp
        35                  40                  45
```

-continued

```
Phe Pro Glu Gln Gly Thr Ser Asp Leu Lys Asp Trp Lys Arg Ile Gly
    50                  55                  60

Lys Glu Leu Lys Gln Ala Gly Arg Lys Gly Asn Ile Ile Pro Leu Thr
65                  70                  75                  80

Val Trp Asn Asp Trp Ala Ile Ile Lys Ala Ala Leu Glu Pro Phe Gln
                85                  90                  95

Thr Glu Glu Asp Ser Ile Ser Val Ser Asp Ala Pro Gly Ser Cys Leu
            100                 105                 110

Ile Asp Cys Asn Glu Asn Thr Arg Lys Lys Ser Gln Lys Glu Thr Glu
        115                 120                 125

Ser Leu His Cys Glu Tyr Val Ala Glu Pro Val Met Ala Gln Ser Thr
    130                 135                 140

Gln Asn Val Asp Tyr Asn Gln Leu Gln Glu Val Ile Tyr Pro Glu Thr
145                 150                 155                 160

Leu Lys Leu Glu Gly Lys Gly Pro Glu Leu Met Gly Pro Ser Glu Ser
                165                 170                 175

Lys Pro Arg Gly Thr Ser Pro Leu Pro Ala Gly Gln Val Leu Val Arg
            180                 185                 190

Leu Gln Pro Gln Lys Gln Val Lys Glu Asn Lys Thr Gln Pro Gln Val
        195                 200                 205

Ala Tyr Gln Tyr Cys Arg Trp Leu Asn Phe Ser Ile Gly His Pro Gln
    210                 215                 220

Lys Val Ser Met Asp Ile Gln Glu Cys Pro Gln His His Arg Ala Gly
225                 230                 235                 240

Arg His Thr Ile Ser Arg Pro Leu Gly Asp Leu Ile Leu Trp His His
                245                 250                 255

Leu Val Asp Arg Val Val Asn Tyr Met Lys Leu Leu Ile Asn Gln Glu
            260                 265                 270

Arg Lys Glu Ile Leu Arg His Gly Asn Ser Gln
        275                 280
```

<210> SEQ ID NO 104
<211> LENGTH: 434
<212> TYPE: PRT
<213> ORGANISM: Homo sapiens

<400> SEQUENCE: 104

```
Met Pro Pro Ala Pro Gln Gly Arg Ala Pro Tyr His Gln Pro Pro Thr
1               5                   10                  15

Arg Arg Leu Asn Pro Met Ala Pro Pro Ser Arg Gln Gly Ser Glu Leu
            20                  25                  30

His Glu Ile Ile Asp Lys Ser Arg Lys Glu Gly Asp Thr Glu Ala Trp
        35                  40                  45

Gln Phe Pro Val Thr Leu Glu Pro Met Pro Pro Gly Glu Gly Ala Gln
    50                  55                  60

Glu Gly Glu Pro Pro Thr Val Glu Ala Arg Tyr Lys Ser Phe Ser Ile
65                  70                  75                  80

Lys Met Leu Lys Asp Met Lys Glu Gly Val Lys Gln Tyr Gly Pro Asn
                85                  90                  95

Ser Pro Tyr Met Arg Thr Leu Leu Asp Ser Ile Ala Tyr Gly His Arg
            100                 105                 110

Leu Ile Pro Tyr Asp Trp Glu Ile Leu Ala Lys Ser Ser Leu Ser Pro
        115                 120                 125

Ser Gln Phe Leu Gln Phe Lys Thr Trp Trp Ile Asp Gly Val Gln Glu
    130                 135                 140
```

-continued

```
Gln Val Arg Arg Asn Arg Ala Ala Asn Pro Pro Val Asn Ile Asp Ala
145                 150                 155                 160

Asp Gln Leu Leu Gly Ile Gly Gln Asn Trp Ser Thr Ile Ser Gln Gln
                165                 170                 175

Ala Leu Met Gln Asn Glu Ala Ile Glu Gln Val Arg Ala Ile Cys Leu
            180                 185                 190

Arg Ala Trp Glu Lys Ile Gln Asp Pro Gly Ser Thr Cys Pro Ser Phe
        195                 200                 205

Asn Thr Val Arg Gln Gly Ser Lys Glu Pro Tyr Pro Asp Phe Val Ala
    210                 215                 220

Arg Leu Gln Asp Val Ala Gln Lys Ser Ile Ala Asp Glu Lys Ala Gly
225                 230                 235                 240

Lys Val Ile Val Glu Leu Met Ala Tyr Glu Asn Ala Asn Pro Glu Cys
                245                 250                 255

Gln Ser Ala Ile Lys Pro Leu Lys Gly Lys Val Pro Ala Gly Ser Asp
            260                 265                 270

Val Ile Ser Glu Tyr Val Lys Ala Cys Asp Gly Ile Gly Gly Ala Met
        275                 280                 285

His Lys Ala Met Leu Met Ala Gln Ala Ile Thr Gly Val Val Leu Gly
    290                 295                 300

Gly Gln Val Arg Thr Phe Gly Gly Lys Cys Tyr Asn Cys Gly Gln Ile
305                 310                 315                 320

Gly His Leu Lys Lys Asn Cys Pro Val Leu Asn Lys Gln Asn Ile Thr
                325                 330                 335

Ile Gln Ala Thr Thr Thr Gly Arg Glu Pro Pro Asp Leu Cys Pro Arg
            340                 345                 350

Cys Lys Lys Gly Lys His Trp Ala Ser Gln Cys Arg Ser Lys Phe Asp
        355                 360                 365

Lys Asn Gly Gln Pro Leu Ser Gly Asn Glu Gln Arg Gly Gln Pro Gln
    370                 375                 380

Ala Pro Gln Gln Thr Gly Ala Phe Pro Ile Gln Pro Phe Val Pro Gln
385                 390                 395                 400

Gly Phe Gln Gly Gln Gln Pro Pro Leu Ser Gln Val Phe Gln Gly Ile
                405                 410                 415

Ser Gln Leu Pro Gln Tyr Asn Asn Cys Pro Ser Pro Gln Ala Ala Val
            420                 425                 430

Gln Gln
```

<210> SEQ ID NO 105
<211> LENGTH: 279
<212> TYPE: DNA
<213> ORGANISM: Homo sapiens

<400> SEQUENCE: 105

```
atggagattt tacattgctt agggccagat aatcaagaaa gtactgttca gccaatgatt     60

acttcaattc ctcttaatct gtggggtcga gatttattac aacaatgggg tgcggaaatc    120

accatgcccg ctccattata tagccccacg agtcaaaaaa tcatgaccaa gatgggatat    180

ataccaggaa agggactagg gaaaaatgaa gatggcatta aagttccagt tgaggctaaa    240

ataaatcaag aaagagaagg aatagggtat ccttttttag                          279
```

<210> SEQ ID NO 106
<211> LENGTH: 92
<212> TYPE: PRT
<213> ORGANISM: Homo sapiens -continued

<400> SEQUENCE: 106

Met Glu Ile Leu His Cys Leu Gly Pro Asp Asn Gln Glu Ser Thr Val
1 5 10 15

Gln Pro Met Ile Thr Ser Ile Pro Leu Asn Leu Trp Gly Arg Asp Leu
20 25 30

Leu Gln Gln Trp Gly Ala Glu Ile Thr Met Pro Ala Pro Leu Tyr Ser
35 40 45

Pro Thr Ser Gln Lys Ile Met Thr Lys Met Gly Tyr Ile Pro Gly Lys
50 55 60

Gly Leu Gly Lys Asn Glu Asp Gly Ile Lys Val Pro Val Glu Ala Lys
65 70 75 80

Ile Asn Gln Glu Arg Glu Gly Ile Gly Tyr Pro Phe
85 90

<210> SEQ ID NO 107
<211> LENGTH: 4086
<212> TYPE: DNA
<213> ORGANISM: Homo sapiens

<400> SEQUENCE: 107
atggggcctc tccaacccgg gttgccctct ccggccatga tcccaaaaga ttggccttta 60
attataattg atctaaagga ttgctttttt accatccctc tggcagagca ggattgtgaa 120
aaatttgcct ttactatacc agccataaat aataaagaac cagccaccag gtttcagtgg 180
aaagtgttac ctcagggaat gcttaatagt ccaactattt gtcagacttt tgtaggtcga 240
gctcttcaac cagtgagaga aaagttttca gactgttata ttattcatta tattgatgat 300
attttatgtg ctgcagaaac gaaagataaa ttaattgact gttatacatt tctgcaagca 360
gaggttgcca atgctggact ggcaatagca tccgataaga tccaaacctc tactcctttt 420
cattatttag ggatgcagat agaaaataga aaaattaagc cacaaaaaat agaaataaga 480
aaagacacat taaaaacact aaatgatttt caaaaattac taggagatat taattggatt 540
cggccaactc taggcattcc tacttatgcc atgtcaaatt tgttctctat cttaagagga 600
gactcagact taaatagtca aagaatatta accccagagg caacaaaaga aattaaatta 660
gtggaagaaa aaattcagtc agcgcaaata aatagaatag atcccttagc cccactccaa 720
cttttgattt ttgccactgc acattctcca acaggcatca ttattcaaaa tactgatctt 780
gtggagtggt cattccttcc tcacagtaca gttaagactt ttacattgta cttggatcaa 840
atagctacat taatcggtca gacaagatta cgaataacaa aattatgtgg aaatgaccca 900
gacaaaatag ttgtcccttt aaccaaggaa caagttagac aagcctttat caattctggt 960
gcatggcaga ttggtcttgc taattttgtg ggacttattg ataatcatta cccaaaaaca 1020
aagatcttcc agttcttaaa attgactact tggattctac ctaaaattac cagacgtgaa 1080
cctttagaaa atgctctaac agtatttact gatggttcca gcaatggaaa agcagcttac 1140
acagggccga aagaacgagt aatcaaaact ccatatcaat cggctcaaag agacgagttg 1200
gttgcagtca ttacagtgtt acaagatttt gaccaaccta tcaatattat atcagattct 1260
gcatatgtag tacaggctac aagggatgtt gagacagctc taattaaata tagcatggat 1320
gatcagttaa accagctatt caatttatta caacaaactg taagaaaaag aaatttccca 1380
ttttatatta cttatattcg agcacacact aatttaccag ggcctttgac taaagcaaat 1440
gaacaagctg acttactggt atcatctgca ctcataaaag cacaagaact tcatgctttg 1500
actcatgtaa atgcagcagg attaaaaaac aaatttgatg tcacatggaa acaggcaaaa 1560

-continued

```
gatattgtac aacattgcac ccagtgtcaa gtcttacacc tgcccactca agaggcagga   1620
gttaatccca gaggtctgtg tcctaatgca ttatggcaaa tggatgtcac gcatgtacct   1680
tcatttggaa gattatcata tgttcatgta acagttgata cttattcaca tttcatatgg   1740
gcaacttgcc aaacaggaga aagtacttcc catgttaaaa aacatttatt gtcttgtttt   1800
gctgtaatgg gagttccaga aaaaatcaaa actgacaatg gaccaggata ttgtagtaaa   1860
gctttccaaa aattcttaag tcagtggaaa atttcacata caacaggaat tccttataat   1920
tcccaaggac aggccatagt tgaaagaact aatagaacac tcaaaactca attagttaaa   1980
caaaaagaag gggagacag taaggagtgt accactcctc agatgcaact taatctagca   2040
ctctatactt taaatttttt aaacatttat agaaatcaga ctactacttc tgcagaacaa   2100
catcttactg gtaaaaagaa cagcccacat gaaggaaaac taatttggtg gaaagataat   2160
aaaaataaga catgggaaat agggaaggtg ataacgtggg ggagaggttt tgcttgtgtt   2220
tcaccaggag aaaatcagct tcctgtttgg ttacccacta gacatttgaa gttctacaat   2280
gaacccatcg gagatgcaaa gaaaagggcc tccacggaga tggtaacacc agtcacatgg   2340
atggataatc ctatagaagt atatgttaat gatagtatat gggtacctgg ccccatagat   2400
gatcgctgcc ctgccaaacc tgaggaagaa gggatgatga taaatatttc cattgggtat   2460
cgttatcctc ctatttgcct agggagagca ccaggatgtt taatgcctgc agtccaaaat   2520
tggttggtag aagtacctac tgtcagtccc atcagtagat tcacttatca catggtaagc   2580
gggatgtcac tcaggccacg ggtaaattat ttacaagact tttcttatca aagatcatta   2640
aaatttagac ctaaagggaa accttgcccc aaggaaattc ccaaagaatc aaaaaataca   2700
gaagttttag tttgggaaga atgtgtggcc aatagtgcgg tgatattata aaacaatgaa   2760
tttggaacta ttatagattg ggcacctcga ggtcaattct accacaattg ctcaggacaa   2820
actcagtcgt gtccaagtgc acaagtgagt ccagctgttg atagcgactt aacagaaagt   2880
ttagacaaac ataagcataa aaaattgcag tctttctacc cttgggaatg gggagaaaaa   2940
ggaatctcta ccccaagacc aaaaatagta agtcctgttt ctggtcctga acatccagaa   3000
ttatggaggc ttactgtggc ctcacaccac attagaattt ggtctggaaa tcaaacttta   3060
gaaacaagag attgtaagcc attttatact gtcgacctaa attccagtct aacagttcct   3120
ttacaaagtt gcgtaaagcc cccttatatg ctagttgtag gaaatatagt tattaaacca   3180
gactcccaga ctataacctg tgaaaattgt agattgctta cttgcattga ttcaactttt   3240
aattggcaac accgtattct gctggtgaga gcaagagagg gcgtgtggat ccctgtgtcc   3300
atggaccgac cgtgggaggc ctcaccatcc gtccatattt tgactgaagt attaaaaggt   3360
gttttaaata gatccaaaag attcattttt actttaattg cagtgattat gggattaatt   3420
gcagtcacag ctacggctgc tgtagcagga gttgcattgc actcttctgt tcagtcagta   3480
aactttgtta atgattggca aaagaattct acaagattgt ggaattcaca atctagtatt   3540
gatcaaaaat tggcaaatca aattaatgat cttagacaaa ctgtcatttg gatgggagac   3600
agactcatga gcttagaaca tcgtttccag ttacaatgtg actggaatac gtcagatttt   3660
tgtattacac cccaaattta taatgagtct gagcatcact gggacatggt tagacgccat   3720
ctacagggaa gagaagataa tctcacttta gacatttcca aattaaaaga acaaattttc   3780
gaagcatcaa aagcccattt aaatttggtg ccaggaactg aggcaattgc aggagttgct   3840
gatggcctcg caaatcttaa ccctgtcact tgggttaaga ccattggaag tacatcgatt   3900
ataaatctca tattaatcct tgtgtgcctg ttttgtctgt tgttagtctg caggtgtacc   3960
```

-continued

```
caacagctcc gaagagacag cgaccatcga gaacgggcca tgatgacgat ggcggttttg   4020

tcgaaaagaa aagggggaaa tgtggggaaa agcaagagag atcaaattgt tactgtgtct   4080

gtgtag                                                              4086


<210> SEQ ID NO 108
<211> LENGTH: 1361
<212> TYPE: PRT
<213> ORGANISM: Homo sapiens
<220> FEATURE:
<221> NAME/KEY: MISC_FEATURE
<222> LOCATION: (1)..(1361)
<223> OTHER INFORMATION: Xaa=Any amino acid

<400> SEQUENCE: 108

Met Gly Pro Leu Gln Pro Gly Leu Pro Ser Pro Ala Met Ile Pro Lys
1               5                   10                  15

Asp Trp Pro Leu Ile Ile Ile Asp Leu Lys Asp Cys Phe Phe Thr Ile
            20                  25                  30

Pro Leu Ala Glu Gln Asp Cys Glu Lys Phe Ala Phe Thr Ile Pro Ala
        35                  40                  45

Ile Asn Asn Lys Glu Pro Ala Thr Arg Phe Gln Trp Lys Val Leu Pro
    50                  55                  60

Gln Gly Met Leu Asn Ser Pro Thr Ile Cys Gln Thr Phe Val Gly Arg
65                  70                  75                  80

Ala Leu Gln Pro Val Arg Glu Lys Phe Ser Asp Cys Tyr Ile Ile His
                85                  90                  95

Tyr Ile Asp Asp Ile Leu Cys Ala Ala Glu Thr Lys Asp Lys Leu Ile
            100                 105                 110

Asp Cys Tyr Thr Phe Leu Gln Ala Glu Val Ala Asn Ala Gly Leu Ala
        115                 120                 125

Ile Ala Ser Asp Lys Ile Gln Thr Ser Thr Pro Phe His Tyr Leu Gly
    130                 135                 140

Met Gln Ile Glu Asn Arg Lys Ile Lys Pro Gln Lys Ile Glu Ile Arg
145                 150                 155                 160

Lys Asp Thr Leu Lys Thr Leu Asn Asp Phe Gln Lys Leu Leu Gly Asp
                165                 170                 175

Ile Asn Trp Ile Arg Pro Thr Leu Gly Ile Pro Thr Tyr Ala Met Ser
            180                 185                 190

Asn Leu Phe Ser Ile Leu Arg Gly Asp Ser Asp Leu Asn Ser Gln Arg
        195                 200                 205

Ile Leu Thr Pro Glu Ala Thr Lys Glu Ile Lys Leu Val Glu Glu Lys
    210                 215                 220

Ile Gln Ser Ala Gln Ile Asn Arg Ile Asp Pro Leu Ala Pro Leu Gln
225                 230                 235                 240

Leu Leu Ile Phe Ala Thr Ala His Ser Pro Thr Gly Ile Ile Ile Gln
                245                 250                 255

Asn Thr Asp Leu Val Glu Trp Ser Phe Leu Pro His Ser Thr Val Lys
            260                 265                 270

Thr Phe Thr Leu Tyr Leu Asp Gln Ile Ala Thr Leu Ile Gly Gln Thr
        275                 280                 285

Arg Leu Arg Ile Thr Lys Leu Cys Gly Asn Asp Pro Asp Lys Ile Val
    290                 295                 300

Val Pro Leu Thr Lys Glu Gln Val Arg Gln Ala Phe Ile Asn Ser Gly
305                 310                 315                 320
```

-continued

```
Ala Trp Gln Ile Gly Leu Ala Asn Phe Val Gly Leu Ile Asp Asn His
                325                 330                 335

Tyr Pro Lys Thr Lys Ile Phe Gln Phe Leu Lys Leu Thr Thr Trp Ile
            340                 345                 350

Leu Pro Lys Ile Thr Arg Arg Glu Pro Leu Glu Asn Ala Leu Thr Val
        355                 360                 365

Phe Thr Asp Gly Ser Ser Asn Gly Lys Ala Ala Tyr Thr Gly Pro Lys
    370                 375                 380

Glu Arg Val Ile Lys Thr Pro Tyr Gln Ser Ala Gln Arg Asp Glu Leu
385                 390                 395                 400

Val Ala Val Ile Thr Val Leu Gln Asp Phe Asp Gln Pro Ile Asn Ile
                405                 410                 415

Ile Ser Asp Ser Ala Tyr Val Val Gln Ala Thr Arg Asp Val Glu Thr
            420                 425                 430

Ala Leu Ile Lys Tyr Ser Met Asp Asp Gln Leu Asn Gln Leu Phe Asn
        435                 440                 445

Leu Leu Gln Gln Thr Val Arg Lys Arg Asn Phe Pro Phe Tyr Ile Thr
    450                 455                 460

Tyr Ile Arg Ala His Thr Asn Leu Pro Gly Pro Leu Thr Lys Ala Asn
465                 470                 475                 480

Glu Gln Ala Asp Leu Leu Val Ser Ser Ala Leu Ile Lys Ala Gln Glu
                485                 490                 495

Leu His Ala Leu Thr His Val Asn Ala Ala Gly Leu Lys Asn Lys Phe
            500                 505                 510

Asp Val Thr Trp Lys Gln Ala Lys Asp Ile Val Gln His Cys Thr Gln
        515                 520                 525

Cys Gln Val Leu His Leu Pro Thr Gln Glu Ala Gly Val Asn Pro Arg
    530                 535                 540

Gly Leu Cys Pro Asn Ala Leu Trp Gln Met Asp Val Thr His Val Pro
545                 550                 555                 560

Ser Phe Gly Arg Leu Ser Tyr Val His Val Thr Val Asp Thr Tyr Ser
                565                 570                 575

His Phe Ile Trp Ala Thr Cys Gln Thr Gly Glu Ser Thr Ser His Val
            580                 585                 590

Lys Lys His Leu Leu Ser Cys Phe Ala Val Met Gly Val Pro Glu Lys
        595                 600                 605

Ile Lys Thr Asp Asn Gly Pro Gly Tyr Cys Ser Lys Ala Phe Gln Lys
    610                 615                 620

Phe Leu Ser Gln Trp Lys Ile Ser His Thr Thr Gly Ile Pro Tyr Asn
625                 630                 635                 640

Ser Gln Gly Gln Ala Ile Val Glu Arg Thr Asn Arg Thr Leu Lys Thr
                645                 650                 655

Gln Leu Val Lys Gln Lys Glu Gly Gly Asp Ser Lys Glu Cys Thr Thr
            660                 665                 670

Pro Gln Met Gln Leu Asn Leu Ala Leu Tyr Thr Leu Asn Phe Leu Asn
        675                 680                 685

Ile Tyr Arg Asn Gln Thr Thr Thr Ser Ala Glu Gln His Leu Thr Gly
    690                 695                 700

Lys Lys Asn Ser Pro His Glu Gly Lys Leu Ile Trp Trp Lys Asp Asn
705                 710                 715                 720

Lys Asn Lys Thr Trp Glu Ile Gly Lys Val Ile Thr Trp Gly Arg Gly
                725                 730                 735
```

-continued

```
Phe Ala Cys Val Ser Pro Gly Glu Asn Gln Leu Pro Val Trp Leu Pro
            740                 745                 750

Thr Arg His Leu Lys Phe Tyr Asn Glu Pro Ile Gly Asp Ala Lys Lys
        755                 760                 765

Arg Ala Ser Thr Glu Met Val Thr Pro Val Thr Trp Met Asp Asn Pro
    770                 775                 780

Ile Glu Val Tyr Val Asn Asp Ser Ile Trp Val Pro Gly Pro Ile Asp
785                 790                 795                 800

Asp Arg Cys Pro Ala Lys Pro Glu Glu Glu Gly Met Met Ile Asn Ile
                805                 810                 815

Ser Ile Gly Tyr Arg Tyr Pro Pro Ile Cys Leu Gly Arg Ala Pro Gly
            820                 825                 830

Cys Leu Met Pro Ala Val Gln Asn Trp Leu Val Glu Val Pro Thr Val
        835                 840                 845

Ser Pro Ile Ser Arg Phe Thr Tyr His Met Val Ser Gly Met Ser Leu
    850                 855                 860

Arg Pro Arg Val Asn Tyr Leu Gln Asp Phe Ser Tyr Gln Arg Ser Leu
865                 870                 875                 880

Lys Phe Arg Pro Lys Gly Lys Pro Cys Pro Lys Glu Ile Pro Lys Glu
                885                 890                 895

Ser Lys Asn Thr Glu Val Leu Val Trp Glu Glu Cys Val Ala Asn Ser
            900                 905                 910

Ala Val Ile Leu Xaa Asn Asn Glu Phe Gly Thr Ile Ile Asp Trp Ala
        915                 920                 925

Pro Arg Gly Gln Phe Tyr His Asn Cys Ser Gly Gln Thr Gln Ser Cys
    930                 935                 940

Pro Ser Ala Gln Val Ser Pro Ala Val Asp Ser Asp Leu Thr Glu Ser
945                 950                 955                 960

Leu Asp Lys His Lys His Lys Lys Leu Gln Ser Phe Tyr Pro Trp Glu
                965                 970                 975

Trp Gly Glu Lys Gly Ile Ser Thr Pro Arg Pro Lys Ile Val Ser Pro
            980                 985                 990

Val Ser Gly Pro Glu His Pro Glu  Leu Trp Arg Leu Thr  Val Ala Ser
        995                 1000                 1005

His His  Ile Arg Ile Trp Ser  Gly Asn Gln Thr Leu  Glu Thr Arg
    1010                 1015                 1020

Asp Cys  Lys Pro Phe Tyr Thr  Val Asp Leu Asn Ser  Ser Leu Thr
    1025                 1030                 1035

Val Pro  Leu Gln Ser Cys Val  Lys Pro Pro Tyr Met  Leu Val Val
    1040                 1045                 1050

Gly Asn  Ile Val Ile Lys Pro  Asp Ser Gln Thr Ile  Thr Cys Glu
    1055                 1060                 1065

Asn Cys  Arg Leu Leu Thr Cys  Ile Asp Ser Thr Phe  Asn Trp Gln
    1070                 1075                 1080

His Arg  Ile Leu Leu Val Arg  Ala Arg Glu Gly Val  Trp Ile Pro
    1085                 1090                 1095

Val Ser  Met Asp Arg Pro Trp  Glu Ala Ser Pro Ser  Val His Ile
    1100                 1105                 1110

Leu Thr  Glu Val Leu Lys Gly  Val Leu Asn Arg Ser  Lys Arg Phe
    1115                 1120                 1125
```

-continued

```
Ile Phe  Thr Leu Ile Ala Val  Ile Met Gly Leu Ile  Ala Val Thr
    1130                 1135                 1140

Ala Thr  Ala Ala Val Ala Gly  Val Ala Leu His Ser  Ser Val Gln
    1145                 1150                 1155

Ser Val  Asn Phe Val Asn Asp  Trp Gln Lys Asn Ser  Thr Arg Leu
    1160                 1165                 1170

Trp Asn  Ser Gln Ser Ser Ile  Asp Gln Lys Leu Ala  Asn Gln Ile
    1175                 1180                 1185

Asn Asp  Leu Arg Gln Thr Val  Ile Trp Met Gly Asp  Arg Leu Met
    1190                 1195                 1200

Ser Leu  Glu His Arg Phe Gln  Leu Gln Cys Asp Trp  Asn Thr Ser
    1205                 1210                 1215

Asp Phe  Cys Ile Thr Pro Gln  Ile Tyr Asn Glu Ser  Glu His His
    1220                 1225                 1230

Trp Asp  Met Val Arg Arg His  Leu Gln Gly Arg Glu  Asp Asn Leu
    1235                 1240                 1245

Thr Leu  Asp Ile Ser Lys Leu  Lys Glu Gln Ile Phe  Glu Ala Ser
    1250                 1255                 1260

Lys Ala  His Leu Asn Leu Val  Pro Gly Thr Glu Ala  Ile Ala Gly
    1265                 1270                 1275

Val Ala  Asp Gly Leu Ala Asn  Leu Asn Pro Val Thr  Trp Val Lys
    1280                 1285                 1290

Thr Ile  Gly Ser Thr Ser Ile  Ile Asn Leu Ile Leu  Ile Leu Val
    1295                 1300                 1305

Cys Leu  Phe Cys Leu Leu Leu  Val Cys Arg Cys Thr  Gln Gln Leu
    1310                 1315                 1320

Arg Arg  Asp Ser Asp His Arg  Glu Arg Ala Met Met  Thr Met Ala
    1325                 1330                 1335

Val Leu  Ser Lys Arg Lys Gly  Gly Asn Val Gly Lys  Ser Lys Arg
    1340                 1345                 1350

Asp Gln  Ile Val Thr Val Ser  Val
    1355                 1360


<210> SEQ ID NO 109
<211> LENGTH: 105
<212> TYPE: PRT
<213> ORGANISM: Homo sapiens

<400> SEQUENCE: 109

Met Asn Pro Ser Glu Met Gln Arg Lys Ala Pro Pro Arg Arg Arg Arg
1               5                   10                  15

His Arg Asn Arg Ala Pro Leu Thr His Lys Met Asn Lys Met Val Thr
            20                  25                  30

Ser Glu Glu Gln Met Lys Leu Pro Ser Thr Lys Lys Ala Gly Pro Pro
        35                  40                  45

Thr Trp Ala Gln Leu Lys Lys Leu Thr Gln Leu Ala Thr Lys Tyr Leu
    50                  55                  60

Glu Asn Thr Lys Val Thr Gln Thr Pro Glu Ser Met Leu Leu Ala Ala
65                  70                  75                  80

Leu Met Ile Val Ser Met Val Ser Ala Gly Val Pro Asn Ser Ser Glu
                85                  90                  95

Glu Thr Ala Thr Ile Glu Asn Gly Pro
            100                 105
```

-continued

<210> SEQ ID NO 110
<211> LENGTH: 20
<212> TYPE: DNA
<213> ORGANISM: Homo sapiens

<400> SEQUENCE: 110
gaaaaaaatc aaaaaaagaa 20

<210> SEQ ID NO 111
<211> LENGTH: 17
<212> TYPE: DNA
<213> ORGANISM: Homo sapiens

<400> SEQUENCE: 111
agccattaat gccataa 17

<210> SEQ ID NO 112
<211> LENGTH: 15
<212> TYPE: DNA
<213> ORGANISM: Homo sapiens

<400> SEQUENCE: 112
taaataggat cactt 15

<210> SEQ ID NO 113
<211> LENGTH: 28
<212> TYPE: DNA
<213> ORGANISM: Homo sapiens

<400> SEQUENCE: 113
ggtgcggaaa tcaccatgcc cgctccat 28

<210> SEQ ID NO 114
<211> LENGTH: 18
<212> TYPE: DNA
<213> ORGANISM: Homo sapiens

<400> SEQUENCE: 114
attatatagc cccacgag 18

<210> SEQ ID NO 115
<211> LENGTH: 21
<212> TYPE: DNA
<213> ORGANISM: Homo sapiens

<400> SEQUENCE: 115
caagatggga tatataccag g 21

<210> SEQ ID NO 116
<211> LENGTH: 18
<212> TYPE: DNA
<213> ORGANISM: Homo sapiens

<400> SEQUENCE: 116
aaaacagaaa aaccggtg 18

<210> SEQ ID NO 117
<211> LENGTH: 16
<212> TYPE: DNA
<213> ORGANISM: Homo sapiens

<400> SEQUENCE: 117
aaatcagtgg ccgcta 16

-continued

<210> SEQ ID NO 118
<211> LENGTH: 17
<212> TYPE: DNA
<213> ORGANISM: Homo sapiens

<400> SEQUENCE: 118
agttagaaaa gggtcac 17

<210> SEQ ID NO 119
<211> LENGTH: 16
<212> TYPE: DNA
<213> ORGANISM: Homo sapiens

<400> SEQUENCE: 119
tgagccttcg ttctca 16

<210> SEQ ID NO 120
<211> LENGTH: 17
<212> TYPE: DNA
<213> ORGANISM: Homo sapiens

<400> SEQUENCE: 120
aggcaaatgg catacgt 17

<210> SEQ ID NO 121
<211> LENGTH: 15
<212> TYPE: DNA
<213> ORGANISM: Homo sapiens

<400> SEQUENCE: 121
ggcctctcca acccg 15

<210> SEQ ID NO 122
<211> LENGTH: 17
<212> TYPE: DNA
<213> ORGANISM: Homo sapiens

<400> SEQUENCE: 122
gagcaggatt gtgaaaa 17

<210> SEQ ID NO 123
<211> LENGTH: 21
<212> TYPE: DNA
<213> ORGANISM: Homo sapiens

<400> SEQUENCE: 123
tcttcaacca gtgagagaaa a 21

<210> SEQ ID NO 124
<211> LENGTH: 20
<212> TYPE: DNA
<213> ORGANISM: Homo sapiens

<400> SEQUENCE: 124
attatattga tgatatttta 20

<210> SEQ ID NO 125
<211> LENGTH: 15
<212> TYPE: DNA
<213> ORGANISM: Homo sapiens

<400> SEQUENCE: 125
aacgaaagat aaatt 15

-continued

<210> SEQ ID NO 126
<211> LENGTH: 15
<212> TYPE: DNA
<213> ORGANISM: Homo sapiens

<400> SEQUENCE: 126
tgactgttat acatt 15

<210> SEQ ID NO 127
<211> LENGTH: 16
<212> TYPE: DNA
<213> ORGANISM: Homo sapiens

<400> SEQUENCE: 127
ttcattattt agggat 16

<210> SEQ ID NO 128
<211> LENGTH: 19
<212> TYPE: DNA
<213> ORGANISM: Homo sapiens

<400> SEQUENCE: 128
agatagaaaa tagaaaaat 19

<210> SEQ ID NO 129
<211> LENGTH: 15
<212> TYPE: DNA
<213> ORGANISM: Homo sapiens

<400> SEQUENCE: 129
attattcaaa atact 15

<210> SEQ ID NO 130
<211> LENGTH: 16
<212> TYPE: DNA
<213> ORGANISM: Homo sapiens

<400> SEQUENCE: 130
aataacaaaa ttatgt 16

<210> SEQ ID NO 131
<211> LENGTH: 15
<212> TYPE: DNA
<213> ORGANISM: Homo sapiens

<400> SEQUENCE: 131
agacaaaata gttgt 15

<210> SEQ ID NO 132
<211> LENGTH: 17
<212> TYPE: DNA
<213> ORGANISM: Homo sapiens

<400> SEQUENCE: 132
tccctttaac caaggaa 17

<210> SEQ ID NO 133
<211> LENGTH: 15
<212> TYPE: DNA
<213> ORGANISM: Homo sapiens

<400> SEQUENCE: 133
aaaagaatga gtcat 15

-continued

<210> SEQ ID NO 134
<211> LENGTH: 15
<212> TYPE: DNA
<213> ORGANISM: Homo sapiens

<400> SEQUENCE: 134
cagtatcact tgact 15

<210> SEQ ID NO 135
<211> LENGTH: 23
<212> TYPE: DNA
<213> ORGANISM: Homo sapiens

<400> SEQUENCE: 135
ttttaatcag tctattaaca ttg 23

<210> SEQ ID NO 136
<211> LENGTH: 16
<212> TYPE: DNA
<213> ORGANISM: Homo sapiens

<400> SEQUENCE: 136
aaaggatatt gagaga 16

<210> SEQ ID NO 137
<211> LENGTH: 16
<212> TYPE: DNA
<213> ORGANISM: Homo sapiens

<400> SEQUENCE: 137
cctaatcaaa tacatt 16

<210> SEQ ID NO 138
<211> LENGTH: 15
<212> TYPE: DNA
<213> ORGANISM: Homo sapiens

<400> SEQUENCE: 138
cgctgtttaa tttgt 15

<210> SEQ ID NO 139
<211> LENGTH: 16
<212> TYPE: DNA
<213> ORGANISM: Homo sapiens

<400> SEQUENCE: 139
tgcattcatg gaagca 16

<210> SEQ ID NO 140
<211> LENGTH: 15
<212> TYPE: DNA
<213> ORGANISM: Homo sapiens

<400> SEQUENCE: 140
actcaggagg caaga 15

<210> SEQ ID NO 141
<211> LENGTH: 16
<212> TYPE: DNA
<213> ORGANISM: Homo sapiens

<400> SEQUENCE: 141
ttaagagaca tttatt 16

-continued

<210> SEQ ID NO 142
<211> LENGTH: 16
<212> TYPE: DNA
<213> ORGANISM: Homo sapiens

<400> SEQUENCE: 142
taaagcagtt caaaaa 16

<210> SEQ ID NO 143
<211> LENGTH: 15
<212> TYPE: DNA
<213> ORGANISM: Homo sapiens

<400> SEQUENCE: 143
aataggaatt ctcta 15

<210> SEQ ID NO 144
<211> LENGTH: 16
<212> TYPE: DNA
<213> ORGANISM: Homo sapiens

<400> SEQUENCE: 144
aaagctcaat tggtta 16

<210> SEQ ID NO 145
<211> LENGTH: 16
<212> TYPE: DNA
<213> ORGANISM: Homo sapiens

<400> SEQUENCE: 145
acggacgatc atttaa 16

<210> SEQ ID NO 146
<211> LENGTH: 666
<212> TYPE: PRT
<213> ORGANISM: Homo sapiens

<400> SEQUENCE: 146

```
Met Gly Gln Thr Lys Ser Lys Ile Lys Ser Lys Tyr Ala Ser Tyr Leu
1               5                   10                  15

Ser Phe Ile Lys Ile Leu Leu Lys Arg Gly Gly Val Lys Val Ser Thr
            20                  25                  30

Lys Asn Leu Ile Lys Leu Phe Gln Ile Ile Glu Gln Phe Cys Pro Trp
        35                  40                  45

Phe Pro Glu Gln Gly Thr Leu Asp Leu Lys Asp Trp Lys Arg Ile Gly
    50                  55                  60

Lys Glu Leu Lys Gln Ala Gly Arg Lys Gly Asn Ile Ile Pro Leu Thr
65                  70                  75                  80

Val Trp Asn Asp Trp Ala Ile Ile Lys Ala Ala Leu Glu Pro Phe Gln
                85                  90                  95

Thr Glu Glu Asp Ser Val Ser Val Ser Asp Ala Pro Gly Ser Cys Ile
            100                 105                 110

Ile Asp Cys Asn Glu Asn Thr Gly Lys Lys Ser Gln Lys Glu Thr Glu
        115                 120                 125

Gly Leu His Cys Glu Tyr Val Ala Glu Pro Val Met Ala Gln Ser Thr
    130                 135                 140

Gln Asn Val Asp Tyr Asn Gln Leu Gln Glu Val Ile Tyr Pro Glu Thr
145                 150                 155                 160

Leu Lys Leu Glu Gly Lys Gly Pro Glu Leu Val Gly Pro Ser Glu Ser
                165                 170                 175
```

-continued

```
Lys Pro Arg Gly Thr Ser Pro Leu Pro Ala Gly Gln Val Pro Val Thr
            180                 185                 190

Leu Gln Pro Gln Lys Gln Val Lys Glu Asn Lys Thr Gln Pro Pro Val
        195                 200                 205

Ala Tyr Gln Tyr Trp Pro Pro Ala Glu Leu Gln Tyr Arg Pro Pro Pro
    210                 215                 220

Glu Ser Gln Tyr Gly Tyr Pro Gly Met Pro Pro Ala Pro Gln Gly Arg
225                 230                 235                 240

Ala Pro Tyr Pro Gln Pro Pro Thr Arg Arg Leu Asn Pro Thr Ala Pro
                245                 250                 255

Pro Ser Arg Gln Gly Ser Lys Leu His Glu Ile Ile Asp Lys Ser Arg
            260                 265                 270

Lys Glu Gly Asp Thr Glu Ala Trp Gln Phe Pro Val Thr Leu Glu Pro
        275                 280                 285

Met Pro Pro Gly Glu Gly Ala Gln Glu Gly Glu Pro Pro Thr Val Glu
    290                 295                 300

Ala Arg Tyr Lys Ser Phe Ser Ile Lys Lys Leu Lys Asp Met Lys Glu
305                 310                 315                 320

Gly Val Lys Gln Tyr Gly Pro Asn Ser Pro Tyr Met Arg Thr Leu Leu
                325                 330                 335

Asp Ser Ile Ala His Gly His Arg Leu Ile Pro Tyr Asp Trp Glu Ile
            340                 345                 350

Gln Ala Lys Ser Ser Leu Ser Pro Ser Gln Phe Leu Gln Phe Lys Thr
        355                 360                 365

Trp Trp Ile Asp Gly Val Gln Glu Gln Val Arg Arg Asn Arg Ala Ala
    370                 375                 380

Asn Pro Pro Val Asn Ile Asp Ala Asp Gln Leu Leu Gly Ile Gly Gln
385                 390                 395                 400

Asn Trp Ser Thr Ile Ser Gln Gln Ala Leu Met Gln Asn Glu Ala Ile
                405                 410                 415

Glu Gln Val Arg Ala Ile Cys Leu Arg Ala Trp Glu Lys Ile Gln Asp
            420                 425                 430

Pro Gly Ser Thr Cys Pro Ser Phe Asn Thr Val Arg Gln Gly Ser Lys
        435                 440                 445

Glu Pro Tyr Pro Asp Phe Val Ala Arg Leu Gln Asp Val Ala Gln Lys
    450                 455                 460

Ser Ile Ala Asp Glu Lys Ala Arg Lys Val Ile Val Glu Leu Met Ala
465                 470                 475                 480

Tyr Glu Asn Ala Asn Pro Glu Cys Gln Ser Ala Ile Lys Pro Leu Lys
                485                 490                 495

Gly Lys Val Pro Ala Gly Ser Asp Val Ile Ser Glu Tyr Val Lys Ala
            500                 505                 510

Cys Asp Gly Ile Gly Gly Ala Met His Lys Ala Met Leu Met Ala Gln
        515                 520                 525

Ala Ile Thr Gly Val Val Leu Gly Gly Gln Val Arg Thr Phe Gly Arg
    530                 535                 540

Lys Cys Tyr Asn Cys Gly Gln Ile Gly His Leu Lys Lys Asn Cys Pro
545                 550                 555                 560

Val Leu Asn Lys Gln Asn Ile Thr Ile Gln Ala Thr Thr Thr Gly Arg
                565                 570                 575

Glu Pro Pro Asp Leu Cys Pro Arg Cys Lys Lys Gly Lys His Trp Ala
            580                 585                 590
```

-continued

Ser Gln Cys Arg Ser Lys Phe Asp Lys Asn Gly Gln Pro Leu Ser Gly
595 600 605

Asn Glu Gln Arg Gly Gln Pro Gln Ala Pro Gln Gln Thr Gly Ala Phe
610 615 620

Pro Ile Gln Pro Phe Val Pro Gln Gly Phe Gln Gly Gln Gln Pro Pro
625 630 635 640

Leu Ser Gln Val Phe Gln Gly Ile Ser Gln Leu Pro Gln Tyr Asn Asn
645 650 655

Cys Pro Pro Pro Gln Ala Ala Val Gln Gln
660 665

<210> SEQ ID NO 147
<211> LENGTH: 333
<212> TYPE: PRT
<213> ORGANISM: Homo sapiens

<400> SEQUENCE: 147

Trp Ala Thr Ile Val Gly Lys Arg Ala Lys Gly Pro Ala Ser Gly Pro
1 5 10 15

Thr Thr Asn Trp Gly Ile Pro Asn Ser Ala Ile Cys Ser Ser Gly Phe
20 25 30

Ser Gly Thr Thr Thr Pro Thr Val Pro Ser Val Ser Gly Asn Lys Pro
35 40 45

Val Thr Thr Ile Gln Gln Leu Ser Pro Ala Thr Ser Gly Ser Ala Ala
50 55 60

Val Asp Leu Cys Thr Ile Gln Ala Val Ser Leu Leu Pro Gly Glu Pro
65 70 75 80

Pro Gln Lys Thr Pro Thr Gly Val Tyr Gly Pro Leu Pro Lys Gly Thr
85 90 95

Val Gly Leu Ile Leu Gly Arg Ser Ser Leu Asn Leu Lys Gly Val Gln
100 105 110

Ile His Thr Ser Val Val Asp Ser Asp Tyr Lys Gly Glu Ile Gln Leu
115 120 125

Val Ile Ser Ser Ser Ile Pro Trp Ser Ala Ser Pro Arg Asp Arg Ile
130 135 140

Ala Gln Leu Leu Leu Leu Pro Tyr Ile Lys Gly Gly Asn Ser Glu Ile
145 150 155 160

Lys Arg Ile Gly Gly Leu Gly Ser Thr Asp Pro Thr Gly Lys Ala Ala
165 170 175

Tyr Trp Ala Ser Gln Val Ser Glu Asn Arg Pro Val Cys Lys Ala Ile
180 185 190

Ile Gln Gly Lys Gln Phe Glu Gly Leu Val Asp Thr Gly Ala Asp Val
195 200 205

Ser Ile Ile Ala Leu Asn Gln Trp Pro Lys Asn Trp Pro Lys Gln Lys
210 215 220

Ala Val Thr Gly Leu Val Gly Ile Gly Thr Ala Ser Glu Val Tyr Gln
225 230 235 240

Ser Thr Glu Ile Leu His Cys Leu Gly Pro Asp Asn Gln Glu Ser Thr
245 250 255

Val Gln Pro Met Ile Thr Ser Ile Pro Leu Asn Leu Trp Gly Arg Asp
260 265 270

Leu Leu Gln Gln Trp Gly Ala Glu Ile Thr Met Pro Ala Pro Ser Tyr
275 280 285

Ser Pro Thr Ser Gln Lys Ile Met Thr Lys Met Gly Tyr Ile Pro Gly
290 295 300

-continued

```
Lys Gly Leu Gly Lys Asn Glu Asp Gly Ile Lys Ile Pro Val Glu Ala
305                 310                 315                 320

Lys Ile Asn Gln Glu Arg Glu Gly Ile Gly Asn Pro Cys
                325                 330


<210> SEQ ID NO 148
<211> LENGTH: 956
<212> TYPE: PRT
<213> ORGANISM: Homo sapiens

<400> SEQUENCE: 148

Asn Lys Ser Arg Lys Arg Arg Asn Arg Glu Ser Leu Leu Gly Ala Ala
1               5                   10                  15

Thr Val Glu Pro Pro Lys Pro Ile Pro Leu Thr Trp Lys Thr Glu Lys
            20                  25                  30

Pro Val Trp Val Asn Gln Trp Pro Leu Pro Lys Gln Lys Leu Glu Ala
        35                  40                  45

Leu His Leu Leu Ala Asn Glu Gln Leu Glu Lys Gly His Ile Glu Pro
    50                  55                  60

Ser Phe Ser Pro Trp Asn Ser Pro Val Phe Val Ile Gln Lys Lys Ser
65                  70                  75                  80

Gly Lys Trp Arg Met Leu Thr Asp Leu Arg Ala Val Asn Ala Val Ile
                85                  90                  95

Gln Pro Met Gly Pro Leu Gln Pro Gly Leu Pro Ser Pro Ala Met Ile
            100                 105                 110

Pro Lys Asp Trp Pro Leu Ile Ile Ile Asp Leu Lys Asp Cys Phe Phe
        115                 120                 125

Thr Ile Pro Leu Ala Glu Gln Asp Cys Glu Lys Phe Ala Phe Thr Ile
    130                 135                 140

Pro Ala Ile Asn Asn Lys Glu Pro Ala Thr Arg Phe Gln Trp Lys Val
145                 150                 155                 160

Leu Pro Gln Gly Met Leu Asn Ser Pro Thr Ile Cys Gln Thr Phe Val
                165                 170                 175

Gly Arg Ala Leu Gln Pro Val Arg Glu Lys Phe Ser Asp Cys Tyr Ile
            180                 185                 190

Ile His Cys Ile Asp Asp Ile Leu Cys Ala Ala Glu Thr Lys Asp Lys
        195                 200                 205

Leu Ile Asp Cys Tyr Thr Phe Leu Gln Ala Glu Val Ala Asn Ala Gly
    210                 215                 220

Leu Ala Ile Ala Ser Asp Lys Ile Gln Thr Ser Thr Pro Phe His Tyr
225                 230                 235                 240

Leu Gly Met Gln Ile Glu Asn Arg Lys Ile Lys Pro Gln Lys Ile Glu
                245                 250                 255

Ile Arg Lys Asp Thr Leu Lys Thr Leu Asn Asp Phe Gln Lys Leu Leu
            260                 265                 270

Gly Asp Ile Asn Trp Ile Arg Pro Thr Leu Gly Ile Pro Thr Tyr Ala
        275                 280                 285

Met Ser Asn Leu Phe Ser Ile Leu Arg Gly Asp Ser Asp Leu Asn Ser
    290                 295                 300

Lys Arg Met Leu Thr Pro Glu Ala Thr Lys Glu Ile Lys Leu Val Glu
305                 310                 315                 320

Glu Lys Ile Gln Ser Ala Gln Ile Asn Arg Ile Asp Pro Leu Ala Pro
                325                 330                 335

Leu Gln Leu Leu Ile Phe Ala Thr Ala His Ser Pro Thr Gly Ile Ile
            340                 345                 350
```

-continued

```
Ile Gln Asn Thr Asp Leu Val Glu Trp Ser Phe Leu Pro His Ser Thr
        355                 360                 365

Val Lys Thr Phe Thr Leu Tyr Leu Asp Gln Ile Ala Thr Leu Ile Gly
    370                 375                 380

Gln Thr Arg Leu Arg Ile Ile Lys Leu Cys Gly Asn Asp Pro Asp Lys
385                 390                 395                 400

Ile Val Val Pro Leu Thr Lys Glu Gln Val Arg Gln Ala Phe Ile Asn
                405                 410                 415

Ser Gly Ala Trp Lys Ile Gly Leu Ala Asn Phe Val Gly Ile Ile Asp
            420                 425                 430

Asn His Tyr Pro Lys Thr Lys Ile Phe Gln Phe Leu Lys Leu Thr Thr
        435                 440                 445

Trp Ile Leu Pro Lys Ile Thr Arg Arg Glu Pro Leu Glu Asn Ala Leu
    450                 455                 460

Thr Val Phe Thr Asp Gly Ser Ser Asn Gly Lys Ala Ala Tyr Thr Gly
465                 470                 475                 480

Pro Lys Glu Arg Val Ile Lys Thr Pro Tyr Gln Ser Ala Gln Arg Ala
                485                 490                 495

Glu Leu Val Ala Val Ile Thr Val Leu Gln Asp Phe Asp Gln Pro Ile
            500                 505                 510

Asn Ile Ile Ser Asp Ser Ala Tyr Val Val Gln Ala Thr Arg Asp Val
        515                 520                 525

Glu Thr Ala Leu Ile Lys Tyr Ser Met Asp Asp Gln Leu Asn Gln Leu
    530                 535                 540

Phe Asn Leu Leu Gln Gln Thr Val Arg Lys Arg Asn Phe Pro Phe Tyr
545                 550                 555                 560

Ile Thr His Ile Arg Ala His Thr Asn Leu Pro Gly Pro Leu Thr Lys
                565                 570                 575

Ala Asn Glu Gln Ala Asp Leu Leu Val Ser Ser Ala Leu Ile Lys Ala
            580                 585                 590

Gln Glu Leu His Ala Leu Thr His Val Asn Ala Ala Gly Leu Lys Asn
        595                 600                 605

Lys Phe Asp Val Thr Trp Lys Gln Ala Lys Asp Ile Val Gln His Cys
    610                 615                 620

Thr Gln Cys Gln Val Leu His Leu Pro Thr Gln Glu Ala Gly Val Asn
625                 630                 635                 640

Pro Arg Gly Leu Cys Pro Asn Ala Leu Trp Gln Met Asp Val Thr His
                645                 650                 655

Val Pro Ser Phe Gly Arg Leu Ser Tyr Val His Val Thr Val Asp Thr
            660                 665                 670

Tyr Ser His Phe Ile Trp Ala Thr Cys Gln Thr Gly Glu Ser Thr Ser
        675                 680                 685

His Val Lys Lys His Leu Leu Ser Cys Phe Ala Val Met Gly Val Pro
    690                 695                 700

Glu Lys Ile Lys Thr Asp Asn Gly Pro Gly Tyr Cys Ser Lys Ala Phe
705                 710                 715                 720

Gln Lys Phe Leu Ser Gln Trp Lys Ile Ser His Thr Thr Gly Ile Pro
                725                 730                 735

Tyr Asn Ser Gln Gly Gln Ala Ile Val Glu Arg Thr Asn Arg Thr Leu
            740                 745                 750

Lys Thr Gln Leu Val Lys Gln Lys Glu Gly Gly Asp Ser Lys Glu Cys
        755                 760                 765
```

-continued

```
Thr Thr Pro Gln Met Gln Leu Asn Leu Ala Leu Tyr Thr Leu Asn Phe
    770                 775                 780

Leu Asn Ile Tyr Arg Asn Gln Thr Thr Thr Ser Ala Glu Gln His Leu
785                 790                 795                 800

Thr Gly Lys Lys Asn Ser Pro His Glu Gly Lys Leu Ile Trp Trp Lys
                805                 810                 815

Asp Asn Lys Asn Lys Thr Trp Glu Ile Gly Lys Val Ile Thr Trp Gly
            820                 825                 830

Arg Gly Phe Ala Cys Val Ser Pro Gly Glu Asn Gln Leu Pro Val Trp
        835                 840                 845

Ile Pro Thr Arg His Leu Lys Phe Tyr Asn Glu Pro Ile Arg Asp Ala
    850                 855                 860

Lys Lys Ser Thr Ser Ala Glu Thr Glu Thr Ser Gln Ser Ser Thr Val
865                 870                 875                 880

Asp Ser Gln Asp Glu Gln Asn Gly Asp Val Arg Arg Thr Asp Glu Val
                885                 890                 895

Ala Ile His Gln Glu Gly Arg Ala Ala Asn Leu Gly Thr Thr Lys Glu
            900                 905                 910

Ala Asp Ala Val Ser Tyr Lys Ile Ser Arg Glu His Lys Gly Asp Thr
        915                 920                 925

Asn Pro Arg Glu Tyr Ala Ala Cys Ser Leu Asp Asp Cys Ile Asn Gly
    930                 935                 940

Gly Lys Ser Pro Tyr Ala Cys Arg Ser Ser Cys Ser
945                 950                 955
```

<210> SEQ ID NO 149
<211> LENGTH: 699
<212> TYPE: PRT
<213> ORGANISM: Homo sapiens

<400> SEQUENCE: 149

```
Met Asn Pro Ser Glu Met Gln Arg Lys Ala Pro Pro Arg Arg Arg Arg
1               5                   10                  15

His Arg Asn Arg Ala Pro Leu Thr His Lys Met Asn Lys Met Val Thr
            20                  25                  30

Ser Glu Glu Gln Met Lys Leu Pro Ser Thr Lys Lys Ala Glu Pro Pro
        35                  40                  45

Thr Trp Ala Gln Leu Lys Lys Leu Thr Gln Leu Ala Thr Lys Tyr Leu
    50                  55                  60

Glu Asn Thr Lys Val Thr Gln Thr Pro Glu Ser Met Leu Leu Ala Ala
65                  70                  75                  80

Leu Met Ile Val Ser Met Val Val Ser Leu Pro Met Pro Ala Gly Ala
                85                  90                  95

Ala Ala Ala Asn Tyr Thr Tyr Trp Ala Tyr Val Pro Phe Pro Pro Leu
            100                 105                 110

Ile Arg Ala Val Thr Trp Met Asp Asn Pro Thr Glu Val Tyr Val Asn
        115                 120                 125

Asp Ser Val Trp Val Pro Gly Pro Ile Asp Asp Arg Cys Pro Ala Lys
    130                 135                 140

Pro Glu Glu Glu Gly Met Met Ile Asn Ile Ser Ile Gly Tyr His Tyr
145                 150                 155                 160

Pro Pro Ile Cys Leu Gly Arg Ala Pro Gly Cys Leu Met Pro Ala Val
                165                 170                 175

Gln Asn Trp Leu Val Glu Val Pro Thr Val Ser Pro Ile Cys Arg Phe
            180                 185                 190
```

-continued

```
Thr Tyr His Met Val Ser Gly Met Ser Leu Arg Pro Arg Val Asn Tyr
        195                 200                 205

Leu Gln Asp Phe Ser Tyr Gln Arg Ser Leu Lys Phe Arg Pro Lys Gly
    210                 215                 220

Lys Pro Cys Pro Lys Glu Ile Pro Lys Glu Ser Lys Asn Thr Glu Val
225                 230                 235                 240

Leu Val Trp Glu Glu Cys Val Ala Asn Ser Ala Val Ile Leu Gln Asn
                245                 250                 255

Asn Glu Phe Gly Thr Ile Ile Asp Trp Ala Pro Arg Gly Gln Phe Tyr
            260                 265                 270

His Asn Cys Ser Gly Gln Thr Gln Ser Cys Pro Ser Ala Gln Val Ser
        275                 280                 285

Pro Ala Val Asp Ser Asp Leu Thr Glu Ser Leu Asp Lys His Lys His
    290                 295                 300

Lys Lys Leu Gln Ser Phe Tyr Pro Trp Glu Trp Gly Glu Lys Gly Ile
305                 310                 315                 320

Ser Thr Pro Arg Pro Lys Ile Val Ser Pro Val Ser Gly Pro Glu His
                325                 330                 335

Pro Glu Leu Trp Arg Leu Thr Val Ala Ser His His Ile Arg Ile Trp
            340                 345                 350

Ser Gly Asn Gln Thr Leu Glu Thr Arg Asp Arg Lys Pro Phe Tyr Thr
        355                 360                 365

Ile Asp Leu Asn Ser Ser Leu Thr Val Pro Leu Gln Ser Cys Val Lys
    370                 375                 380

Pro Pro Tyr Met Leu Val Val Gly Asn Ile Val Ile Lys Pro Asp Ser
385                 390                 395                 400

Gln Thr Ile Thr Cys Glu Asn Cys Arg Leu Leu Thr Cys Ile Asp Ser
                405                 410                 415

Thr Phe Asn Trp Gln His Arg Ile Leu Leu Val Arg Ala Arg Glu Gly
            420                 425                 430

Val Trp Ile Pro Val Ser Met Asp Arg Pro Trp Glu Ala Ser Pro Ser
        435                 440                 445

Val His Ile Leu Thr Glu Val Leu Lys Gly Val Leu Asn Arg Ser Lys
    450                 455                 460

Arg Phe Ile Phe Thr Leu Ile Ala Val Ile Met Gly Leu Ile Ala Val
465                 470                 475                 480

Thr Ala Thr Ala Ala Val Ala Gly Val Ala Leu His Ser Ser Val Gln
                485                 490                 495

Ser Val Asn Phe Val Asn Asp Trp Gln Lys Asn Ser Thr Arg Leu Trp
            500                 505                 510

Asn Ser Gln Ser Ser Ile Asp Gln Lys Leu Ala Asn Gln Ile Asn Asp
        515                 520                 525

Leu Arg Gln Thr Val Ile Trp Met Gly Asp Arg Leu Met Ser Leu Glu
    530                 535                 540

His Arg Phe Gln Leu Gln Cys Asp Trp Asn Thr Ser Asp Phe Cys Ile
545                 550                 555                 560

Thr Pro Gln Ile Tyr Asn Glu Ser Glu His His Trp Asp Met Val Arg
                565                 570                 575

Arg His Leu Gln Gly Arg Glu Asp Asn Leu Thr Leu Asp Ile Ser Lys
            580                 585                 590

Leu Lys Glu Gln Ile Phe Glu Ala Ser Lys Ala His Leu Asn Leu Val
        595                 600                 605
```

-continued

```
Pro Gly Thr Glu Ala Ile Ala Gly Val Ala Asp Gly Leu Ala Asn Leu
    610                 615                 620

Asn Pro Val Thr Trp Val Lys Thr Ile Gly Ser Thr Thr Ile Ile Asn
625                 630                 635                 640

Leu Ile Leu Ile Leu Val Cys Leu Phe Cys Leu Leu Leu Val Cys Arg
                645                 650                 655

Cys Thr Gln Gln Leu Arg Arg Asp Ser Asp His Arg Glu Arg Ala Met
            660                 665                 670

Met Thr Met Ala Val Leu Ser Lys Arg Lys Gly Gly Asn Val Gly Lys
        675                 680                 685

Ser Lys Arg Asp Gln Ile Val Thr Val Ser Val
    690                 695
```

<210> SEQ ID NO 150
<211> LENGTH: 968
<212> TYPE: DNA
<213> ORGANISM: Homo sapiens

<400> SEQUENCE: 150

```
tgtggggaaa agcaagagag atcagattgt tactgtgtct gtgtagaaag aagtagacat     60

aggagactcc attttgttat gtactaagaa aaattcttct gccttgagat tctgttaatc    120

tatgacctta cccccaaccc cgtgctctct gaaacatgtg ctgtgtccac tcagggttaa    180

atggattaag ggcggtgcag gatgtgcttt gttaaacaga tgcttgaagg cagcatgctc    240

cttaagagtc atcaccactc cctaatctca agtacccagg gacacaaaaa ctgcggaagg    300

ccgcagggac ctctgcctag gaaagccagg tattgtccaa cgtttctccc catgtgatag    360

cctgaaatat ggcctcgtgg gaagggaaag acctgaccgt cccccagccc gacacccgta    420

aagggtctgt gctgaggagg attagtaaaa gaggaaggaa tgcctcttgc agttgagaca    480

agaggaaggc atctgtctcc tgcctgtccc tgggcaatgg aatgtctcgg tataaaaccc    540

gattgtatgc tccatctact gagataggga aaaaccgcct tagggctgga ggtgggacct    600

gcgggcagca atactgcttt gtaaagcact gagatgttta tgtgtatgca tatctaaaag    660

cacagcactt aatcctttac attgtctatg atgcaaagac ctttgttcac atgtttgtct    720

gctgaccctc tccccacaat tgtcttgtga ccctgacaca tccccctctt cgagaaacac    780

ccacagatga tcagtaaata ctaagggaac tcagaggctg gcgggatcct ccatatgctg    840

aacgctggtt ccccgggtcc ccttctttct ttctctatac tttgtctctg tgtctttttc    900

ttttccaaat ctctcgtccc accttacgag aaacacccac aggtgtgtag gggcaaccca    960

cccctaca                                                             968
```

<210> SEQ ID NO 151
<211> LENGTH: 962
<212> TYPE: DNA
<213> ORGANISM: Homo sapiens

<400> SEQUENCE: 151

```
tgtggggaaa agcaagagag atcagattgt cactgtatct gtgtagaaag aagtagacat     60

gggagactcc attttgttat gtactaagaa aaattcttct gccttgagat tctgtgacct    120

tacccccaac cccgtgctct ctgaaacatg tgctgtgtca aactcagggt taaatggatt    180

aagggcggtg caggatgtgc tttgttaaac agatgcttga aggcagcatg ctccttaaga    240

gtcatcacca ctccctaatc tcaagtaccc agggacacaa acactgcgga aggccgcagg    300

gacctctgcc taggaaagcc aggtattgtc caaggtttct ccccatgtga tagtctgaaa    360
```

-continued

```
tatggcctcg tgggaaggga aagacctgac cgtcccccag cccgacaccc gtaaagggtc    420

tgtgctgagg aggattagta aaagaggaag gcatgcctct tgcagttgag acaagaggaa    480

ggcatctgtc tcctgcccgt ccctgggcaa tggaatgtct cggtataaaa ccggattgta    540

cgttccatct actgagatag ggaaaaaccg ccttagggct ggaggtggga cctgcgggca    600

gcaatactgc tttttaaagc attgagatgt ttatgtgtat gcatatctaa aagcacagca    660

cttaatcctt taccttgtct atgatgcaaa gatctttgtt cacgtgtttg tctgctgacc    720

ctctccccac tattgtcttg tgaccctgac acatcccccct ctcggagaaa cacccacgaa    780

tgaccaataa atactaaagg gaactcagag gctggcggga tcctccatat gctgaacgct    840

ggttccccgg gccccttat ttctttctct acactttgtc tctgtgtctt tttctttcct    900

aagtctctcg ttccaccta cgagaaacac ccacaggtgt ggaggggcaa cccaccccta    960

ca                                                                  962
```

```
<210> SEQ ID NO 152
<211> LENGTH: 968
<212> TYPE: DNA
<213> ORGANISM: Homo sapiens

<400> SEQUENCE: 152

tgtggggaaa agcaagagag atcagattgt tactgtgtct gtgtagaaag aagtagacat     60

gggagactcc attttgttat gtgctaagaa aaattcttct gccttgagat tctgttaatc    120

tatgacctta cccccaaccc cgtgctctct gaaacatgtg ctgtgtcaac tcagggttga    180

atggattaag ggcggtgcag gatgtgcttt gttaaacaga tgcttgaagg cagcatgctc    240

cttaagagtc atcaccactc cctaatctca agtacccagg gacacaaaaa ctgcggaagg    300

ccgcagggac ctctgcctag gaaagccagg tattgtccaa ggtttctccc catgtgatag    360

tctgaaatat ggcctcgtgg gaagggaaag acctgaccat cccccagccc gacacccata    420

aagggtctgt gctgaggagg attagtataa gaggaaggca tgcctcttgc agttgagaca    480

agaggaaggc atctgtctcc tgcctgtccc tgggcaatgg aatgtctcgg tataaaaccc    540

gattgtatgc tccatctact gagataggga aaaaccgcct tagggctgga ggtgggacct    600

gcgggcagca atactgcctt gtaaagcatt gagatgttta tgtgtatgca tatctaaaag    660

cacagcactt aatcctttac attgtctatg atgcaaagac ctttgttcac gtgtttgtct    720

gctgaccctc tccccacaat tgtcttgtga ccctgacaca tccccctctt tgagaaacac    780

ccacagatga tcaataaata ctaagggaac tcagaggctg gcgggatcct ccatatgctg    840

aacgctggtt ccccggttcc ccttatttct ttctctatac tttgtctctg tgtctttttc    900

ttttccaaat ctctcgtccc accttacgag aaacacccac aggtgtgtag ggcaacccca    960

cccctaca                                                            968
```

```
<210> SEQ ID NO 153
<211> LENGTH: 968
<212> TYPE: DNA
<213> ORGANISM: Homo sapiens

<400> SEQUENCE: 153

tgtggggaaa agcaagagag atcagattgt tacagtgtct gtgtagaaag aagtagacat     60

aggagactcc attttgttct gtactaagaa aaattcttct gccttgaaat tctgttaatc    120

tataacctta cccccaaccc cgtgctcttt gaaacatgtg ctgtgtcaac tcagagttaa    180
```

-continued

```
atggattaag tgcggtgcaa gatgtgcttt gttaaacaga tgcttgaagg cagcatgctc    240

cttgagagtc atcaccactc cctaatctca agtacccagg gacacaaaaa ctgcggaagg    300

cctcagggac ctctgcctag gaaagccagg tattgtccaa ggtttctccc catgtgatag    360

tctgaaatat ggcctcgtgg gaagggaaag acctgaccat cccccagccc gacacccgta    420

aagggtctgt gctgaggagg attagtaaaa gaggaaggaa cgcctcttgc agttgagaca    480

agaggaaggc atctgtctcc tgcctgtccc tgggcaatgg aatgtcccgg tataaaaccc    540

gattgtatgc tccatctact gagataggga aaaaccgcct tagggctgga ggtgggacct    600

gcgggcagca atactgcttt gtaaagcatt gagctgttta tgtgtatgca tatctaaaag    660

cacagcactt aatcctttac attgtctatg atgcaaagac ctttgttcac gtgtttgtct    720

gctgaccctc tccccacaat tgtcttgtga ccctgacaca tccccctctt cgagaaacac    780

ccacgaatga tgaataaata ctaagggaac tcagaggctg gcgggatcct ccatatgctg    840

aacgctggtt ccccgggtcc ccttacttct ttctctgtac tttgtctctg tgtctttttc    900

tttcctaagt ctctcgttcc accttacgag aaatacccac aggtgtggag gggcaaccca    960

cccctaca                                                             968
```

<210> SEQ ID NO 154
<211> LENGTH: 968
<212> TYPE: DNA
<213> ORGANISM: Homo sapiens

<400> SEQUENCE: 154

```
tgtggggaaa agcaagagag atcagattgt tactgtgtct gtgtagaaag aagtagacat     60

aggagactcc attttgttct gtactaagaa aaattcttct gccttgagat tctgttaatc    120

tataacctta cccccaaccc cgtgctctct gaaacatgtg ctatgtcaac tcagagttga    180

atggattaag ggcggtgcaa gatgtgcttt gttaaacaga tgcttgaagg cagcacgctc    240

cttaagagtc atcaccactc cctaatctca agtacccagg gacacaaaaa ctgcggaagg    300

ccgcagggac ctctgcctag gaaagccagg tattgtccaa ggtttctccc catgtgatag    360

tctgaaatat ggcctcgtgg gaagggaaag acctgaccat cccccagccc gacacctgta    420

aagggtctgt gctgaggagg attagtataa gaggaaggca tgcctcttgc agttgagaca    480

agaggaaggc atctgtctcc tgcccgtccc tgggcaatgg aatgtctcgg tataaaaccc    540

gattgtatgt tccatctact gagataggga aaaaccgcct tagggctgga ggtgggacct    600

gcgggcagca atactgcttt gtaaagcatt gagatgttta tgtgtatgca tatctaaaag    660

cacagcactt aatcctttac cttgtctatg atgcaaagac ctttgttcac gtgtttgtct    720

gctgaccctc tccccacgat tgtcttgtga ccctgacaca tccccgtctt cgagaaacac    780

ccacgaatga tcaataaata ctaagggaac tcagaggctg gcgggatcct ccatatgctg    840

aacgctggtt ccccaggtcc ccttatttct ttctctatac tttgtctctg tgtctttttc    900

ttttccaagt ctctcgttcc atcttacgag aaacacccac aggtgtggag gggcaaccca    960

cccctaca                                                             968
```

<210> SEQ ID NO 155
<211> LENGTH: 150
<212> TYPE: DNA
<213> ORGANISM: Homo sapiens -continued

<400> SEQUENCE: 155
gagataggga aaaaccgcct tagggctgga ggtgggacct gcgggcagca atactgcttt 60
gtaaagcact gagatgttta tgtgtatgca tatctaaaag cacagcactt aatcctttac 120
attgtctatg atgcaaagac ctttgttcac 150

<210> SEQ ID NO 156
<211> LENGTH: 258
<212> TYPE: DNA
<213> ORGANISM: Homo sapiens

<400> SEQUENCE: 156
atgtttgtct gctgaccctc tccccacaat tgtcttgtga ccctgacaca tccccctctt 60
cgagaaacac ccacagatga tcagtaaata ctaagggaac tcagaggctg gcgggatcct 120
ccatatgctg aacgctggtt ccccgggtcc ccttctttct ttctctatac tttgtctctg 180
tgtctttttc ttttccaaat ctctcgtccc accttacgag aaacacccac aggtgtgtag 240
gggcaaccca cccctaca 258

<210> SEQ ID NO 157
<211> LENGTH: 2707
<212> TYPE: DNA
<213> ORGANISM: Homo sapiens
<220> FEATURE:
<221> NAME/KEY: misc_feature
<222> LOCATION: (1)..(2707)
<223> OTHER INFORMATION: N=A,G,C,T

<400> SEQUENCE: 157
nnnnnnnnnn nnnnnnnnnn nnnnnnnnnn nnnnnnnnnn nnnnnnnnnn nnnnnnnnnn 60
nnnacatttg aagttctaca atgaacccat cngagatgca aagaaannnn nnnnnnagcn 120
cctccncgga gacggaaaca ccgcaatcga gcancnnnnn nnnnnnnnnt ngactcacaa 180
gatgaanaaa atggtgannt cagaagaaca gatgaagttg ccatccacca agaangcnga 240
gccgccgact tgggcacaan taaagaagct gacacagtta gctanaaaan nnnnnctnga 300
gaacacaaag gtgacacaaa ctccagagan tatgctgctt gcagctttga tgattgtatc 360
aatggtggta agtctcccna tgcctgcagg agcagctgca gctaantata cntactgggc 420
ctatgtgcct ttcccgccct taattcgggc agtcacatgg atggataatc ctattgaagt 480
atatgttaat aatagtgtat gggntacctg gccccacaga tgatcgttgc cctgccaaac 540
ctgaggaaga aggaatgatg ataaatattt ccattgggta tcnttatcct cctatttgcc 600
tagggagagc accaggatgt ttaatngcct gcantccaaa attggttggt agaagtacct 660
actgtcagtn ccancagtag attcacttat cacatggtaa gnggnatgtc actcaggcca 720
cnggtaaatn atttacanga cttttcttat caaagatcat taaaatttag ncctaaaggg 780
aaaccttgcc ccaaggaaat tcccaaagna tcaaaanann cagaagtttt agtttgggaa 840
gaatgtgtgg cnaatagtgc ngtgatatta caaaacaatg aatttggaac tattatagat 900
tgggcacctc gaggtcaatt ctancacann nnnnnnnnnn nnnnnnnnnn nnattgcnca 960
ggncaaactc antcntgtcc nagngcacaa gnnnnnnnnn nnnnnagtcc agctgttgat 1020
agngacttaa cagaaagtnt agacnaannt nannntanaa nnttanantc nntctanccn 1080
tggnaatggg gngaaaangg aatntcnncn nnnnnnnnnn nnnnnnnnnn nnnnnnnnnn 1140
nnnnnnnnnn nnnnnnnnnn nnnnnnnnnn nnnnnnnnnn nnnnnnnnnn nnnnnnnnnn 1200
nnnnnnnnnn nnnnnnnnnn nnnnnnnnnn nnnnnnnnnn nnnnnnnnnn nnnnnnnnnn 1260

-continued

```
nnnnnnnnnn nnnnnnnnnn nnnnnnnnnn nnnnnnnnnn nnnnnnnnnn nnnnnnnnnn   1320

nnnnnnnnnn nnnnnnnnnn nnnnnnnnnn nnnnnnnnnn nnnnnnnnnn nnnnnnnnnn   1380

nnnnnnnnnn nnnnnnnnnn nnnnnnnnnn nnnnnnnnnn nnnnnnnnnn nnnnnnnnnn   1440

nnnnnnnnnn nccnngacca aanntantna gtcctgttnc tggtcctgaa catccagaat   1500

tatggangct tactgtggcc tcannaccac attagaattt ggtctggaaa tcaanctnta   1560

gaaacaagag atcntaagcc atnttatact atcnacctaa attccagtct nacanttcct   1620

ttncaaagtt gngtaaagcc cccttatatn gctagttgta ggaaatannt agttattaaa   1680

ccagantccc aaactatann acctgtgaaa attgtagatt gtttacttgc attgattcaa   1740

cttttaattg gcagcaccgt attctgctng tgagagcaag aganggngtg tggatccctg   1800

tgtccatgga ccgaccgtgg gaggcntcnc catccntcca tattttnacn gaagtattaa   1860

aaggnnttnt aantagatcc aaaagattca tttttacttt aattgcagtg attatgggnn   1920

tnattgcagt cacagctacn gctgcngnng cngganttgc nttncactcn tctgttcann   1980

cngnanantn tgtnaatnat tggcaaaana anttcnncaa nattgtggaa ttcncananc   2040

nnnnatngat caaaaattgg caaatcaaat taatgatctt agacaaactg tcatttggat   2100

gggaganagn ctcatgagct tngaanatcn tttncagtta cantgtgact ggaatacgtc   2160

agatttttgt attacaccnc aannntataa tgagtctgag catcactggg acatggttag   2220

angccatcta canggaagag aagataatct nactttagac atttcnaaat taaaagaann   2280

nnnnnnnnnn nncaaatttt nnaancatca aaagcccatt taaatttggt gccaggaact   2340

gaggcaatng nnnnagntgc tgatggcctc ncaaatctta accctgtcac ttgggttaan   2400

accatnngaa gtncnacnat tntaaatntc atattaatcc ttgtntgcct gttntgtctg   2460

ttgttnnagt ctncaggtgt anccancagc tccgaagaga cagcgaccan cnagaacggg   2520

ccatgatgac gatggnggtt ttgtcnaaaa gaaaaggggg nnanatgtng ggaaaagnna   2580

gagagatcag antgttactg tngtctntgt agaaanangn agacatanga gactccattt   2640

tgnnntgtac nnnnnnnnnn nnnnnnnnnn nnnnnnnnnn nnnnnnnnnn nnnnnnnnnn   2700

nnnnnnn                                                             2707


<210> SEQ ID NO 158
<211> LENGTH: 673
<212> TYPE: PRT
<213> ORGANISM: Homo sapiens
<220> FEATURE:
<221> NAME/KEY: MISC_FEATURE
<222> LOCATION: (1)..(673)
<223> OTHER INFORMATION: Xaa=Any amino acid

<400> SEQUENCE: 158

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Cys Pro Trp Phe Pro Glu Gln Gly Xaa Leu Asp Leu Xaa Asp
    50                  55                  60

Trp Lys Arg Ile Gly Xaa Glu Leu Lys Gln Ala Gly Arg Lys Gly Asn
65                  70                  75                  80

Xaa Xaa Xaa Xaa Xaa Xaa Xaa Xaa Xaa Xaa Xaa Xaa Xaa Xaa Xaa Xaa
                85                  90                  95
```

-continued

```
Xaa Xaa Xaa Xaa Xaa Xaa Xaa Xaa Xaa Xaa Xaa Xaa Xaa Xaa Asp Ala
            100                 105                 110

Pro Gly Ser Cys Ile Ile Asp Cys Asn Glu Xaa Thr Xaa Lys Lys Ser
        115                 120                 125

Gln Lys Glu Thr Glu Xaa Leu His Cys Glu Tyr Val Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Ala Gly
            180                 185                 190

Gln Val Xaa Val Thr Leu Gln Pro Gln Xaa Gln Val Lys Glu Asn Lys
        195                 200                 205

Thr Gln Xaa Pro Val Ala Tyr Gln Tyr Trp Pro Pro Xaa Xaa Xaa Xaa
    210                 215                 220

Xaa Xaa Xaa Xaa Xaa Xaa Ser Gln Tyr Gly Tyr Xaa Gly Met Pro Pro
225                 230                 235                 240

Ala Xaa Gln Xaa Arg Xaa Pro Tyr Pro Gln Pro Pro Thr Xaa Arg Xaa
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa Xaa
    370                 375                 380

Xaa Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa Xaa
                405                 410                 415

Xaa Xaa Xaa Xaa Xaa Xaa Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa Xaa Xaa Xaa
    450                 455                 460

Xaa Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa Xaa
                485                 490                 495

Xaa Xaa Xaa Xaa Xaa Xaa Xaa Xaa Xaa Xaa Xaa Xaa Xaa Xaa Xaa Xaa
            500                 505                 510
```

-continued

```
Xaa Xaa Xaa Xaa Xaa Xaa Xaa Xaa Xaa Xaa Xaa Xaa Xaa Xaa Xaa Xaa
        515                 520                 525

Xaa Xaa Xaa Xaa Xaa Xaa Xaa Xaa Xaa Xaa Xaa Xaa Xaa Xaa Xaa Xaa
    530                 535                 540

Xaa Xaa Xaa Xaa Xaa Xaa Xaa Xaa Xaa Xaa Xaa Xaa Xaa Xaa Xaa Xaa
545                 550                 555                 560

Xaa Xaa Xaa Xaa Xaa Xaa Xaa Xaa Xaa Xaa Xaa Xaa Xaa Xaa Xaa Xaa
                565                 570                 575

Xaa Xaa Xaa Xaa Xaa Xaa Xaa Xaa Xaa Xaa Xaa Xaa Xaa Xaa Xaa Xaa
            580                 585                 590

Xaa Xaa Xaa Xaa Xaa Xaa Xaa Xaa Cys Xaa Ser Lys Phe Asp Lys Xaa
        595                 600                 605

Gly Gln Pro Leu Ser Gly Asn Xaa Xaa Xaa Xaa Xaa Xaa Xaa Xaa Xaa
    610                 615                 620

Xaa Xaa Xaa Xaa Xaa Xaa Xaa Xaa Xaa Xaa Xaa Xaa Xaa Xaa Xaa Xaa
625                 630                 635                 640

Xaa Xaa Xaa Xaa Xaa Xaa Xaa Xaa Xaa Xaa Xaa Xaa Xaa Xaa Xaa Xaa
                645                 650                 655

Xaa Xaa Xaa Xaa Xaa Xaa Xaa Xaa Xaa Xaa Xaa Xaa Xaa Xaa Xaa Xaa
            660                 665                 670

Xaa


<210> SEQ ID NO 159
<211> LENGTH: 1035
<212> TYPE: PRT
<213> ORGANISM: Homo sapiens
<220> FEATURE:
<221> NAME/KEY: MISC_FEATURE
<222> LOCATION: (1)..(1035)
<223> OTHER INFORMATION: Xaa=Any amino acid

<400> SEQUENCE: 159

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190
```

-continued

```
Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Asp Xaa Leu Ala Pro Leu
                245                 250                 255

Gln Leu Leu Ile Phe Ala Thr Ala His Ser Xaa Thr Gly Ile Ile Ile
            260                 265                 270

Gln Asn Thr Asp Leu Val Glu Trp Ser Phe Leu Pro His Ser Thr Val
        275                 280                 285

Lys Thr Phe Thr Leu Tyr Leu Asp Gln Met Ala Thr Leu Ile Gly Gln
    290                 295                 300

Xaa Arg Leu Arg Ile Ile Xaa Leu Cys Gly Asn Asp Pro Asp Lys Ile
305                 310                 315                 320

Xaa Val Pro Xaa Xaa Lys Xaa Gln Val Arg Gln Ala Phe Ile Xaa Ser
                325                 330                 335

Gly Ala Trp Xaa Ile Gly Leu Ala Asn Phe Leu Gly Ile Ile Asp Asn
            340                 345                 350

His Tyr Pro Lys Thr Lys Ile Phe Gln Phe Leu Lys Leu Thr Thr Trp
        355                 360                 365

Ile Leu Pro Lys Ile Thr Arg Arg Glu Pro Leu Glu Asn Ala Leu Thr
    370                 375                 380

Val Phe Thr Asp Gly Ser Ser Asn Gly Lys Ala Ala Tyr Thr Gly Pro
385                 390                 395                 400

Lys Glu Arg Val Ile Lys Thr Pro Tyr Gln Ser Ala Gln Arg Ala Glu
                405                 410                 415

Leu Val Ala Val Ile Thr Val Leu Gln Asp Phe Asp Gln Pro Ile Asn
            420                 425                 430

Ile Ile Ser Asp Ser Ala Tyr Val Val Gln Ala Thr Arg Asp Val Glu
        435                 440                 445

Thr Ala Leu Ile Lys Tyr Ser Xaa Asp Asp Xaa Leu Asn Gln Leu Phe
    450                 455                 460

Asn Leu Leu Gln Gln Thr Val Arg Lys Arg Asn Phe Pro Phe Tyr Ile
465                 470                 475                 480

Thr His Ile Arg Ala His Thr Asn Leu Pro Gly Pro Leu Thr Lys Ala
                485                 490                 495

Asn Glu Gln Ala Asp Leu Leu Val Ser Ser Ala Xaa Ile Lys Ala Gln
            500                 505                 510

Glu Leu Xaa Ala Leu Thr His Val Asn Ala Ala Gly Leu Lys Asn Lys
        515                 520                 525

Phe Asp Val Thr Trp Lys Gln Ala Lys Asp Ile Val Gln His Cys Thr
    530                 535                 540

Gln Cys Gln Val Leu His Leu Xaa Thr Gln Glu Ala Gly Val Asn Pro
545                 550                 555                 560

Arg Gly Leu Cys Pro Asn Ala Leu Trp Gln Met Asp Xaa Thr His Val
                565                 570                 575

Xaa Ser Phe Gly Arg Leu Ser Tyr Val His Val Thr Val Asp Thr Tyr
            580                 585                 590

Ser His Phe Ile Trp Ala Thr Cys Gln Thr Gly Glu Ser Thr Ser His
        595                 600                 605
```

-continued

```
Val Lys Lys His Leu Leu Ser Cys Phe Ala Val Met Gly Val Pro Glu
    610                 615                 620

Lys Ile Lys Thr Asp Asn Gly Pro Gly Tyr Cys Ser Lys Ala Phe Gln
625                 630                 635                 640

Lys Phe Leu Ser Gln Trp Lys Ile Ser His Thr Thr Gly Ile Pro Tyr
                645                 650                 655

Asn Ser Gln Gly Gln Ala Ile Val Glu Arg Thr Asn Arg Thr Leu Lys
            660                 665                 670

Thr Gln Leu Val Lys Gln Lys Glu Gly Gly Asp Ser Lys Glu Cys Thr
        675                 680                 685

Thr Pro Gln Met Gln Leu Asn Leu Ala Leu Tyr Thr Leu Asn Phe Leu
    690                 695                 700

Asn Ile Tyr Arg Asn Gln Thr Thr Thr Ser Ala Xaa Gln His Leu Thr
705                 710                 715                 720

Gly Lys Lys Xaa Ser Pro His Glu Gly Lys Leu Ile Trp Trp Lys Asp
                725                 730                 735

Xaa Lys Asn Lys Thr Trp Glu Ile Gly Lys Val Ile Thr Trp Gly Arg
            740                 745                 750

Gly Phe Ala Cys Val Ser Pro Gly Glu Asn Gln Leu Pro Val Trp Ile
        755                 760                 765

Pro Thr Arg His Leu Lys Phe Tyr Asn Glu Pro Ile Xaa Asp Ala Lys
    770                 775                 780

Lys Xaa Xaa Ser Xaa Glu Xaa Xaa Thr Xaa Xaa Xaa Xaa Xaa Xaa Xaa
785                 790                 795                 800

Xaa Xaa Xaa Xaa Xaa Xaa Xaa Xaa Xaa Xaa Xaa Xaa Xaa Xaa Xaa Xaa
                805                 810                 815

Xaa Xaa Xaa Xaa Xaa Xaa Xaa Xaa Xaa Xaa Xaa Xaa Xaa Xaa Xaa Xaa
            820                 825                 830

Xaa Xaa Xaa Xaa Xaa Xaa Xaa Xaa Xaa Xaa Xaa Xaa Xaa Xaa Xaa Xaa
        835                 840                 845

Xaa Xaa Xaa Xaa Xaa Xaa Xaa Xaa Xaa Xaa Xaa Xaa Xaa Xaa Xaa Xaa
    850                 855                 860

Xaa Xaa Xaa Xaa Xaa Xaa Xaa Xaa Xaa Xaa Xaa Xaa Xaa Xaa Xaa Xaa
865                 870                 875                 880

Xaa Xaa Xaa Xaa Xaa Xaa Xaa Xaa Xaa Xaa Xaa Xaa Xaa Xaa Xaa Xaa
                885                 890                 895

Xaa Xaa Xaa Xaa Xaa Xaa Xaa Xaa Xaa Xaa Xaa Xaa Xaa Xaa Xaa Xaa
            900                 905                 910

Xaa Xaa Xaa Xaa Xaa Xaa Xaa Xaa Xaa Xaa Xaa Xaa Xaa Xaa Xaa Xaa
        915                 920                 925

Xaa Xaa Xaa Xaa Xaa Xaa Xaa Xaa Xaa Xaa Xaa Thr Ile Xaa Xaa Xaa
    930                 935                 940

Xaa Xaa Xaa Xaa Xaa Xaa Xaa Xaa Xaa Xaa Xaa Xaa Xaa Xaa Xaa Xaa
945                 950                 955                 960

Xaa Xaa Xaa Xaa Xaa Xaa Xaa Xaa Ala Xaa Xaa Xaa Asp Xaa Xaa Xaa
                965                 970                 975

Xaa Xaa Xaa Lys Xaa Xaa Xaa Xaa Xaa Xaa Xaa Xaa Xaa Xaa Pro Xaa
            980                 985                 990

Glu Trp Gly Xaa Xaa Xaa Ile Xaa  Xaa Xaa Xaa Xaa Xaa  Xaa Xaa Ser
        995                 1000                1005
```

-continued

```
Pro Xaa  Ser Xaa Xaa Xaa Xaa  Xaa Xaa Xaa Xaa Xaa  Xaa Xaa Xaa
    1010                 1015                 1020

Xaa Xaa  Xaa Xaa Xaa Xaa Xaa  Xaa Xaa Xaa Xaa Xaa
    1025                 1030                 1035


<210> SEQ ID NO 160
<211> LENGTH: 1081
<212> TYPE: PRT
<213> ORGANISM: Homo sapiens
<220> FEATURE:
<221> NAME/KEY: MISC_FEATURE
<222> LOCATION: (1)..(1081)
<223> OTHER INFORMATION: Xaa=Any amino acid

<400> SEQUENCE: 160

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa Xaa
305                 310                 315                 320
```

-continued

```
Xaa Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa Xaa
    370                 375                 380

Xaa Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa Xaa
                405                 410                 415

Xaa Xaa Xaa Xaa Xaa Xaa Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa Xaa Xaa Xaa
    450                 455                 460

Xaa Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Leu Ile Xaa
                485                 490                 495

Xaa Val Thr Trp Met Asp Asn Pro Xaa Glu Val Tyr Val Asn Asp Ser
            500                 505                 510

Val Trp Val Pro Gly Pro Xaa Asp Asp Xaa Cys Pro Ala Lys Pro Glu
        515                 520                 525

Glu Glu Gly Met Met Ile Asn Ile Ser Ile Xaa Tyr Xaa Tyr Pro Pro
    530                 535                 540

Ile Cys Leu Gly Arg Ala Pro Gly Cys Leu Met Pro Ala Val Gln Asn
545                 550                 555                 560

Trp Leu Val Glu Val Pro Thr Val Ser Pro Xaa Xaa Arg Phe Thr Tyr
                565                 570                 575

His Met Val Ser Gly Met Ser Leu Arg Pro Arg Val Asn Xaa Leu Gln
            580                 585                 590

Asp Phe Ser Tyr Gln Arg Ser Leu Lys Phe Arg Pro Lys Gly Lys Pro
        595                 600                 605

Cys Pro Lys Glu Ile Pro Lys Glu Ser Lys Asn Thr Glu Val Leu Val
    610                 615                 620

Trp Glu Glu Cys Val Ala Asn Ser Xaa Val Ile Leu Gln Asn Asn Glu
625                 630                 635                 640

Phe Gly Thr Ile Ile Asp Trp Ala Pro Arg Gly Gln Phe Tyr His Asn
                645                 650                 655

Cys Ser Gly Gln Thr Gln Ser Cys Xaa Ser Ala Gln Val Ser Pro Ala
            660                 665                 670

Val Asp Ser Asp Leu Thr Glu Ser Leu Asp Lys His Lys His Lys Lys
        675                 680                 685

Leu Gln Ser Phe Tyr Pro Trp Glu Trp Gly Glu Lys Gly Ile Ser Thr
    690                 695                 700

Pro Arg Pro Xaa Ile Ile Ser Pro Val Ser Gly Pro Glu His Pro Glu
705                 710                 715                 720

Leu Trp Xaa Xaa Xaa Xaa Xaa Xaa Xaa Xaa Xaa Arg Ile Xaa Xaa Xaa
                725                 730                 735
```

-continued

```
Xaa Xaa Xaa Xaa Xaa Xaa Xaa Xaa Xaa Xaa Xaa Xaa Xaa Xaa Xaa Xaa
            740                 745                 750

Leu Asn Ser Xaa Leu Thr Val Pro Leu Gln Ser Cys Val Lys Pro Xaa
        755                 760                 765

Xaa Xaa Xaa Xaa Xaa Xaa Xaa Xaa Xaa Xaa Xaa Xaa Xaa Xaa Xaa Xaa
    770                 775                 780

Xaa Xaa Xaa Xaa Xaa Xaa Xaa Xaa Xaa Xaa Xaa Xaa Asp Ser Thr Xaa
785                 790                 795                 800

Xaa Trp Xaa Xaa Xaa Ile Xaa Leu Xaa Xaa Xaa Xaa Xaa Xaa Xaa Xaa
                805                 810                 815

Xaa Xaa Xaa Xaa Xaa Xaa Xaa Xaa Xaa Xaa Xaa Xaa Xaa Xaa Xaa Xaa
            820                 825                 830

Xaa Xaa Xaa Xaa Xaa Xaa Xaa Xaa Xaa Xaa Xaa Xaa Xaa Xaa Xaa Xaa
        835                 840                 845

Xaa Xaa Xaa Xaa Xaa Xaa Xaa Xaa Xaa Xaa Xaa Xaa Xaa Xaa Xaa Xaa
    850                 855                 860

Xaa Xaa Xaa Xaa Xaa Xaa Xaa Xaa Xaa Xaa Xaa Xaa Xaa Xaa Xaa Xaa
865                 870                 875                 880

Xaa Xaa Xaa Xaa Xaa Xaa Xaa Xaa Xaa Xaa Xaa Xaa Xaa Xaa Xaa Xaa
                885                 890                 895

Xaa Xaa Xaa Xaa Xaa Xaa Xaa Xaa Xaa Xaa Xaa Xaa Xaa Xaa Xaa Xaa
            900                 905                 910

Xaa Xaa Xaa Xaa Xaa Xaa Xaa Xaa Xaa Xaa Xaa Xaa Xaa Xaa Xaa Xaa
        915                 920                 925

Xaa Xaa Xaa Xaa Xaa Xaa Xaa Xaa Xaa Xaa Xaa Xaa Xaa Xaa Xaa Xaa
    930                 935                 940

Xaa Xaa Xaa Xaa Xaa Xaa Xaa Xaa Xaa Xaa Xaa Xaa Xaa Xaa Xaa Xaa
945                 950                 955                 960

Xaa Xaa Xaa Xaa Xaa Xaa Xaa Xaa Xaa Xaa Xaa Xaa Xaa Xaa Xaa Xaa
                965                 970                 975

Xaa Xaa Xaa Xaa Xaa Xaa Xaa Xaa Xaa Xaa Xaa Xaa Xaa Xaa Xaa Xaa
            980                 985                 990

Xaa Xaa Xaa Xaa Xaa Xaa Xaa Xaa  Xaa Xaa Xaa Xaa Xaa  Xaa Xaa Xaa
        995                 1000                 1005

Xaa Xaa  Xaa Xaa Xaa Xaa Xaa  Xaa Xaa Xaa Xaa Xaa  Xaa Xaa Xaa
    1010                 1015                 1020

Xaa Xaa  Xaa Xaa Xaa Xaa Xaa  Xaa Xaa Xaa Xaa Xaa  Xaa Xaa Arg
    1025                 1030                 1035

Cys Thr  Gln Gln Leu Arg Arg  Asp Ser Asp Xaa Xaa  Xaa Xaa Xaa
    1040                 1045                 1050

Xaa Xaa  Xaa Xaa Xaa Xaa Xaa  Xaa Xaa Xaa Xaa Xaa  Xaa Xaa Xaa
    1055                 1060                 1065

Xaa Xaa  Xaa Xaa Xaa Xaa Xaa  Xaa Xaa Xaa Xaa Xaa  Xaa
    1070                 1075                 1080
```

<210> SEQ ID NO 161
<211> LENGTH: 15
<212> TYPE: DNA
<213> ORGANISM: Homo sapiens

<400> SEQUENCE: 161
taggcctttg aggga 15

-continued

<210> SEQ ID NO 162
<211> LENGTH: 17
<212> TYPE: DNA
<213> ORGANISM: Homo sapiens

<400> SEQUENCE: 162
taggccttat tttaggg 17

<210> SEQ ID NO 163
<211> LENGTH: 17
<212> TYPE: DNA
<213> ORGANISM: Homo sapiens

<400> SEQUENCE: 163
gagaaggagc ccaagag 17

<210> SEQ ID NO 164
<211> LENGTH: 15
<212> TYPE: DNA
<213> ORGANISM: Homo sapiens

<400> SEQUENCE: 164
gagcctccca cagtt 15

<210> SEQ ID NO 165
<211> LENGTH: 17
<212> TYPE: DNA
<213> ORGANISM: Homo sapiens

<400> SEQUENCE: 165
aggccagata caagtct 17

<210> SEQ ID NO 166
<211> LENGTH: 18
<212> TYPE: DNA
<213> ORGANISM: Homo sapiens

<400> SEQUENCE: 166
ttttcgataa aaatgcta 18

<210> SEQ ID NO 167
<211> LENGTH: 16
<212> TYPE: DNA
<213> ORGANISM: Homo sapiens

<400> SEQUENCE: 167
ttatatgagg acatta 16

<210> SEQ ID NO 168
<211> LENGTH: 18
<212> TYPE: DNA
<213> ORGANISM: Homo sapiens

<400> SEQUENCE: 168
ttatggacat agactcat 18

<210> SEQ ID NO 169
<211> LENGTH: 18
<212> TYPE: DNA
<213> ORGANISM: Homo sapiens

<400> SEQUENCE: 169
ttgggagatt ctggcaaa 18

-continued

<210> SEQ ID NO 170
<211> LENGTH: 16
<212> TYPE: DNA
<213> ORGANISM: Homo sapiens

<400> SEQUENCE: 170
aatcgtctct ctcacc 16

<210> SEQ ID NO 171
<211> LENGTH: 20
<212> TYPE: DNA
<213> ORGANISM: Homo sapiens

<400> SEQUENCE: 171
aatttttaca atttaagact 20

<210> SEQ ID NO 172
<211> LENGTH: 15
<212> TYPE: DNA
<213> ORGANISM: Homo sapiens

<400> SEQUENCE: 172
gtccgaagaa atagg 15

<210> SEQ ID NO 173
<211> LENGTH: 16
<212> TYPE: DNA
<213> ORGANISM: Homo sapiens

<400> SEQUENCE: 173
tgccaatcct ccagtt 16

<210> SEQ ID NO 174
<211> LENGTH: 22
<212> TYPE: DNA
<213> ORGANISM: Homo sapiens

<400> SEQUENCE: 174
aacatagatg cagatcaact at 22

<210> SEQ ID NO 175
<211> LENGTH: 18
<212> TYPE: DNA
<213> ORGANISM: Homo sapiens

<400> SEQUENCE: 175
agtactatta gtcaacaa 18

<210> SEQ ID NO 176
<211> LENGTH: 20
<212> TYPE: DNA
<213> ORGANISM: Homo sapiens

<400> SEQUENCE: 176
gtcaacaagc attaatgcaa 20

<210> SEQ ID NO 177
<211> LENGTH: 18
<212> TYPE: DNA
<213> ORGANISM: Homo sapiens

<400> SEQUENCE: 177
ccattgagca agttagag 18

-continued

<210> SEQ ID NO 178
<211> LENGTH: 18
<212> TYPE: DNA
<213> ORGANISM: Homo sapiens

<400> SEQUENCE: 178
gagctatctg ccttagag 18

<210> SEQ ID NO 179
<211> LENGTH: 20
<212> TYPE: DNA
<213> ORGANISM: Homo sapiens

<400> SEQUENCE: 179
cttgggaaaa aatccaagac 20

<210> SEQ ID NO 180
<211> LENGTH: 30
<212> TYPE: DNA
<213> ORGANISM: Homo sapiens

<400> SEQUENCE: 180
gaagtacctg cccctcattt aatacagtaa 30

<210> SEQ ID NO 181
<211> LENGTH: 15
<212> TYPE: DNA
<213> ORGANISM: Homo sapiens

<400> SEQUENCE: 181
ccctaccctg atttt 15

<210> SEQ ID NO 182
<211> LENGTH: 16
<212> TYPE: DNA
<213> ORGANISM: Homo sapiens

<400> SEQUENCE: 182
aaggctccaa gatgtt 16

<210> SEQ ID NO 183
<211> LENGTH: 19
<212> TYPE: DNA
<213> ORGANISM: Homo sapiens

<400> SEQUENCE: 183
tcaattgccg atgaaaaag 19

<210> SEQ ID NO 184
<211> LENGTH: 17
<212> TYPE: DNA
<213> ORGANISM: Homo sapiens

<400> SEQUENCE: 184
cggtaaggtc atagtgg 17

<210> SEQ ID NO 185
<211> LENGTH: 17
<212> TYPE: DNA
<213> ORGANISM: Homo sapiens

<400> SEQUENCE: 185
tggagttgat ggcatat 17

-continued

<210> SEQ ID NO 186
<211> LENGTH: 17
<212> TYPE: DNA
<213> ORGANISM: Homo sapiens

<400> SEQUENCE: 186
aaacgccaat cctgagt 17

<210> SEQ ID NO 187
<211> LENGTH: 15
<212> TYPE: DNA
<213> ORGANISM: Homo sapiens

<400> SEQUENCE: 187
tcaatcagcc attaa 15

<210> SEQ ID NO 188
<211> LENGTH: 21
<212> TYPE: DNA
<213> ORGANISM: Homo sapiens

<400> SEQUENCE: 188
aaaggttcct gcaggatcag a 21

<210> SEQ ID NO 189
<211> LENGTH: 19
<212> TYPE: DNA
<213> ORGANISM: Homo sapiens

<400> SEQUENCE: 189
aggatcagat gtaatctca 19

<210> SEQ ID NO 190
<211> LENGTH: 17
<212> TYPE: DNA
<213> ORGANISM: Homo sapiens

<400> SEQUENCE: 190
aatatgtaaa agcctgt 17

<210> SEQ ID NO 191
<211> LENGTH: 16
<212> TYPE: DNA
<213> ORGANISM: Homo sapiens

<400> SEQUENCE: 191
ataaagctat gcttat 16

<210> SEQ ID NO 192
<211> LENGTH: 20
<212> TYPE: DNA
<213> ORGANISM: Homo sapiens

<400> SEQUENCE: 192
aataacagga gttgttttag 20

<210> SEQ ID NO 193
<211> LENGTH: 16
<212> TYPE: DNA
<213> ORGANISM: Homo sapiens

<400> SEQUENCE: 193
acatttggag gaaaat 16

-continued

<210> SEQ ID NO 194
<211> LENGTH: 17
<212> TYPE: DNA
<213> ORGANISM: Homo sapiens

<400> SEQUENCE: 194
attggtcact taaaaaa 17

<210> SEQ ID NO 195
<211> LENGTH: 17
<212> TYPE: DNA
<213> ORGANISM: Homo sapiens

<400> SEQUENCE: 195
attggtcact taaaaaa 17

<210> SEQ ID NO 196
<211> LENGTH: 22
<212> TYPE: DNA
<213> ORGANISM: Homo sapiens

<400> SEQUENCE: 196
ggtagagagc cacctgactt at 22

<210> SEQ ID NO 197
<211> LENGTH: 15
<212> TYPE: DNA
<213> ORGANISM: Homo sapiens

<400> SEQUENCE: 197
aagatgtaaa aaagg 15

<210> SEQ ID NO 198
<211> LENGTH: 16
<212> TYPE: DNA
<213> ORGANISM: Homo sapiens

<400> SEQUENCE: 198
gctagtcaat gtcgtt 16

<210> SEQ ID NO 199
<211> LENGTH: 15
<212> TYPE: DNA
<213> ORGANISM: Homo sapiens

<400> SEQUENCE: 199
gggaaacgag caaag 15

<210> SEQ ID NO 200
<211> LENGTH: 16
<212> TYPE: DNA
<213> ORGANISM: Homo sapiens

<400> SEQUENCE: 200
ccaattcagc catttg 16

<210> SEQ ID NO 201
<211> LENGTH: 19
<212> TYPE: DNA
<213> ORGANISM: Homo sapiens

<400> SEQUENCE: 201
ccactgtccc aagtgtttc 19

-continued

<210> SEQ ID NO 202
<211> LENGTH: 16
<212> TYPE: DNA
<213> ORGANISM: Homo sapiens

<400> SEQUENCE: 202
aataagccag ttacca 16

<210> SEQ ID NO 203
<211> LENGTH: 15
<212> TYPE: DNA
<213> ORGANISM: Homo sapiens

<400> SEQUENCE: 203
acaatacaac aattg 15

<210> SEQ ID NO 204
<211> LENGTH: 23
<212> TYPE: DNA
<213> ORGANISM: Homo sapiens

<400> SEQUENCE: 204
ctcaccacaa gcggcagtgc agc 23

<210> SEQ ID NO 205
<211> LENGTH: 35
<212> TYPE: DNA
<213> ORGANISM: Homo sapiens

<400> SEQUENCE: 205
tactatacaa gcagtctctc tgcttccagg ggagc 35

<210> SEQ ID NO 206
<211> LENGTH: 16
<212> TYPE: DNA
<213> ORGANISM: Homo sapiens

<400> SEQUENCE: 206
aaaaaatccc tacagg 16

<210> SEQ ID NO 207
<211> LENGTH: 18
<212> TYPE: DNA
<213> ORGANISM: Homo sapiens

<400> SEQUENCE: 207
cactgcctga ggggactg 18

<210> SEQ ID NO 208
<211> LENGTH: 17
<212> TYPE: DNA
<213> ORGANISM: Homo sapiens

<400> SEQUENCE: 208
gactaatctt gggaaga 17

<210> SEQ ID NO 209
<211> LENGTH: 18
<212> TYPE: DNA
<213> ORGANISM: Homo sapiens

<400> SEQUENCE: 209
aaatctaaaa ggagttca 18

-continued

<210> SEQ ID NO 210
<211> LENGTH: 21
<212> TYPE: DNA
<213> ORGANISM: Homo sapiens

<400> SEQUENCE: 210
ctagtgtggt tgattcagac t 21

<210> SEQ ID NO 211
<211> LENGTH: 20
<212> TYPE: DNA
<213> ORGANISM: Homo sapiens

<400> SEQUENCE: 211
cgaaattcaa ttggttatta 20

<210> SEQ ID NO 212
<211> LENGTH: 15
<212> TYPE: DNA
<213> ORGANISM: Homo sapiens

<400> SEQUENCE: 212
tcttcaattc cttgg 15

<210> SEQ ID NO 213
<211> LENGTH: 17
<212> TYPE: DNA
<213> ORGANISM: Homo sapiens

<400> SEQUENCE: 213
agtccaagag acaggat 17

<210> SEQ ID NO 214
<211> LENGTH: 19
<212> TYPE: DNA
<213> ORGANISM: Homo sapiens

<400> SEQUENCE: 214
ttattactcc tgccatata 19

<210> SEQ ID NO 215
<211> LENGTH: 19
<212> TYPE: DNA
<213> ORGANISM: Homo sapiens

<400> SEQUENCE: 215
cattagaaaa aggacattg 19

<210> SEQ ID NO 216
<211> LENGTH: 17
<212> TYPE: DNA
<213> ORGANISM: Homo sapiens

<400> SEQUENCE: 216
ttggaattct gtttgta 17

<210> SEQ ID NO 217
<211> LENGTH: 16
<212> TYPE: DNA
<213> ORGANISM: Homo sapiens

<400> SEQUENCE: 217
taactgagcc attaat 16

-continued

<210> SEQ ID NO 218
<211> LENGTH: 21
<212> TYPE: DNA
<213> ORGANISM: Homo sapiens

<400> SEQUENCE: 218
agccatggtc ccctttaatt a 21

<210> SEQ ID NO 219
<211> LENGTH: 17
<212> TYPE: DNA
<213> ORGANISM: Homo sapiens

<400> SEQUENCE: 219
ttttaccaca ccagcct 17

<210> SEQ ID NO 220
<211> LENGTH: 15
<212> TYPE: DNA
<213> ORGANISM: Homo sapiens

<400> SEQUENCE: 220
ttgtcagctc aagct 15

<210> SEQ ID NO 221
<211> LENGTH: 15
<212> TYPE: DNA
<213> ORGANISM: Homo sapiens

<400> SEQUENCE: 221
tacatcgttc actat 15

<210> SEQ ID NO 222
<211> LENGTH: 15
<212> TYPE: DNA
<213> ORGANISM: Homo sapiens

<400> SEQUENCE: 222
ttaaaagcat taaat 15

<210> SEQ ID NO 223
<211> LENGTH: 17
<212> TYPE: DNA
<213> ORGANISM: Homo sapiens

<400> SEQUENCE: 223
agaagtccca attgagg 17

<210> SEQ ID NO 224
<211> LENGTH: 15
<212> TYPE: DNA
<213> ORGANISM: Homo sapiens

<400> SEQUENCE: 224
ggtcttgccg atttt 15

<210> SEQ ID NO 225
<211> LENGTH: 15
<212> TYPE: DNA
<213> ORGANISM: Homo sapiens

<400> SEQUENCE: 225
acaatcgtta ccaca 15

ENDOGENOUS RETROVIRUSES UP-REGULATED IN PROSTATE CANCER

CROSS-REFERENCE TO RELATED APPLICATION

This application claims the benefit of U.S. Provisional Patent Application No. 60/251,830, filed Dec. 7, 2000, where this provisional application is incorporated hereby by reference in its entirety.

All documents cited herein are incorporated by reference in their entirety.

TECHNICAL FIELD

The present invention relates to the diagnosis of cancer, particularly prostate cancer. In particular, it relates to a subgroup of human endogenous retroviruses (HERVs) which show up-regulated expression in tumors, particularly prostate tumors.

BACKGROUND ART

Prostate cancer is the most common type of cancer in men in the USA. Benign prostatic hyperplasia (BPH) is the abnormal growth of benign prostate cells in which the prostate grows and pushes against the urethra and bladder, blocking the normal flow of urine. More than half of the men in the USA between the ages of 60 and 70 and as many as 90 percent between the ages of 70 and 90 have symptoms of BPH. Although this condition is seldom a threat to life, it may require treatment to relieve symptoms.

Cancer that begins in the prostate is called primary prostate cancer (or prostatic cancer). Prostate cancer may remain in the prostate gland, or it may spread to nearby lymph nodes and may also spread to the bones, bladder, rectum, and other organs. Prostate cancer is diagnosed by measuring the levels of prostate-specific antigen (PSA) and prostatic acid phosphatase (PAP) in the blood. The level of PSA in blood may rise in men who have prostate cancer, BPH, or an infection in the prostate. The level of PAP rises above normal in many prostate cancer patients, especially if the cancer has spread beyond the prostate. However, one cannot diagnose prostate cancer with these tests alone because elevated PSA or PAP levels may also indicate other, non-cancerous problems.

In order to help determine whether conditions of the prostate are benign or malignant further tests such as transrectal ultrasonography, intravenous pyelogram, and cystoscopy are usually performed. If these test results suggest that cancer may be present, the patient must undergo a biopsy as the only sure way to diagnose prostate cancer. Consequently, it is desirable to provide a simple and direct test for the early detection and diagnosis of prostate cancer without having to undergo multiple rounds of cumbersome testing procedures. It is also desirable and necessary to provide compositions and methods for the prevention and/or treatment of prostate cancer.

It is an object of the invention to provide materials that can be used in the prevention, treatment and diagnosis of prostate cancer. It is a further object to provide improvements in the prevention, treatment and diagnosis of prostate cancer.

DISCLOSURE OF THE INVENTION

It has been found that human endogenous retroviruses (HERVs) of the HML-2 subgroup of the HERV-K family show up-regulated expression in prostate tumors. This finding can be used in prostate cancer screening, diagnosis and therapy.

The invention provides a method for diagnosing cancer, especially prostate cancer, the method comprising the step of detecting the presence or absence of an expression product of a HML-2 endogenous retrovirus in a patient sample. Higher levels of expression product relative to normal tissue indicate that the patient from whom the sample was taken has cancer.

The HML-2 expression product which is detected is either a mRNA transcript or a polypeptide translated from such a transcript. These expression products may be detected directly or indirectly. A direct test uses an assay which detects HML-2 RNA or polypeptide in a patient sample. An indirect test uses an assay which detects biomolecules which are not directly expressed in vivo from HML-2 e.g. an assay to detect cDNA which has been reverse-transcribed from a HML-2 mRNA, or an assay to detect an antibody which has been raised in response to a HML-2 polypeptide.

A—The Patient Sample

Where the diagnostic method of the invention is based on HML-2 mRNA, the patient sample will generally comprise cells, preferably, prostate cells. These may be present in a sample of tissue, preferably, prostate tissue, or may be cells, preferably, prostate cells which have escaped into circulation (e.g. during metastasis). Instead of or as well as comprising prostate cells, the sample may comprise virions which contain mRNA from HML-2.

Where the diagnostic method of the invention is based on HML-2 polypeptides, the patient sample may comprise cells, preferably, prostate cells and/or virions (as described above for mRNA), or may comprise antibodies which recognize HML-2 polypeptides. Such antibodies will typically be present in circulation.

In general, therefore, the patient sample is tissue sample (e.g. a biopsy), preferably, a prostate sample (e.g. a biopsy) or a blood sample.

The patient is generally a human, preferably human male, and more preferably an adult human male.

Expression products may be detected in the patient sample itself, or it may be detected in material derived from the sample (e.g. the supernatant of a cell lysate, or a RNA extract, or cDNA generated from a RNA extract, or polypeptides translated from a RNA extract, or cells derived from culture of cells extracted from a patient etc.). These are still considered to be "patient samples" within the meaning of the invention.

Methods of the invention can be conducted in vitro or in vivo.

Other possible sources of patient samples include isolated cells, whole tissues, or bodily fluids (e.g. blood, plasma, serum, urine, pleural effusions, cerebro-spinal fluid, etc.)

B—The mRNA Expression Product

Where the diagnostic method of the invention is based on mRNA detection, it typically involves detecting a RNA comprising six basic regions. From 5' to 3', these are:

A sequence which has at least 75% identity to SEQ ID NO:155 (e.g. 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9%, 100% identity); or a sequence which has at least 50% identity to SEQ ID NO:155 (e.g. 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9%, 100% identity) and is expressed at least 1.5 fold (e.g. 2, 2.5, 5, 10, 20, 50, etc., fold)

higher level relative to expression in a normal (i.e., non cancerous) cell with at least a 95% confidence level; or a sequence which has at least 80% identity (e.g. 81%, 82%, 83%, 84%, 85%, 86%, 87%, 88%, 89%, 90%, 91%, 92%, 93%, 94%, 95%, 96%, 97%, 98%, 99%, 99.5%, 99.9%, 100% identity) to at least a 20 contiguous nucleotide fragment (e.g. 25, 30, 35, 40, 45, 50, 55, 60, 65, 70, 75, 80, 85, 90, 95, 100, 110, 115, 120, 125, 130, 135, 140, 145, etc., contiguous nucleotides) of SEQ ID NO:155; or a sequence which has at least 80% identity (e.g. 81%, 82%, 83%, 84%, 85%, 86%, 87%, 88%, 89%, 90%, 91%, 92%, 93%, 94%, 95%, 96%, 97%, 98%, 99%, 99.5%, 99.9%, 100% identity) to at least a 20 contiguous nucleotide fragment (e.g. 25, 30, 35, 40, 45, 50, 55, 60, 65, 70, 75, 80, 85, 90, 95, 100, 110, 115, 120, 125, 130, 135, 140, 145, etc., contiguous nucleotides) of SEQ ID NO:155 and is expressed at least 1.5 fold (e.g. 2, 2.5, 5, 10, 20, 50, etc., fold) higher level relative to expression in a normal (i.e., non cancerous) cell with at least a 95% confidence level. This sequence will typically be at the 5' end of the RNA. SEQ ID NO:155 is the nucleotide sequence of the start of R region in the LTR of the 'ERVK6' HML-2 virus [ref. 1]. This portion of the R region is found in all full-length HML-2 transcripts.

A downstream region comprising a sequence which has at least 75% sequence identity to SEQ ID NO:156 (e.g. 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9%, 100% identity); or a sequence which has at least 50% identity to SEQ ID NO:156 (e.g. 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9%, 100% identity) and is expressed at least 1.5 fold (e.g. 2, 2.5, 5, 10, 20, 50, etc., fold) higher level relative to expression in a normal (i.e., non cancerous) cell with at least a 95% confidence level; or a sequence which has at least 80% identity (e.g. 81%, 82%, 83%, 84%, 85%, 86%, 87%, 88%, 89%, 90%, 91%, 92%, 93%, 94%, 95%, 96%, 97%, 98%, 99%, 99.5%, 99.9%, 100% identity) to at least a 20 contiguous nucleotide fragment (e.g. 25, 30, 35, 40, 45, 50, 55, 60, 65, 70, 75, 80, 85, 90, 95, 100, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, etc., contiguous nucleotides) of SEQ ID NO:156; or a sequence which has at least 80% identity (e.g. 81%, 82%, 83%, 84%, 85%, 86%, 87%, 88%, 89%, 90%, 91%, 92%, 93%, 94%, 95%, 96%, 97%, 98%, 99%, 99.5%, 99.9%, 100% identity) to at least a 20 contiguous nucleotide fragment (e.g. 25, 30, 35, 40, 45, 50, 55, 60, 65, 70, 75, 80, 85, 90, 95, 100, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, etc., contiguous nucleotides) of SEQ ID NO:156 and is expressed at least 1.5 fold (e.g. 2, 2.5, 5, 10, 20, 50, etc., fold) higher level relative to expression in a normal (i.e., non cancerous) cell with at least a 95% confidence level. SEQ ID NO:156 is the nucleotide sequence of the RU5 region downstream of SEQ ID NO:155 in the ERVK6 LTR. This region is found in full-length HML-2 transcripts, but may not be present in all mRNAs transcribed from a HML-2 LTR promoter.

A downstream region comprising a sequence which has at least 75% sequence identity to SEQ ID NO:6 (e.g. 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9%, 100% identity); or a sequence which has at least 50% identity to SEQ ID NO:6 (e.g. 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9%, 100% identity) and is expressed at least 1.5 fold (e.g. 2, 2.5, 5, 10, 20, 50, etc., fold) higher level relative to expression in a normal (i.e., non cancerous) cell with at least a 95% confidence level; or a sequence which has at least 80% identity (e.g. 81%, 82%, 83%, 84%, 85%, 86%, 87%, 88%, 89%, 90%, 91%, 92%, 93%, 94%, 95%, 96%, 97%, 98%, 99%, 99.5%, 99.9%, 100% identity) to at least a 20 contiguous nucleotide fragment (e.g. 25, 30, 35, 40, 45, 50, 55, 60, 65, 70, 75, 80, 85, 90, 95, 100, etc., contiguous nucleotides) of SEQ ID NO:6; or a sequence which has at least (1, 80% identity (e.g. 81%, 82%, 83%, 84%, 85%, 86%, 87%, 88%, 89%, 90%, 91%, 92%, 93%, 94%, 95%, 96%, 97%, 98%, 99%, 99.5%, 99.9%, 100% identity) to at least a 20 contiguous nucleotide fragment (e.g. 25, 30, 35, 40, 45, 50, 55, 60, 65, 70, 75, 80, 85, 90, 95, 100, etc., contiguous nucleotides) of SEQ ID NO:6 and is expressed at least 1.5 fold (e.g. 2, 2.5, 5, 10, 20, 50, etc., fold) higher level relative to expression in a normal (i.e., non cancerous) cell with at least a 95% confidence level. SEQ ID NO:6 is the nucleotide sequence of the region of the ERVK6 virus between the U5 region and the first 5' splice site. This region is found in full-length HML-2 transcripts, but has been lost by some variants and, like region 2 above, may not be present in all mRNAs transcribed from a HML-2 LTR promoter.

4. A downstream region comprising any RNA sequence. This region will typically comprise the coding sequence of one or more HML-2 polypeptides, but may alternatively comprise: a mutant viral coding sequence; a viral or non-viral non-coding sequence; or a non-viral coding sequence. Transcription of any of these sequences can come under the control of a HML-2 LTR.

A downstream region comprising a sequence which has at least 75% sequence identity to SEQ ID NO:5 (e.g. 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9%, 100% identity); or a sequence which has at least 50% identity to SEQ ID NO:5 (e.g. 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9%, 100% identity) and is expressed at least 1.5 fold (e.g. 2, 2.5, 5, 10, 20, 50, etc., fold) higher level relative to expression in a normal (i.e., non cancerous) cell with at least a 95% confidence level; or a sequence which has at least 80% identity (e.g. 81%, 82%, 83%, 84%, 85%, 86%, 87%, 88%, 89%, 90%, 91%, 92%, 93%, 94%, 95%, 96%, 97%, 98%, 99%, 99.5%, 99.9%, 100% identity) to at least a 20 contiguous nucleotide fragment (e.g. 25, 30, 35, 40, 45, 50, 55, 60, 65, 70, 75, 80, 85, 90, 95, 100, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 350, 400, 450, 500, 550, 600, 650, 700, 750, 800, etc., contiguous nucleotides) of SEQ ID NO:5; or a sequence which has at least 80% identity (e.g. 81%, 82%, 83%, 84%, 85%, 86%, 87%, 88%, 89%, 90%, 91%, 92%, 93%, 94%, 95%, 96%, 97%, 98%, 99%, 99.5%, 99.9%, 100% identity) to at least a 20 contiguous nucleotide fragment (e.g. 25, 30, 35, 40, 45, 50, 55, 60, 65, 70, 75, 80, 85, 90, 95, 100, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 350, 400, 450, 500, 550, 600, 650, 700, 750, 800, etc., contiguous nucleotides) of SEQ ID NO:5 and is expressed at least 1.5 fold (e.g. 2, 2.5, 5, 10, 20, 50, etc., fold) higher level relative to expression in a normal (i.e., non cancerous) cell with at least a 95% confidence level. SEQ ID NO:5 is the nucleotide sequence of the U3R region in the 3' end of ERVK6. This sequence will typically be near the 3' end of the RNA, immediately preceding any polyA tail.

6. A 3' polyA tail.

The percent identity of the sequences described above are determined by the Smith-Waterman algorithm using the default parameters: open gap penalty=−20 and extension penalty=−5.

These mRNA molecules are referred to below as "PCA-mRNA" molecules ("prostate cancer associated mRNA"), and endogenous viruses which express these PCA-mRNAs are referred to as PCAVs ("prostate cancer associated viruses"). Nevertheless, said PCAVs may also be associated with other types of cancer.

Although some PCA-mRNAs include all six of these regions, most HERVs are defective in that they have accumulated multiple stop codons, frameshifts, or larger deletions etc. This means that many PCA-mRNAs do not include all six regions. As all PCA-mRNAs are transcribed under the control of the same group of LTRs, however, transcription of all PCA-mRNAs is up-regulated in prostate tumors even though the mRNA may not encode functional polypeptides.

Where a mRNA to be detected is driven by 5' LTR of HML-2 in genomic DNA, the first of these regions will always be present, but the remaining five are optional. Conversely, where a mRNA to be detected is controlled by 3' LTR of HML-2, the fifth of these regions will always be present, but the remaining five are optional.

In general, therefore, the mRNA to be detected has the formula $N_1$-$N_2$-$N_3$-$N_4$-$N_5$-polyA, wherein:

N1 has at least 75% sequence identity to SEQ ID NO:155; or has at least 50% identity to SEQ ID NO:155 and is expressed at least 1.5 fold higher relative to expression in a normal (i.e., non cancerous) cell with at least a 95% confidence level; or has at least 80% identity to at least a 20 contiguous nucleotide fragment of SEQ ID NO:155; or has at least 80% identity to at least a 20 contiguous nucleotide fragment of SEQ ID NO:155 and is expressed at least 1.5 fold higher relative to expression in a normal (i.e., non cancerous) cell with at least a 95% confidence level;

N2 has at least 75% sequence identity to SEQ ID NO:156; or has at least 50% identity to SEQ ID NO:156 and is expressed at least 1.5 fold higher relative to expression in a normal (i.e., non cancerous) cell with at least a 95% confidence level; or has at least 80% identity to at least a 20 contiguous nucleotide fragment of SEQ ID NO:156; or has at least 80% identity to at least a 20 contiguous nucleotide fragment of SEQ ID NO:156 and is expressed at least 1.5 fold higher relative to expression in a normal (i.e., non cancerous) cell with at least a 95% confidence level;

N3 has at least 75% sequence identity to SEQ ID NO:6; or has at least 50% identity to SEQ ID NO:6 and is expressed at least 1.5 fold higher relative to expression in a normal (i.e., non cancerous) cell with at least a 95% confidence level; or has at least 80% identity to at least a 20 contiguous nucleotide fragment of SEQ ID NO:6; or has at least 80% identity to at least a 20 contiguous nucleotide fragment of SEQ ID NO:6 and is expressed at least 1.5 fold higher relative to expression in a normal (i.e., non cancerous) cell with at least a 95% confidence level;

N4 comprises any RNA sequence;

N5 has at least 75% sequence identity to SEQ ID NO:5; or has at least 50% identity to SEQ ID NO:5 and is expressed at least 1.5 fold higher relative to expression in a normal (i.e., non cancerous) cell with at least a 95% confidence level; or has at least 80% identity to at least a 20 contiguous nucleotide fragment of SEQ ID NO:5; or has at least 80% identity to at least a 20 contiguous nucleotide fragment of SEQ ID NO:5 and is expressed at least 1.5 fold higher relative to expression in a normal (i.e., non cancerous) cell with at least a 95% confidence level; and at least one of $N_1$, $N_2$, $N_3$, $N_4$ or $N_5$ is present, but polyA is optional.

Although only at least one of $N_1$, $N_2$, $N_3$, $N_4$ or $N_5$ needs to be present, it is preferred that two, three, four or five of these regions are present. It is preferred that at least one of $N_1$ and/or $N_5$ is present.

$N_1$ is preferably present in the mRNA to be detected (i.e. the invention is preferably based on the detection of mRNA driven by a 5' LTR). More preferably, at least $N_1$-$N_2$ is present.

Where $N_1$ is present, it is preferably at the 5' end of the mRNA (i.e. 5'$N_1$- . . . ).

Where $N_5$ is present, it is preferably immediately before a 3' polyA tail (i.e. . . . -$N_5$-polyA-3').

Where $N_4$ is present, it preferably comprises a polypeptide-coding sequence (e.g. encoding a HML-2 polypeptide). Examples of HML-2 polypeptide-coding sequences are described below.

The RNA will generally have a 5' cap.

B.1 Enriching RNA in a Sample

Where diagnosis is based on mRNA detection, the method of the invention preferably comprises an initial step of: (a) extracting RNA (e.g. mRNA) from a patient sample; (b) removing DNA from a patient sample without removing mRNA; and/or (c) removing or disrupting DNA which comprises SEQ ID NO:4, but not RNA which comprises SEQ ID NO:4, from a patient sample. This is necessary because the genomes of both normal and cancerous prostate cells contain multiple PCAV DNA templates, whereas increased PCA-mRNA levels are only found in cancerous cells. As an alternative, a RNA-specific assay can be used which is not affected by the presence of homologous DNA.

Methods for extracting RNA from biological samples are well known [e.g. refs. 2 & 8] and include methods based on guanidinium buffers, lithium chloride, SDS/potassium acetate etc. After total cellular RNA has been extracted, mRNA may be enriched e.g. using oligo-dT techniques.

Methods for removing DNA from biological samples without removing mRNA are well known [e.g. appendix C of ref. 2] and include DNase digestion.

Methods for removing DNA, but not RNA, comprising PCA-mRNA sequences will use a reagent which is specific to a sequence within a PCA-mRNA e.g. a restriction enzyme which recognizes a DNA sequence within SEQ ID NO:4, but which does not cleave the corresponding RNA sequence.

Methods for specifically purifying PCA-mRNAs from a sample may also be used. One such method uses an affinity support which binds to PCA-mRNAs. The affinity support may include a polypeptide sequence which binds to the PCAV-mRNA e.g. the cORF polypeptide, which binds to the LTR of HERV-K mRNAs in a sequence-specific manner, or HIV Rev protein, which has been shown to recognize the HERV-K LTR [3].

B.2 Direct Detection of RNA

Various techniques are available for detecting the presence or absence of a particular RNA sequence in a sample [e.g. refs. 2 & 8]. If a sample contains genomic PCAV DNA, the detection technique will generally be RNA-specific; if the sample contains no PCAV DNA, the detection technique may or may not be RNA-specific.

Hybridization-based detection techniques may be used, in which a polynucleotide probe complementary to a region of PCA-mRNA is contacted with a RNA-containing sample under hybridizing conditions. Detection of hybridization indicates that nucleic acid complementary to the probe is present. Hybridization techniques for use with RNA include Northern blots, in situ hybridization and arrays.

Sequencing may also be used, in which the sequence(s) of RNA molecules in a sample are obtained. These techniques reveal directly whether a sequence of interest is present in a sample. Sequence determination of the 5' end of a RNA corresponding to $N_1$ will generally be adequate.

Amplification-based techniques may also be used. These include PCR, SDA, SSSR, LCR, TMA, NASBA, T7 amplification etc. The technique preferably gives exponential amplification. A preferred technique for use with RNA is RT-PCR [e.g. see chapter 15 of ref. 2]. RT-PCR of mRNA from prostate cells is reported in references 4, 5, 6 & 7.

B.3 Indirect Detection of RNA

Rather than detect RNA directly, it may be preferred to detect molecules which are derived from RNA (i.e. indirect detection of RNA). A typical indirect method of detecting mRNA is to prepare cDNA by reverse transcription and then to directly detect the cDNA. Direct detection of cDNA will generally use the same techniques as described above for direct detection of RNA (but it will be appreciated that methods such as RT-PCR are not suitable for DNA detection and that cDNA is double-stranded, so detection techniques can be based on a sequence, on its complement, or on the double-stranded molecule).

B.4 Polynucleotide Materials

The invention provides polynucleotide materials for use in the detection of PCAV nucleic acids.

The invention provides an isolated polynucleotide comprising: (a) the nucleotide sequence $N_1$-$N_2$-$N_3$-$N_4$-$N_5$-polyA as defined above; (b) a fragment of at least x nucleotides of nucleotide sequence $N_1$-$N_2$-$N_3$-$N_4$-$N_5$ as defined above; (c) a nucleotide sequence having at least s % identity to nucleotide sequence $N_1$-$N_2$-$N_3$-$N_4$-$N_5$ as defined above; or (d) the complement of (a), (b) or (c). These polynucleotides include variants of nucleotide sequence $N_1$-$N_2$-$N_3$-$N_4$-$N_5$-polyA (e.g. degenerate variants, allelic variants, homologs, orthologs, mutants etc.).

Fragment (b) is preferably a fragment of $N_1$.

The value of x is at least 7 (e.g. at least 8, 9, 10, 11, 12, 13, 14, 15, 16, 17, 18, 19, 20, 21, 22, 23, 24, 25, 30, 35, 40, 45, 50, 60, 70, 75, 80, 90, 100 etc.). The value of x may be less than 2000 (e.g. less than 1000, 500, 100, or 50).

The value of s is preferably at least 50 (e.g. at least 55, 60, 65, 70, 75, 80, 85, 90, 91, 92, 93, 94, 95, 96, 97, 98, 99, 99.5, 99.9 etc.).

The invention also provides an isolated polynucleotide having formula 5'-A-B-C-3', wherein: -A- is a nucleotide sequence consisting of a nucleotides; -C- is a nucleotide sequence consisting of c nucleotides; -B- is a nucleotide sequence consisting of either (a) a fragment of b nucleotides of nucleotide sequence $N_1$-$N_2$-$N_3$-$N_4$-$N_5$ as defined above or (b) the complement of a fragment of b nucleotides of nucleotide sequence $N_1$-$N_2$-$N_3$-$N_4$-$N_5$ as defined above; and said polynucleotide is neither (a) a fragment of nucleotide sequence $N_1$-$N_2$-$N_3$-$N_4$-$N_5$ or (b) the complement of a fragment of nucleotide sequence $N_1$-$N_2$-$N_3$-$N_4$-$N_5$.

The -B- moiety is preferably a fragment of $N_1$-$N_2$, and more preferably a fragment of $N_1$. The -A- and/or -C- moieties may comprise a promoter sequence (or its complement) e.g. for use in TMA.

The value of a+c is at least 1 (e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100 etc.). The value of b is at least 7 (e.g. at least 8, 9, 10, 11, 12, 13, 14, 15, 16, 17, 18, 19, 20, 21, 22, 23, 24, 25, 30, 35, 40, 45, 50, 60, 70, 80, 90, 100 etc.). It is preferred that the value of a+b+c is at least 9 (e.g. at least 10, 11, 12, 13, 14, 15, 16, 17, 18, 19, 20, 21, 22, 23, 24, 25, 30, 35, 40, 45, 50, 60, 70, 80, 90, 100 etc.). It is preferred that the value of a+b+c is at most 500 (e.g. at most 450, 400, 350, 300, 250, 200, 190, 180, 170, 160, 150, 140, 130, 120, 110, 100, 90, 80, 70, 60, 50, 40, 30, 25, 20, 19, 18, 17, 16, 15, 14, 13, 12, 11, 10, 9).

Where -B- is a fragment of $N_1$-$N_2$-$N_3$-$N_4$-$N_5$, the nucleotide sequence of -A- typically shares less than n % sequence identity to the a nucleotides which are 5' of sequence -B- in $N_1$-$N_2$-$N_3$-$N_4$-$N_5$ and/or the nucleotide sequence of -C- typically shares less than n % sequence identity to the c nucleotides which are 3' of sequence -C- in $N_1$-$N_2$-$N_3$-$N_4$-$N_5$. Similarly, where -B- is the complement of a fragment of $N_1$-$N_2$-$N_3$-$N_4$-$N_5$, the nucleotide sequence of -A- typically shares less than n % sequence identity to the complement of the a nucleotides which are 5' of the complement of sequence -B- in $N_1$-$N_2$-$N_3$-$N_4$-$N_5$ and/or the nucleotide sequence of -C- typically shares less than n % sequence identity to the complement of the c nucleotides which are 3' of the complement of sequence -C- in $N_1$-$N_2$-$N_3$-$N_4$-$N_5$. The value of n is generally 60 or less (e.g. 50, 40, 30, 20, 10 or less).

The invention also provides an isolated polynucleotide which selectively hybridizes to a nucleic acid having nucleotide sequence $N_1$-$N_2$-$N_3$-$N_4$-$N_5$ as defined above or to a nucleic acid having the complement of nucleotide sequence $N_1$-$N_2$-$N_3$-$N_4$-$N_5$ as defined above. The polynucleotide preferably hybridizes to at least $N_1$.

Hybridization reactions can be performed under conditions of different "stringency". Conditions that increase stringency of a hybridization reaction of widely known and published in the art [e.g. page 7.52 of reference 8]. Examples of relevant conditions include (in order of increasing stringency): incubation temperatures of 25° C., 37° C., 50° C., 55° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or de-ionized water. Hybridization techniques are well known in the art [e.g. see references 2, 8, 9, 10, 11 etc.]. Depending upon the particular polynucleotide sequence and the particular domain encoded by that polynucleotide sequence, hybridization conditions upon which to compare a polynucleotide of the invention to a known polynucleotide may differ, as will be understood by the skilled artisan.

In some embodiments, the isolated polynucleotide of the invention selectively hybridizes under low stringency conditions; in other embodiments it selectively hybridizes under intermediate stringency conditions; in other embodiments, it selectively hybridizes under high stringency conditions. An exemplary set of low stringency hybridization conditions is 50° C. and 10×SSC. An exemplary set of intermediate stringency hybridization conditions is 55° C. and 1×SSC. An exemplary set of high stringent hybridization conditions is 68° C. and 0.1×SSC.

The polynucleotides of the invention are particularly useful as probes and/or as primers for use in hybridization and/or amplification reactions.

More than one polynucleotide of the invention can hybridize to the same nucleic acid target (e.g. more than one can hybridize to a single RNA).

References to a percentage sequence identity between two nucleic acid sequences mean that, when aligned, that percentage of bases are the same in comparing the two sequences. This alignment and the percent homology or sequence identity can be determined using software programs known in the art, for example those described in section 7.7.18 of reference 11. A preferred alignment program is GCG Gap (Genetics Computer Group, Wisconsin, Suite Version 10.1), preferably using default parameters, which are as follows: open gap=3; extend gap=1.

Polynucleotides of the invention may take various forms e.g. single-stranded, double-stranded, linear, circular, vectors, primers, probes etc.

Polynucleotides of the invention can be prepared in many ways e.g. by chemical synthesis (at least in part), by digesting longer polynucleotides using restriction enzymes, from genomic or cDNA libraries, from the organism itself etc.

Polynucleotides of the invention may be attached to a solid support (e.g. a bead, plate, filter, film, slide, resin, etc.)

Polynucleotides of the invention may include a detectable label (e.g. a radioactive or fluorescent label, or a biotin label). This is particularly useful where the polynucleotide is to be used in nucleic acid detection techniques e.g. where the nucleic acid is a primer or as a probe for use in techniques such as PCR, LCR, TMA, NASBA, bDNA etc.

The term "polynucleotide" in general means a polymeric form of nucleotides of any length, which contain deoxyribonucleotides, ribonucleotides, and/or their analogs. It includes DNA, RNA, DNA/RNA hybrids, and DNA or RNA analogs, such as those containing modified backbones or bases, and also peptide nucleic acids (PNA) etc. The term "polynucleotide" is not intended to be limiting as to the length or structure of a nucleic acid unless specifically indicated, and the following are non-limiting examples of polynucleotides: a gene or gene fragment, exons, introns, mRNA, tRNA, rRNA, ribozymes, cDNA, recombinant polynucleotides, branched polynucleotides, plasmids, vectors, any isolated DNA from any source, any isolated RNA from any sequence, nucleic acid probes, and primers. Polynucleotides may have any three-dimensional structure, and may perform any function, known or unknown. Unless otherwise specified or required, any embodiment of the invention that includes a polynucleotide encompasses both the double-stranded form and each of two complementary single-stranded forms known or predicted to make up the double stranded form.

Polynucleotides of the invention may be isolated and obtained in substantial purity, generally as other than an intact chromosome. Usually, the polynucleotides will be obtained substantially free of other naturally-occurring nucleic acid sequences, generally being at least about 50% (by weight) pure, usually at least about 90% pure.

Polynucleotides of the invention (particularly DNA) are typically "recombinant" e.g. flanked by one or more nucleotides with which it is not normally associated on a naturally-occurring chromosome.

The polynucleotides can be used, for example: to produce polypeptides; as probes for the detection of nucleic acid in biological samples; to generate additional copies of the polynucleotides; to generate ribozymes or antisense oligonucleotides; and as single-stranded DNA probes or as triple-strand forming oligonucleotides. The polynucleotides are preferably uses to detect PCA-mRNAs.

A "vector" is a polynucleotide construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, "viral vectors" which is designed to result in the production of a recombinant virus or virus-like particle, or "shuttle vectors", which comprise the attributes of more than one type of vector.

A "host cell" includes an individual cell or cell culture which can be or has been a recipient of exogenous polynucleotides. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a polynucleotide of this invention.

B.5 Nucleic Acid Detection Kits

The invention provides a kit comprising primers (e.g. PCR primers) for amplifying a template sequence contained within a PCAV nucleic acid, the kit comprising a first primer and a second primer, wherein the first primer is substantially complementary to said template sequence and the second primer is substantially complementary to a complement of said template sequence, wherein the parts of said primers which have substantial complementarity define the termini of the template sequence to be amplified. The first primer and/or the second primer may include a detectable label.

The invention also provides a kit comprising first and second single-stranded oligonucleotides which allow amplification of a PCAV template nucleic acid sequence contained in a single- or double-stranded nucleic acid (or mixture thereof), wherein: (a) the first oligonucleotide comprises a primer sequence which is substantially complementary to said template nucleic acid sequence; (b) the second oligonucleotide comprises a primer sequence which is substantially complementary to the complement of said template nucleic acid sequence; (c) the first oligonucleotide and/or the second oligonucleotide comprise(s) sequence which is not complementary to said template nucleic acid; and (d) said primer sequences define the termini of the template sequence to be amplified. The non-complementary sequence(s) of feature (c) are preferably upstream of (i.e. 5' to) the primer sequences. One or both of the (c) sequences may comprise a restriction site [12] or promoter sequence [13]. The first and/or the second oligonucleotide may include a detectable label.

The kit of the invention may also comprise a labeled polynucleotide which comprises a fragment of the template sequence (or its complement). This can be used in a hybridization technique to detect amplified template.

The primers and probes used in these kits are preferably polynucleotides as described in section B.4.

The template is preferably a sequence as defined in section B.1 above.

C—Polypeptide Expression Product

Where the method is based on polypeptide detection, it will involve detecting expression of a polypeptide encoded by a PCAV-mRNA. This will typically involve detecting one or more of the following HML-2 polypeptides: gag, prt, pol, env, cORF. Although some PCA-mRNAs encode all of these polypeptides (e.g. ERVK6 [1]), the polypeptide-coding regions of most HERVs (including PCAVs) contain mutations which mean that one or more coding-regions in the mRNA transcript are either mutated or absent. Thus not all PCAVs have the ability to encode all HML-2 polypeptides.

The transcripts which encode HML-2 polypeptides are generated by alternative splicing of the full-length mRNA copy of the endogenous genome [e.g. FIG. 4 of ref. 143].

HML-2 gag polypeptide is encoded by the first long ORF in a complete HML-2 genome [140]. Full-length gag polypeptide is proteolytically cleaved.

Examples of gag nucleotide sequences are: SEQ ID NOS: 7, 8, 9 & 11 [HERV-K(CH)]; SEQ ID NO:85 [HERV-K108]; SEQ ID NO:91 [HERV-K(C7)]; SEQ ID NO:97 [HERV-K (II)]; SEQ ID NO:102 [HERV-K10].

Examples of gag polypeptide sequences are: SEQ ID NOS: 46, 47, 48, 49, 56 & 57 [HERV-K(CH)]; SEQ ID NO:92 [HERV-K(C7)]; SEQ ID NO:98 [HERV-K(II)]; SEQ ID NOS:103 & 104 [HERV-K10]; SEQ ID NO:146 ['ERVK6'].

An alignment of gag polypeptide sequences is shown in FIG. 7.

HML-2 prt polypeptide is encoded by the second long ORF in a complete HML-2 genome. It is translated as a gag-prt fusion polypeptide. The fusion polypeptide is proteolytically cleaved to give a protease.

Examples of part nucleotide sequences are: SEQ ID NO:86 [HERV-K(108)]; SEQ ID NO:99 [HERV-K(II)]; SEQ ID NO:105 [HERV-K10].

Examples of prt polypeptide sequences are: SEQ ID NO:106 [HERV-K10]; SEQ ID NO:147 ['ERVK6'].

HML-2 pol polypeptide is encoded by the third long ORF in a complete HML-2 genome. It is translated as a gag-prt-pol fusion polypeptide. The fusion polypeptide is proteolytically cleaved to give three pol products—reverse transcriptase, endonuclease and integrase [14].

Examples of pol nucleotide sequences are: SEQ ID NO:87 [HERV-K(108)]; SEQ ID NO:93 [HERV-K(C7)]; SEQ ID NO:100 [HERV-K(II)]; SEQ ID NO:107 [HERV-K10].

Examples of pol polypeptide sequences are: SEQ ID NO:94 [HERV-K(C7)]; SEQ ID NO:108 [HERV-K10]; SEQ ID NO:148 ['ERVK6'].

An alignment of pol polypeptide sequences is shown in FIG. 8.

HML-2 env polypeptide is encoded by the fourth long ORF in a complete HML-2 genome. The translated polypeptide is proteolytically cleaved.

Examples of env nucleotide sequences are: SEQ ID NO:88 [HERV-K(108)]; SEQ ID NO:95 [HERV-K C7]; SEQ ID NO:101 [HERV-K(II)]; SEQ ID NO:107 [HERV-K10].

Examples of env polypeptide sequences are: SEQ ID NO:96 [HERV-K(C7)]; SEQ ID NO:108 [HERV-K10]; SEQ ID NO:149 ['ERVK6'].

Alignments of env polynucleotide and polypeptide sequences are shown in FIGS. 6 and 9.

HML-2 cORF polypeptide is encoded by an ORF which shares the same 5' region and start codon as env. After amino acid 87, a splicing event removes env-coding sequences and the cORF-coding sequence continues in the reading frame+1 relative to that of env [15, 16; see below]. cORF has also been called Rec [17].

Examples of cORF nucleotide sequences are: SEQ ID NO:89 and SEQ ID NO:90 [HERV-K(108)].

Examples of cORF polypeptide sequences are SEQ ID NO:109.

C.1 Direct Detection of HML-2 Polypeptides

Various techniques are available for detecting the presence or absence of a particular polypeptides in a sample. These are generally immunoassay techniques which are based on the specific interaction between an antibody and an antigenic amino acid sequence in the polypeptide. Suitable techniques include standard immunohistological methods, immunoprecipitation, immunofluorescence, ELISA, RIA, FIA, etc.

In general, therefore, the invention provides a method for detecting the presence of and/or measuring a level of a polypeptide of the invention in a biological sample, wherein the method uses an antibody specific for the polypeptide. The method generally comprises the steps of: a) contacting the sample with an antibody specific for the polypeptide; and b) detecting binding between the antibody and polypeptides in the sample.

Polypeptides of the invention can also be detected by functional assays e.g. assays to detect binding activity or enzymatic activity. For instance, a functional assay for cORF is disclosed in references 16, 129 & 130. A functional assay for the protease is disclosed in reference 140.

Another way for detecting polypeptides of the invention is to use standard proteomics techniques e.g. purify or separate polypeptides and then use peptide sequencing. For example, polypeptides can be separated using 2D-PAGE and polypeptide spots can be sequenced (e.g. by mass spectroscopy) in order to identify if a sequence is present in a target polypeptide.

Detection methods may be adapted for use in vivo (e.g. to locate or identify sites where cancer cells are present). In these embodiments, an antibody specific for a target polypeptide is administered to an individual (e.g. by injection) and the antibody is located using standard imaging techniques (e.g. magnetic resonance imaging, computed tomography scanning, etc.). Appropriate labels (e.g. spin labels etc.) will be used. Using these techniques, cancer cells are differentially labeled.

An immunofluorescence assay can be easily performed on cells without the need for purification of the target polypeptide. The cells are first fixed onto a solid support, such as a microscope slide or microtiter well. The membranes of the cells are then permeablized in order to permit entry of polypeptide-specific antibody (NB: fixing and permeabilization can be achieved together). Next, the fixed cells are exposed to an antibody which is specific for the encoded polypeptideand which is fluorescently labeled. The presence of this label (e.g. visualized under a microscope) identifies cells which express the target PCAV polypeptide. To increase the sensitivity of the assay, it is possible to use a second antibody to bind to the anti-PCAV antibody, with the label being carried by the second antibody. [18]

C.2 Indirect Detection of HML-2 Polypeptides

Rather than detect polypeptides directly, it may be preferred to detect molecules which are produced by the body in response to a polypeptide (i.e. indirect detection of a polypeptide). This will typically involve the detection of antibodies, so the patient sample will generally be a blood sample. Antibodies can be detected by conventional immunoassay techniques e.g. using PCAV polypeptides of the invention, which will typically be immobilized.

Antibodies against HERV-K polypeptides have been detected in humans [143].

C.3—Polypeptide Materials

The invention provides polypeptides for use in the detection methods of the invention. In general, these polypeptides will be encoded by PCA-mRNAs e.g. by sequence(s) in the $-N_4-$ region.

The invention provides an isolated polypeptide comprising: (a) an amino acid sequence selected from the group consisting of SEQ ID NOS:109 (cORF), 146 (gag), 147 (prt), 148 (pol), 149 (env); (b) a fragment of at least x amino acids of (a); or (c) a polypeptide sequence having at least s % identity to (a). These polypeptides include variants (e.g. allelic variants, homologs, orthologs, mutants etc.).

The value of x is at least 5 (e.g. at least 6, 7, 8, 9, 10, 11, 12, 13, 14, 15, 16, 17, 18, 19, 20, 21, 22, 23, 24, 25, 30, 35, 40, 45, 50, 60, 70, 75, 80, 90, 100 etc.). The value of x may be less than 2000 (e.g. less than 1000, 500, 100, or 50).

The value of s is preferably at least 50 (e.g. at least 55, 60, 65, 70, 75, 80, 85, 90, 91, 92, 93, 94, 95, 96, 97, 98, 99, 99.5, 99.9 etc.).

The invention also provides an isolated polypeptide having formula NH2-A-B-C-COOH, wherein: A is a polypeptide sequence consisting of a amino acids; C is a polypeptide sequence consisting of c amino acids; B is a polypeptide sequence consisting of a fragment of b amino acids of an amino acid sequence selected from the group consisting of SEQ ID NOS:109, 146, 147, 148, 149; and said polypeptide is not a fragment of polypeptide sequence SEQ ID NO:109, 146, 147, 148 or 149.

The value of a+c is at least 1 (e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100 etc.). The value of b is at least 5 (e.g. at least 6, 7, 8, 9, 10, 11, 12, 13, 14, 15, 16, 17, 18, 19, 20, 21, 22, 23, 24, 25, 30, 35, 40, 45, 50, 60, 70, 80, 90, 100 etc.). It is preferred that the value of a+b+c is at least 9 (e.g. at least 10, 11, 12, 13, 14, 15, 16, 17, 18, 19, 20, 21, 22, 23, 24, 25, 30, 35, 40, 45, 50, 60, 70, 80, 90, 100 etc.). It is preferred that the value of a+b+c is at most 500 (e.g. at most 450, 400, 350, 300, 250, 200, 190, 180, 170, 160, 150, 140, 130, 120, 110, 100, 90, 80, 70, 60, 50, 40, 30, 25, 20, 19, 18, 17, 16, 15, 14, 13, 12, 11, 10, 9).

The amino acid sequence of -A- typically shares less than n % sequence identity to the a amino acids which are N-terminal of sequence -B- in SEQ ID NO:109, 146, 147, 148 or 149 and the amino acid sequence of -C- typically shares less than n % sequence identity to the c amino acids which are C-terminal of sequence -B- in SEQ ID NO:109, 146, 147, 148 or 149. The value of n is generally 60 or less (e.g. 50, 40, 30, 20, 10 or less).

The fragment of (b) may comprise a T-cell or, preferably, a B-cell epitope of SEQ ID NO:109, 146, 147, 148 or 149. T- and B-cell epitopes can be identified empirically (e.g. using the PEPSCAN method [19, 20] or similar methods), or they can be predicted (e.g. using the Jameson-Wolf antigenic index [21], matrix-based approaches [22], TEPITOPE [23], neural networks [24], OptiMer & EpiMer [25, 26], ADEPT [27], Tsites [28], hydrophilicity [29], antigenic index [30] or the methods disclosed in reference 31 etc.).

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of reference 11. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is taught in reference 32.

Polypeptides of the invention can be prepared in many ways e.g. by chemical synthesis (at least in part), by digesting longer polypeptides using proteases, by translation from RNA, by purification from cell culture (e.g. from recombinant expression), from the organism itself (e.g. isolation from prostate tissue), from a cell line source etc.

Polypeptides of the invention can be prepared in various forms (e.g. native, fusions, glycosylated, non-glycosylated etc.).

Polypeptides of the invention may be attached to a solid support.

Polypeptides of the invention may comprise a detectable label (e.g. a radioactive or fluorescent label, or a biotin label).

In general, the polypeptides of the subject invention are provided in a non-naturally occurring environment e.g. they are separated from their naturally-occurring environment. In certain embodiments, the subject polypeptide is present in a composition that is enriched for the polypeptide as compared to a control. As such, purified polypeptide is provided, whereby purified is meant that the polypeptide is present in a composition that is substantially free of other expressed polypeptides, where by substantially free is meant that less than 90%, usually less than 60% and more usually less than 50% of the composition is made up of other expressed polypeptides.

The term "polypeptide" refers to amino acid polymers of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Polypeptides can occur as single chains or associated chains. Polypeptides of the invention can be naturally or non-naturally glycosylated (i.e. the polypeptide has a glycosylation pattern that differs from the glycosylation pattern found in the corresponding naturally occurring polypeptide).

Mutants can include amino acid substitutions, additions or deletions. The amino acid substitutions can be conservative amino acid substitutions or substitutions to eliminate non-essential amino acids, such as to alter a glycosylation site, a phosphorylation site or an acetylation site, or to minimize misfolding by substitution or deletion of one or more cysteine residues that are not necessary for function. Conservative amino acid substitutions are those that preserve the general charge, hydrophobicity/hydrophilicity, and/or steric bulk of the amino acid substituted. Variants can be designed so as to retain or have enhanced biological activity of a particular region of the polypeptide (e.g. a functional domain and/or, where the polypeptide is a member of a polypeptide family, a region associated with a consensus sequence). Selection of amino acid alterations for production of variants can be based upon the accessibility (interior vs. exterior) of the amino acid (e.g. ref. 33), the thermostability of the variant polypeptide (e.g. ref. 34), desired glycosylation sites (e.g. ref. 35), desired disulfide bridges (e.g. refs. 36 & 37), desired metal binding sites (e.g. refs. 38 & 39), and desired substitutions with in proline loops (e.g. ref. 40). Cysteine-depleted muteins can be produced as disclosed in reference 41.

C.4 Antibody Materials

The invention also provides isolated antibodies, or antigen-binding fragments thereof, that bind to a polypeptide of the invention. The invention also provides isolated antibodies or antigen binding fragments thereof, that bind to a polypeptide encoded by a polynucleotide of the invention.

Antibodies of the invention may be polyclonal or monoclonal and may be produced by any suitable means (e.g. by recombinant expression).

Antibodies of the invention may include a label. The label may be detectable directly, such as a radioactive or fluorescent label. Alternatively, the label may be detectable indirectly, such as an enzyme whose products are detectable (e.g. luciferase, β-galactosidase, peroxidase etc.).

Antibodies of the invention may be attached to a solid support.

Antibodies of the invention may be prepared by administering (e.g. injecting) a polypeptide of the invention to an appropriate animal (e.g. a rabbit, hamster, mouse or other rodent).

Antigen-binding fragments of antibodies include Fv, scFv, Fc, Fab, $F(ab')_2$ etc.

To increase compatibility with the human immune system, the antibodies may be chimeric or humanized [e.g. refs. 42 & 43], or fully human antibodies may be used. Because humanized antibodies are far less immunogenic in humans than the original non-human monoclonal antibodies, they can be used for the treatment of humans with far less risk of anaphylaxis. Thus, these antibodies may be preferred in therapeutic applications that involve in vivo administration to a human such as, use as radiation sensitizers for the treatment of neoplastic disease or use in methods to reduce the side effects of cancer therapy.

Humanized antibodies may be achieved by a variety of methods including, for example: (1) grafting non-human complementarity determining regions (CDRs) onto a human framework and constant region ("humanizing"), with the optional transfer of one or more framework residues from the non-human antibody; (2) transplanting entire non-human variable domains, but "cloaking" them with a human-like surface by replacement of surface residues ("veneering"). In the present invention, humanized antibodies will include both "humanized" and "veneered" antibodies. [44, 45, 46, 47, 48, 49, 50].

CDRs are amino acid sequences which together define the binding affinity and specificity of a Fv region of a native immunoglobulin binding site [e.g. refs. 51 & 52].

The phrase "constant region" refers to the portion of the antibody molecule that confers effector functions. In chimeric antibodies, mouse constant regions are substituted by human constant regions. The constant regions of humanized antibodies are derived from human immunoglobulins. The heavy chain constant region can be selected from any of the 5 isotypes: alpha, delta, epsilon, gamma or mu.

One method of humanizing antibodies comprises aligning the heavy and light chain sequences of a non-human antibody to human heavy and light chain sequences, replacing the non-human framework residues with human framework residues based on such alignment, molecular modeling of the conformation of the humanized sequence in comparison to the conformation of the non-human parent antibody, and repeated back mutation of residues in the framework region which disturb the structure of the non-human CDRs until the predicted conformation of the CDRs in the humanized sequence model closely approximates the conformation of the non-human CDRs of the parent non-human antibody. Such humanized antibodies may be further derivatized to facilitate uptake and clearance e.g, via Ashwell receptors. [refs. 53 & 54]

Humanized or fully-human antibodies can also be produced using transgenic animals that are engineered to contain human immunoglobulin loci. For example, ref. 55 discloses transgenic animals having a human Ig locus wherein the animals do not produce functional endogenous immunoglobulins due to the inactivation of endogenous heavy and light chain loci. Ref. 56 also discloses transgenic non-primate mammalian hosts capable of mounting an immune response to an immunogen, wherein the antibodies have primate constant and/or variable regions, and wherein the endogenous immunoglobulin-encoding loci are substituted or inactivated. Ref. 57 discloses the use of the Cre/Lox system to modify the immunoglobulin locus in a mammal, such as to replace all or a portion of the constant or variable region to form a modified antibody molecule. Ref. 58 discloses non-human mammalian hosts having inactivated endogenous Ig loci and functional human Ig loci. Ref. 59 discloses methods of making transgenic mice in which the mice lack endogenous heavy claims, and express an exogenous immunoglobulin locus comprising one or more xenogeneic constant regions.

Using a transgenic animal described above, an immune response can be produced to a PCAV polypeptide, and antibody-producing cells can be removed from the animal and used to produce hybridomas that secrete human monoclonal antibodies. Immunization protocols, adjuvants, and the like are known in the art, and are used in immunization of, for example, a transgenic mouse as described in ref. 60. The monoclonal antibodies can be tested for the ability to inhibit or neutralize the biological activity or physiological effect of the corresponding polypeptide.

D—Comparison with Control Samples

D.1—The Control

HML-2 transcripts are up-regulated in tumors, including prostate tumors. To detect such up-regulation, a reference point is needed i.e. a control. Analysis of the control sample gives a standard level of RNA and/or protein expression against which a patient sample can be compared.

A negative control gives a background or basal level of expression against which a patient sample can be compared. Higher levels of expression product relative to a negative control indicate that the patient from whom the sample was taken has, for example, prostate cancer. Typically, for prostate cancer, for example, negative controls would include lifetime baseline levels of expression or the expression level observed in pooled normals. Conversely, equivalent levels of expression product indicate that the patient does not have a HML-2-related cancer such as prostate cancer.

A positive control gives a level of expression against which a patient sample can be compared. Equivalent or higher levels of expression product relative to a positive control indicate that the patient from whom the sample was taken has cancer such as prostate cancer. Conversely, lower levels of expression product indicate that the patient does not have a HML-2 related cancer such as prostate cancer.

For direct or indirect RNA measurement, or for direct polypeptide measurement, a negative control will generally comprise cells which are not from a tumor cell, e.g. a prostate tumor cell. For indirect polypeptide measurement, a negative control will generally be a blood sample from a patient who does not have a prostate tumor. The negative control could be a sample from the same patient as the patient sample, but from a tissue in which HML-2 expression is not up-regulated e.g. a non-tumor non-prostate cell. The negative control could be a prostate cell from the same patient as the patient sample, but taken at an earlier stage in the patient's life. The negative control could be a cell from a patient without a prostate tumor. This cell may or may not be a prostate cell. The negative control cell could be a prostate cell from a patient with BPH.

For direct or indirect RNA measurement, or for direct polypeptide measurement, a positive control will generally comprise cells from a tumor cell e.g. a prostate tumor. For indirect polypeptide measurement, a positive control will generally be a blood sample from a patient who has a prostate tumor. The positive control could be a prostate tumor cell from the same patient as the patient sample, but taken at an earlier stage in the patient's life (e.g. to monitor remission). The positive control could be a cell from another patient with a prostate tumor. The positive control could be a prostate cell line.

Other suitable positive and negative controls will be apparent to the skilled person.

HML-2 expression in the control can be assessed at the same time as expression in the patient sample. Alternatively, HML-2 expression in the control can be assessed separately (earlier or later).

Rather than actually compare two samples, however, the control may be an absolute value i.e. a level of expression which has been empirically determined from samples taken from prostate tumor patients (e.g. under standard conditions).

D.2—Degree of Up-Regulation

The up-regulation relative to the control (100%) will usually be at least 150% (e.g. 200%, 250%, 300%, 400%, 500%, 600% or more).

D.3—Diagnosis

The invention provides a method for diagnosing prostate cancer. It will be appreciated that "diagnosis" according to the invention can range from a definite clinical diagnosis of disease to an indication that the patient should undergo further testing which may lead to a definite diagnosis. For example, the method of the invention can be used as part of a screening process, with positive samples being subjected to further analysis.

Furthermore, diagnosis includes monitoring the progress of cancer in a patient already known to have the cancer. Cancer can also be staged by the methods of the invention. Preferably, the cancer is prostate cancer.

The efficacy of a treatment regimen (therametrics) of a cancer associated can also monitored by the method of the invention e.g. to determine its efficacy.

Susceptibility to a cancer can also be detected e.g. where up-regulation of expression has occurred, but before cancer has developed. Prognostic methods are also encompassed.

All of these techniques fall within the general meaning of "diagnosis" in the present invention.

E—Pharmaceutical Compositions

The invention provides a pharmaceutical composition comprising polynucleotide, polypeptide, or antibody as defined above. The invention also provides their use as medicaments, and their use in the manufacture of medicaments for treating prostate cancer. The invention also provides a method for raising an immune response, comprising administering an immunogenic dose of polynucleotide or polypeptide of the invention to an animal.

Pharmaceutical compositions encompassed by the present invention include as active agent, the polynucleotides, polypeptides, or antibodies of the invention disclosed herein in a therapeutically effective amount. An "effective amount" is an amount sufficient to effect beneficial or desired results, including clinical results. An effective amount can be administered in one or more administrations. For purposes of this invention, an effective amount is an amount that is sufficient to palliate, ameliorate, stabilize, reverse, slow or delay the symptoms and/or progression of prostate cancer.

The compositions can be used to treat cancer as well as metastases of primary cancer. In addition, the pharmaceutical compositions can be used in conjunction with conventional methods of cancer treatment, e.g. to sensitize tumors to radiation or conventional chemotherapy. The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e. arresting its development; or (c) relieving the disease symptom, i.e. causing regression of the disease or symptom.

Where the pharmaceutical composition comprises an antibody that specifically binds to a gene product encoded by a differentially expressed polynucleotide, the antibody can be coupled to a drug for delivery to a treatment site or coupled to a detectable label to facilitate imaging of a site comprising cancer cells, such as prostate cancer cells. Methods for coupling antibodies to drugs and detectable labels are well known in the art, as are methods for imaging using detectable labels.

The term "therapeutically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms. The precise effective amount for a subject will depend upon the subject's size and health, the nature and extent of the condition, and the therapeutics or combination of therapeutics selected for administration. The effective amount for a given situation is determined by routine experimentation and is within the judgment of the clinician. For purposes of the present invention, an effective dose will generally be from about 0.01 mg/kg to about 5 mg/kg, or about 0.01 mg/kg to about 50 mg/kg or about 0.05 mg/kg to about 10 mg/kg of the compositions of the present invention in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art. Pharmaceutically acceptable carriers in therapeutic compositions can include liquids such as water, saline, glycerol and ethanol. Auxiliary substances, such as wetting or emulsifying agents, pH. buffering substances, and the like, can also be present in such vehicles. Typically, the therapeutic compositions are prepared as injectables, either as liquid solutions or suspensions; solid forms suitable for solution in, or suspension in, liquid vehicles prior to injection can also be prepared. Liposomes are included within the definition of a pharmaceutically acceptable carrier. Pharmaceutically acceptable salts can also be present in the pharmaceutical composition, e.g. mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in *Remington: The Science and Practice of Pharmacy* (1995) Alfonso Gennaro, Lippincott, Williams, & Wilkins.

The composition is preferably sterile and/or pyrogen-free. It will typically be buffered around pH 7.

Once formulated, the compositions contemplated by the invention can be (1) administered directly to the subject (e.g. as polynucleotide, polypeptides, small molecule agonists or antagonists, and the like); or (2) delivered ex vivo, to cells derived from the subject (e.g. as in ex vivo gene therapy). Direct delivery of the compositions will generally be accomplished by parenteral injection, e.g. subcutaneously, intraperitoneally, intravenously or intramuscularly, intratumoral or to the interstitial space of a tissue. Other modes of administration include oral and pulmonary administration, suppositories, and transdermal applications, needles, and gene guns or hyposprays. Dosage treatment can be a single dose schedule or a multiple dose schedule.

Methods for the ex vivo delivery and reimplantation of transformed cells into a subject are known in the art [e.g. ref. 61]. Examples of cells useful in ex vivo applications include, for example, stem cells, particularly hematopoetic, lymph cells, macrophages, dendritic cells, or tumor cells. Generally, delivery of nucleic acids for both ex vivo and in vitro applications can be accomplished by, for example, dextran-mediated transfection, calcium phosphate precipitation, polybrene mediated transfection, protoplast fusion, electroporation, encapsulation of the polynucleotide(s) in liposomes, and direct microinjection of the DNA into nuclei, all well known in the art.

Differential expression PCAV polynucleotides has been found to correlate with prostate tumors. The tumor can be amenable to treatment by administration of a therapeutic agent based on the provided polynucleotide, corresponding polypeptide or other corresponding molecule (e.g. antisense, ribozyme, etc.). In other embodiments, the disorder can be amenable to treatment by administration of a small molecule drug that, for example, serves as an inhibitor (antagonist) of the function of the encoded gene product of a gene having increased expression in cancerous cells relative to normal cells or as an agonist for gene products that are decreased in expression in cancerous cells (e.g. to promote the activity of gene products that act as tumor suppressors).

The dose and the means of administration of the inventive pharmaceutical compositions are determined based on the specific qualities of the therapeutic composition, the condition, age, and weight of the patient, the progression of the disease, and other relevant factors. For example, administration of polynucleotide therapeutic compositions agents includes local or systemic administration, including injection, oral administration, particle gun or catheterized administration, and topical administration. Preferably, the therapeutic polynucleotide composition contains an expression construct comprising a promoter operably linked to a polynucleotide of the invention. Various methods can be used to administer the therapeutic composition directly to a specific site in the body. For example, a small metastatic lesion is located and the therapeutic composition injected several times in several different locations within the body of tumor. Alternatively, arteries which serve a tumor are identified, and the therapeutic composition injected into such an artery, in order to deliver the composition directly into the tumor. A tumor that has a necrotic center is aspirated and the composition injected directly into the now empty center of the tumor. An antisense composition is directly administered to the surface of the tumor, for example, by topical application of the composition. X-ray imaging is used to assist in certain of the above delivery methods.

Targeted delivery of therapeutic compositions containing an antisense polynucleotide, subgenomic polynucleotides, or antibodies to specific tissues can also be used. Receptor-mediated DNA delivery techniques are described in, for example, references 62 to 67. Therapeutic compositions containing a polynucleotide are administered in a range of about 100 ng to about 200 mg of DNA for local administration in a gene therapy protocol. Concentration ranges of about 500 ng to about 50 mg, about 1 μg to about 2 mg, about 5 μg to about 500 μg, and about 20 μg to about 100 μg of DNA can also be used during a gene therapy protocol. Factors such as method of action (e.g. for enhancing or inhibiting levels of the encoded gene product) and efficacy of transformation and expression are considerations which will affect the dosage required for ultimate efficacy of the antisense subgenomic polynucleotides. Where greater expression is desired over a larger area of tissue, larger amounts of antisense subgenomic polynucleotides or the same amounts re-administered in a successive protocol of administrations, or several administrations to different adjacent or close tissue portions of, for example, a tumor site, may be required to effect a positive therapeutic outcome. In all cases, routine experimentation in clinical trials will determine specific ranges for optimal therapeutic effect.

The therapeutic polynucleotides and polypeptides of the present invention can be delivered using gene delivery vehicles. The gene delivery vehicle can be of viral or non-viral origin (see generally references 68, 69, 70 and 71). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (e.g. references 72 to 82), alphavirus-based vectors (e.g. Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), adenovirus vectors, and adeno-associated virus (AAV) vectors (e.g. see refs. 83 to 88). Administration of DNA linked to killed adenovirus [89] can also be employed.

Non-viral delivery vehicles and methods can also be employed, including, but not limited to, polycationic condensed DNA linked or unlinked to killed adenovirus alone [e.g. 89], ligand-linked DNA [90], eukaryotic cell delivery vehicles cells [e.g. refs. 91 to 95] and nucleic charge neutralization or fusion with cell membranes. Naked DNA can also be employed. Exemplary naked DNA introduction methods are described in refs. 96 and 97. Liposomes that can act as gene delivery vehicles are described in refs. 98 to 102. Additional approaches are described in refs. 103 & 104.

Further non-viral delivery suitable for use includes mechanical delivery systems such as the approach described in ref. 104. Moreover, the coding sequence and the product of expression of such can be delivered through deposition of photopolymerized hydrogel materials or use of ionizing radiation [e.g. refs. 105 & 106]. Other conventional methods for gene delivery that can be used for delivery of the coding sequence include, for example, use of hand-held gene transfer particle gun or use of ionizing radiation for activating transferred gene [108 & 109].

Vaccine Compositions

The invention provides a composition comprising a polypeptide or polynucleotide of the invention and a pharmaceutically acceptable carrier.

The composition may additionally comprise an adjuvant. For example, the composition may comprise one or more of the following adjuvants: (1) oil-in-water emulsion formulations (with or without other specific immunostimulating agents such as muramyl peptides (see below) or bacterial cell wall components), such as for example (a) MF59™ [110; Chapter 10 in ref. 111], containing 5% Squalene, 0.5% Tween 80, and 0.5% Span 85 (optionally containing MTP-PE) formulated into submicron particles using a microfluidizer, (b) SAF, containing 10% Squalane, 0.4% Tween 80, 5% pluronic-blocked polymer L121, and thr-MDP either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (2) saponin adjuvants, such as QS21 or Stimulon™ (Cambridge Bioscience, Worcester, Mass.) may be used or particles generated therefrom such as ISCOMs (immunostimulating complexes), which ISCOMS may be devoid of additional detergent [112]; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 etc.), interferons (e.g. gamma interferon), macrophage colony stimulating factor (M-CSF), tumor necrosis factor (TNF), etc.; (5) monophosphoryl lipid A (MPL) or 3-O-deacylated MPL (3dMPL) [e.g. 113, 114]; (6) combinations of 3dMPL with, for example, QS21 and/or oil-in-water emulsions [e.g. 115, 116, 117]; (7) oligonucleotides comprising CpG motifs i.e. containing at least one CG dinucleotide, with 5-methylcytosine optionally being used in place of cytosine; (8) a polyoxyethylene ether or a polyoxyethylene ester [118]; (9) a polyoxyethylene sorbitan ester surfactant in combination with an octoxynol [119] or a polyoxyethylene alkyl ether or ester surfactant in combination with at least one additional non-ionic surfactant such as an octoxynol [120]; (10) an immunostimulatory oligonucleotide (e.g. a CpG oligonucleotide) and a saponin [121]; (11) an immunostimulant and a particle of metal salt [122]; (12) a saponin and an oil-in-water emulsion [123]; (13) a saponin (e.g. QS21)+3dMPL+IL-12 (optionally+a sterol) [124]; (14) aluminium salts, preferably hydroxide or phosphate, but any other suitable salt may also be used (e.g. hydroxyphosphate, oxyhydroxide, orthophosphate, sulphate etc. [chapters 8 & 9 of ref. 111]). Mixtures of different aluminium salts may also be used. The salt may take any suitable form (e.g. gel, crystalline, amorphous etc.); (15) chitosan; (16) cholera toxin or *E. coli* heat labile toxin, or detoxified mutants thereof [125]; (17) microparticles of poly(α-hydroxy)acids, such as PLG; (18) other substances that act as immunostimulating agents to enhance the efficacy of the composition. Aluminium salts and/or MF59™ are preferred.

The composition is preferably sterile and/or pyrogen-free. It will typically be buffered around pH 7.

The composition is preferably an immunogenic composition and is more preferably a vaccine composition. The composition can be used to raise antibodies in a mammal (e.g. a human).

Vaccines of the invention may be prophylactic (i.e. to prevent disease) or therapeutic (i.e. to reduce or eliminate the symptoms of a disease).

Efficacy can be tested by monitoring expression of polynucleotides and/or polypeptides of the invention after administration of the composition of the invention.

F—Screening Methods and Drug Design

The invention provides methods of screening for compounds with activity against cancer, comprising: contacting a test compound with a tissue sample derived from a cell in which HML-2 expression is up-regulated; or a cell line; and monitoring HML-2 expression in the sample. A decrease in expression indicates potential anti-cancer efficacy of the test compound.

The invention also provides methods of screening for compounds with activity against prostate cancer, comprising: contacting a test compound with a polynucleotide or polypeptide of the invention; and detecting a binding interaction between the test compound and the polynucleotide/polypeptide. A binding interaction indicates potential anti-cancer efficacy of the test compound.

The invention also provides methods of screening for compounds with activity against prostate cancer, comprising: contacting a test compound with a polypeptide of the invention; and assaying the function of the polypeptide. Inhibition of the polypeptide's function (e.g. loss of protease activity, loss of RNA export, loss of reverse transcriptase activity, loss of endonuclease activity, loss of integrase activity etc.) indicates potential anti-cancer efficacy of the test compound.

Typical test compounds include, but are not restricted to, peptides, peptoids, proteins, lipids, metals, nucleotides, nucleosides, small organic molecules, antibiotics, polyamines, and combinations and derivatives thereof. Small organic molecules have a molecular weight of more than 50 and less than about 2,500 daltons, and most preferably between about 300 and about 800 daltons. Complex mixtures of substances, such as extracts containing natural products, or the products of mixed combinatorial syntheses, can also be tested and the component that binds to the target RNA can be purified from the mixture in a subsequent step.

Test compounds may be derived from large libraries of synthetic or natural compounds. For instance, synthetic compound libraries are commercially available from Maybridge Chemical Co. (Trevillet, Cornwall, UK) or Aldrich (Milwaukee, Wis.). Alternatively, libraries of natural compounds in the form of bacterial, fungal, plant and animal extracts may be used. Additionally, test compounds may be synthetically produced using combinatorial chemistry either as individual compounds or as mixtures.

Agonists or antagonists of the polypeptides of the invention can be screened using any available method known in the art, such as signal transduction, antibody binding, receptor binding, mitogenic assays, chemotaxis assays, etc. The assay conditions ideally should resemble the conditions under which the native activity is exhibited in vivo, that is, under physiologic pH, temperature, and ionic strength. Suitable agonists or antagonists will exhibit strong inhibition or enhancement of the native activity at concentrations that do not cause toxic side effects in the subject. Agonists or antagonists that compete for binding to the native polypeptide can require concentrations equal to or greater than the native concentration, while inhibitors capable of binding irreversibly to the polypeptide can be added in concentrations on the order of the native concentration.

Such screening and experimentation can lead to identification of an agonist or antagonist of a HML-2 polypeptide. Such agonists and antagonists can be used to modulate, enhance, or inhibit HML-2 expression and/or function. [126]

The present invention relates to methods of using the polypeptides of the invention (e.g. recombinantly produced HML-2 polypeptides) to screen compounds for their ability to bind or otherwise modulate, such as, inhibit, the activity of HML-2 polypeptides, and thus to identify compounds that can serve, for example, as agonists or antagonists of the HML-2 polypeptides. In one screening assay, the HML-2 polypeptide is incubated with cells susceptible to the growth stimulatory activity of HML-2, in the presence and absence of a test compound. The HML-2 activity altering or binding potential of the test compound is measured. Growth of the cells is then determined. A reduction in cell growth in the test sample indicates that the test compound binds to and thereby inactivates the HML-2 polypeptide, or otherwise inhibits the HML-2 polypeptide activity.

Transgenic animals (e.g. rodents) that have been transformed to over-express HML-2 genes can be used to screen compounds in vivo for the ability to inhibit development of tumors resulting from HML-2 over-expression or to treat such tumors once developed. Transgenic animals that have prostate tumors of increased invasive or malignant potential can be used to screen compounds, including antibodies or peptides, for their ability to inhibit the effect of HML-2 polypeptides. Such animals can be produced, for example, as described in the examples herein.

Screening procedures such as those described above are useful for identifying agents for their potential use in pharmacological intervention strategies in prostate cancer treatment. Additionally, polynucleotide sequences corresponding to HML-2, including LTRs, may be used to assay for inhibitors of elevated gene expression.

Potent inhibitors of HERV-K protease are already known [127]. Inhibition of HERV-K protease by HIV-1 protease inhibitors has also been reported [128]. These compounds can be studied for use in prostate cancer therapy, and are also useful lead compounds for drug design.

Transdominant negative mutants of cORF have also been reported [129,130]. Transdominant cORF mutants can be studied for use in prostate cancer therapy.

Antisense oligonucleotides complementary to HML-2 mRNA can be used to selectively diminish or oblate the expression of the polypeptide. More specifically, antisense constructs or antisense oligonucleotides can be used to inhibit the production of HML-2 polypeptide(s) in prostate tumor cells. Antisense mRNA can be produced by transfecting into target cancer cells an expression vector with a HML-2 polynucleotide of the invention oriented in an antisense direction relative to the direction of PCAV-mRNA transcription. Appropriate vectors include viral vectors, including retroviral vectors, as well as non-viral vectors. Alternately, antisense oligonucleotides can be introduced directly into target cells to achieve the same goal. Oligonucleotides can be selected/designed to achieve the highest level of specificity and, for example, to bind to a PCAV-mRNA at the initiator ATG.

Monoclonal antibodies to HML-2 polypeptides can be used to block the action of the polypeptides and thereby control growth of cancer cells. This can be accomplished by infusion of antibodies that bind to HML-2 polypeptides and block their action.

The invention also provides high-throughput screening methods for identifying compounds that bind to a polynucleotide or polypeptide of the invention. Preferably, all the biochemical steps for this assay are performed in a single solution in, for instance, a test tube or microtitre plate, and the test compounds are analyzed initially at a single compound concentration. for the purposes of high throughput screening, the experimental conditions are adjusted to achieve a proportion of test compounds identified as "positive" compounds from amongst the total compounds screened. The assay is preferably set to identify compounds with an appreciable affinity towards the target e.g., when 0.1% to 1% of the total test compounds from a large compound library are shown to bind to a given target with a $K_i$ of 10 μM or less (e.g. 1 μM, 100 nM, 10 nM, or less)

G—The HML-2 Family of Human Endogenous Retroviruses

Genomes of all eukaryotes contain multiple copies of sequences related to infectious retroviruses. These endogenous retroviruses have been well studied in mice where both true infectious forms and thousands of defective retrovirus-like elements (e.g. the IAP and Etn sequence families) exist. Some members of the IAP and Etn families are "active" retrotransposons since insertions of these elements have been documented which cause germ line mutations or oncogenic transformation.

Endogenous retroviruses were identified in human genomic DNA by their homology to retroviruses of other vertebrates [131, 132]. It is believed that the human genome probably contains numerous copies of endogenous proviral DNAs, but little is known about their function. Most HERV families have relatively few members (1-50) but one family (HERV-H) consists of ~1000 copies per haploid genome distributed on all chromosomes. The large numbers and general transcriptional activity of HERVs in embryonic and tumor cell lines suggest that they could act as disease-causing insertional mutagens or affect adjacent gene expression in a neutral or beneficial way.

The K family of human endogenous retroviruses (HERV-K) is well known [133]. It is related to the mouse mammary tumor virus (MMTV) and is present in the genomes of humans, apes and old world monkeys, but several human HERV-K proviruses are unique to humans [134]. The HERV-K family is present at 30-50 full-length copies per haploid human genome and possesses long open reading frames that potentially are translated into viral proteins [135, 136]. Two types of proviral genomes are known, which differ by the presence (type 2) or absence (type 1) of a stretch of 292 nucleotides in the overlapping boundary of the pol and env genes [137]. Some members of the HERV-K family are known to code for the gag protein and retroviral particles, which are both detectable in germ cell tumors and derived cell lines [138]. Analysis of the RNA expression pattern of full-length HERV-K has also identified a doubly-spliced RNA that encodes a 105 amino acid protein termed central ORF ('cORF') which is a sequence-specific nuclear RNA export factor that is functionally equivalent to the Rev protein of HIV [139]. HERV-K10 has been shown to encode a full-length gag homologous 73 kDa protein and a functional protease [140].

Patients suffering from germ cell tumors show high antibody titers against HERV-K gag and env proteins at the time of tumor detection [141]. In normal testis and testicular tumors the HERV-K transmembrane envelope protein has been detected both in germ cells and tumor cells, but not in the surrounding tissue. In the case of testicular tumor, correlations between the expression of the env-specific mRNA, the presence of the transmembrane env, cORF and gag proteins and antibodies against HERV-K specific peptides in the serum of the patients, have been reported. Reference 142 reports that HERV-K10 gag and/or env proteins are synthesized in seminoma cells and that patients with those tumors exhibit relatively high antibody titers against gag and/or env.

Gag proteins released in form of particles from HERV-K have been identified in the cell culture supernatant of the teratocarcinoma derived cell line Tera 1. These retrovirus-like particles (termed "human teratocarcinoma derived virus" or HTDV) have been shown to have a 90% sequence homology to the HERV-K10 genome [138, 143].

While the HERV-K family is present in the genome of every human cell, a high level of expression of mRNAs, proteins and particles is observed only in human teratocarcinoma cell lines [144]. In other tissues and cell lines, only a basal level of expression of mRNA has been demonstrated even using very sensitive methods. The expression of retroviral proviruses is generally regulated by elements of the 5' long terminal repeat (LTR). Furthermore, the activation of expression of an endogenous retrovirus may trigger the expression of a downstream gene that triggers a neoplastic effect.

The sequence of HERV-K(II), which locates to chromosome 3, has been disclosed [145].

HML-2 is a subgroup of the HERV-K family [146]. HERV isolates which are members of the HML-2 subgroup include HERV-K10 [137,142], the 27 HML-2 viruses shown in FIG. 4 of reference 147, HERV-K(C7) [148], HERV-K(II) [145], HERV-K(CH) Table 11 provides a list of all known members of the HML-2 subgroup of the HERV-K family as determined by searching the DoubleTwist database containing all genomic contigs with the sequence AF074086 using the Smith-Waterman algorithm with the default parameters: open gap penalty=−20 and extension penalty=−5.

The invention is based on the finding that HML-2 mRNA expression is up-regulated in prostate tumors. Because HML-2 is a well-recognized family, the skilled person will be able to determine without difficulty whether any particular endogenous retroviruses is or is not a HML-2. Preferred members of the HML-2 family for use in accordance with the present invention are those whose proviral genome has an LTR which has at least 75% sequence identity to SEQ ID NO:150 (the LTR sequence from HML-2.HOM [1]). Example LTRs include SEQ ID NOS:151-154.

H—HERV-K(CH)

The present invention is based on the discovery of elevated levels of multiple HML-2 polynucleotides in prostate tumor samples as compared to normal prostate tissue. One particular HML-2 whose mRNA was found to be up-regulated is designated herein as 'HERV-K(CH)'.

Sequences from HERV-K(CH) are shown in SEQ ID NOS: 14-39 and have been deposited with the ATCC (see Table 7). The skilled person will be able to classify any further HERV as HERV-K(CH) or not based on sequence identity to these HERV-K(CH) polynucleotides. Preferably such a comparison is to one or more, or all, of the polynucleotide sequences disclosed herein or of the polynucleotide inserts in the ATCC-deposited isolates. Alternatively, the skilled artisan can determine the sequence identity based on a comparison to any one or more, or all, of the sequences in SEQ ID NOS:7-10 and SEQ ID NOS:14-39 taking into consideration the spontaneous mutation rate associated with retroviral replication. Thus, it will be apparent when the differences in the sequences are consistent with a HERV-K(CH) isolate or consistent with another HERV.

HERV-K(CH) is therefore a specific member of the HML-2 subgroup which can be used in the invention as described above. It can also be used in methods previously described in relation to HERV-K e.g. the diagnosis of testicular cancer [142], autoimmune diseases, multiple sclerosis [149], insulin-dependent diabetes mellitus (IDDM) [150] etc.

H.1—HERV-K(CH) Nucleic Acids

H.1.1—HERV-K(CH) Genomic Sequences

The invention provides an isolated polynucleotide comprising: (a) the nucleotide sequence of any of SEQ ID NOS: 7-10; (b) the nucleotide sequence of any of SEQ ID NOS:27-39; (c) the complement of a nucleotide sequence of any of SEQ ID NOS:7-10; or (d) the complement of the nucleotide sequence of any of SEQ ID NOS:27-39.

H.1.2—HERV-K(CH) Fragments

The invention also provides an isolated polynucleotide comprising a fragment of: (a) a nucleotide sequence shown in SEQ ID NOS:7-10; (b) the nucleotide sequence shown in any of SEQ ID NOS:27-39; (c) the complement of a nucleotide sequence shown in SEQ ID NOS:7-10; or (d) the complement of the nucleotide sequence shown in any of SEQ ID NOS:27-39.

The fragment is preferably at least x nucleotides in length, wherein x is at least 7 (e.g. at least 8, 9, 10, 11, 12, 13, 14, 15, 16, 17, 18, 19, 20, 21, 22, 23, 24, 25, 30, 35, 40, 45, 50, 60, 70, 75, 80, 90, 100 etc.). The value of x may be between about 150 and about 200 or be between about 250 and about 300. The value of x may be about 350, about 400, about 450, about 500, about 550, about 600, about 650, about 700, or about 750. The value of x may be less than 2000 (e.g. less than 1000, 500, 100, or 50).

The fragment is preferably neither one of the following sequences nor a fragment of one of the following sequences: (i) the nucleotide sequence shown in SEQ ID NO:42; (ii) the nucleotide sequence shown in SEQ ID NO:43; (iii) the nucleotide sequence shown in SEQ ID NO:44; (iv) the nucleotide sequence shown in SEQ ID NO:45; (v) a known polynucleotide; or (vi) a polynucleotide known as of 7 Dec. 2000 (e.g. a polynucleotide available in a public database such as GenBank of GeneSeq before 7 Dec. 2000).

The fragment is preferably a contiguous sequence of one of polynucleotides of (a), (b), (c) or (d) that remains unmasked following application of a masking program for masking low complexity (e.g. XBLAST) to the sequence (i.e. one would select an unmasked region, as indicated by the polynucleotides outside the poly-n stretches of the masked sequence produced by the masking program).

These polynucleotides are particularly useful as probes. In general, a probe in which x=15 represents sufficient sequence for unique identification. Probes can be used, for example, to determine the presence or absence of a polynucleotide of the invention (or variants thereof) in a sample. By using probes, particularly labeled probes of DNA sequences, one can isolate homologous or related genes. The source of homologous genes can be any species e.g. primate species, particularly human; rodents, such as rats and mice; canines; felines; bovines; ovines; equines; yeast; nematodes; etc.

Probes from more than one polynucleotide sequence of the invention can hybridize with the same nucleic acid if the nucleic acid from which they were derived corresponds to a single sequence (e.g. more than, one can hybridize to a single cDNA derived from the same mRNA).

Preferred fragments (e.g. for the identification of HERV-K (CH) polynucleotides associated with cancer) which do not correspond identically in their entirety to any portion of the sequence(s) shown in SEQ ID NOS:42-45 are: SEQ ID NO:59 (from gag region), SEQ ID NOS:60-70 (from pol region) and SEQ ID NOS:71-82 (from 3' pol region).

Preferred fragments (e.g. for the simultaneous identification of HERV-K(CH) polynucleotides, HERV-KII polynucleotides and/or HERV-K10 polynucleotides) which do correspond identically in their entirety to any portion of the sequence(s) shown in SEQ ID NOS:44 & 45 are SEQ ID NOS:83 & 84 (from gag region).

Polynucleotide probes unique to HERV-K(CH), HERV-KII and HERV-K10 gag regions are provided in Table 1; polynucleotide probes unique to HERV-K(CH), HERV-KII, and HERV-K10 protease 3' and polymerase 5' regions are provided in Table 2; polynucleotide probes unique to HERV-K(CH), HERV-KII, and HERV-K10 3' pol only regions are provided in Table 3.

H.1.3—HERV-K(CH) Fragments Plus Heterologous Sequences

The invention also provides an isolated polynucleotide comprising (a) a segment that is a fragment of the sequence shown in SEQ ID NOS:7-10 or SEQ ID NOS:27-39, wherein (i) said fragment is at least 10 nucleotides in length and (ii) corresponds identically in its entirety to a portion of SEQ ID NO:44 and/or 45; and, optionally, (b) one or more segments flanking the segment defined in (a), wherein the presence of said optional segment(s) causes said polynucleotide to not correspond identically to any portion of a sequence shown in SEQ ID NOS:7-10 or SEQ ID NOS:27-39. In some embodiments, the optional flanking segments share less than 40% sequence identity to the nucleic acid sequences shown in SEQ ID NOS:7-10, SEQ ID NO:44 and/or SEQ ID NO:45. In other embodiments, the optional flanking segments have no contiguous sequence of 10, 12, 15 or 20 nucleotides in common with SEQ ID NOS:7-10, SEQ ID NO:44 and/or SEQ ID NO:45. In yet other embodiments, the optional flanking segment is not present. In further embodiments, a fragment of the polynucleotide sequence is up to at least 30, 40, 50, 60, 70, 80, 90, 100, 200, 300, 400, 500, 1000, or 1500 nucleotides in length.

The invention also provides an isolated polynucleotide having formula 5'-A-B-C-3', wherein: A is a nucleotide sequence consisting of a nucleotides; B is a nucleotide sequence consisting of a fragment of b nucleotides from (i) the nucleotide sequence shown in SEQ ID NOS:7-10, (ii) the nucleotide sequence shown in any of SEQ ID NOS:27-39, (iii) the complement of the nucleotide sequence shown in SEQ ID NOS:7-10, or (iv) the complement of the nucleotide sequence shown in any of SEQ ID NOS:27-39; C is a nucleotide sequence consisting of c nucleotides; and wherein said polynucleotide is not a fragment of (i) the nucleotide sequence shown in SEQ ID NOS:7-10, (ii) the nucleotide sequence shown in any of SEQ ID NOS:27-39, (iii) the complement of the nucleotide sequence shown in SEQ ID NOS:7-10, or (iv) the complement of the nucleotide sequence shown in any of SEQ ID NOS:27-39.

In this polynucleotide, a+c is at least 1 (e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100 etc.) and b is at least 7 (e.g. at least 8, 9, 10, 11, 12, 13, 14, 15, 16, 17, 18, 19, 20, 21, 22, 23, 24, 25, 30, 35, 40, 45, 50, 60, 70, 80, 90, 100 etc.). It is preferred that the value of a+b+c is at least 9 (e.g. at least 10, 11, 12, 13, 14, 15, 16, 17, 18, 19, 20, 21, 22, 23, 24, 25, 30, 35, 40, 45, 50, 60, 70, 80, 90, 100 etc.). It is preferred that the value of a+b+c is at most 200 (e.g. at most 190, 180, 170, 160, 150, 140, 130, 120, 110, 100, 90, 80, 70, 60, 50, 40, 30, 25, 20, 19, 18, 17, 16, 15, 14, 13, 12, 11, 10, 9).

A and/or C may comprise a promoter sequence (or its complement).

H.1.4—Homologous Sequences

The invention provides a polynucleotide having at least s % identity to: (a) SEQ ID NOS:7-10; (b) a fragment of x nucleotides of SEQ ID NOS:7-10; (c) SEQ ID NOS:11-13; (b) a fragment of x nucleotides of SEQ ID NOS:11-13. The value of s is at least 50 (e.g. at least 55, 60, 65, 70, 75, 80, 85, 90, 91, 92, 93, 94, 95, 96, 97, 98, 99, 99.5, 99.9 etc.). The value of x is at least 7 (e.g. 8, 9, 10, 11, 12, 13, 14, 15, 16, 17, 18, 19, 20, 21, 22, 23, 24, 25, 30, 35, 40, 45, 50, 60, 70, 80, 90, 100 etc.).

These polynucleotides include naturally-occurring variants (e.g. degenerate variants, allelic variants, etc.), homologs, orthologs, and functional mutants.

Variants can be identified by hybridization of putative variants with the polynucleotide sequences disclosed in SEQ ID NOS:14-39 herein, preferably by hybridization under stringent conditions. For example, by using appropriate wash conditions, variants can be identified where the allelic variant exhibits at most about 25-30% base pair (bp) mismatches relative to the selected polynucleotide probe. In general, allelic variants contain 15-25% by mismatches, and can contain as little as even 5-15%, or 2-5%, or 1-2% by mismatches, as well as a single by mismatch.

The invention also encompasses homologs corresponding to any one of the polynucleotide sequences provided herein, where the source of homologous genes can be any mammalian species (e.g. primate species, particularly human; rodents, such as rats, etc.). Between mammalian species (e.g. human and primate), homologs generally have substantial sequence similarity (e.g. at least 75% sequence identity, usually at least 90%, more usually at least 95%) between nucleotide sequences. Sequence similarity is calculated based on a reference sequence, which may be a subset of a larger sequence, such as a conserved motif, coding region, flanking region, domain, etc. A reference sequence will usually be at least about 18 contiguous nt long, more usually at least about 30 nt long, and may extend to the complete sequence that is being compared. Algorithms for sequence analysis are known in the art.

A preferred HERV-K(CH) isolate is an isolate sequence which is shown in SEQ ID NOS:7-10. Another preferred class of HERV-K(CH) isolates are those having a nucleotide sequence identity of at least 90%, preferably at least 95% to the 3' polymerase region shown in SEQ ID NO:13 which relates to integrase, as measured by the alignment program GCG Gap (Suite Version 10.1) using the default parameters: open gap=3 and extend gap=1. Another preferred class of HERV-K(CH) isolates are those having a nucleotide sequence identity of at least 98%, more preferably at least 99% to the 5' polymerase region shown in SEQ ID NO:12 which relates to reverse transcriptase, as measured by the alignment program GCG Gap (Suite Version 10.1) using the default parameters: open gap=3 and extend gap=1. Another typical classification of the relationship of retroviruses is based on the amino acid sequence similarities in the reverse transcriptase protein. Thus, an even more preferred class of HERV-K(CH) isolates are those having an amino acid sequence identity of at least 90%, more preferably 95% to the 5' polymerase region encoded by the nucleotide sequence shown in SEQ ID NO:12, as determined by the Smith-Waterman homology search algorithm using an affine gap search with a gap open penalty of 12 and a gap extension penalty of 2, BLOSUM matrix of 62. Thus, these prostate cancer-associated polynucleotide sequences define a class of human endogenous retroviruses, designated herein as HERV-K(CH), whose members comprise variations which, without wanted to be bound by theory, may be due to the presence of polymorphisms or allelic variations.

H.1.5—HERV-K(CH) Hybridizable Sequences

The invention provides an isolated polynucleotide comprising a polynucleotide that selectively hybridizes, relative to a known polynucleotide, to: (a) the nucleotide sequence shown in SEQ ID NOS:7-10; (b) the nucleotide sequence shown in any of SEQ ID NOS:27-39; (c) the complement of the nucleotide sequence shown in SEQ ID NOS:7-10; (d) the complement of the nucleotide sequence shown in any of SEQ ID NOS:27-39; (e) a fragment of the nucleotide sequence shown in SEQ ID NOS:7-10; (f) a fragment of the nucleotide sequence shown in any of SEQ ID NOS:27-39; (g) the complement of a fragment of the nucleotide sequence shown in SEQ ID NOS:7-10; (h) the complement of a fragment of the nucleotide sequence shown in any of SEQ ID NOS:27-39; (j) a nucleotide sequence shown in SEQ ID NOS:14-39; or (k) polynucleotides found in ATCC deposits having ATCC accession numbers given in Table 7. The fragment of (e), (f), (g) or (h) is preferably at least x nucleotides in length, wherein x is as defined in H.1.2 above, and is preferably not one of the sequences (i), (ii), (iii), (iv), (v) or (vi) as defined H.1.2 above.

Hybridization reactions can be performed under conditions of different "stringency", as described in B.4 above. In some embodiments, the polynucleotide hybridizes under low stringency conditions; in other embodiments it hybridizes under intermediate stringency conditions; in other embodiments, it hybridizes under high stringency conditions.

H.1.6—Deposited HERV-K Sequences

The invention also provides an isolated polynucleotide comprising: (a) a HERV-K(CH) cDNA insert as deposited at the ATCC and having an ATCC accession number given in Table 7; (b) a HERV-K(CH) sequence as shown in any one of SEQ ID NOS:14-26; (c) a HERV-K(CH) sequence as shown in any one of SEQ ID NOS:27-39; or (d) a fragment of (a), (b) or (c). The fragment of (d) is preferably at least x nucleotides in length, wherein x is at least 7 (e.g. at least 8, 9, 10, 11, 12, 13, 14, 15, 16, 17, 18, 19, 20, 21, 22, 23, 24, 25, 30, 35, 40, 45, 50, 60, 70, 80, 90, 100 etc.

H.1.7—Preferred HERV-K(CH) Sequences

Preferred polynucleotides of the invention are those having a sequence set forth in any one of the polynucleotide sequences SEQ ID NOS:7-10 and SEQ ID NOS:14-39 provided herein; polynucleotides obtained from the biological materials described herein, in particular, polynucleotide sequences present in the isolates deposited with the ATCC and having ATCC accession numbers given in Table 7 or other biological sources (particularly human sources) or by hybridization to the above mentioned sequences under stringent conditions (particularly conditions of high stringency); genes corresponding to the provided polynucleotides; variants of the provided polynucleotides and their corresponding genes particularly those variants that retain a biological activity of the encoded gene product (e.g. a biological activity ascribed to a gene product corresponding to the provided polynucleotides as a result of the assignment of the gene product to a protein family(ies) and/or identification of a functional domain present in the gene product). Other polynucleotides and polynucleotide compositions contemplated by and within the scope of the present invention will be readily apparent to one of ordinary skill in the art when provided with the disclosure here.

H.1.8—General Features of Polynucleotides of the Invention

General features of the polynucleotides described in this section H.1 are the same as those described in section B.4 above.

The isolated polynucleotides preferably comprise a polynucleotide having a HERV-K(CH) sequence.

A polynucleotide of the invention can encode all or a part of a polypeptide, such as the gag region, 5' pol region or 3' pol region of a human endogenous retrovirus. Double or single stranded fragments can be obtained from the DNA sequence by chemically synthesizing oligonucleotides in accordance with conventional methods, by restriction enzyme digestion, by PCR amplification, etc.

Polynucleotides of the invention can be cDNAs or genomic DNAs, as well as fragments thereof, particularly fragments that encode a biologically active gene product and/or are useful in the methods disclosed herein (e.g. in diagnosis, as a unique identifier of a differentially expressed gene of interest, etc.). The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, being removed by nuclear RNA splicing, to create a continuous open reading frame encoding a polypeptide. mRNA species can also exist with both exons and introns, where the introns may be removed by alternative splicing. Furthermore it should be noted that different species of mRNAs encoded by the same genomic sequence can exist at varying levels in a cell, and detection of these various levels of mRNA species can be indicative of differential expression of the encoded gene product in the cell.

A genomic sequence of interest comprises the nucleic acid present between the initiation codon and the stop codon, as defined in the listed sequences, including all of the introns that are normally present in a native chromosome. It can further include the 3' and 5' untranslated regions found in the mature mRNA. It can further include specific transcriptional and translational regulatory sequences, such as promoters, enhancers, etc., including about 1 kb, but possibly more, of flanking genomic DNA at either the 5' and 3' end of the transcribed region. The genomic DNA can be isolated as a fragment of 100 kbp or smaller; and substantially free of flanking chromosomal sequence. The genomic DNA flanking the coding region, either 3' and 5', or internal regulatory sequences as sometimes found in introns, contains sequences required for proper tissue, stage-specific, or disease-state specific expression.

Polynucleotides of the invention can be provided as linear molecules or within circular molecules, and can be provided within autonomously replicating molecules (vectors) or within molecules without replication sequences. Expression of the polynucleotides can be regulated by their own or by other regulatory sequences known in the art. The polynucleotides can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

A polynucleotide sequence that is "shown in" or "depicted in" a SEQ ID NO or Figure means that the sequence is present as an identical contiguous sequence in the SEQ ID NO or Figure. The term encompasses portions, or regions of the SEQ ID NO or Figure as well as the entire sequence contained within the SEQ ID NO or Figure.

H.2—HERV-K(CH) Polypeptides

H.2.1—HERV-K(CH) Open Reading Frames

The invention provides an isolated polypeptide: (a) encoded within a HERV-K(CH) open reading frame; (b) encoded by a polynucleotide shown in SEQ ID NO:11, 12 or 13; or (c) comprising an amino acid sequence as shown in any one of SEQ ID NOS:46-49, 50-55, 56-57 or 58.

Deduced polypeptides encoded by the HERV-K(CH) polynucleotides of the invention include the gag translations shown in SEQ IDS 46-49 and the 3' pol translations shown in SEQ ID NOS:50-55. A polypeptide sequence encoded by the polynucleotide having the sequence shown in SEQ ID NO:15 is provided in SEQ ID NO:56; a polypeptide sequence encoded by the polynucleotide having the sequence shown in SEQ ID NO:14, is shown in SEQ ID NO:57. A consensus 3' pol polypeptide sequence encoded by the polynucleotides having the sequence shown in SEQ ID NOS:21-27, inclusive, is provided in SEQ ID NO:58.

The polypeptides encompassed by the present invention include those encoded by polynucleotides of the invention, e.g. SEQ ID NOS:7-10 and SEQ ID NOS:14-39, as well as polynucleotides deposited with the ATCC as disclosed herein, as well as nucleic acids that, by virtue of the degeneracy of the genetic code, are not identical in sequence to the disclosed polynucleotides and encode the polypeptides. Thus, the invention includes within its scope a polypeptide encoded by a polynucleotide having the sequence of any one of the polynucleotide sequences provided herein, or a variant thereof.

While the over-expression of the polynucleotides associated with prostate tumor is observed, elevated levels of expression of the polypeptides encoded by these polynucleotides may likely play a role in prostate tumors.

Typically, in retroviruses, a single large gag polypeptide is synthesized (e.g. a 73 kDa gag protein in HERV-K10) which is subsequently cleaved into multiple functional peptides by a functional protease encoded by the pol or protease region of the genome. Overexpression of sequences corresponding to both gag and pol domains of the HERV-K(CH) suggest such a mechanism. Sequences corresponding to the env and the nuclear RNA transport protein cORF region of the HERV-K (CH) genome may also be overexpressed. The polypeptides encoded by the open reading frames within the over-expressed polynucleotide sequences may play a significant role in the progression of prostate tumors.

The detection of these polypeptides by antibodies or other reagents that specifically recognize them may aid in the early diagnosis of prostate tumor or any other cancers associated with the overexpression of these HERV-K(CH) sequences.

Furthermore, inhibition of the function of these polypeptides may suggest means for therapy and treatment of prostatic or other HERV-K(CH) sequence related cancers. One method of accomplishing such inhibition is by administration of vaccines as a preventative therapy or antibody-mediated drug therapy as a post-neoplasia regimen for treatment of such cancers.

H.2.2—HERV-K(CH) Fragments

The invention provides an isolated polypeptide comprising a fragment of (a) a polypeptide sequence encoded within a HERV-K(CH) open reading frame; (b) a polypeptide sequence encoded by a polynucleotide shown in SEQ ID NO:11, 12 or 13; or (c) an amino acid sequence as shown in any one of SEQ ID NOS:46-49, 50-55, 56-57 or 58.

The fragment is preferably at least x amino acids in length, wherein x is at least 5 (e.g. at least 6, 7, 8, 9, 10, 11, 12, 13, 14, 15, 16, 17, 18, 19, 20, 21, 22, 23, 24, 25, 30, 35, 40, 45, 50, 60, 70, 75, 80, 90, 100, 125, 150, 200, 300, 400, 500 or more etc.). The value of x will typically not exceed 1000.

The fragment may include an epitope e.g. an epitope of the amino acid sequence shown in SEQ ID NOS:56, 57 or 58.

SEQ ID NOS:46-49 provide a translation of the HERV-K (CH) polynucleotides having a sequence shown in SEQ ID NOS:14, 15, 16 and 40 (the sequence of SEQ ID NO:40 is from a polynucleotide found in a normal prostate library) corresponding to polynucleotides encoding the gag region. SEQ ID NOS:50-55 provide a translation of the HERV-K (CH) polynucleotides having a sequence shown in SEQ ID NOS:21-26, inclusive, corresponding to the 3' region of pol. SEQ ID NOS:56 & 57 provide translations of the HERV-K (CH) polynucleotide of SEQ ID NO:15 and SEQ ID NO:14, respectively. SEQ ID NO:58 provides a consensus translation of the polynucleotide from the 3' pol region (SEQ ID NOS: 21-26, inclusive). Encompassed with the present invention are polypeptide fragments, such as, epitopes, of at least 5 amino acids, at least 6 amino acids, at least 8 amino acids, at least 10 amino acids, at least 11 amino acids, at least amino acids, at least 13 amino acids, at least 14 amino acids and at least 15 amino acids of the translations shown in SEQ ID NOS:46-49 and 50-55. In a preferred embodiment, the HERV-K(CH) epitopes of the amino acid sequence as shown in SEQ ID NOS:56-58 were determined by the Jameson-Wolf antigenic index [21].

The following regions in 3' pol (SEQ ID NO:58) were determined to be antigenic by Jameson-Wolf algorithm: amino acids: 1-10; 15-35; 45-55; 60-85; 100-115; 125-140; 170-190; 195-215; 230-268. Additional epitope-containing fragments include amino acids 1-8; 2-10; 1-15; 5-15; 7-15; 10-20; 12-20; 15-23; 20-28; 28-35; 15-30; 15-40; 20-30; 45-52; 48-55; 60-68; 60-70; 65-73; 70-78; 75-83; 70-80; 65-75; 68-75; 75-85; 78-85; 65-85; 60-75; 100-108; 103-110; 105-113; 108-115; 125-133; 128-135; 132-140; 170-178; 175-182; 180-187; 182-190; 195-202; 200-208; 205-212; 208-215; 230-237; 235-242; 240-247; 245-252; 250-257; 255-262; 260-268; 230-250; 235-255; 240-260; 245-268; 230-245; 235-245; 235-250; 240-255; 245-260; 250-268; 15-55; 170-215; 45-85.

The following regions in gag (SEQ ID NO:56) were determined to be antigenic by Jameson-Wolf algorithm: amino acids: 1-40; 45-60; 80-105; 130-145; 147-183; 186-220; 245-253; 255-288. Additional epitope-containing fragments include amino acids 1-8; 2-10; 1-15; 5-15; 7-15; 10-20; 12-20; 15-23; 20-28; 28-35; 30-37; 33-40; 1-20; 20-40; 1-15; 15-30; 15-40; 45-52; 50-57; 55-62; 50-60; 1-60; 80-87; 85-92; 80-90; 90-97; 95-102; 98-105; 85-100; 90-105; 80-100; 85-105; 130-137; 135-142; 140-147; 145-152; 150-157; 155-162; 160-167; 165-172; 170-177; 175-183; 180-187; 185-192; 190-197; 195-202; 200-207; 205-212; 210-217; 213-220; 185-220; 190-220; 195-220; 200-220; 205-220; 255-262; 260-267; 265-272; 270-277; 275-282; 280-288; 245-288; 250-288; 260-288; 265-288; 270-288.

The following regions in gag (SEQ ID NO:57) were determined to be antigenic by Jameson-Wolf algorithm: amino acids: 1-40; 80-105; 145-180; 185-225; 240-335. Additional epitope-containing fragments include amino acids 1-8; 2-10; 1-15; 5-15; 7-15; 10-20; 12-20; 15-23; 20-28; 28-35; 30-37; 33-40; 1-20; 20-40; 1-15; 15-30; 15-40; 80-87; 85-92; 80-90; 90-97; 95-102; 98-105; 85-100; 90-105; 80-100; 85-105; 145-152; 150-157; 155-162; 160-167; 165-172; 170-177; 175-182; 180-187; 185-192; 190-197; 195-202; 200-207; 205-212; 210-217; 215-212; 218-225; 145-160; 150-165; 155-170; 160-175; 170-185; 180-225; 185-225; 190-225; 195-225; 200-225; 205-225; 210-225; 215-225; 240-247; 245-252; 250-257; 255-262; 260-267; 265-272; 270-277; 275-282; 280-287; 285-292; 290-297; 295-302; 300-307; 305-312; 310-317; 315-322; 320-327; 325-332; 328-335; 245-285; 250-285; 260-285; 265-285; 270-295; 275-300; 280-305; 285-310; 295-315; 300-320; 305-325; 325-335; 245-335; 250-335; 255-335; 260-335; 270-335; 275-335; 280-335; 285-335; 290-335; 295-335; 305-335; 310-335; 315-335; 320-335.

H.2.3—HERV-K(CH) Fragments Plus Heterologous Sequences

The invention also provides an isolated polypeptide having formula 5'-A-B-C-3', wherein: A is an amino acid sequence consisting of a amino acids; B is an amino acid sequence consisting of a fragment of b amino acids from (i) the amino acid sequence encoded by a polynucleotide shown in SEQ ID NO:11, 12 or 13; (ii) any one of SEQ ID NOS:46-49, 50-55, 56-57 or 58; C is an amino acid sequence consisting of c amino acids; and wherein said polypeptide is not a fragment of the amino acid sequence defined in (i) or (ii).

In this polypeptide, a+c is at least 1 (e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100 etc.) and b is at least 7 (e.g. at least 8, 9, 10, 11, 12, 13, 14, 15, 16, 17, 18, 19, 20, 21, 22, 23, 24, 25, 30, 35, 40, 45, 50, 60, 70, 80, 90, 100 etc.). It is preferred that the value of a+b+c is at least 9 (e.g. at least 10, 11, 12, 13, 14, 15, 16, 17, 18, 19, 20, 21, 22, 23, 24, 25, 30, 35, 40, 45, 50, 60, 70, 80, 90, 100 etc.). It is preferred that the value of a+b+c is at most 200 (e.g. at most 190, 180, 170, 160, 150, 140, 130, 120, 110, 100, 90, 80, 70, 60, 50, 40, 30, 25, 20, 19, 18, 17, 16, 15, 14, 13, 12, 11, 10, 9).

H.2.4—Homologous Sequences

The invention provides a polypeptide having at least s % identity to: (a) the polypeptide sequences encoded by SEQ ID NOS:7-45; (b) a fragment of x amino acids of the polypeptide sequences encoded by SEQ ID NOS:7-45; (c) the polypeptide sequences SEQ ID NOS:46-58; (d) a fragment of x amino acids of the polypeptide sequences SEQ ID NOS:46-58. The value of s is at least 35 (e.g. at least 40, 45, 50, 55, 60, 65, 70, 75, 80, 81, 82, 83, 84, 85, 86, 87, 88, 89, 90, 91, 92, 93, 94, 95, 96, 97, 98, 99, 99.5, 99.9 etc.). The value of x is at least 7 (e.g. 8, 9, 10, 11, 12, 13, 14, 15, 16, 17, 18, 19, 20, 21, 22, 23, 24, 25, 30, 35, 40, 45, 50, 60, 70, 80, 90, 100.

These polypeptides include naturally-occurring variants (e.g. allelic variants, etc.), homologs, orthologs, and functional mutants.

The invention thus encompasses variants of the naturally-occurring polypeptides, wherein such variants are homologous or substantially similar to the naturally occurring polypeptide, and can be of an origin of the same or different species as the naturally occurring polypeptide (e.g. human, murine, or some other species that naturally expresses the recited polypeptide, usually a mammalian species). These polypeptide variants are encoded by polynucleotides that are within the scope of the invention, and the genetic code can be used to select appropriate codons to construct the corresponding variants.

H.2.5—Preferred HERV-K(CH) Sequences

The invention provides polypeptides, such as those shown in SEQ ID NO: encoded by HERV-K(CH) polynucleotides that are differentially expressed in prostate cancer cells. Such polypeptides are referred to herein as "polypeptides associated with prostate cancer" or "HERV-K(CH) polypeptides". The polypeptides can be used to generate antibodies specific for a polypeptide associated with prostate cancer, which antibodies are in turn useful in diagnostic methods, prognostic methods, therametric methods, and the like as discussed in more detail herein. Polypeptides are also useful as targets for therapeutic intervention, as discussed in more detail herein.

Preferred polypeptides are encoded by polynucleotides of the invention.

H.2.6—General Features of Polypeptides of the Invention

General features of the polypeptides described in this section H.2 are the same as those described in section C.3 above.

The isolated polypeptides of the invention preferably comprise a polypeptide having a HERV-K(CH) sequence.

Polypeptides, such as polypeptides of the gag regions or polypeptides of the pol regions, encoded by the polynucleotides disclosed herein, such as polynucleotides having the sequences as shown in SEQ ID NOS:7-10 and SEQ ID NOS: 14-39, and in isolates deposited with the ATCC and having ATCC accession numbers given in Table 7 and/or their corresponding full length genes, can be used to screen peptide libraries to identify binding partners, such as receptors, from among the encoded polypeptides. Peptide libraries can be synthesized according to methods known in the art (e.g. see refs. &).

In general, the term "polypeptide" as used herein refers to both the full length polypeptide encoded by the recited polynucleotide, the polypeptide encoded by the gene represented by the recited polynucleotide, as well as portions or fragments thereof.

A polypeptide sequence that is "shown in" or "depicted in" a SEQ ID NO or Figure means that the sequence is present as an identical contiguous sequence in the SEQ ID NO or Figure. The term encompasses portions, or regions of the SEQ ID NO or Figure as well as the entire sequence contained within the SEQ ID NO or Figure.

H.3 Anti-HERV-K(CH) Antibodies

The present invention also provides isolated antibodies or antigen binding fragments thereof, that bind to a polypeptide of the present invention. The present invention also provides isolated antibodies or antigen binding fragments thereof, that bind to a polypeptide encoded by a polynucleotide of the present invention. The present invention also provides isolated antibodies that bind to a polypeptide of the invention, or antigen binding fragment thereof, encoded by a polynucleotide made by the method comprising the following steps i) immunizing a host animal with a composition comprising said polypeptide of the present invention, or antigen binding fragment thereof, and ii) collecting cells from said host expressing antibodies against the antigen or antigen binding fragment thereof. The present invention also provides isolated antibodies that bind to a polypeptide, or antigen binding fragment thereof, encoded by a polynucleotide of the present invention made by the method comprising the following steps: providing a cell line producing an antibody, wherein said antibody binds to a polypeptide of the present invention, or antigen binding fragment thereof, encoded by a polynucleotide of the present invention and culturing said cell line under conditions wherein said antibodies are produced. In additional embodiments, the antibodies are collected and monoclonal antibodies are produced using the collected host cells or genetic material derived from the collected host cells. In additional embodiments, the antibody is a polyclonal antibody. In a further embodiment, the antibody is attached to a solid surface or further comprises a detectable label.

The present invention further provides antibodies, which may be isolated antibodies, that bind a polypeptide encoded by a polynucleotide described herein. Antibodies can be provided in a composition comprising the antibody and a buffer and/or a pharmaceutically acceptable excipient. Antibodies specific for a polypeptide associated with cancer are useful in a variety of diagnostic and therapeutic methods, as discussed in detail herein.

Expression products of a polynucleotide described herein, as well as the corresponding mRNA (particularly mRNAs having distinct secondary and/or tertiary structures), cDNA, or complete gene, or fragments of said expression products can be prepared and used for raising antibodies for experimental, diagnostic, and therapeutic purposes. For polynucleotides to which a corresponding gene has not been assigned, this provides an additional method of identifying the corresponding gene. The polynucleotide or related cDNA is expressed as described above, and antibodies are prepared. These antibodies are specific to an epitope on the polypeptide encoded by the polynucleotide, and can precipitate or bind to the corresponding native polypeptide in a cell or tissue preparation or in a cell-free extract of an in vitro expression system.

Polyclonal or monoclonal antibodies to the HERV-K(CH) polypeptides or an epitope thereof can be made for use in immunoassays by any of a number of methods known in the art. By epitope reference is made to an antigenic determinant of a polypeptide. The presence of an epitope is demonstrated by the ability of an antibody to bind a polypeptide with specificity. Two antibodies are considered to be directed to the same epitope if they cross block each others binding to the same polypeptide.

One approach for preparing antibodies to a polypeptide is the selection and preparation of an amino acid sequence of all or part of the polypeptide, chemically synthesizing the sequence and injecting it into an appropriate animal, typically a rabbit, hamster or a mouse.

Oligopeptides can be selected as candidates for the production of an antibody to the HERV-K(CH) polypeptide based upon the oligopeptides lying in hydrophilic regions, which are thus likely to be exposed in the mature polypeptide. Additional oligopeptides can be determined using, for example, the Antigenicity Index [30].

In other embodiments of the present invention, humanized monoclonal antibodies are provided, wherein the antibodies are specific for HERV-K(CH) polypeptides and do not appreciably bind other HERV polypeptides. The phrase "humanized antibody" refers to an antibody derived from a non-human antibody, typically a mouse monoclonal antibody. Alternatively, a humanized antibody may be derived from a chimeric antibody that retains or substantially retains the antigen-binding properties of the parental, non-human, antibody but which exhibits diminished immunogenicity in humans as compared to the parental antibody. The phrase "chimeric antibody," as used herein, refers to an antibody containing sequence derived from two different antibodies (see, e.g. ref. 153) which typically originate from different species. Most typically, chimeric antibodies comprise human and murine antibody fragments, generally human constant and mouse variable regions.

In the present invention, HERV-K(CH) polypeptides of the invention and variants thereof are used to immunize a transgenic animal as described above. Monoclonal antibodies are made using methods known in the art, and the specificity of the antibodies is tested using isolated HERV-K(CH) polypeptides.

Methods for preparation of the human or primate HERV-K(CH) or an epitope thereof include, but are not limited to chemical synthesis, recombinant DNA techniques or isolation from biological samples. Chemical synthesis of a peptide can be performed, for example, by the classical Merrifeld method of solid phase peptide synthesis [154] or the FMOC strategy on a Rapid Automated Multiple Peptide Synthesis system (E.I. du Pont de Nemours Company, Wilmington, Del.) [155].

Polyclonal antibodies can be prepared by immunizing rabbits or other animals by injecting antigen followed by subsequent boosts at appropriate intervals. The animals are bled and sera assayed against purified HERV-K(CH) usually by ELISA or by bioassay based upon the ability to block the action of HERV-K(CH). When using avian species, e.g. chicken, turkey and the like, the antibody can be isolated from the yolk of the egg. Monoclonal antibodies can be prepared after the method of Milstein and Kohler by fusing splenocytes from immunized mice with continuously replicating tumor cells such as myeloma or lymphoma cells. [156, 157, 158]. The hybridoma cells so formed are then cloned by limiting dilution methods and supernates assayed for antibody production by ELISA, RIA or bioassay.

The unique ability of antibodies to recognize and specifically bind to target polypeptides provides an approach for treating an overexpression of the polypeptide. Thus, another aspect of the present invention provides for a method for preventing or treating diseases involving overexpression of a HERV-K(CH) polypeptide by treatment of a patient with specific antibodies to the HERV-K(CH) polypeptide.

Specific antibodies, either polyclonal or monoclonal, to the HERV-K(CH) polypeptides can be produced by any suitable method known in the art as discussed above. For example, murine or human monoclonal antibodies can be produced by hybridoma technology or, alternatively, the HERV-K(CH) polypeptides, or an immunologically active fragment thereof, or an anti-idiotypic antibody, or fragment thereof can be administered to an animal to elicit the production of antibodies capable of recognizing and binding to the HERV-K(CH) polypeptides. Such antibodies can be from any class of antibodies including, but not limited to IgG, IgA, IgM, IgD, and IgE or in the case of avian species, IgY and from any subclass of antibodies.

H.4—HERV-K(CH) Vectors and Host Cells

The present invention also encompasses vectors and host cells comprising an isolated polynucleotide of the present invention.

H.5—HERV-K(CH) Kits, Libraries and Arrays

The invention provides kits, electronic libraries and arrays comprising polynucleotides of the invention, for use in diagnosing the presence of cancer in a test sample.

In general, a library of polynucleotides is a collection of sequence information, which information is provided in either biochemical form (e.g. as a collection of polynucleotide molecules), or in electronic form (e.g. as a collection of polynucleotide sequences stored in a computer-readable form, as in a computer system and/or as part of a computer program). The sequence information of the polynucleotides can be used in a variety of ways, e.g. as a resource for gene discovery, as a representation of sequences expressed in a selected cell type (e.g. cell type markers), and/or as markers of a given disease or disease state. In general, a disease marker is a representation of a gene product that is present in all cells affected by disease either at an increased or decreased level relative to a normal cell (e.g. a cell of the same or similar type that is not substantially affected by disease). For example, a polynucleotide sequence in a library can be a polynucleotide that represents an mRNA, polypeptide, or other gene product encoded by the polynucleotide, that is either over-expressed or under-expressed in a tissue affected by cancer, such as prostate cancer relative to a normal (i.e. substantially disease-free) tissue, such as normal prostate tissue.

The nucleotide sequence information of the library can be embodied in any suitable form, e.g. electronic or biochemical forms. For example, a library of sequence information embodied in electronic form comprises an accessible computer data file (or, in biochemical form, a collection of nucleic acid molecules) that contains the representative nucleotide sequences of genes that are differentially expressed (e.g. over-expressed or under-expressed) as between, for example, i) a cancerous cell and a normal cell; ii) a cancerous cell and a dysplastic cell; iii) a cancerous cell and a cell affected by a disease or condition other than cancer; iv) a metastatic cancerous cell and a normal cell and/or non-metastatic cancerous cell; v) a malignant cancerous cell and a non-malignant cancerous cell (or a normal cell) and/or vi) a dysplastic cell relative to a normal cell. Other combinations and comparisons of cells affected by various diseases or stages of disease will be readily apparent to the ordinarily skilled artisan. Biochemical embodiments of the library include a collection of nucleic acids that have the sequences of the genes in the library, where the nucleic acids can correspond to the entire gene in the library or to a fragment thereof, as described in greater detail below.

The polynucleotide libraries of the subject invention generally comprise sequence information of a plurality of polynucleotide sequences, where at least one of the polynucleotides has a sequence of any of sequence described herein. By plurality is meant at least 2, usually at least 3 and can include up to all of the sequences described herein. The length and number of polynucleotides in the library will vary with the nature of the library, e.g. if the library is an oligonucleotide array, a cDNA array, a computer database of the sequence information, etc.

Where the library is an electronic library, the nucleic acid sequence information can be present in a variety of media. "Media" refers to a manufacture, other than an isolated nucleic acid molecule, that contains the sequence information of the present invention. Such a manufacture provides the genome sequence or a subset thereof in a form that can be examined by means not directly applicable to the sequence as it exists in a nucleic acid. For example, the nucleotide sequence of the present invention, e.g. the nucleic acid sequences of any of the polynucleotides of the sequences described herein, can be recorded on computer readable media, e.g. any medium that can be read and accessed directly by a computer. Such media include, but are not limited to: magnetic storage media, such as a floppy disc, a hard disc storage medium, and a magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present sequence information. "Recorded" refers to a process for storing information on computer readable medium, using any such methods as known in the art. Any convenient data storage structure can be chosen, based on the means used to access the stored information. A variety of data processor programs and formats can be used for storage, e.g. word processing text file, database format, etc. In addition to the sequence information, electronic versions of libraries comprising one or more sequence described herein can be provided in conjunction or connection with other computer-readable information and/or other types of computer-readable files (e.g. searchable files, executable files, etc, including, but not limited to, for example, search program software, etc.).

By providing the nucleotide sequence in computer readable form, the information can be accessed for a variety of purposes. Computer software to access sequence information is publicly available. For example, the gapped BLAST [159] and BLAZE [160] search algorithms on a Sybase system can be used to identify open reading frames (ORFs) within the genome that contain homology to ORFs from other organisms.

As used herein, "a computer-based system" refers to the hardware means, software means, and data storage means used to analyze the nucleotide sequence information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means can comprise any manufacture comprising a recording of the present sequence information as described above, or a memory access means that can access such a manufacture.

"Search means" refers to one or more programs implemented on the computer-based system, to compare a target sequence or target structural motif, or expression levels of a polynucleotide in a sample, with the stored sequence information. Search means can be used to identify fragments or regions of the genome that match a particular target sequence or target motif. A variety of known algorithms are publicly known and commercially available, e.g. MacPattern (EMBL), BLASTN and BLASTX (NCBI). A "target sequence" can be any polynucleotide or amino acid sequence of six or more contiguous nucleotides or two or more amino acids, preferably from about 10 to 100 amino acids or from about 30 to 300 nt A variety of comparing means can be used to accomplish comparison of sequence information from a sample (e.g. to analyze target sequences, target motifs, or relative expression levels) with the data storage means. A skilled artisan can readily recognize that any one of the publicly available homology search programs can be used as the search means for the computer based systems of the present invention to accomplish comparison of target sequences and motifs. Computer programs to analyze expression levels in a sample and in controls are also known in the art.

A "target structural motif," or "target motif," refers to any rationally selected sequence or combination of sequences in which the sequence(s) are chosen based on a three-dimensional configuration that is formed upon the folding of the target motif, or on consensus sequences of regulatory or active sites. There are a variety of target motifs known in the art. Protein target motifs include, but arc not limited to, enzyme active sites and signal sequences. Nucleic acid target motifs include, but are not limited to, hairpin structures, promoter sequences and other expression elements such as binding sites for transcription factors.

A variety of structural formats for the input and output means can be used to input and output the information in the computer-based systems of the present invention. One format for an output means ranks the relative expression levels of different polynucleotides. Such presentation provides a skilled artisan with a ranking of relative expression levels to determine a gene expression profile.

As discussed above, the "library" as used herein also encompasses biochemical libraries of the polynucleotides of the sequences described herein, e.g. collections of nucleic acids representing the provided polynucleotides. The biochemical libraries can take a variety of forms, e.g. a solution of cDNAs, a pattern of probe nucleic acids stably associated with a surface of a solid support (i.e. an array) and the like. Of particular interest are nucleic acid arrays in which one or more of the genes described herein is represented by a sequence on the array. By array is meant an article of manufacture that has at least a substrate with at least two distinct nucleic acid targets on one of its surfaces, where the number of distinct nucleic acids can be considerably higher, typically being at least 10 nt, usually at least 20 nt and often at least 25 nt. A variety of different array formats have been developed and are known to those of skill in the art. The arrays of the subject invention find use in a variety of applications, including gene expression analysis, drug screening, mutation analysis and the like, as disclosed in the above-listed exemplary patent documents.

In addition to the above nucleic acid libraries, analogous libraries of polypeptides are also provided, where the where the polypeptides of the library will represent at least a portion of the polypeptides encoded by a gene corresponding to a sequence described herein.

Polynucleotide arrays provide a high throughput technique that can assay a large number of polynucleotides or polypeptides in a sample. This technology can be used as a tool to test for differential expression. A variety of methods of producing arrays, as well as variations of these methods, are known in the art and contemplated for use in the invention. For example, arrays can be created by spotting polynucleotide probes onto a substrate (e.g. glass, nitrocellulose, etc.) in a two-dimensional matrix or array having bound probes. The probes can be bound to the substrate by either covalent bonds or by non-specific interactions, such as hydrophobic interactions. Samples of polynucleotides can be detectably labeled (e.g. using radioactive or fluorescent labels) and then hybridized to the probes. Double stranded polynucleotides, comprising the labeled sample polynucleotides bound to probe polynucleotides, can be detected once the unbound portion of the sample is washed away. Alternatively, the polynucleotides of the test sample can be immobilized on the array, and the probes detectably labeled. Techniques for constructing arrays and methods of using these arrays are described in, for example, references 161 to 177.

Arrays can be used to, for example, examine differential expression of genes and can be used to determine gene function. For example, arrays can be used to detect differential expression of a gene corresponding to a polynucleotide described herein, where expression is compared between a test cell and control cell (e.g. cancer cells and normal cells). For example, high expression of a particular message in a cancer cell, which is not observed in a corresponding normal cell, can indicate a cancer specific gene product. Exemplary uses of arrays are further described in, for example, references 178 and 179. Furthermore, many variations on methods of detection using arrays are well within the skill in the art and within the scope of the present invention. For example, rather than immobilizing the probe to a solid support, the test sample can be immobilized on a solid support which is then contacted with the probe.

A gene or polynucleotide that is differentially expressed in a cancer cell when the polynucleotide is detected at higher or lower levels in cancer compared with a cell of the same cell type that is not cancerous. Typically, screening for polynucleotides differentially expressed focuses on a polynucleotide that is expressed such that, for example, mRNA is found at levels at least about 25%, at least about 50% to about 75%, at least about 90%, preferably at least about 2-fold, more preferably at least about 5-fold, at least about 10-fold, or at least about 50-fold or more, higher (e.g. overexpressed) or lower (e.g. underexpressed) in a cancer cell when compared with a cell of the same cell type that is not cancerous. The comparison can be made between two tissues, for example, if one is using in situ hybridization or another assay method that allows some degree of discrimination among cell types in the tissue. The comparison may also be made between cells removed from their tissue source. Thus, a polypeptide encoded by a polynucleotide that is differentially expressed in a cancer cell would be of clinical significance with respect to cancer.

In one preferred embodiment of the present invention, an array comprises at least two polynucleotides, each having a sequence selected from the group consisting of SEQ ID NOS: 14-39 and polynucleotides present in isolates deposited with the ATCC and having ATCC accession numbers PTA-2561, PTA-2572, PTA-2566, PTA-2571, PTA-2562, PTA-2573, PTA-2560, PTA-2565, PTA-2568, PTA-2564, PTA-2569, PTA-2567, PTA-2559, PTA-2563, PTA-2570. In another preferred embodiment, an array comprises at least one polynucleotide having a sequence selected from the group consisting of SEQ ID NOS:14-39 and polynucleotides present in isolates deposited with the ATCC and having ATCC accession numbers PTA-2561, PTA-2572, PTA-2566, PTA-2571, PTA-2562, PTA-2573, PTA-2560, PTA-2565, PTA-2568, PTA-2564, PTA-2569, PTA-2567, PTA-2559, PTA-2563, PTA-2570 and at least one of a polynucleotide having a sequence shown in SEQ ID NO:42 or 43.

The polynucleotides described herein, as well as their gene products, are of particular interest as genetic or biochemical markers (e.g. in blood or tissues) that will detect the earliest changes along the carcinogenesis pathway and/or to monitor the efficacy of various therapies and preventive interventions. For example, the level of expression of certain polynucleotides can be indicative of a poorer prognosis, and therefore warrant more aggressive chemo- or radio-therapy for a patient or vice versa. The correlation of novel surrogate tumor specific features with response to treatment and outcome in patients can define prognostic indicators that allow the design of tailored therapy based on the molecular profile of the tumor. These therapies include antibody targeting, antagonists (e.g. small molecules), and gene therapy. Determining expression of certain polynucleotides and comparison of a patients profile with known expression in normal tissue and variants of the disease allows a determination of the best possible treatment for a patient, both in terms of specificity of treatment and in terms of comfort level of the patient. Polynucleotide expression can also be used to better classify, and thus diagnose and treat, different forms and disease states of cancer. Two classifications widely used in oncology that can benefit from identification of the expression levels of the genes corresponding to the polynucleotides described herein are staging of the cancerous disorder, and grading the nature of the cancerous tissue.

The polynucleotides that correspond to differentially expressed genes, as well as their encoded gene products, can be useful to monitor patients having or susceptible to cancer to detect potentially malignant events at a molecular level before they are detectable at a gross morphological level. In addition, the polynucleotides described herein, as well as the genes corresponding to such polynucleotides, can be useful as therametrics, e.g. to assess the effectiveness of therapy by using the polynucleotides or their encoded gene products, to assess, for example, tumor burden in the patient before, during, and after therapy.

Furthermore, a polynucleotide identified as corresponding to a gene that is differentially expressed in, and thus is important for, one type of cancer can also have implications for development or risk of development of other types of cancer, e.g. where a polynucleotide represents a gene differentially expressed across various cancer types.

In another embodiment, the diagnostic and/or prognostic methods of the invention involve detection of expression of a selected set of genes in a test sample to produce a test expression pattern (TEP). The TEP is compared to a reference expression pattern (REP), which is generated by detection of expression of the selected set of genes in a reference sample (e.g. a positive or negative control sample). The selected set of genes includes at least one of the genes of the invention, which genes correspond to the polynucleotide sequences described herein. Of particular interest is a selected set of genes that includes gene differentially expressed in the disease for which the test sample is to be screened.

"Reference sequences" or "reference polynucleotides" as used herein in the context of differential gene expression analysis and diagnosis/prognosis refers to a selected set of polynucleotides, which selected set includes at least one or more of the differentially expressed polynucleotides described herein. A plurality of reference sequences, preferably comprising positive and negative control sequences, can be included as reference sequences. Additional suitable reference sequences are found in GenBank, Unigene, and other nucleotide sequence databases (including, e.g. expressed sequence tag (EST), partial, and full-length sequences).

"Reference array" means an array having reference sequences for use in hybridization with a sample, where the reference sequences include all, at least one of, or any subset of the differentially expressed polynucleotides described herein. Usually such an array will include at least 2 different reference sequences, and can include any one or all of the provided differentially expressed sequences. Arrays of interest can further comprise sequences, including polymorphisms, of other genetic sequences, particularly other sequences of interest for screening for a disease or disorder (e.g. cancer, dysplasia, or other related or unrelated diseases, disorders, or conditions). The oligonucleotide sequence on the array will usually be at least about 12 nt in length, and can be of about the length of the provided sequences, or can extend into the flanking regions to generate fragments of 100 nt to 200 nt in length or more. Reference arrays can be produced according to any suitable methods known in the art. For example, methods of producing large arrays of oligonucleotides are described in references 180 & 181 using light-directed synthesis techniques. Using a computer controlled system, a heterogeneous array of monomers is converted, through simultaneous coupling at a number of reaction sites, into a heterogeneous array of polymers. Alternatively, microarrays are generated by deposition of presynthesized oligonucleotides onto a solid substrate, for example as described in reference 182.

A "reference expression pattern" or "REP" as used herein refers to the relative levels of expression of a selected set of genes, particularly of differentially expressed genes, that is associated with a selected cell type, e.g. a normal cell, a cancerous cell, a cell exposed to an environmental stimulus, and the like. A "test expression pattern" or "TEP" refers to relative levels of expression of a selected set of genes, particularly of differentially expressed genes, in a test sample (e.g. a cell of unknown or suspected disease state, from which mRNA is isolated).

REPs can be generated in a variety of ways according to methods well known in the art. For example, REPs can be generated by hybridizing a control sample to an array having a selected set of polynucleotides (particularly a selected set of differentially expressed polynucleotides), acquiring the hybridization data from the array, and storing the data in a format that allows for ready comparison of the REP with a TEP. Alternatively, all expressed sequences in a control sample can be isolated and sequenced, e.g. by isolating mRNA from a control sample, converting the mRNA into cDNA, and sequencing the cDNA. The resulting sequence information roughly or precisely reflects the identity and relative number of expressed sequences in the sample. The sequence information can then be stored in a format (e.g. a computer-readable format) that allows for ready comparison of the REP with a TEP. The REP can be normalized prior to or after data storage, and/or can be processed to selectively remove sequences of expressed genes that are of less interest or that might complicate analysis (e.g. some or all of the sequences associated with housekeeping genes can be eliminated from REP data).

TEPs can be generated in a manner similar to REPs, e.g. by hybridizing a test sample to an array having a selected set of polynucleotides, particularly a selected set of differentially expressed polynucleotides, acquiring the hybridization data from the array, and storing the data in a format that allows for ready comparison of the TEP with a REP. The REP and TEP to be used in a comparison can be generated simultaneously, or the TEP can be compared to previously generated and stored REPs.

In one embodiment of the invention, comparison of a TEP with a REP involves hybridizing a test sample with an array, where the reference array has one or more reference sequences for use in hybridization with a sample. The reference sequences include all, at least one of, or any subset of the differentially expressed polynucleotides described herein. Hybridization data for the test sample is acquired, the data normalized, and the produced TEP compared with a REP generated using an array having the same or similar selected set of differentially expressed polynucleotides. Probes that correspond to sequences differentially expressed between the two samples will show decreased or increased hybridization efficiency for one of the samples relative to the other.

Methods for collection of data from hybridization of samples with a reference arrays are well known in the art. For example, the polynucleotides of the reference and test samples can be generated using a detectable fluorescent label, and hybridization of the polynucleotides in the samples detected by scanning the microarrays for the presence of the detectable label using, for example, a microscope and light source for directing light at a substrate. A photon counter detects fluorescence from the substrate, while an x-y translation stage varies the location of the substrate. A confocal detection device that can be used in the subject methods is described in reference 183. A scanning laser microscope is described in reference 163. A scan, using the appropriate excitation line, is performed for each fluorophore used. The digital images generated from the scan are then combined for subsequent analysis. For any particular array element, the ratio of the fluorescent signal from one sample (e.g. a test sample) is compared to the fluorescent signal from another sample (e.g. a reference sample), and the relative signal intensity determined.

Methods for analyzing the data collected from hybridization to arrays are well known in the art. For example, where detection of hybridization involves a fluorescent label, data analysis can include the steps of determining fluorescent intensity as a function of substrate position from the data collected, removing outliers, i.e. data deviating from a predetermined statistical distribution, and calculating the relative binding affinity of the targets from the remaining data. The resulting data can be displayed as an image with the intensity in each region varying according to the binding affinity between targets and probes.

In general, the test sample is classified as having a gene expression profile corresponding to that associated with a disease or non-disease state by comparing the TEP generated from the test sample to one or more REPs generated from reference samples (e.g. from samples associated with cancer or specific stages of cancer, dysplasia, samples affected by a disease other than cancer, normal samples, etc.). The criteria for a match or a substantial match between a TEP and a REP include expression of the same or substantially the same set of reference genes, as well as expression of these reference genes at substantially the same levels (e.g. no significant difference between the samples for a signal associated with a selected reference sequence after normalization of the samples, or at least no greater than about 25% to about 40% difference in signal strength for a given reference sequence. In general, a pattern match between a TEP and a REP includes a match in expression, preferably a match in qualitative or quantitative expression level, of at least one of, all or any subset of the differentially expressed genes of the invention.

Pattern matching can be performed manually, or can be performed using a computer program. Methods for preparation of substrate matrices (e.g. arrays), design of oligonucleotides for use with such matrices, labeling of probes, hybridization conditions, scanning of hybridized matrices, and analysis of patterns generated, including comparison analysis, are described e.g. in reference 184.

H.6—HERV-K(CH)-Based Diagnostic Methods

The invention provides methods for diagnosing the presence of cancer in a test sample associated with expression of a polynucleotide in a test cell sample, comprising the steps of: i) detecting a level of expression of at least one polynucleotide of the invention, or a fragment thereof, or at least one polynucleotide found in an isolate selected from the group consisting of ATCC accession numbers given in Table 7, or a fragment thereof; and ii) comparing said level of expression of the polynucleotide in the test sample with a level of expression of polynucleotide in the control cell sample, wherein differential expression of the polynucleotide in the test cell sample relative to the level of polynucleotide expression in the control cell sample is indicative of the presence of cancer in the test cell sample.

In some embodiments of the present invention, the cancer is prostate cancer. In other embodiments of the present invention, the cancer is testicular cancer.

In yet other embodiments of the present invention, the detecting is measuring the level of an RNA transcript; measuring the level of a polynucleotide; or measuring by a method including PCR, TMA, bDNA, NAT or Nasba. In further embodiments, the polynucleotide is attached to a solid support.

The present invention also provides compositions comprising a test cell sample and an isolated polynucleotide of the present invention. The present invention further provides methods for detecting cancer associated with expression of a polypeptide in a test cell sample, comprising the steps of: i) detecting a level of expression of at least one polypeptide of the invention, or a fragment thereof and ii) comparing said level of expression of the polypeptide in the test sample with a level of expression of polypeptide in the control cell sample, wherein an altered level of expression of the polypeptide in the test cell sample relative to the level of expression of the polypeptide in the control cell sample is indicative of the presence of cancer in the test cell sample. The present invention also provides methods for detecting cancer associated with the presence of an antibody in a test cell sample, comprising the steps of: i) detecting a level of an antibody of the present invention, and ii) comparing said level of said antibody in the test sample with a level of said antibody in the control cell sample, wherein an altered level of antibody in said test cell sample relative to the level of antibody in the control cell sample is indicative of the presence of cancer in the test cell sample. In some embodiments, the cancer is prostate cancer and in other embodiments, the cancer is testicular cancer.

This invention also provides methods for detecting cancer associated with elevated levels of HERV-K(CH) polynucleotides, in particular in prostate cancer, by means of (i) detecting polynucleotides having at least 65%, at least 70%, at least 75%, at least 80%, at least 85%, at least 90% at least 91%, at least 92%, at least 93%, at least 94%, at least 95%, at least 96%, at least 97%, at least 98%, at least 99% or at least 100% identity to the polynucleotide shown in SEQ ID NOS:7-10 or to polynucleotides in isolates deposited with the ATCC and having ATCC deposit accession numbers PTA-2561, PTA-2572, PTA-2566, PTA-2571, PTA-2562, PTA-2573, PTA-2560, PTA-2565, PTA-2568, PTA-2564, PTA-2569, PTA-2567, PTA-2559, PTA-2563, PTA-2570, as measured by the alignment program GCG Gap (Suite Version 10.1) using the default parameters: open gap=3 and extend gap=1 or polynucleotides hybridizing under high stringency conditions to the polynucleotide shown in SEQ ID NOS:7-10; (ii) detecting polypeptides, or fragments thereof encoded by the sequences of (i); and (iii) detecting antibodies specific for one or more of the polypeptides. Furthermore, (iv) detecting particles associated with overexpression of HERV-K(CH) polynucleotides may also be used in the diagnosis of cancer, in particular, prostate cancer, and monitoring its progression.

The treatment regimen of a prostate or other cancer associated with elevated levels of HERV-K(CH) polynucleotides may also monitored by detecting levels of the polynucleotides and polypeptides in order to assess the staging of the cancer and/or efficacy of particular cancer therapies.

The present invention provides methods of using the polynucleotides described herein for detecting cancer cells, in particular prostate cancer cells, facilitating diagnosis of cancer and the severity of a cancer (e.g. tumor grade, tumor burden, and the like) in a subject, facilitating a determination of the prognosis of a subject, and assessing the responsiveness of the subject to therapy (e.g. by providing a measure of therapeutic effect through, for example, assessing tumor burden during or following a chemotherapeutic regimen). Detection can be based on detection of a polynucleotide that is differentially expressed in a cancer cell, and/or detection of a polypeptide encoded by a polynucleotide that is differentially expressed in a cancer cell. The detection methods of the invention can be conducted in vitro or in vivo, on isolated cells, or in whole tissues or a bodily fluid e.g. blood, plasma, serum, urine, and the like).

The detection methods can be provided as part of a kit. Thus, the invention further provides kits for detecting the presence and/or a level of a polynucleotide that is differentially expressed in a cancer cell (e.g. by detection of an mRNA encoded by the differentially expressed gene of interest), and/or a polypeptide encoded thereby, in a biological sample. Procedures using these kits can be performed by clinical laboratories, experimental laboratories, medical practitioners, or private individuals. The kits of the invention for detecting a polypeptide encoded by a polynucleotide that is differentially expressed in a cancer cell may comprise a moiety that specifically binds the polypeptide, which may be an antibody that binds the polypeptide or fragment thereof. The kits of the invention used for detecting a polynucleotide that is differentially expressed in a prostate cancer cell may comprise a moiety that specifically hybridizes to such a polynucleotide. The kit may optionally provide additional components that are useful in the procedure, including, but not limited to, buffers, developing reagents, labels, reacting surfaces, means for detection, control samples, standards, instructions, and interpretive information.

Accordingly, the present invention provides kits for detecting prostate cancer comprising at least one of polynucleotides having the sequence as shown in SEQ ID NOS:7-10, SEQ ID NOS:14-39, or fragments thereof, or having the sequence found in an isolate deposited with the ATCC and having ATCC accession numbers PTA-2561, PTA-2572, PTA-2566, PTA-2571, PTA-2562, PTA-2573, PTA-2560, PTA-2565, PTA-2568, PTA-2564, PTA-2569, PTA-2567, PTA-2559, PTA-2563, PTA-2570 or fragments thereof.

In some embodiments, methods are provided for detecting a polypeptide encoded by a gene differentially expressed in a prostate cancer cell. Any of a variety of known methods can be used for detection, including, but not limited to, immunoassay, using antibody that binds the polypeptide, e.g. by enzyme-linked immunosorbent assay (ELISA), radioimmunoassay (MA), and the like; and functional assays for the encoded polypeptide, e.g. binding activity or enzymatic activity.

As will be readily apparent to the ordinarily skilled artisan upon reading the present specification, the detection methods and other methods described herein can be readily varied. Such variations are within the intended scope of the invention. For example, in the above detection scheme, the probe for use in detection can be immobilized on a solid support, and the test sample contacted with the immobilized probe. Binding of the test sample to the probe can then be detected in a variety of ways, e.g. by detecting a detectable label bound to the test sample to facilitate detected of test sample-immobilized probe complexes.

The present invention further provides methods for detecting the presence of and/or measuring a level of a polypeptide in a biological sample, which polypeptide is encoded by a polynucleotide that is differentially expressed in a prostate cancer cell, using an antibody specific for the encoded polypeptide. The methods generally comprise: a) contacting the sample with an antibody specific for a polypeptide encoded by a polynucleotide that is differentially expressed in a prostate cancer cell; and b) detecting binding between the antibody and molecules of the sample.

Detection of specific binding of the antibody specific for the encoded prostate cancer-associated polypeptide, when compared to a suitable control is an indication that encoded polypeptide is present in the sample. Suitable controls include a sample known not to contain the encoded polypeptide or known not to contain elevated levels of the polypeptide; such as normal prostate tissue, and a sample contacted with an antibody not specific for the encoded polypeptide, e.g. an anti-idiotype antibody. A variety of methods to detect specific antibody-antigen interactions are known in the art and can be used in the method, including, but not limited to, standard immunohistological methods, immunoprecipitation, an enzyme immunoassay, and a radioimmunoassay. In general, the specific antibody will be detectably labeled, either directly or indirectly. Direct labels include radioisotopes; enzymes whose products are detectable (e.g. luciferase, β-galactosidase, and the like); fluorescent labels (e.g. fluorescein isothiocyanate, rhodamine, phycoerythrin, and the like); fluorescence emitting metals, e.g. $^{152}$Eu, or others of the lanthanide series, attached to the antibody through metal chelating groups such as EDTA; chemiluminescent compounds, e.g. luminol, isoluminol, acridinium salts, and the like; bioluminescent compounds, e.g. luciferin, aequorin (green fluorescent protein), and the like. The antibody may be attached (coupled) to an insoluble support, such as a polystyrene plate or a bead. Indirect labels include second antibodies specific for antibodies specific for the encoded polypeptide ("first specific antibody"), wherein the second antibody is labeled as described above; and members of specific binding pairs, e.g. biotin-avidin, and the like. The biological sample may be brought into contact with and immobilized on a solid support or carrier, such as nitrocellulose, that is capable of immobilizing cells, cell particles, or soluble proteins. The support may then be washed with suitable buffers, followed by contacting with a detectably-labeled first specific antibody. Detection methods are known in the art and will be chosen as appropriate to the signal emitted by the detectable label. Detection is generally accomplished in comparison to suitable controls, and to appropriate standards.

In some embodiments, the methods are adapted for use in vivo, e.g. to locate or identify sites where cancer cells, such as prostate cancer cells, are present.

In some embodiments, methods are provided for detecting a cancer cell by detecting expression in the cell of a transcript that is differentially expressed in a cancer cell. Any of a variety of known methods can be used for detection, including, but not limited to, detection of a transcript by hybridization with a polynucleotide that hybridizes to a polynucleotide that is differentially expressed in a prostate cancer cell; detection of a transcript by a polymerase chain reaction using specific oligonucleotide primers; in situ hybridization of a cell using as a probe a polynucleotide that hybridizes to a gene that is differentially expressed in a prostate cancer cell. The methods can be used to detect and/or measure mRNA levels of a gene that is differentially expressed in a prostate cancer cell. In some embodiments, the methods comprise: a) contacting a sample with a polynucleotide that corresponds to a differentially expressed gene described herein under conditions that allow hybridization; and b) detecting hybridization, if any.

Detection of differential hybridization, when compared to a suitable control, is an indication of the presence in the sample of a polynucleotide that is differentially expressed in a cancer cell. Appropriate controls include, for example, a sample which is known not to contain a polynucleotide that is differentially expressed in a cancer cell, and use of a labeled polynucleotide of the same "sense" as the polynucleotide that is differentially expressed in the cancer cell. In a preferred embodiment, the cancer cell is a prostate cancer cell. Conditions that allow hybridization are known in the art, and have been described in more detail above. Detection can also be accomplished by any known method, including, but not limited to, in situ hybridization, PCR (polymerase chain reaction), RT-PCR (reverse transcription-PCR), TMA, bDNA, and Nasba and "Northern" or RNA blotting, or combinations of such techniques, using a suitably labeled polynucleotide. A variety of labels and labeling methods for polynucleotides are known in the art and can be used in the assay methods of the invention. Specific hybridization can be determined by comparison to appropriate controls.

Polynucleotide generally comprising at least 10 nt, at least 12 nt or at least 15 contiguous nucleotides of a polynucleotide provided herein, such as, for example, those having the sequence as depicted in SEQ ID NOS:7-10, and 3-28, are used for a variety of purposes, such as probes for detection of and/or measurement of, transcription levels of a polynucleotide that is differentially disclosed herein should provide a detection signal at least 5-, 10-, or 20-fold higher than the expressed in a prostate cancer cell. A probe that hybridizes specifically to a polynucleotide background hybridization provided with other unrelated sequences. It should be noted that "probe" as used herein is meant to refer to a polynucleotide sequence used to detect a differentially expressed gene product in a test sample. As will be readily appreciated by the ordinarily skilled artisan, the probe can be detectably labeled and contacted with, for example, an array comprising immobilized polynucleotides obtained from a test sample (e.g. mRNA). Alternatively, the probe can be immobilized on an array and the test sample detectably labeled. These and other variations of the methods of the invention are well within the skill in the art and are within the scope of the invention.

Nucleotide probes are used to detect expression of a gene corresponding to the provided polynucleotide. In Northern blots, mRNA is separated electrophoretically and contacted with a probe. A probe is detected as hybridizing to an mRNA species of a particular size. The amount of hybridization can be quantitated to determine relative amounts of expression, for example under a particular condition. Probes are used for in situ hybridization to cells to detect expression. Probes can also be used in vivo for diagnostic detection of hybridizing sequences. Probes are typically labeled with a radioactive isotope. Other types of detectable labels can be used such as chromophores, fluorophores, and enzymes. Other examples of nucleotide hybridization assays are described in refs. 185 and 186.

PCR is another means for detecting small amounts of target nucleic acids (see, e.g. refs. 187, 188 & 189). Two primer polynucleotides nucleotides that hybridize with the target nucleic acids are used to prime the reaction. The primers can be composed of sequence within or 3' and 5' to the HERV-K (CH) polynucleotides disclosed herein. Alternatively, if the primers are 3' and 5' to these polynucleotides, they need not hybridize to them or the complements. After amplification of the target with a thermostable polymerase, the amplified target nucleic acids can be detected by methods known in the art (e.g. Southern blot). mRNA or cDNA can also be detected by traditional blotting techniques (e.g. Southern blot, Northern blot, etc.) described in ref. 8 (e.g. without PCR amplification). In general, mRNA or cDNA generated from mRNA using a polymerase enzyme can be purified and separated using gel electrophoresis, and transferred to a solid support, such as nitrocellulose. The solid support is exposed to a labeled probe, washed to remove any unhybridized probe, and duplexes containing the labeled probe are detected.

Methods using PCR amplification can be performed on the DNA from a single cell, although it is convenient to use at least about $10^5$ cells. The use of the polymerase chain reaction is described in ref. 190, and a review of techniques may be found in pages 14.2 to 14.33 of reference 8. A detectable label may be included in the amplification reaction. Suitable detectable labels include fluorochromes, (e.g. fluorescein isothiocyanate (FITC), rhodamine, Texas Red, phycoerythrin, allophycocyanin, 6-carboxyfluorescein (6-FAM), 6-carboxy-X-rhodamine (ROX), 2',7'-dimethoxy-4',5'-dichloro-6-carboxyfluorescein, 5-carboxyfluorescein (5-FAM), N,N,N',N'-tetramethyl-6-carboxyrhodamine (TAMRA), or 6-carboxy-2',4',7',4,7-hexachlorofluorescein (HEX)), radioactive labels, (e.g. $^{32}P$, $^{35}S$, $^{3}H$, etc.), and the like. The label may be a two stage system, where the polynucleotides is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The present invention further relates to methods of detecting/diagnosing a neoplastic or preneoplastic condition in a mammal (for example, a human).

Examples of conditions that can be detected/diagnosed in accordance with these methods include, but are not limited to prostate cancers. Polynucleotides corresponding to genes that exhibit the appropriate expression pattern can be used to detect prostate cancer in a subject. Reference 191 reviews markers of cancer.

One detection/diagnostic method comprises: (a) obtaining from a mammal (eg a human) a biological sample, (b) detecting the presence in the sample of a HERV-K(CH) polypeptide and (c) comparing the amount of product present with that in a control sample. In accordance with this method, the presence in the sample of elevated levels of a HERV-K(CH) gene product indicates that the subject has a neoplastic or preneoplastic condition.

The compound is preferably a binding protein, e.g. an antibody, polyclonal or monoclonal, or antigen binding fragment thereof, which can be labeled with a detectable marker (eg fluorophore, chromophore or isotope, etc). Where appropriate, the compound can be attached to a solid support. Determination of formation of the complex can be effected by contacting the complex with a further compound (eg an antibody) that specifically binds to the first compound (or complex). Like the first compound, the further compound can be attached to a solid support and/or can be labeled with a detectable marker.

The identification of elevated levels of HERV-K(CH) polypeptide in accordance with the present invention makes possible the identification of subjects (patients) that are likely to benefit from adjuvant therapy. For example, a biological sample from a post-primary therapy subject (e.g. subject having undergone surgery) can be screened for the presence of circulating HERV-K(CH) polypeptide, the presence of elevated levels of the polypeptide, determined by studies of normal populations, being indicative of residual tumor tissue. Similarly, tissue from the cut site of a surgically removed tumor can be examined (e.g. by immunofluorescence), the presence of elevated levels of product (relative to the surrounding tissue) being indicative of incomplete removal of the tumor. The ability to identify such subjects makes it possible to tailor therapy to the needs of the particular subject. Subjects undergoing non-surgical therapy (e.g. chemotherapy or radiation therapy) can also be monitored, the presence in samples from such subjects of elevated levels of HERV-K(CH) polypeptide being indicative of the need for continued treatment. Staging of the disease (for example, for purposes of optimizing treatment regimens) can also be effected, for example, by prostate biopsy e.g. with antibody specific for a HERV-K(CH) polypeptide.

The present invention also relates to a kit that can be used in the detection of a HERV-K(CH) polypeptide. The kit can comprise a compound that specifically binds a HERV-K(CH) polypeptide, such as, for example, binding proteins including antibodies or binding fragments thereof (e.g. $F(ab')_2$ fragments) disposed within a container means. The kit can further comprise ancillary reagents, for processing the binding assay.

Definitions

The term "comprising" means "including" as well as "consisting" e.g. a composition "comprising" X may consist exclusively of X or may include something additional e.g. X+Y.

The term "about" in relation to a numerical value x means, for example, x±10%.

The terms "neoplastic cells", "neoplasia", "tumor", "tumor cells", "cancer" and "cancer cells", (used interchangeably) refer to cells which exhibit relatively autonomous growth, so that they exhibit an aberrant growth phenotype characterized by a significant loss of control of cell proliferation (i.e. deregulated cell division). Neoplastic cells can be malignant or benign and include prostate cancer derived tissue.

MODES FOR CARRYING OUT THE INVENTION

Figure 1:
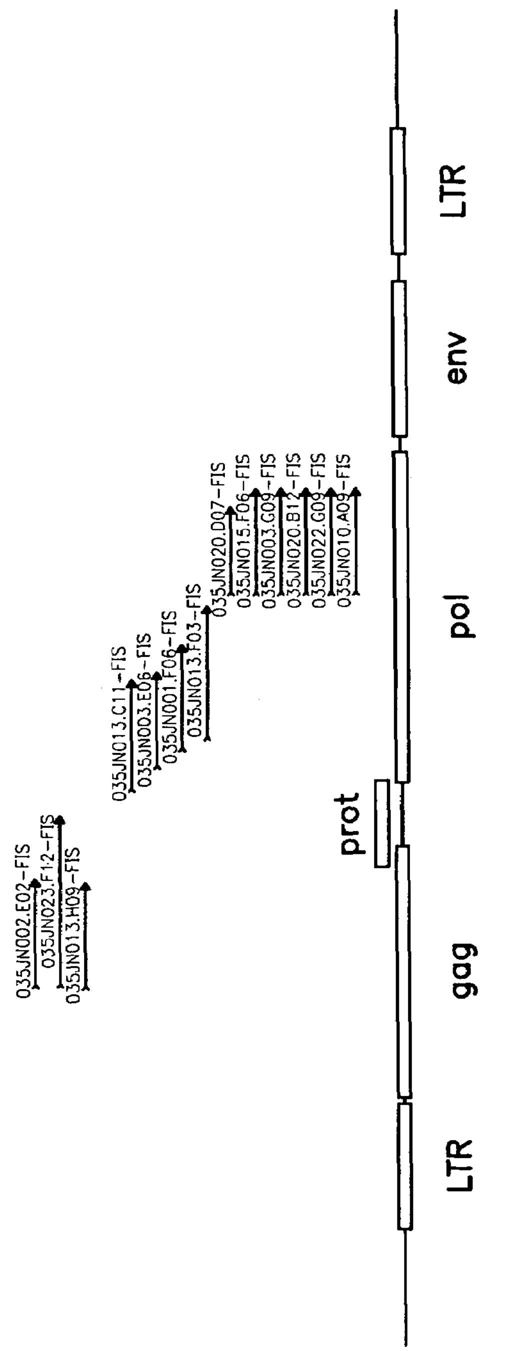
FIG. 1 is a schematic representation of a human endogenous retrovirus with a depiction of the HERV-K(CH) polynucleotides and their position relative to the retrovirus.
Figure 2:
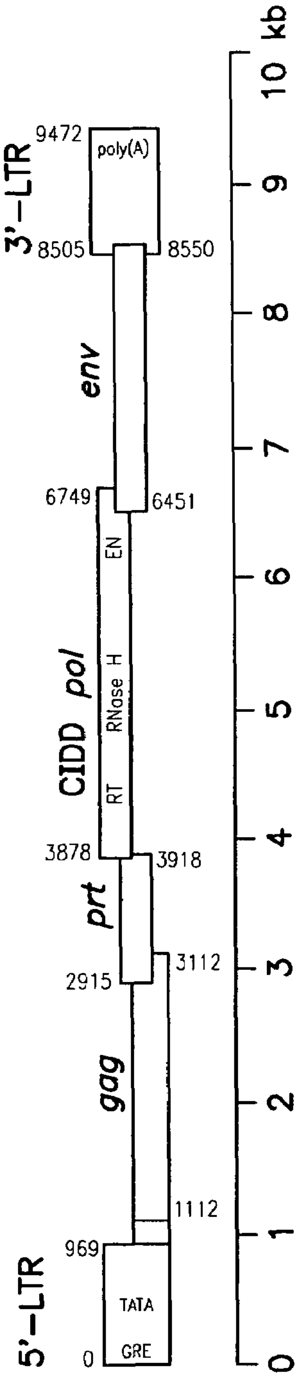
FIG. 2 is a schematic representation of open reading frames within the HERV-K(HML-2.HOM) (also known as 'ERVK6') genome [1].
Figure 3:
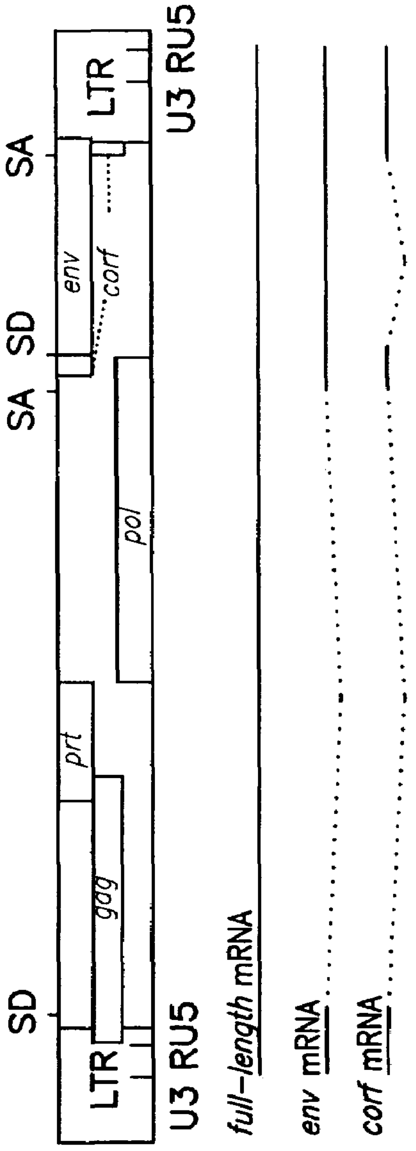
FIG. 3 shows splicing events described in the prior art [16] for HERV-K mRNAs.
Figure 4:
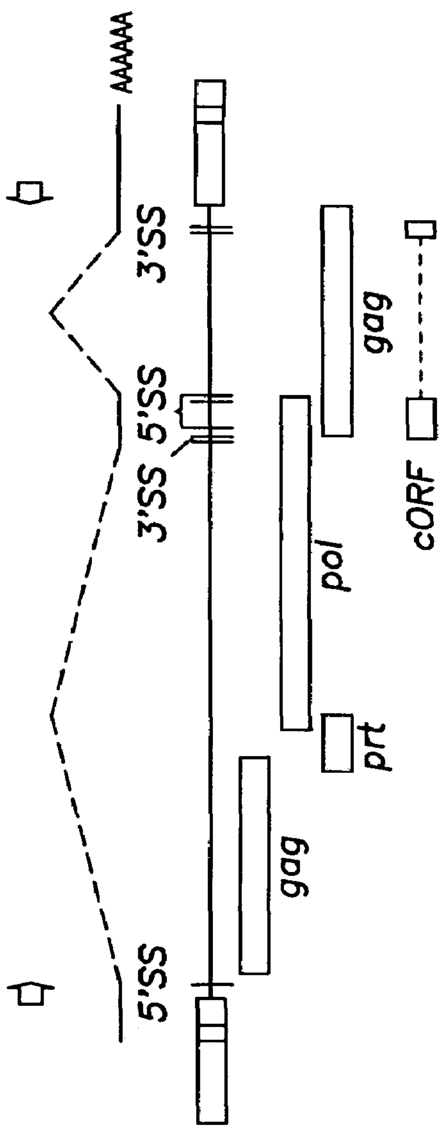
FIG. 4 shows splice sites identified near the 5' and 3' ends of the env ORF. The three reading frames are shaded differently.

Certain aspects of the present invention are described in greater detail in the non-limiting examples that follow. The examples are put forth so as to provide those of ordinary skill in the art with a complete disclosure and description of how to make and use the present invention, and are not intended to limit the scope of what the inventors regard as their invention nor are they intended to represent that the experiments below are all and only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Source of Human Prostate Cell Samples and Isolation of Polynucleotides Expressed by them Candidate polynucleotides that may represent genes differentially expressed in cancer were obtained from both publicly-available sources and from cDNA libraries generated from selected cell lines and patient tissues. A normalized cDNA library was prepared from one patient tumor tissue and cloned polynucleotides for spotting on microarrays were isolated from the library. Normal and tumor tissues from 13 patients were processed to generate T7 RNA polymerase transcribed polynucleotides, which were, in turn, assessed for expression in the microarrays. The tissues that served as sources for these libraries and polynucleotides are summarized in Table 4.

Normalization: The objective of normalization is to generate a cDNA library in which all transcripts expressed in a particular cell type or tissue are equally represented [refs. 192 & 193], and therefore isolation of as few as 30,000 recombinant clones in an optimally normalized library may represent the entire gene expression repertoire of a cell, estimated to number 10,000 per cell. The source materials for generating the normalized prostate libraries were cryopreserved prostate tumor tissue from a patient with Gleason grade 3+3 adenocarcinoma and normal prostate biopsies from a pool of at-risk subjects under medical surveillance. Prostate epithelia were harvested directly from frozen sections of tissue by laser capture microdissection (LCM, Arcturus Engineering Inc., Mountain View, Calif.), carried out according to methods well known in the art (e.g. ref. 194), to provide substantially homogenous cell samples.

Total RNA was extracted from LCM-harvested cells using RNeasy™ Protect Kit (Qiagen, Valencia, Calif.), following manufacturer's recommended procedures. RNA was quantified using RiboGreen™ RNA quantification kit (Molecular Probes, Inc. Eugene, Oreg.). One μg of total RNA was reverse transcribed and PCR amplified using SMART™ PCR cDNA synthesis kit (ClonTech, Palo Alto, Calif.). The cDNA products were size-selected by agarose gel electrophoresis using standard procedures (ref. 8). The cDNA was extracted using Bio 101Geneclean® II kit (Qbiogene, Carlsbad, Calif.). Normalization of the cDNA was carried out using kinetics of hybridization principles: 1.0 μg of cDNA was denatured by heat at 100° C. for 10 minutes, then incubated at 42° C. for 42 hours in the presence of 120 mM NaCl, 10 mM Tris.HCl (pH=8.0), 5 mM EDTA.$Na^+$ and 50% formamide. Single-stranded cDNA ("normalized" cDNA) was purified by hydroxyapatite chromatography (#130-0520, BioRad, Hercules, Calif.) following the manufacturer's recommended procedures, amplified and converted to double-stranded cDNA by three cycles of PCR amplification, and cloned into plasmid vectors using standard procedures (ref. 8). All primers/adaptors used in the normalization and cloning process are provided by the manufacturer in the SMART™ PCR cDNA synthesis kit (ClonTech, Palo Alto, Calif.). Supercompetent cells (XL-2 Blue Ultracompetent Cells, Stratagene, Calif.) were transfected with the normalized cDNA libraries, plated on plated on solid media and grown overnight at 36° C.

Characterization of normalized libraries: The sequences of 10,000 recombinants per library were analyzed by capillary sequencing using the ABI PRISM 3700 DNA Analyzer (Applied Biosystems, California). To determine the representation of transcripts in a library, BLAST analysis was performed on the clone sequences to assign transcript identity to each isolated clone, i.e. the sequences of the isolated polynucleotides were first masked to eliminate low complexity sequences using the XBLAST masking program (refs. 195, 196 and 197). Generally, masking does not influence the final search results, except to eliminate sequences of relative little interest due to their low complexity, and to eliminate multiple "hits" based on similarity to repetitive regions common to multiple sequences e.g. Alu repeats. The remaining sequences were then used in a BLASTN vs. GenBank search. The sequences were also used as query sequence in a BLASTX vs. NRP (non-redundant proteins) database search.

Automated sequencing reactions were performed using a Perkin-Elmer PRISM Dye Terminator Cycle Sequencing Ready Reaction Kit containing AmpliTaq DNA Polymerase, FS, according to the manufacturer's directions. The reactions were cycled on a GeneAmp PCR System 9600 as per manufacturer's instructions, except that they were annealed at 20° C. or 30° C. for one minute. Sequencing reactions were ethanol precipitated, pellets were resuspended in 8 microliters of loading buffer, 1.5 microliters was loaded on a sequencing gel, and the data was collected by an ABI PRISM 3700 DNA Sequencer. (Applied Biosystems, Foster City, Calif.).

The number of times a sequence is represented in a library is determined by performing sequence identity analysis on cloned cDNA sequences and assigning transcript identity to each isolated clone. First, each sequence was checked to see if it was a mitochondrial, bacterial or ribosomal contaminant. Such sequences were excluded from the subsequent analysis. Second, sequence artifacts (e.g. vector and repetitive elements) were masked and/or removed from each sequence.

The remaining sequences were compared via BLAST [198] to GenBank and EST databases for gene identification and were compared with each other via FastA [199] to calculate the frequency of cDNA appearance in the normalized cDNA library. The sequences were also searched against the GenBank and GeneSeq nucleotide databases using the BLASTN program (BLASTN 1.3 MP [198]). Fourth, the sequences were analyzed against a non-redundant protein (NRP) database with the BLASTX program (BLASTX 1.3 MP [198]). This protein database is a combination of the Swiss-Prot, PIR, and NCBI GenPept protein databases. The BLASTX program was run using the default BLOSUM-62 substitution matrix with the filter parameter: "xnu+seg". The score cutoff utilized was 75.

Assembly of overlapping clones into contigs was done using the program Sequencher (Gene Codes Corp.; Ann Arbor, Mich.). The assembled contigs were analyzed using the programs in the GCG package (Genetic Computer Group, University Research Park, 575 Science Drive, Madison, Wis. 53711) Suite Version 10.1.

Summary of polynucleotides described herein: Table 6 provides a summary of polynucleotides isolated as described above and identified as corresponding to a differentially expressed gene (see below). Specifically, Table 6 provides: 1) the HERVK ORF for each clone ID; 2) the clone ID assigned to each sequence; 3) the % patients having the expression ratio of >/=2×; >/=2-5×; >/=5×; and less than ½ X; and the Tumor/Normal mRNA Expression Ratio per patient "Pat", eg, patient 93, patient 95, patient 96, etc.

Detection of Elevated Levels of cDNA Associated with Prostate Cancer Using Arrays cDNA sequences representing a variety of candidate genes to be screened for differential expression in prostate cancer were assayed by hybridization on polynucleotide arrays. The cDNA sequences included cDNA clones isolated from cell lines or tissues as described above. The cDNA sequences analyzed also included polynucleotides comprising sequence overlap with sequences in the Unigene database, and which encode a variety gene products of various origins, functionality, and levels of characterization. cDNAs were spotted onto reflective slides (Amersham) according to methods well known in the art at a density of 9,216 spots per slide representing 4608 sequences (including controls) spotted in duplicate, with approximately 0.8 μl of an approximately 200 ng/μl solution of cDNA.

PCR products of selected cDNA clones corresponding to the gene products of interest were prepared in a 50% DMSO solution. These PCR products were spotted onto Amersham aluminum microarray slides at a density of 9216 clones per array using a Molecular Dynamics Generation III spotting robot. Clones were spotted in duplicate, for a total of 4608 different sequences per chip.

cDNA probes were prepared from total RNA obtained by laser capture microdissection (LCM, Arcturus Enginering Inc., Mountain View, Calif.) of tumor tissue samples and normal tissue samples isolated from the patients described above.

Total RNA was first reverse transcribed into cDNA using a primer containing a T7 RNA polymerase promoter, followed by second strand DNA synthesis. cDNA was then transcribed in vitro to produce antisense RNA using the T7 promoter-mediated expression (e.g. ref. 200), and the antisense RNA was then converted into cDNA. The second set of cDNAs were again transcribed in vitro, using the T7 promoter, to provide antisense RNA. This antisense RNA was then fluorescently labeled, or the RNA was again converted into cDNA, allowing for third round of T7-mediated amplification to produce more antisense RNA. Thus the procedure provided for two or three rounds of in vitro transcription to produce the final RNA used for fluorescent labeling. Probes were labeled by making fluorescently labeled cDNA from the RNA starting material. Fluorescently-labeled cDNAs prepared from the tumor RNA sample were compared to fluorescently labeled cDNAs prepared from normal cell RNA sample. For example, the cDNA probes from the normal cells were labeled with Cy3 fluorescent dye (green) and cDNA probes prepared from the tumor cells were labeled with Cy5 fluorescent dye (red).

The differential expression assay was performed by mixing equal amounts of probes from tumor cells and normal cells of the same patient. The arrays were pre-hybridized by incubation for about 2 hrs at 60° C. in 5×SSC/0.2% SDS/1 mM EDTA, and then washed three times in water and twice in isopropanol. Following pre-hybridization of the array, the probe mixture was then hybridized to the array under conditions of high stringency (overnight at 42° C. in 50% formamide, 5×SSC, and 0.2% SDS. After hybridization, the array was washed at 55° C. three times as follows: 1) first wash in 1×SSC/0.2% SDS; 2) second wash in 0.1×SSC/0.2% SDS; and 3) third wash in 0.1×SSC.

The arrays were then scanned for green and red fluorescence using a Molecular Dynamics Generation III dual color laser-scanner/detector. The images were processed using BioDiscovery Autogene software, and the data from each scan set normalized. The experiment was repeated, this time labeling the two probes with the opposite color in order to perform the assay in both "color directions." Each experiment was sometimes repeated with two more slides (one in each color direction). The data from each scan was normalized, and the level fluorescence for each sequence on the array expressed as a ratio of the geometric mean of 8 replicate spots/genes from the four arrays or 4 replicate spots/gene from 2 arrays or some other permutation.

Table 6 summarizes the results for gene products differentially expressed in the prostate tumor samples relative to normal cells. The ratio of differential expression is expressed as the normalized hybridization signal associated with the tumor probe divided by the normalized hybridization signal with the normal probe; thus, a ratio greater than 1 indicates that the gene product is increased in expression in cancerous cells relative to normal cells, while a ratio of less than 1 indicates the opposite. The results from each patient are identified by "Pat" with the corresponding patient identification number. "Concordance" indicates the % of patients in which differential expression of the selected gene product in tumor cells was at least a two-fold different from normal cells.

In at least 79% of prostate patients assayed, 8 out of 10 genes, whose expression was elevated by at least 500%, were represented in HERV-K(CH) sequences.

Table 6 provides those gene products that were differentially expressed and were classified as gag, 5'-pol (reverse transcriptase) and 3'-pol (integrase) related sequences. It may be possible to examine the function of these gene products in development of cancer and metastasis through use of small molecule inhibitors known to affect the activity of such enzymes.

Analysis of the Prostate Cancer Associated Sequences

In order to determine whether there was homology to any known sequences, the PCR products of 16 different clones from one prostate tumor patient were sequenced. PCR products from these and other clones from the same library were spotted on DNA microarrays. RNA from 13 prostate tumor patients were assayed on the microarrays and then the full inserts of some of the 16 clones were sequenced (Table 6).

The 16 isolates were initially determined in a first pass sequencing reaction to have the sequences as shown in SEQ ID NOS:27-39, inclusive. The isolate from the normal prostate tissue was initially determined in a first pass sequencing reaction to have the sequence as shown in SEQ ID NO:41. A first pass sequencing reaction refers to a high-throughput process, where PCR reactions generate the sequencing template then sequencing is performed with one of the PCR primers, in a single direction. A search of public databases revealed that these 16 isolates have some degree of identity to regions of the human endogenous retrovirus HERV-K(II)

sequence disclosed in Genbank accession number AB047240 and shown in SEQ ID NO:44, and also to HERV-K(10), but are nonetheless unique.

The isolates were subjected to a second round of nucleic acid sequencing and were found to have the sequences as shown in SEQ ID NOS:14-26, inclusive. The isolate from the normal prostate tissue was subjected to a second round of nucleic acid sequencing and found to have the sequence as shown in SEQ ID NO:40. This second round of sequencing is a customized process, where sequencing is performed on purified dsDNA template in a DNA vector. Sequencing is done from both ends of the template, forward and reverse, with primers designed from the flanking regions of the vector, and new primers are synthesized for every additional reaction needed to span the entire insert.

The Genbank disclosure of HERV-K(II) provides only an incomplete characterization of its genetic features and no association with any disease. The Genbank disclosure characterizes HERV-KII as having a gag gene located at nucleotide 2113-4116 and an env gene located at nucleotide 7437-8174. Detailed analysis of the reported HERV-K(II) sequence indicates that the HERV-K(II) genome includes regions related to gag, protease, 5'-end of pol (reverse transcriptase) and 3'-end of pol (integrase) domains of a retrovirus. Specifically, the location of the protease gene is from about nucleotide 3917 to about 4920 and the location of the polymerase domain is from about nucleotide 4797 to about 7468.

Composite HERV-K(CH) polynucleotide sequences are s own in SEQ NOS:7, 8, 9 and 10 and FIG. 1 provides a schematic illustration of a human endogenous retrovirus and the HERV-K(CH) species within the schematic illustration. SEQ ID NO:7 is a composite sequence of the polynucleotides SEQ ID NOS:14-16, inclusive, and has a consensus sequence as shown in SEQ ID NO:11. This region corresponds to the gag region of a human endogenous retrovirus. SEQ ID NOS:8 and 9 are composites sequence of the polynucleotides having a sequence as shown in SEQ ID NOS:17-20, inclusive, and has a consensus sequence as shown in SEQ ID NO:12. This region corresponds to the 5' pol region of a human endogenous retrovirus. SEQ ID NO:10 is a composite sequence of the polynucleotides having a sequence as shown in SEQ ID NOS:21-26, inclusive, and has a consensus sequence as shown in SEQ ID NO:13. This region corresponds to the 3' pol region of a human enddogenous retrovirus.

Homology to HERV-K(II) gag region varied from 87% to 99%. Homology to HERV-K(II) 5'-pol (reverse transcriptase) region varied from 87% to 97%. Homology to HERV-K(II) 3'-pol (integrase) region was approximately 89%. When compared to the human endogenous provirus HERV-K10, the homology of the gag region clones was approximately 79%, the 5'-pol region between 81% and 89% and the 3'-pol region was approximately 89%. Table 5 illustrates the homology of the sequences of the individual clones with the corresponding HERV-K(II) and HERV-K(10) regions. Because the presence of polyA stretches in the HERV-K(CH) sequences (and deposited isolates) may be an artifact of cloning, the % identity shown in Table 5 was determined with alignments performed with polynucleotides excluding the terminal polyA stretch.

Consensus polynucleotide sequences SEQ ID NOS:11-13 were generated with Multiple Sequence Alignment (MSA), a web implementation of the GCG Pileup and Pretty programs. The program uses a clustering algorithm similar to the Clustal program described in reference. The default values for the alignments and consensus extraction were 8 for gap open and 2 for gap extension. The poling plurality or minimum number of like sequences specified to assign a residue to the consensus sequence was 2.

The polynucleotide sequences shown in SEQ ID NOS:14-16, inclusive, were used for the consensus polynucleotide sequence shown in SEQ ID NO:11. The polynucleotide sequences shown in SEQ ID NOS:17-20, inclusive, were used for the consensus polynucleotide sequence shown in SEQ ID NO:12. The polynucleotide sequences shown in SEQ ID NOS:21-26, inclusive, were used for the consensus polynucleotide shown in SEQ ID NO:13. The "N" represents where there is no qualifying minimum representative base. i.e. at least two sequences with the same base at that site.

Figure 5:
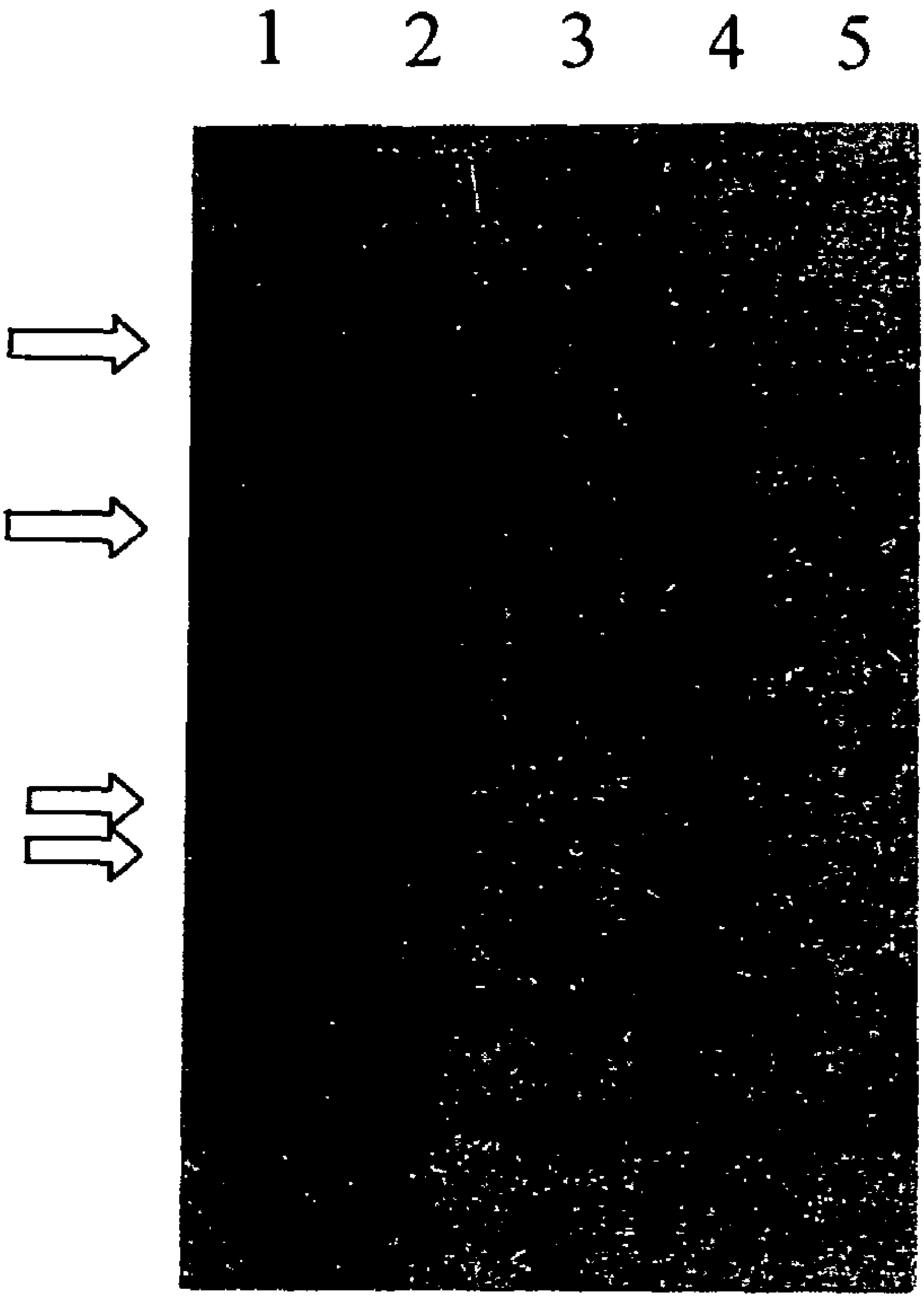
FIG. 5 shows northern blot analysis of PCAV transcripts in cancer cell lines. The top arrow on the left shows the position of the genomic mRNA transcript. The next arrow shows the position of the env transcript. The bottom two arrows show the positions of other ORFs. The lanes contain RNA from the following cell lines: (1) Tera 1; (2) DU145; (3) PC3; (4) MDA Pca-2b; (5) LNCaP. Tera 1 is a teratocarcinoma cell line; the others are prostatic carcinoma cell lines.
Figures 2, 6:
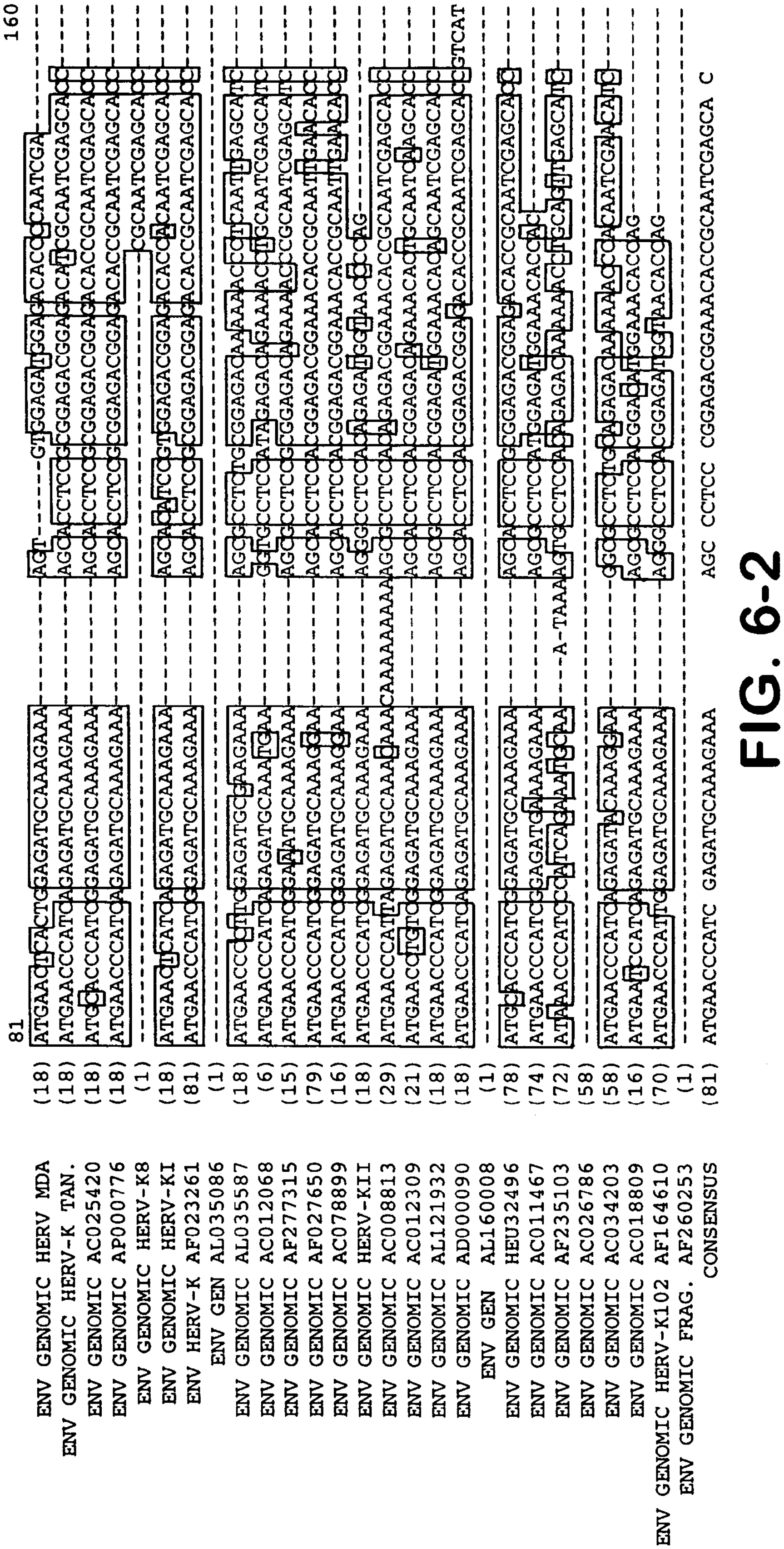
FIG. 6 shows an alignment of env genomic DNA sequences from 27 HERV-K viruses. A consensus sequence (SEQ ID NO:157) is shown on the bottom line.
Figures 5, 6:
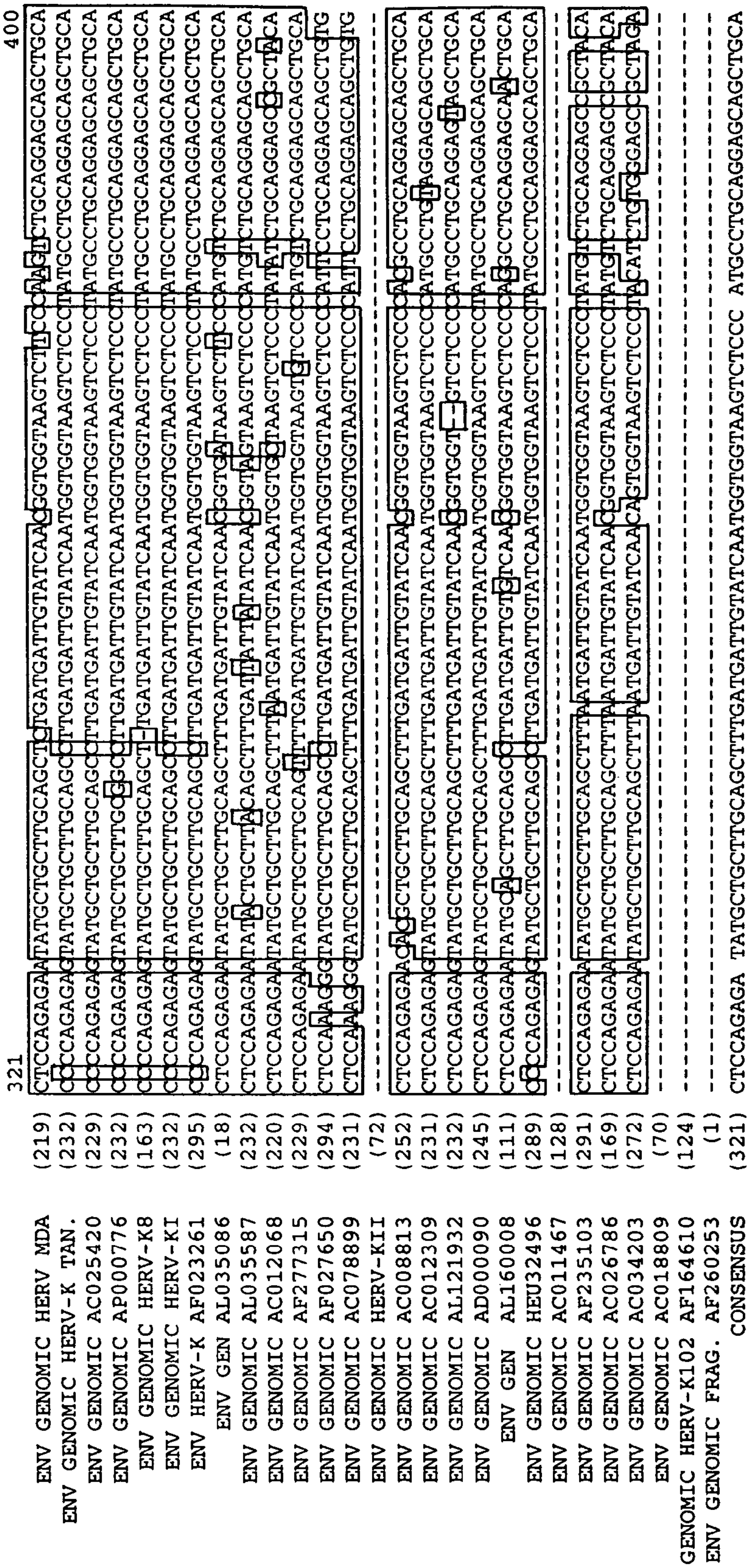
Figure 6:
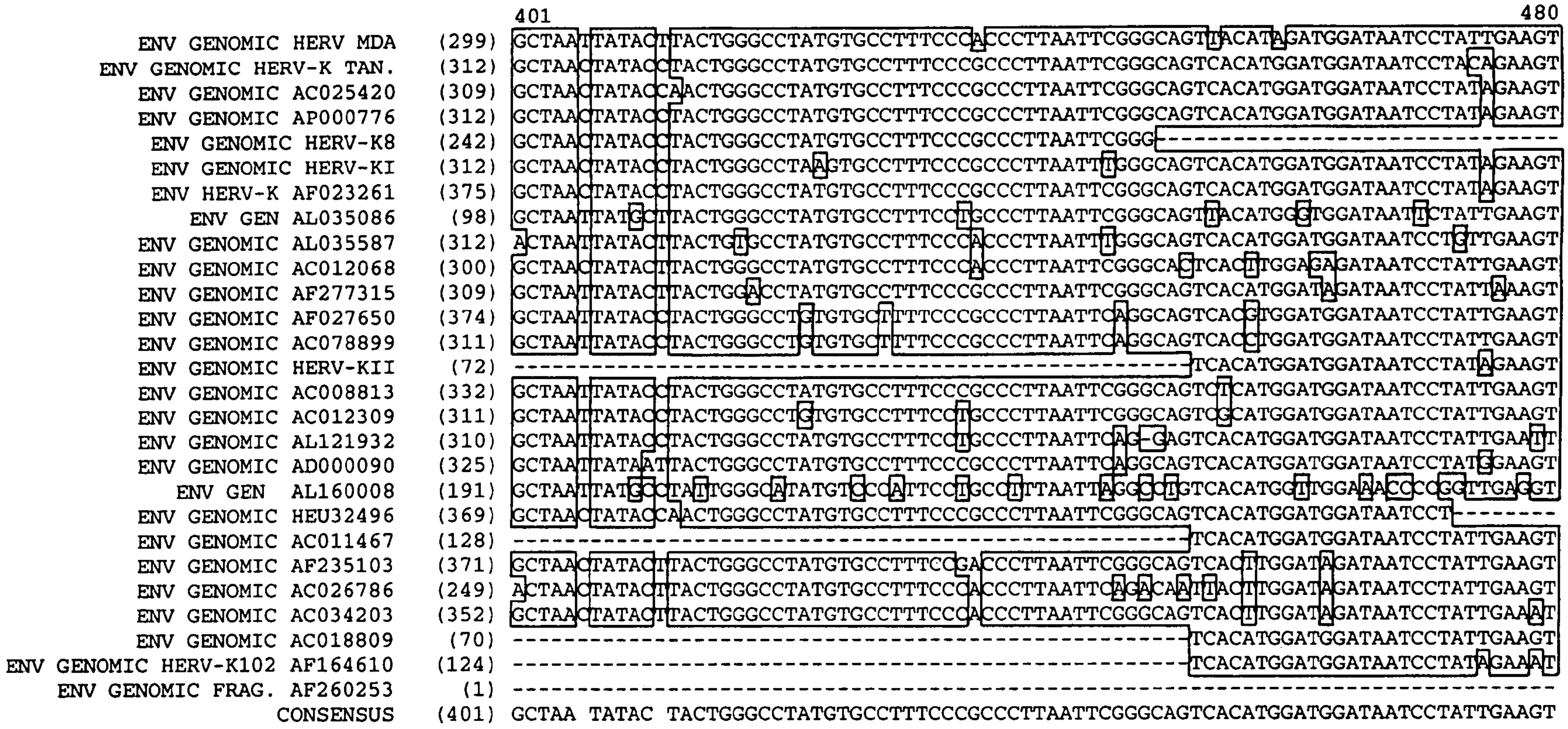
Figures 6, 7, 8, 9, 10, 11, 12, 13:
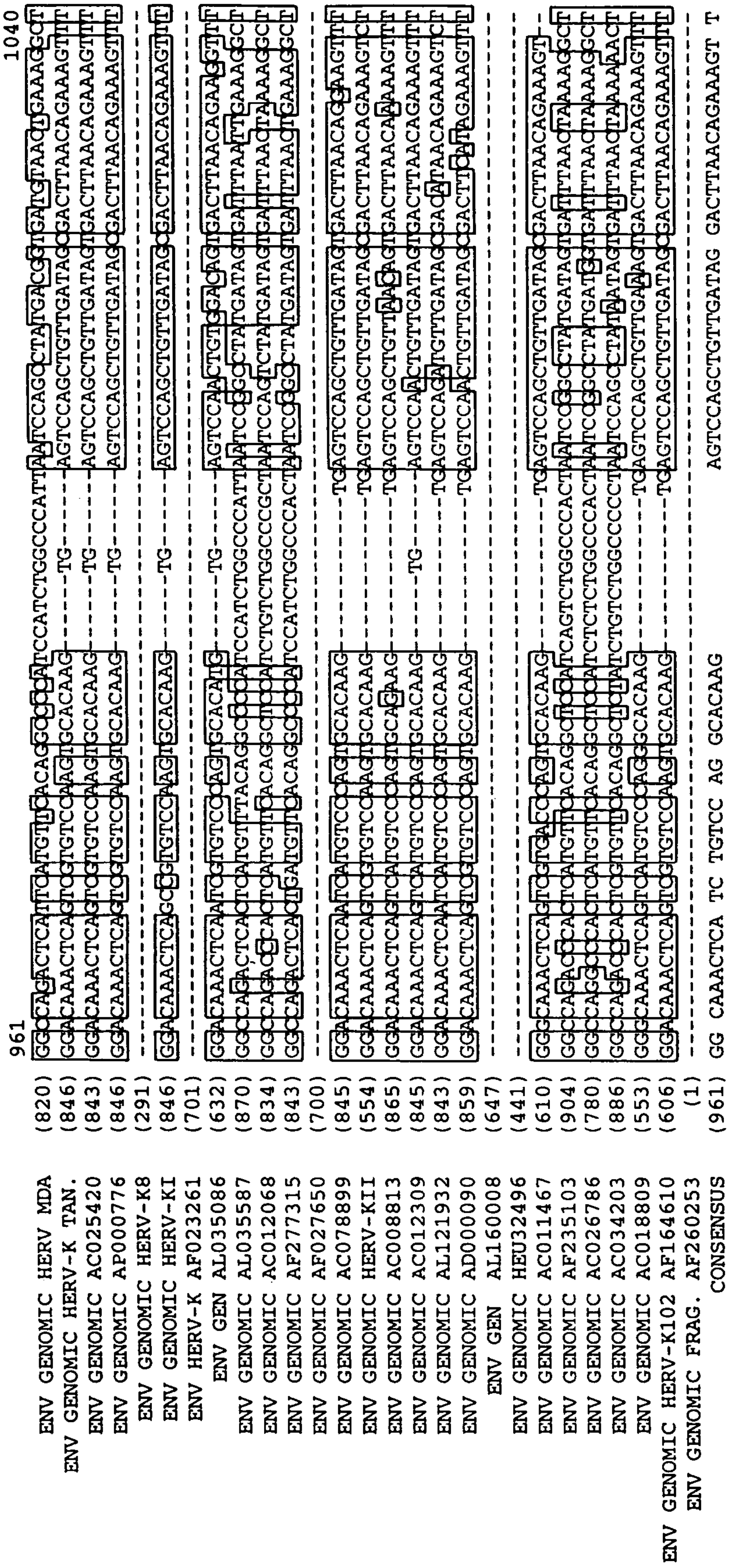
FIGS. 7-9 show alignments of inferred polypeptide sequences for gag (7), pol (8) and env (9) from various HERV-K viruses, together with consensus sequences (SEQ ID NOS:158-160).
Figures 6, 7, 8, 9, 10, 11, 12, 13, 14:
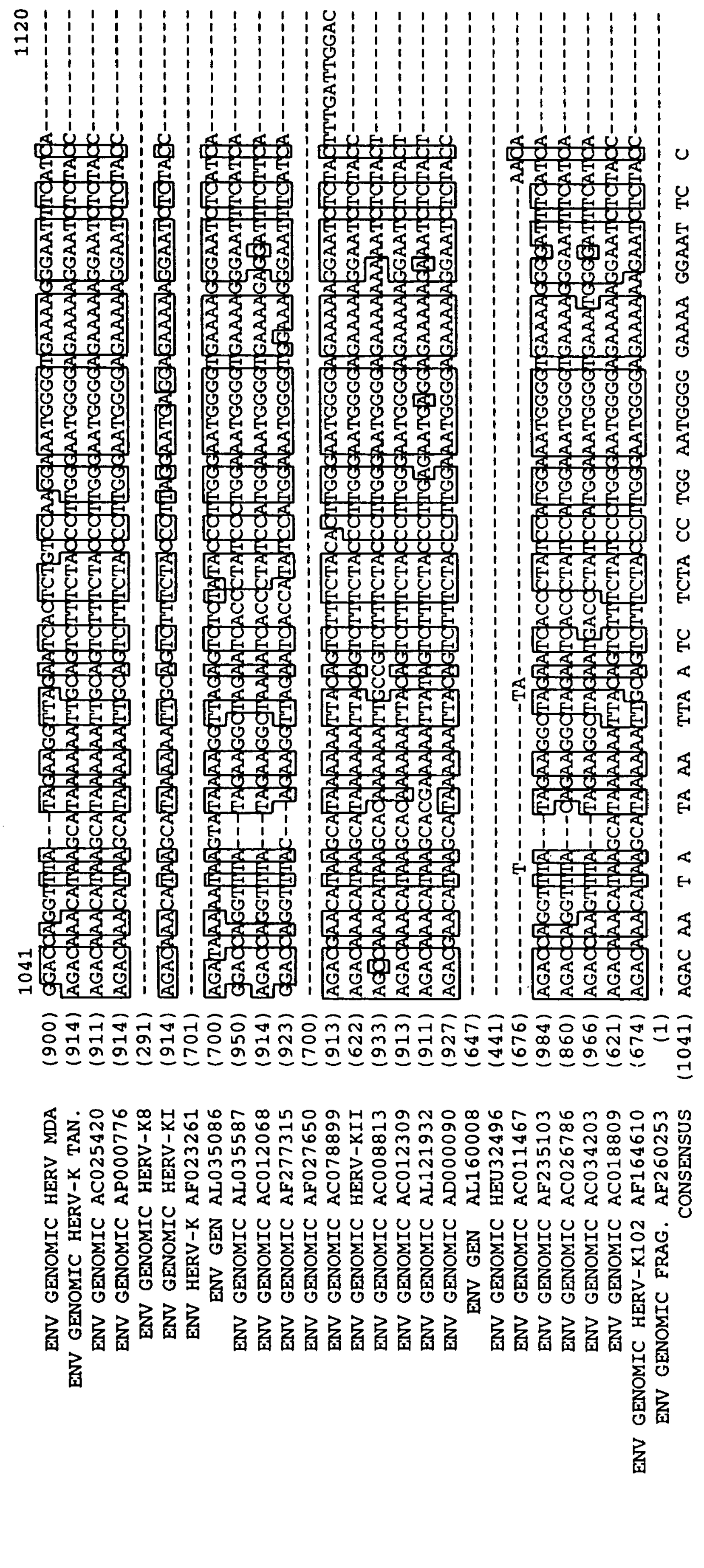
Figures 6, 7, 8, 9, 10, 11, 12, 13, 14, 15, 16, 17, 18, 19:
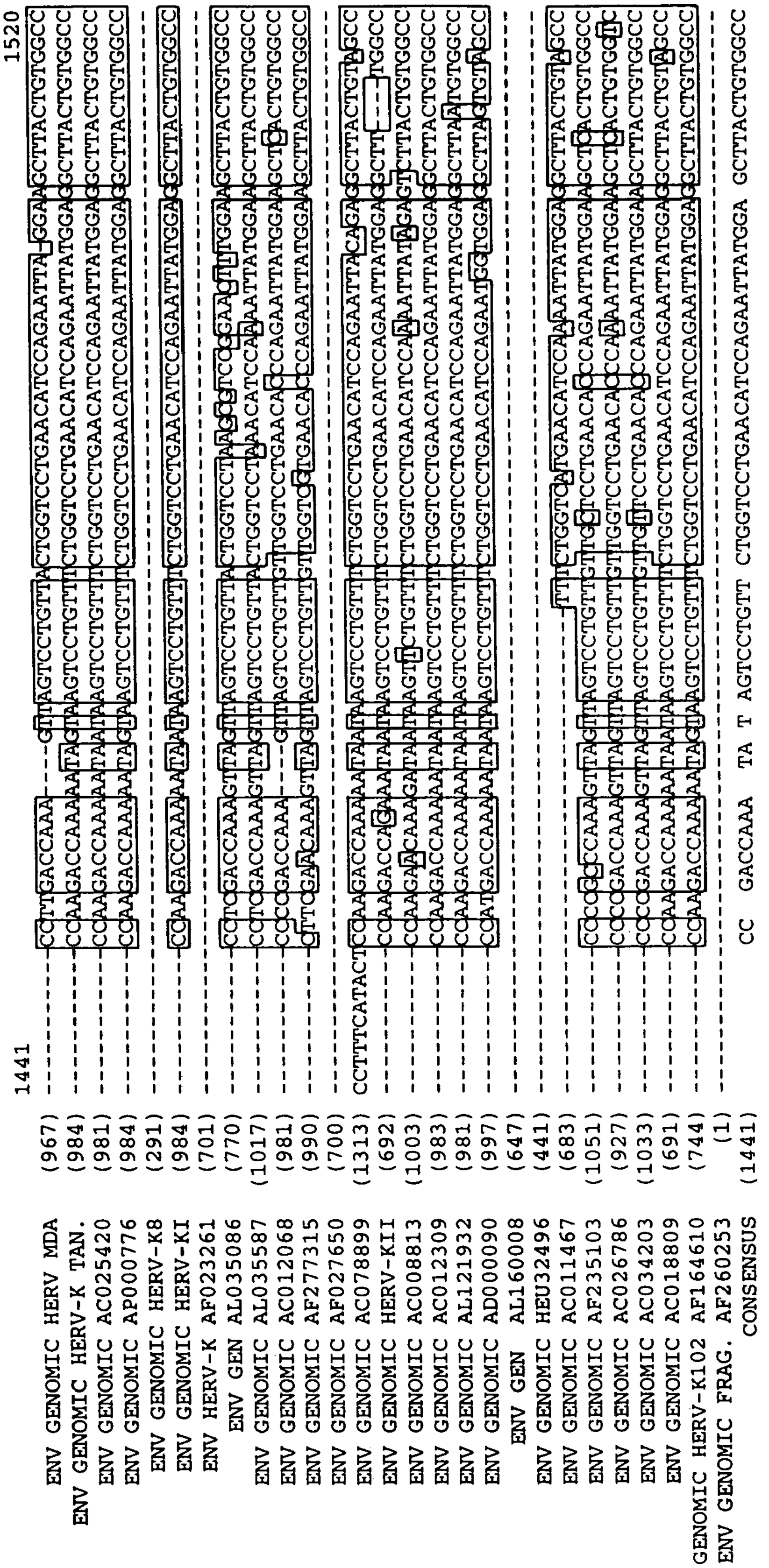
Figures 6, 7, 8, 9, 10, 11, 12, 13, 14, 15, 16, 17, 18, 19, 20, 21, 22, 23:
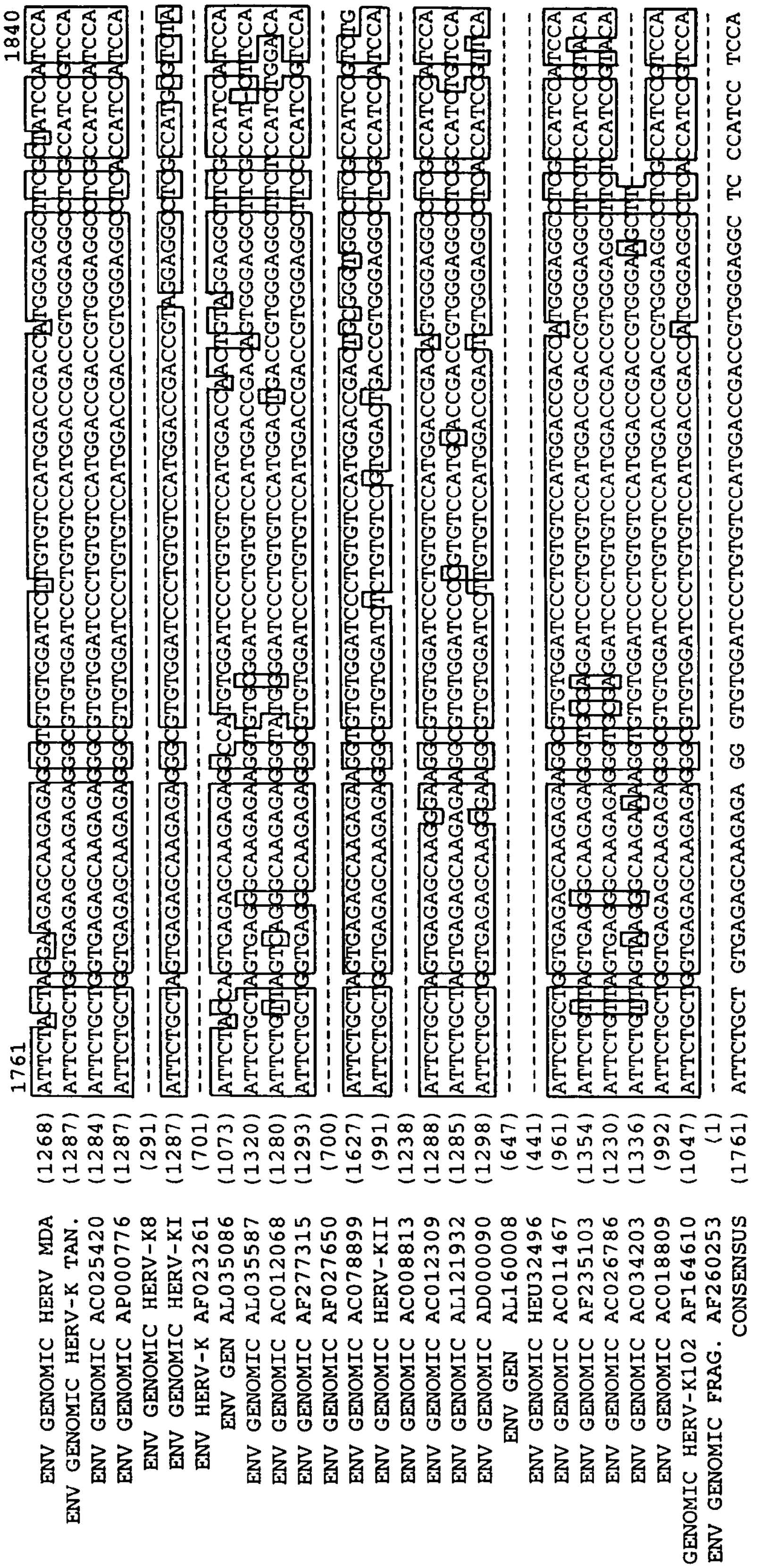
Figures 6, 7, 8, 9, 10, 11, 12, 13, 14, 15, 16, 17, 18, 19, 20, 21, 22, 23, 24, 25:
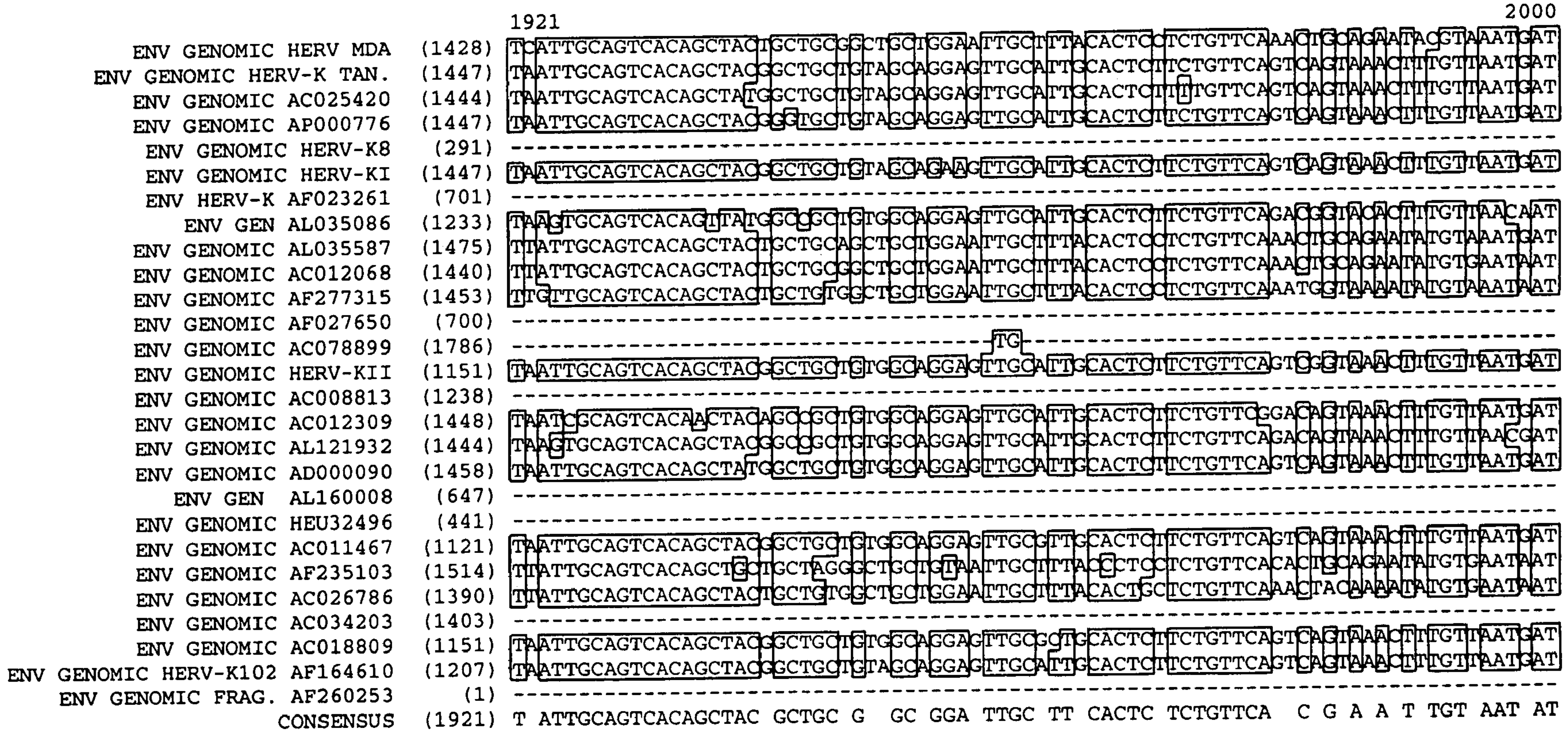
Figures 6, 7, 8, 9, 10, 11, 12, 13, 14, 15, 16, 17, 18, 19, 20, 21, 22, 23, 24, 25, 26, 27, 28, 29:
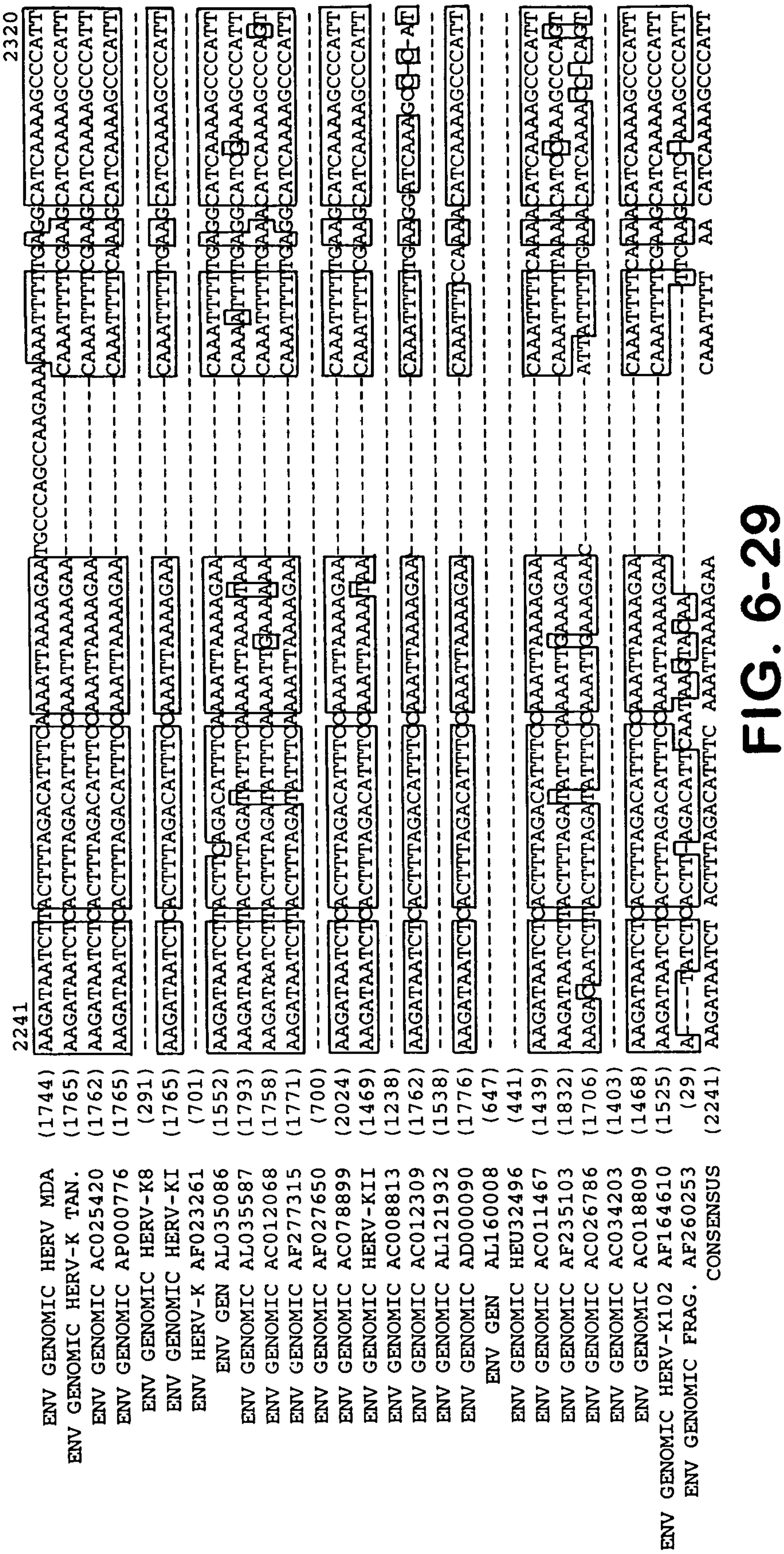
Figures 6, 7, 8, 9, 10, 11, 12, 13, 14, 15, 16, 17, 18, 19, 20, 21, 22, 23, 24, 25, 26, 27, 28, 29, 30, 31, 32, 33:
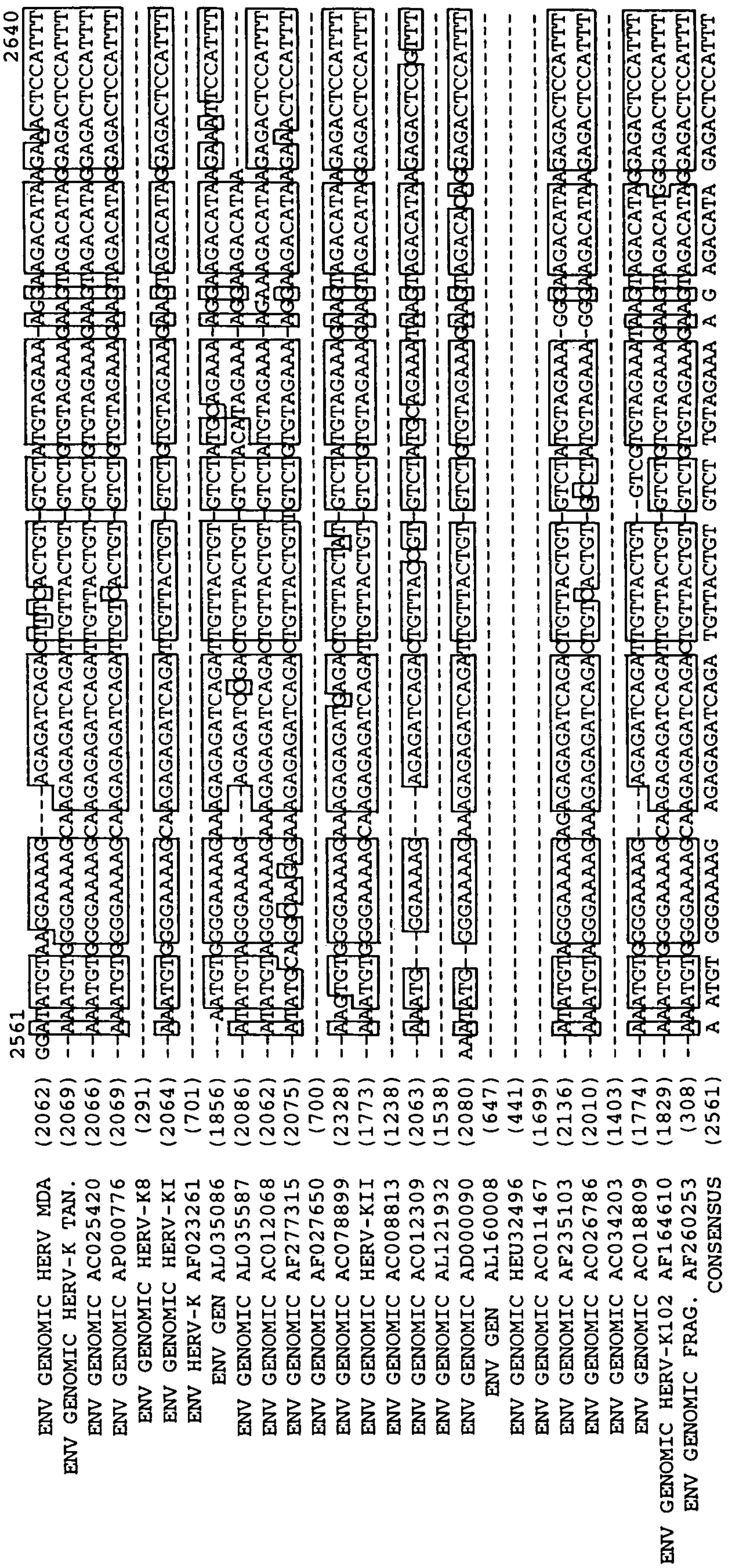

Northern blotting of prostate cancer cell lines using nucleotides 243-end of SEQ ID NO:150 labeled as a probe indicates that they express PCAV transcripts of several sizes, corresponding to both full-length viral genomic sequences and to sub-genomic spliced transcripts (FIG. 5). Expression of such transcripts have also been observed in teratocarcinoma cell lines [15], as shown in lane 1 of FIG. 14.

Investigation of Other Human Endogenous Retroviruses

HERV-K(CH) is a member of the HML-2 subgroup of the HERV-K family. HERV-K(II) and HERV-K(10) are also members of this sub-group.

The same microarray techniques as described above were used to study the expression of members of the HERV-K family in the HML-2 and HML-6 subgroups in prostate tumor tissue. The expression of HERV-H viruses was also studied.

The results in table 9 show that HERV-His not up-regulated in prostate tumors. The HML-6 subgroup of HERV-K is also not up-regulated. The only endogenous retroviruses that are up-regulated in prostate tumors are in the HML-2 subgroup.

Investigation of Tumors Other than Prostate Tumors

HML-2 endogenous retroviruses are up-regulated in prostate tumors. Tumor samples taken from patients with breast and colon cancer were investigated for up-regulation of HML-2 and HML-6 HERV-K viruses using the microarray techniques described above.

The results in table 10 show that the HML-2 viruses are up-regulated in tissue from prostate tumors, but not from colon or breast tumors. HML-6 expression is not up-regulated in any of the tumors.

Detection of HERV-K(CH) Sequences in Human Prostate Cancer Cells and Tissues.

DNA from prostate cancer tissue and other human cancer tissues, human colon, normal human tissues including non-cancerous prostate, and from other human cell lines are extracted following the procedure of ref. 202. The DNA is re-suspended in a solution containing 0.05 M Tris HCl buffer, pH 7.8, and 0.1 mM EDTA, and the amount of DNA recovered is determined by microfluorometry using Hoechst 33258 dye [ref. 203].

Polymerase chain reaction (PCR) is performed using Taq polymerase following the conditions recommended by the manufacturer (Perkin Elmer Cetus) with regard to buffer, $Mg^{2+}$, and nucleotide concentrations. Thermocycling is performed in a DNA cycler by denaturation at 94° C. for 3 min. followed by either 35 or 50 cycles of 94° C. for 1.5 min., 50° C. for 2 min. and 72° C. for 3 min. The ability of the PCR to amplify the selected regions of the HERV-K(CH) gene is tested by using a cloned HERV-K(CH) polynucleotide(s) as a positive template(s). Optimal $Mg^{2+}$, primer concentrations and requirements for the different cycling temperatures are determined with these templates. The master mix recommended by the manufacturer is used. To detect possible contamination of the master mix components, reactions without template are routinely tested.

Southern blotting and hybridization are performed as described in reference 204, using the cloned sequences labeled by the random primer procedure [205]. Prehybridization and hybridization are performed in a solution containing 6×SSPE, 5% Denhardt's, 0.5% SDS, 50% formamide, 100 μg/ml denaturated salmon testis DNA, incubated for 18 hrs at 42° C., followed by washings with 2×SSC and 0.5% SDS at room temperature and at 37° C. and finally in 0.1×SSC with 0.5% SDS at 68° C. for 30 min (ref. 8). For paraffin-embedded tissue sections the conditions described in ref. 206 are followed using primers designed to detect a 250 by sequence.

Expression of Cloned Polynucleotides in Host Cells.

To study the polypeptide products of HERV-K(CH) cDNA, restriction fragments from the HERV-K(CH) cDNA are cloned into the expression vector pMT2 (pages 16.17-16.22 of ref. 8) and transfected into COS cells grown in DMEM supplemented with 10% FCS. Transfections are performed employing calcium phosphate techniques (pages 16.32-16.40 of ref. 8) and cell lysates are prepared forty-eight hours after transfection from both transfected and untransfected COS cells. Lysates are subjected to analysis by immunoblotting using anti-peptide antibody.

In immunoblotting experiments, preparation of cell lysates and electrophoresis are performed according to standard procedures. Protein concentration is determined using BioRad protein assay solutions. After semi-dry electrophoretic transfer to nitro-cellulose, the membranes are blocked in 500 mM NaCl, 20 mM Tris, pH 7.5, 0.05% Tween-20 (TTBS) with 5% dry milk. After washing in TTBS and incubation with secondary antibodies (Amersham), enhanced chemiluminescence (ECL) protocols (Amersham) are performed as described by the manufacturer to facilitate detection.

Generation of Antibodies Against Polypeptides.

Polypeptides, unique to HERV-K(CH) are synthesized or isolated from bacterial or other (e.g. yeast, baculovirus) expression systems and conjugated to rabbit serum albumin (RSA) with m-maleimido benzoic acid N-hydroxysuccinimide ester (MBS) (Pierce, Rockford, Ill.). Immunization protocols with these peptides are performed according to standard methods. Initially, a pre-bleed of the rabbits is performed prior to immunization. The first immunization includes Freund's complete adjuvant and 500 μg conjugated peptide or 100 μg purified peptide. All subsequent immunizations, performed four weeks after the previous injection, include Freund's incomplete adjuvant with the same amount of protein. Bleeds are conducted seven to ten days after the immunizations.

For affinity purification of the antibodies, the corresponding HERV-K(CH) polypeptide is conjugated to RSA with MBS, and coupled to CNBr-activated Sepharose (Pharmacia, Sweden). Antiserum is diluted 10-fold in 10 mM Tris-HCl, pH 7.5, and incubated overnight with the affinity matrix. After washing, bound antibodies are eluted from the resin with 100 mM glycine, pH 2.5.

ELISA Assay for Detecting HERV-K(CH) Gag and/or Pol Related Sequences.

To test blood samples for antibodies that bind specifically to recombinantly produced HERV-K(CH) antigens, the following procedure is employed. After the recombinant HERV-K(CH) pol or gag or env related polypeptides are purified, the recombinant polypeptide is diluted in PBS to a concentration of 5 μg/ml (500 ng/100 μl). 100 microliters of the diluted antigen solution is added to each well of a 96-well Immulon 1 plate (Dynatech Laboratories, Chantilly, Va.), and the plate is then incubated for 1 hour at room temperature, or overnight at 4° C., and washed 3 times with 0.05% Tween 20 in PBS. Blocking to reduce nonspecific binding of antibodies is accomplished by adding to each well 200 μl of a 1% solution of bovine serum albumin in PBS/Tween 20 and incubation for 1 hour. After aspiration of the blocking solution, 100 μl of the primary antibody solution (anticoagulated whole blood, plasma, or serum), diluted in the range of 1/16 to 1/2048 in blocking solution, is added and incubated for 1 hour at room temperature or overnight at 4° C. The wells are then washed 3 times, and 100 μl goat anti-human IgG antibody conjugated to horseradish peroxidase (organon Teknika, Durham, N.C.), diluted 1/500 or 1/1000 in PBS/Tween 20, 100 μl of o-phenylenediamine dihydrochloride (OPD, Sigma) solution is added to each well and incubated for 5-15 minutes. The OPD solution is prepared by dissolving a 5 mg OPD tablet in 50 ml 1% methanol in $H_2O$ and adding 50 μl 30% $H_2O$ immediately before use. The reaction is stopped by adding 25 1 of 4M $H_2SO_4$ Absorbance are read at 490 nm in a microplate reader (Bio-Rad).

Preparation of Vaccines.

The present invention also relates to a method of stimulating an immune response against cells that express HERV-K(CH) polypeptides in a patient using HERV-K(CH) gag, and/or pol polypeptides of the invention that acts as an antigen produced by or associated with a malignant cell. This aspect of the invention provides a method of stimulating an immune response in a human against prostate cells or cells that express a HERV-K(CH) pol or gag polynucleotides and polypeptides. The method comprises the step of administering to a human an immunogenic amount of a polypeptide comprising: (a) the amino acid sequence of a human endogenous retrovirus HERV-K(CH) polypeptide or (b) a mutein or variant of a polypeptide comprising the amino acid sequence of a human endogenous retrovirus HERV-K(CH) polypeptide.

Generation of Transgenic Animals Expressing Polypeptides as a Means for Testing Therapeutics.

HERV-K(CH) nucleic acids are used to generate genetically modified non-human animals, or site specific gene modifications thereof, in cell lines, for the study of function or regulation of prostate tumor-related genes, or to create animal models of diseases, including prostate cancer. The term "transgenic" is intended to encompass genetically modified animals having an exogenous HERV-K(CH) gene(s) that is stably transmitted in the host cells where the gene(s) may be altered in sequence to produce a modified polypeptide, or having an exogenous HERV-K(CH) LTR promoter operably linked to a reporter gene. Transgenic animals may be made through a nucleic acid construct randomly integrated into the genome. Vectors for stable integration include plasmids, retroviruses and other animal viruses, YACs, and the like. Of interest are transgenic mammals, e.g. cows, pigs, goats, horses, etc., and particularly rodents, e.g. rats, mice, etc.

The modified cells or animals are useful in the study of HERV-K(CH) gene function and regulation. For example, a series of small deletions and/or substitutions may be made in the HERV-K(CH) gene to determine the role of different domains in prostate tumorigenesis. Specific constructs of interest include, but are not limited to, anti-sense constructs to block HERV-K(CH) gene expression, expression of dominant negative HERV-K(CH) gene mutations, and over-expression of a HERV-K(CH) gene. Expression of a HERV-K (CH) gene or variants thereof in cells or tissues where it is not normally expressed or at abnormal times of development is provided. In addition, by providing expression of polypeptides derived from HERV-K(CH) in cells in which it is otherwise not normally produced, changes in cellular behavior can be induced.

DNA constructs for random integration need not include regions of homology to mediate recombination. Conveniently, markers for positive and negative selection are included. For various techniques for transfecting mammalian cells, see ref. 207.

For embryonic stem (ES) cells, an ES cell line is employed, or embryonic cells is obtained freshly from a host, e.g. mouse, rat, guinea pig, etc. Such cells are grown on an appropriate fibroblast-feeder layer or grown in the presence of appropriate growth factors, such as leukemia inhibiting factor (LIF). When ES cells are transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting chimeric animals screened for cells bearing the construct. By providing for a different phenotype of the blastocyst and the ES cells, chimeric progeny can be readily detected.

The chimeric animals are screened for the presence of the modified gene and males and females having the modification are mated to produce homozygous progeny. If the gene alterations cause lethality at some point in development, tissues or organs are maintained as allogeneic or congenic grafts or transplants, or in in vitro culture. The transgenic animals may be any non-human mammal, such as laboratory animals, domestic animals, etc. The transgenic animals are used in functional studies, drug screening, etc., e.g. to determine the effect of a candidate drug on prostate cancer, to test potential therapeutics or treatment regimens, etc.

Diagnostic Imaging Using HERV-K(CH) Specific Antibodies

The present invention encompasses the use of antibodies to HERV-K(CH) polypeptides to accurately stage prostate cancer patients at initial presentation and for early detection of metastatic spread of prostate cancer. Radioimmunoscintigraphy using monoclonal antibodies specific for HERV-K(CH) gag or HERV-K(CH) pol or portions thereof or other HERV-K(CH) polypeptides can provide an additional tumor-specific diagnostic test. The monoclonal antibodies of the instant invention are used for histopathological diagnosis of prostate carcinomas.

Subcutaneous human xenografts of prostate cancer cells in nude mice is used to test whether a technetium-99m ($^{99m}$Tc)-labeled monoclonal antibody of the invention can successfully image the xenografted prostate cancer by external gamma scintography as described for seminoma cells in ref. 208. Each monoclonal antibody specific for a HERV-K(CH) polypeptide is purified from ascitic fluid of BALB/c mice bearing hybridoma tumors by affinity chromatography on polypeptide A-Sepharose. Purified antibodies, including control monoclonal antibodies such as an avidin-specific monoclonal antibody [209] are labeled with $^{99m}$Tc following reduction, using the methods of refs. 210 and 211. Nude mice bearing human prostate cancer cells are injected intraperitoneally with 200-500 μCi of $^{99nm}$Tc-labeled antibody. Twenty-four hours after injection, images of the mice are obtained using a Siemens ZLC3700 gamma camera equipped with a 6 mm pinhole collimator set approximately 8 cm from the animal. To determine monoclonal antibody biodistribution following imaging, the normal organs and tumors are removed, weighed, and the radioactivity of the tissues and a sample of the injectate are measured. Additionally, HERV-K (CH)-specific antibodies conjugated to antitumor compounds are used as prostate cancer-specific chemotherapy.

Deposits

The materials listed in Table 7 were deposited with the American Type Culture Collection.

All publications and patent applications mentioned in this specification are incorporated herein by reference to the same extent as if each individual publication or patent application were specifically and individually indicated to be incorporated by reference.

The foregoing description of preferred embodiments of the invention has been presented by way of illustration and example for purposes of clarity and understanding. It is not intended to be exhaustive or to limit the invention to the precise forms disclosed. It will be readily apparent to those of ordinary skill in the art in light of the teachings of this invention that many changes and modifications may be made thereto without departing from the spirit of the invention. It is intended that the scope of the invention be defined by the appended claims and their equivalents.

TABLE 1

GAG protease (5') probes, isolate specific

| Isolate | Nucleotides | SEQ ID |
|---|---|---|
| K(CH) | 1224-1238 | 161 |
| KII | 2098-2114 | 162 |
| K10 | 874-890 | 163 |
| | 894-908 | 164 |
| | 910-927 | 165 |
| | 927-944 | 166 |
| | 989-1004 | 167 |
| | 1019-1036 | 168 |
| | 1046-1063 | 169 |
| | 1063-1078 | 170 |
| | 1084-1103 | 171 |
| | 1131-1145 | 172 |
| | 1148-1163 | 173 |
| | 1164-1185 | 174 |
| | 1206-1223 | 175 |

TABLE 1-continued

| GAG protease (5') probes, isolate specific | | |
|---|---|---|
| Isolate | Nucleotides | SEQ ID |
| | 1216-1235 | 176 |
| | 1243-1260 | 177 |
| | 1258-2375 | 178 |
| | 1277-1295 | 179 |
| | 1300-1329 | 180 |
| | 1347-1361 | 181 |
| | 1367-1382 | 182 |
| | 1392-1410 | 183 |
| | 1412-1428 | 184 |
| | 1426-1442 | 185 |
| | 1445-1461 | 186 |
| | 1463-1477 | 187 |
| | 1490-1510 | 188 |
| | 1502-1520 | 189 |
| | 1522-1538 | 190 |
| | 1561-1576 | 191 |
| | 1586-1605 | 192 |
| | 1620-1635 | 193 |
| | 1653-1669 | 194 |
| | 1698-1723 | 195 |
| | 1722-1743 | 196 |
| | 1748-1762 | 197 |
| | 1773-1788 | 198 |
| | 1820-1834 | 199 |
| | 1872-1887 | 200 |
| | 1917-1935 | 201 |
| | 1940-1955 | 202 |
| | 1955-1969 | 203 |
| | 1973-1995 | 204 |
| | 2008-2042 | 205 |
| | 2049-2064 | 206 |
| | 2076-2093 | 207 |
| | 2097-2113 | 208 |
| | 2122-2139 | 209 |
| | 2148-2118 | 210 |
| | 2176-2196 | 211 |
| | 2198-2212 | 212 |
| | 2219-2235 | 213 |
| | 2246-2261 | 214 |

TABLE 2

| Protease (3'seq) Polymerase (5'seq) Probes | | |
|---|---|---|
| Isolate | Nucleotides | SEQ ID |
| K(CH) | 170-188 | 215 |
| consensus | 205-221 | 216 |
| | 253-268 | 217 |
| | 316-336 | 218 |
| | 401-417 | 219 |
| | 490-504 | 220 |
| | 538-552 | 221 |
| | 872-886 | 222 |
| K(CH) | 109-125 | 223 |
| | 1374-1388 | 224 |
| | 1402-1416 | 225 |
| KII | 140-159 | 110 |
| | 410-426 | 111 |
| | 1127-1141 | 112 |
| K10 | 11-38 | 113 |
| | 37-54 | 114 |
| | 70-90 | 115 |
| | 226-243 | 116 |
| | 249-264 | 117 |
| | 308-324 | 118 |
| | 327-342 | 119 |
| | 381-397 | 120 |

TABLE 2-continued

| Protease (3'seq) Polymerase (5'seq) Probes | | |
|---|---|---|
| Isolate | Nucleotides | SEQ ID |
| | 440-454 | 121 |
| | 541-557 | 122 |
| | 678-698 | 123 |
| | 722-741 | 124 |
| | 753-767 | 125 |
| | 771-785 | 126 |
| | 854-869 | 127 |
| | 872-890 | 128 |
| | 1195-1209 | 129 |
| | 1308-1323 | 130 |
| | 1335-1349 | 131 |
| | 1349-1365 | 132 |

TABLE 3

| 3' POL probes only | | |
|---|---|---|
| Isolate | Nucleotides | SEQ ID |
| K(CH) consensus | 3-17 | 133 |
| | 25-39 | 134 |
| | 82-104 | 135 |
| | 136-151 | 136 |
| | 154-169 | 137 |
| | 189-203 | 138 |
| | 322-337 | 139 |
| | 461-475 | 140 |
| | 630-645 | 141 |
| | 712-727 | 142 |
| | 757-771 | 143 |
| | 818-833 | 144 |
| KII | 1636-1651 | 145 |

TABLE 4

| ORFS and sources of initial isolates/clones from prostate cDNA libraries | | |
|---|---|---|
| HERVK ORF | Chiron Clone ID | Source of Clone |
| gag | 035JN002.E02 | Prostate Cancer Tissue, Patient 101, Gleason Grade 3 + 3 |
| gag | 035JN013.H09 | Prostate Cancer Tissue, Patient 101, Gleason Grade 3 + 3 |
| gag | 035JN023.F12 | Prostate Cancer Tissue, Patient 101, Gleason Grade 3 + 3 |
| gag | 037XN001.D10 | Normal Prostate Tissue, Pooled from 10 individuals |
| pol5' | 035JN001.F06 | Prostate Cancer Tissue, Patient 101, Gleason Grade 3 + 3 |
| pol5' | 035JN003.E06 | Prostate Cancer Tissue, Patient 101, Gleason Grade 3 + 3 |
| pol5' | 035JN013.C11 | Prostate Cancer Tissue, Patient 101, Gleason Grade 3 + 3 |
| pol5' | 035JN013.F03 | Prostate Cancer Tissue, Patient 101, Gleason Grade 3 + 3 |
| pol3' | 035JN003.G09 | Prostate Cancer Tissue, Patient 101, Gleason Grade 3 + 3 |
| pol3' | 035JN010.A09 | Prostate Cancer Tissue, Patient 101, Gleason Grade 3 + 3 |

TABLE 4-continued

ORFS and sources of initial isolates/clones from prostate cDNA libraries

| HERVK ORF | Chiron Clone ID | Source of Clone |
|---|---|---|
| pol3' | 035JN015.F06 | Prostate Cancer Tissue, Patient 101, Gleason Grade 3 + 3 |
| pol3' | 035JN020.B12 | Prostate Cancer Tissue, Patient 101, Gleason Grade 3 + 3 |
| pol3' | 035JN020.D07 | Prostate Cancer Tissue, Patient 101, Gleason Grade 3 + 3 |
| pol3' | 035JN022.G09 | Prostate Cancer Tissue, Patient 101, Gleason Grade 3 + 3 |
| pol3' | 035JN015.H02 | Prostate Cancer Tissue, Patient 101, Gleason Grade 3 + 3 |
| pol3' | 035JN016.H02 | Prostate Cancer Tissue, Patient 101, Gleason Grade 3 + 3 |

TABLE 5

Identity of HERV-K(CH) polynucleotides with HERV-K(II) and HERV-K(10)

| Clone ID | Region | % Identity HERV-K(II) | % Identity HERV-K(10) |
|---|---|---|---|
| 035JN003.G09 | 3'-pol | 89.423 | 89.423 |
| 035JN010.A09 | 3'-pol | 89.663 | 89.663 |
| 035JN015.F06 | 3'-pol | 89.423 | 89.423 |
| 035JN020.B12 | 3'-pol | 89.303 | 89.303 |
| 035JN020.D07 | 3'-pol | 89.614 | 89.614 |
| 035JN022.G09 | 3'-pol | 89.354 | 89.354 |
| 035JN002.E02 | gag | 99.524 | 79.881 |
| 035JN013.H09 | gag | 99.017 | 79.975 |
| 035JN023.F12 | gag | 98.849 | 79.335 |
| 035XN001.D10 | gag | 87.383 | 79.947 |
| 035JN001.F06 | 5'-pol | 97.211 | 88.844 |
| 035JN003.E06 | 5'-pol | 97.450 | 86.723 |
| 035JN013.C11 | 5'-pol | 97.156 | 85.444 |
| 035JN013.F03 | 5'-pol | 87.962 | 81.521 |

TABLE 6

DNA microarray results: 13 patients tumor vs. normal prostate, expression of HERV-K RNA

| | | Percent Patient with Expression Ratio | | | | Tumor/Normal mRNA Expression Ratio | | | | |
|---|---|---|---|---|---|---|---|---|---|---|
| HERVK ORF | Chiron Clone ID | >=2x | >=2.5x | >=5x | <= halfx | Pat 93 | Pat 95 | Pat 96 | Pat 97 | Pat 151 |
| gag | 035JN002.E02 | 57.1 | 42.9 | 7.1 | 0.0 | 4.8 | 3.0 | 2.1 | 1.0 | 2.3 |
| gag | 035JN013.H09 | 78.6 | 78.6 | 50.0 | 0.0 | 9.3 | 4.5 | 5.2 | 1.4 | 5.5 |
| gag | 035JN023.F12 | 78.6 | 78.6 | 57.1 | 0.0 | 9.1 | 4.1 | 5.1 | 1.6 | 5.5 |
| gag | 037XN001.D10 | 64.3 | 64.3 | 14.3 | 0.0 | 5.4 | 3.4 | 2.5 | 1.5 | 3.6 |
| pol5prime | 035JN001.F06 | 42.9 | 21.4 | 7.1 | 0.0 | 2.0 | 2.6 | 1.8 | 1.5 | 2.7 |
| pol5prime | 035JN003.E06 | 42.9 | 21.4 | 7.1 | 0.0 | 2.1 | 2.6 | 1.8 | 1.4 | 2.6 |
| pol5prime | 035JN013.C11 | 85.7 | 78.6 | 57.1 | 0.0 | 6.9 | 5.6 | 6.9 | 2.0 | 7.4 |
| pol5prime | 035JN013.F03 | 85.7 | 71.4 | 21.4 | 0.0 | 4.6 | 3.4 | 3.7 | 2.2 | 4.6 |
| pol3prime | 035JN003.G09 | 71.4 | 57.1 | 7.1 | 0.0 | 4.1 | 3.3 | 3.3 | 1.6 | 4.9 |
| pol3prime | 035JN010.A09 | 85.7 | 78.6 | 71.4 | 0.0 | 8.0 | 4.4 | 12.6 | 2.1 | 12.4 |
| pol3prime | 035JN015.F06 | 85.7 | 78.6 | 71.4 | 0.0 | 7.6 | 4.0 | 12.8 | 2.2 | 11.9 |
| pol3prime | 035JN020.B12 | 85.7 | 78.6 | 64.3 | 0.0 | 7.0 | 4.0 | 10.5 | 2.2 | 11.9 |
| pol3prime | 035JN020.D07 | 85.7 | 78.6 | 57.1 | 0.0 | 6.0 | 3.2 | 8.7 | 2.0 | 13.7 |
| pol3prime | 035JN022.G09 | 78.6 | 78.6 | 57.1 | 0.0 | 6.6 | 4.2 | 6.6 | 2.0 | 8.8 |
| pol3prime | 035JN015.H02 | 85.7 | 78.6 | 57.1 | 0.0 | 7.9 | 4.2 | 9.0 | 2.1 | 10.7 |
| pol3prime | 035JN016.H02 | 71.4 | 71.4 | 14.3 | 0.0 | 3.8 | 3.0 | 3.4 | 1.9 | 4.3 |

| | | Tumor/Normal mRNA Expression Ratio | | | | | | | |
|---|---|---|---|---|---|---|---|---|---|
| HERVK ORF | Chiron Clone ID | Pat 155 | Pat 231 | Pat 232 | Pat 251 | Pat 282 | Pat 286 | Pat 294 | Pat 351 |
| gag | 035JN002.E02 | 2.5 | 1.9 | 1.7 | 6.9 | 1.5 | 0.6 | 2.6 | 2.9 |
| gag | 035JN013.H09 | 13.8 | 4.2 | 3.5 | 31.2 | 4.5 | 1.0 | 12.1 | 8.6 |
| gag | 035JN023.F12 | 17.0 | 4.5 | 3.2 | 28.2 | 5.2 | 1.0 | 12.7 | 7.3 |
| gag | 037XN001.D10 | 4.6 | 2.9 | 1.8 | 10.0 | 1.7 | 1.0 | 3.5 | 4.3 |
| pol5prime | 035JN001.F06 | 1.8 | 2.0 | 1.8 | 7.8 | 1.2 | 1.0 | 1.9 | 2.3 |
| pol5prime | 035JN003.E06 | 1.9 | 2.0 | 1.7 | 7.7 | 1.2 | 1.0 | 1.8 | 2.1 |
| pol5prime | 035JN013.C11 | 24.0 | 4.8 | 4.3 | 37.4 | 4.4 | 1.0 | 13.1 | 8.8 |
| pol5prime | 035JN013.F03 | 8.4 | 4.1 | 3.4 | 21.8 | 2.3 | 1.0 | 5.0 | 5.8 |
| pol3prime | 035JN003.G09 | 3.3 | 2.2 | 3.5 | 14.9 | 1.5 | 1.0 | 2.5 | 3.9 |
| pol3prime | 035JN010.A09 | 55.9 | 5.1 | 9.5 | 70.0 | 5.8 | 1.0 | 26.3 | 9.7 |
| pol3prime | 035JN015.F06 | 53.4 | 5.1 | 8.0 | 69.7 | 5.9 | 1.0 | 25.3 | 9.1 |
| pol3prime | 035JN020.B12 | 34.9 | 5.0 | 6.8 | 44.5 | 5.2 | 1.0 | 15.2 | 8.1 |
| pol3prime | 035JN020.D07 | 22.9 | 4.6 | 8.6 | 58.2 | 3.8 | 1.0 | 15.0 | 7.6 |
| pol3prime | 035JN022.G09 | 12.7 | 4.5 | 5.3 | 28.0 | 2.6 | 1.0 | 5.9 | 7.8 |
| pol3prime | 035JN015.H02 | 35.3 | 4.7 | 7.5 | 49.5 | 4.8 | 1.0 | 18.2 | 8.7 |
| pol3prime | 035JN016.H02 | 5.0 | 3.0 | 3.1 | 14.1 | 1.7 | 1.0 | 2.6 | 5.0 |

TABLE 7

| DEPOSITS | | |
|---|---|---|
| Cell Line | CMCC Accession No. | ATCC Accession No. |
| 035JN003G09 | 5400 | PTA 2561 |
| 035JN010A09 | 5401 | PTA 2572 |
| 035JN015F06 | 5402 | PTA 2566 |
| 035JN015H02 | 5403 | PTA 2571 |
| 035JN020B12 | 5405 | PTA 2562 |
| 035JN020D07 | 5406 | PTA 2573 |
| 035JN022G09 | 5413 | PTA 2560 |
| 035JN002E02 | 5404 | PTA 2565 |
| 035JN013H09 | 5408 | PTA 2568 |
| 035JN023F12 | 5409 | PTA 2564 |
| 035XN001D10 | 5410 | PTA 2569 |
| 035JN001F06 | 5411 | PTA 2567 |
| 035JN003E06 | 5412 | PTA 2559 |
| 035JN013C11 | 5407 | PTA 2563 |
| 035JN013F03 | 5415 | PTA 2570 |

ATCC = American Type Culture Collection
CMCC = Chiron Master Culture Collection
All deposits made 10th April 2000

TABLE 8

| Sequence listing | |
|---|---|
| SEQ ID | DESCRIPTION |
| 1 | U5 region of herv-k(hml-2.hom) [GenBank AF074086] |
| 2 | U3 region of herv-k(hml-2.hom) |
| 3 | R region of herv-k(hml-2.hom) |
| 4 | RU5 region of herv-k(hml-2.hom) |
| 5 | U3R region of herv-k(hml-2.hom) |
| 6 | Non-coding region between U5 and first 5' splice site of herv-k(hml-2.hom) |
| 7 | Composite of three HERV-K(CH) polynucleotides [SEQ IDs 14-16] positioned in the gag region. |
| 8 & 9 | Composite of four HERV-K(CH) polynucleotides [SEQ IDs 17-20] positioned in the 5' pol region |
| 10 | Composite of six HERV-K(CH) polynucleotides [SEQ IDs 21-26] positioned in the 3' pol region |
| 11 | Consensus sequence of HERV-K(CH) gag region |
| 12 | Consensus sequence of HERV-K(CH) 5' pol region |
| 13 | Consensus sequence of HERV-K(CH) 3' pol region |
| 14 | Sequence for clone 035JN002.E02. |
| 15 | Sequence for clone 035JN023.F12. |
| 16 | Sequence for clone 035JN013.H09. |
| 17 | Sequence for clone 035JN013.C11 |
| 18 | Sequence for clone 035JN003.E06. |
| 19 | Sequence for clone 35JN001.F06. |
| 20 | Sequence for clone 035JN013.F03. |
| 21 | Sequence for clone 035JN020.D07. |
| 22 | Sequence for clone 035JN015.F06. |
| 23 | Sequence for clone 035JN003.G09. |
| 24 | Sequence for clone 035JN020.B12. |
| 25 | Sequence for clone 035JN022.G09. |
| 26 | Sequence for clone 035JN010.A09. |
| 27 | Sequence for clone 035JN002.E02. |
| 28 | Sequence for clone 035JN023.F12. |
| 29 | Sequence for clone 035JN013.H09. |
| 30 | Sequence for clone 035JN013.C11. |
| 31 | Sequence for clone 035JN003.E06. |
| 32 | Sequence for clone 035JN001.F06. |
| 33 | Sequence for clone 035JN013.F03. |
| 34 | Sequence for clone 035JN020.D07. |
| 35 | Sequence for clone 035JN015.F06. |
| 36 | Sequence for clone 035JN003.G09. |
| 37 | Sequence for clone 035JN020.B12. |
| 38 | Sequence for clone 035JN022.G09. |
| 39 | Sequence for clone 035JN010.A09. |
| 40 | Sequence for clone 037XN001.D10 and isolated from normal prostate tissue. |

TABLE 8-continued

| Sequence listing | |
|---|---|
| SEQ ID | DESCRIPTION |
| 41 | Sequence for clone 037XN001.D10 and isolated from normal prostate tissue. |
| 42 | EST polynucleotide sequence shown in GenBank accession number Q60732. |
| 43 | EST polynucleotide sequence SEQ ID 407 of WO 00/04149 |
| 44 | Polynucleotide sequence for HERV-KII |
| 45 | Polynucleotide sequence for HERV-K10 |
| 46-49 | Amino acid translations of SEQ IDs 11, 14, 15, 16 |
| 50-55 | Amino acid translations of SEQ IDs 21-26 (note PSFGK motifs) |
| 56-57 | Amino acid translations of SEQ IDs 27 & 28 |
| 58 | Consensus polypeptide sequence inferred from SEQ IDs 21-26 |
| 59-82 | Polynucleotide probes not in SEQ IDs 42-45 |
| 83 & 84 | Polynucleotide probes shared with SEQ IDs 42-45 |
| 85 | HERV-K108 gag CDS |
| 86 | HERV-K108 prt CDS |
| 87 | HERV-K108 pol CDS |
| 88 | HERV-K108 env CDS |
| 89 | HERV-K108 cORF 5' CDS |
| 90 | HERV-K108 cORF 3' CDS |
| 91 | HERV-K(C7) gag CDS |
| 92 | HERV-K(C7) gag amino acid sequence |
| 93 | HERV-K(C7) pol CDS |
| 94 | HERV-K(C7) pol amino acid sequence |
| 95 | HERV-K(C7) env CDS |
| 96 | HERV-K(C7) env amino acid sequence |
| 97 | HERV-K(II) gag CDS |
| 98 | HERV-K(II) gag amino acid sequence |
| 99 | HERV-K(II) prt CDS |
| 100 | HERV-K(II) pol CDS |
| 101 | HERV-K(II) env CDS |
| 102 | HERV-K10 gag CDS |
| 103 | HERV-K10 gag(i) |
| 104 | HERV-K10 gag(ii) |
| 105 | HERV-K10 prt CDS |
| 106 | HERV-K10 prt amino acid sequence |
| 107 | HERV-K10 pol/env CDS |
| 108 | HERV-K10 pol/env amino acid sequence |
| 109 | cORF amino acid sequence |
| 110-132 | Table 2 probes (cont[d] at SEQ IDs 215-225) |
| 133-145 | Table 3 probes |
| 146 | HML-2.HOM (‘ERVK6’) gag amino acid sequence |
| 147 | HML-2.HOM (‘ERVK6’) prt amino acid sequence |
| 148 | HML-2.HOM (‘ERVK6’) pol amino acid sequence |
| 149 | HML-2.HOM (‘ERVK6’) env amino acid sequence |
| 150 | LTR of herv-k(hml-2.hom) |
| 151-154 | HML-2 LTR sequences |
| 155 & 156 | herv-k(hml-2.hom) RU5 region (5' and 3' regions, respectively) |
| 157 | Env consensus nucleic acid sequence (FIG. 6) |
| 158 | Gag consensus sequence (FIG. 7) |
| 159 | Pol consensus sequence (FIG. 8) |
| 160 | Env consensus sequence (FIG. 9) |
| 161-214 | Table 1 probes |
| 215-225 | Table 2 probes (cont[d] from SEQ IDs 110-132) |

TABLE 9

| Expression of HERV-H and HERV-K in prostate tumors | | | |
|---|---|---|---|
| GenBank ID | HERV | HML Subgroup | Result |
| AB047240 | K | HML-2 | 65 |
| AF164611 | K | HML-2 | 63 |

TABLE 9-continued

| Expression of HERV-H and HERV-K in prostate tumors | | | |
|---|---|---|---|
| GenBank ID | HERV | HML Subgroup | Result |
| AF164612 | K | HML-2 | 63 |
| AF079797 | K | HML-6 | 3 |
| BC005351 | H | — | 0 |
| XM__054932 | H | — | 0 |

The "Result" column gives the % of patient samples which showed up-regulation of the GenBank sequence given in the first column in tumor tissue relative to non-tumor tissue.

TABLE 10

| Expression of HERV-K viruses in colon and breast tumors | | | | | |
|---|---|---|---|---|---|
| | | | Result | | |
| GenBank ID | HERV | HML Subgroup | Prostate | Breast | Colon |
| AB047240 | K | HML-2 | 65 | 0 | 2 |
| AF079797 | K | HML-6 | 3 | 6 | 0 |
| AF164611 | K | HML-2 | 63 | 0 | 2 |
| AF164612 | K | HML-2 | 63 | 6 | 2 |

The "Result" columns give the % of patient samples which showed up-regulation of the GenBank sequence given in the first column in tumor tissue relative to non-tumor tissue.

TABLE 11

HML-2-subgroup of HERV-K Family

| Query | Query Length | Target Locus | Target Description | Target Length | Score | Pscore |
|---|---|---|---|---|---|---|
| N4 | 7428 | NT__022283S1.2 | /contig__orient = none/start = 1/end = 160119/chrom = 2 Homo | 102399 | 72570 | 3.9E−47 |
| N4 | 7428 | NT__007386S1.3 | /contig__orient = complement/start = 1/end = 250001/chrom = 6 | 102399 | 72570 | 3.9E−47 |
| N4 | 7428 | NT__009509S2.3 | /contig__orient = forward/start = 250002/end = 500002/chrom = 12 | 102399 | 72379 | 5.3E−47 |
| N4 | 7428 | NT__009151S32.3 | /contig__orient = complement/start = 7623180/end = 7873180 | 102399 | 72707 | 3.1E−47 |
| N4 | 7428 | NT__023901S1.2 | /contig__orient = none/start = 1/end = 166310/chrom = 8 | 102399 | 70366 | 1.3E−45 |
| N4 | 7428 | NT__025820S3.2 | /contig__orient = complement/start = 4556361/end = 661270 | 102399 | 67986 | 5.9E−44 |
| N4 | 7428 | NT__024249S1.2 | /contig__orient = none/start = 1/end = 167403/chrom = Homo | 102399 | 67986 | 5.9E−44 |
| N4 | 7428 | NT__011519S9.5 | /contig__orient = forward/start = 2016320/end = 2266320 | 102399 | 68342 | 3.4E−44 |
| N4 | 7428 | NT__006788S1.3 | /contig__orient = complement/start = 1/end = 250000/chrom = 5 | 102399 | 68610 | 2.6E−44 |
| N4 | 7428 | NT__004858S5.3 | /contig__orient = complement/start = 999278/end = 1248551 | 102399 | 68624 | 2.1E−44 |
| N4 | 7428 | NT__005795S3.3 | /contig__orient = forward/start = 405779/end = 655779/chrom = 3 | 102399 | 67968 | 6.1E−44 |
| N4 | 7428 | NT__025140S3.3 | /contig__orient = none/start = 449919/end = 649836/chrom = 19 | 97618 | 68168 | 4.4E−44 |
| N4 | 7428 | NT__009334S8.3 | /contig__orient = complement/start = 1574760/end = 1824759 | 102399 | 65447 | 3.4E−42 |
| N4 | 7428 | NT__004406S4.3 | /contig__orient = forward/start = 797371/end = 985557/chrom = 1 | 85887 | 65099 | 6E−42 |
| N4 | 7428 | NT__011192S4.3 | /contig__orient = forward/start = 750004/end = 949429/chrom = 19 | 102399 | 62351 | 4.9E−40 |
| N4 | 7428 | NT__007592S14.3 | /contig__orient = forward/start = 3276099/end = 3526099/chrom = 6 | 102399 | 56493 | 5.7E−36 |
| N4 | 7428 | NT__011512S23.3 | /contig__orient = forward/start = 5505084/end = 5755084 | 102399 | 64096 | 3E−41 |
| N4 | 7428 | NT__019638S1.3 | /contig__orient = none/start = 1/end = 250001/chrom = 19 | 102399 | 57114 | 2.1E−36 |
| N4 | 7428 | NT__022411S1.3 | /contig__orient = none/start = 1/end = 163648/chrom = 3 | 61348 | 65630 | 2.6E−42 |
| N4 | 7428 | NT__005632S1.3 | /contig__orient = complement/start = 1/end = 214350/chrom = 3 | 102399 | 62739 | 2.6E−40 |
| N4 | 7428 | NT__022504S1.3 | /contig__orient = forward/start = 1/end = 271641/chrom = 3 | 102399 | 56001 | 1.3E−35 |
| N4 | 7428 | NT__023397S2.3 | /contig__orient = complement/start = 250002/end = 455242 | 102399 | 49492 | 4.1E−31 |
| N4 | 7428 | NT__011520S13.5 | /contig__orient = forward/start = 3068083/end = 3318083 | 102399 | 47530 | 9.6E−30 |
| N4 | 7428 | NT__019483S4.3 | /contig__orient = forward/start = 750003/end = 1000003/chrom = 8 | 102399 | 50179 | 1.4E−31 |
| N4 | 7428 | NT__019483S2.3 | /contig__orient = forward/start = 250001/end = 500001/chrom = 8 | 102399 | 50122 | 1.5E−31 |
| N4 | 7428 | NT__024033S5.3 | /contig__orient = forward/start = 1000005/end = 1250005 | 102399 | 57370 | 1.4E−36 |
| N4 | 7428 | NT__023628S1.3 | /contig__orient = complement/start1/end = 151365/chrom = 7 | 102399 | 56440 | 6.2E−36 |
| N4 | 7428 | NT__023323S1.2 | /contig__orient = none/start = 1/end = 103061/chrom = 5 Homo | 102399 | 45124 | 4.5E−28 |

| Percent Alignment | Percent Query | Matches | Similarities | Query Start | Query End | Target Start | Target End | Open Gap Penalty | Extension Penalty |
|---|---|---|---|---|---|---|---|---|---|
| 98 | 98 | 7334 | 7334 | 7428 | 1 | 13506 | 20899 | −20 | −5 |
| 98 | 98 | 7334 | 7334 | 1 | 7428 | 29800 | 37193 | −20 | −5 |
| 98 | 98 | 7329 | 7329 | 7428 | 1 | 136539 | 143951 | −20 | −5 |
| 98 | 98 | 7345 | 7345 | 1 | 7428 | 114716 | 122137 | −20 | −5 |
| 97 | 97 | 7222 | 7222 | 7428 | 1 | 94194 | 101616 | −20 | −5 |
| 95 | 95 | 7112 | 7112 | 1 | 7428 | 164603 | 172033 | −20 | −5 |
| 95 | 95 | 7112 | 7112 | 1 | 7428 | 18873 | 26303 | −20 | −5 |
| 95 | 95 | 7058 | 7058 | 1 | 7428 | 62776 | 69910 | −20 | −5 |
| 95 | 95 | 7066 | 7066 | 1 | 7428 | 144115 | 151250 | −20 | −5 |
| 95 | 95 | 7072 | 7072 | 7428 | 1 | 23642 | 30777 | −20 | −5 |
| 94 | 94 | 7040 | 7040 | 1 | 7428 | 122036 | 129165 | −20 | −5 |
| 94 | 94 | 7049 | 7049 | 7428 | 1 | 174979 | 182103 | −20 | −5 |
| 93 | 93 | 6913 | 6913 | 7428 | 1 | 116705 | 123823 | −20 | −5 |
| 92 | 93 | 6910 | 6910 | 1 | 7428 | 103675 | 110860 | −20 | −5 |
| 90 | 92 | 6844 | 6844 | 7428 | 1 | 17828 | 25313 | −20 | −5 |
| 79 | 91 | 6795 | 6795 | 1 | 7428 | 141741 | 150230 | −20 | −5 |
| 92 | 91 | 6818 | 6818 | 7428 | 38 | 93282 | 100383 | −20 | −5 |
| 82 | 90 | 6273 | 6273 | 7427 | 1 | 179318 | 187384 | −20 | −5 |
| 95 | 90 | 6734 | 6734 | 7024 | 1 | 140614 | 147637 | −20 | −5 |
| 91 | 89 | 6630 | 6630 | 7428 | 7428 | 48116 | 55040 | −20 | −5 |

TABLE 11-continued

| HML-2-subgroup of HERV-K Family | | | | | | | | | |
|---|---|---|---|---|---|---|---|---|---|
| 86 | 86 | 6420 | 6420 | 7428 | 1 | 176629 | 183705 | −20 | −5 |
| 79 | 84 | 6275 | 6275 | 1 | 7428 | 25289 | 33146 | −20 | −5 |
| 77 | 83 | 6166 | 6166 | 1 | 7425 | 146733 | 154470 | −20 | −5 |
| 82 | 83 | 6184 | 6184 | 7428 | 1 | 13951 | 21321 | −20 | −5 |
| 82 | 83 | 6177 | 6177 | 7428 | 1 | 131375 | 138737 | −20 | −5 |
| 97 | 78 | 5859 | 5859 | 1 | 5981 | 41571 | 47546 | −20 | −5 |
| 99 | 76 | 5651 | 5651 | 1772 | 7428 | 1 | 5656 | −20 | −5 |
| 82 | 75 | 5600 | 5600 | 6704 | 1 | 1 | 6758 | −20 | −5 |

REFERENCES

The Contents of which are Hereby Incorporated in Full by Reference

1 Mayer et al. (1999) *Nat. Genet.* 21. (3), 257-258 (1999)
2 Farrell (1998) *RNA Methodologies* (Academic Press; ISBN 0-12-249695-7).
3 Yang et al. (1999) *Proc Natl Acad Sci USA* 96(23):13404-8
4 Robbins et al. (1997) *Clin Lab Sci* 10(5):265-71.
5 Ylikoski et al. (1999) *Clin Chem* 45(9):1397-407
6 Ylikoski et al. (2001) *Biotechniques.* 30:832-840
7 Shirahata & Pegg (1986) *J. Biol. Chem.* 261(29):13833-7.
8 Sambrook et al. (1989) *Molecular Cloning: A Laboratory Manual. NY*, Cold Spring Harbor Laboratory
9 *Short protocols in molecular biology* (4th edition, 1999) Ausubel et al. eds. ISBN 0-471-32938-X.
10 U.S. Pat. No. 5,707,829
11 *Current Protocols in Molecular Biology* (F. M. Ausubel et al., eds., 1987) Supplement 30.
12 EP-B-0509612
13 EP-B-0505012
14 Berkhout et al. (1999) *J. Virol.* 73:2365-2375.
15 Löwer et al. (1995) *J. Virol.* 69:141-149.
16 Magin et al. (1999) *J. Virol.* 73:9496-9507.
17 Magin-Lachmann (2001) *J. Virol.* 75(21):10359-71.
18 Hashido et al. (1992) Biochem. Biophys. Res. Comm. 187:1241-1248.
19 Geysen et al. (1984) *PNAS USA* 81:3998-4002.
20 Carter (1994) *Methods Mol Biol* 36:207-23.
21 Jameson, B A et al., 1988, *CABIOS* 4(1):181-186.
22 Raddrizzani & Hammer (2000) *Brief Bioinform* 1(2):179-89.
23 De Lalla et al. (1999) *J. Immunol.* 163:1725-29.
24 Brusic et al. (1998) *Bioinformatics* 14(2):121-30
25 Meister et al. (1995) *Vaccine* 13(6):581-91.
26 Roberts et al. (1996) *AIDS Res Hum Retroviruses* 12(7): 593-610.
27 Maksyutov & Zagrebelnaya (1993) *Comput Appl Biosci* 9(3):291-7.
28 Feller & de la Cruz (1991) *Nature* 349(6311):720-1.
29 Hopp (1993) *Peptide Research* 6:183-190.
30 Welling et al. (1985) *FEBS Lett.* 188:215-218.
31 Davenport et al. (1995) *Immunogenetics* 42:392-297.
32 Smith and Waterman, Adv. Appl. Math. (1981) 2: 482-489.
33 Go et al, Int. J. Peptide Protein Res. (1980) 15:211
34 Querol et al., Prot. Eng. (1996) 9:265
35 Olsen and Thomsen, J. Gen. Microbiol. (1991) 137:579
36 Clarke et al., Biochemistry (1993) 32:4322
37 Wakarchuk et al., Protein Eng. (1994) 7:1379
38 Toma et al., Biochemistry (1991) 30:97
39 Haezerbrouck et al., Protein Eng. (1993) 6:643
40 Masul et al., Appl. Env. Microbiol. (1994) 60:3579
41 U.S. Pat. No. 4,959,314
42 Breedveld (2000) *Lancet* 355(9205):735-740.
43 Gorman & Clark (1990) *Semin. Immunol.* 2:457-466
44 Jones et al., *Nature* 321:522-525 (1986)
45 Morrison et al., *Proc. Natl. Acad. Sci, U.S.A.,* 81:6851-6855 (1984)
46 Morrison and Oi, *Adv. Immunol.,* 44:65-92 (1988)
47 Verhoeyer et al., *Science* 239:1534-1536 (1988)
48 Padlan, *Molec. Immun.* 28:489-498 (1991)
49 Padlan, *Molec. Immunol.* 31(3):169-217 (1994).
50 Kettleborough, C. A. et al., *Protein Eng.* 4(7):773-83. (1991).
51 Chothia et al., *J. Mol. Biol.* 196:901-917 (1987)
52 Kabat et al., U.S. Dept. of Health and Human Services NIH Publication No. 91-3242 (1991)
53 U.S. Pat. No. 5,530,101.
54 U.S. Pat. No. 5,585,089.
55 WO 98/24893
56 WO 91/10741
57 WO 96/30498
58 WO 94/02602
59 U.S. Pat. No. 5,939,598.
60 WO 96/33735
61 WO 93/14778
62 Findeis et al., *Trends Biotechnol.* (1993) 11:202
63 Chiou et al. (1994) *Gene Therapeutics: Methods And Applications Of Direct Gene Transfer*. ed. Wolff
64 Wu et al., *J. Biol. Chem.* (1988) 263:621
65 Wu et al., *J. Biol. Chem.* (1994) 269:542
66 Zenke et al., *Proc. Natl. Acad. Sci.* (*USA*) (1990) 87:3655
67 Wu et al., *J. Biol. Chem.* (1991) 266:338
68 Jolly, *Cancer Gene Therapy* (1994) 1:51
69 Kimura, *Human Gene Therapy* (1994) 5:845
70 Connelly, *Human Gene Therapy* (1995) 1:185
71 Kaplitt, *Nature Genetics* (1994) 6:148
72 WO 90/07936
73 WO 94/03622
74 WO 93/25698
75 WO 93/25234
76 U.S. Pat. No. 5,219,740
77 WO 93/11230
78 WO 93/10218
79 U.S. Pat. No. 4,777,127
80 GB Patent No. 2,200,651
81 EP-A-0 345 242
82 WO 91/02805
83 WO 94/12649
84 WO 93/03769
85 WO 93/19191
86 WO 94/28938
87 WO 95/11984
88 WO 95/00655
89 Curiel, *Hum. Gene Ther.* (1992). 3:147

90 Wu, *J. Biol. Chem.* (1989) 264:16985
91 U.S. Pat. No. 5,814,482
92 WO 95/07994
93 WO 96/17072
94 WO 95/30763
95 WO 97/42338
96 WO 90/11092
97 U.S. Pat. No. 5,580,859
98 U.S. Pat. No. 5,422,120
99 WO 95/13796
100 WO 94/23697
101 WO 91/14445
102 EP 0524968
103 Philip, *Mol. Cell Biol.* (1994)14:2411
104 Woffendin, *Proc. Natl. Acad. Sci.* (1994) 91:11581
105U.S. Pat. No. 5,206,152
106 WO 92/11033
107U.S. Pat. No. 5,149,655
108U.S. Pat. No. 5,206,152
109 WO 92/11033
110 WO90/14837
111 *Vaccine Design—the subunit and adjuvant approach* (1995) ed. Powell & Newman
112 WO00/07621
113 GB-2220221
114 EP-A-0689454
115 EP-A-0835318
116 EP-A-0735898
117 EP-A-0761231
118 WO99/52549
119 WO01/21207
120 WO01/21152
121 WO00/62800
122 WO00/23105
123 WO99/11241
124 WO98/57659
125 WO93/13202.
126 McSharry (1999) *Antiviral Res* 43(1):1-21.
127 Kuhelj et al. (2001) *J Biol Chem* 276(20):16674-82.
128 Schommer et al. (1996) *J Gen Virol* 77:375-379.
129 Magin et al. (2000) *Virology* 274:11-16.
130. Boese et al. (2001) *FEBS Lett* 493(2-3):117-21.
131 Larsson, E., et al., Current Topics in Microbiology and Immunology 148:115 (1989)
132 Mariani-Costantini, et al., J. Virol. 63:4982 (1989) and Shih, et al., Virology 182:495 (1991)
133. Tönjes et al. (1996) *J. AIDS Hum. Retrovir.* 13(Suppl 1):S261-S267.
134 Barbulescu et al., Curr. Biol. 9:861 (1999)
135 Ono, et al., J. Virol. 58:937 (1986)
136 Löwer et al., Proc. Natl. Acad. Sci USA 90:4480 (1993)
137 Ono et al., (1986) *J. Virol.* 60:589
138 Boller, et al., Virol. 196:349 (1993)
139 Yang et al., Proc. Natl. Acad. Sci USA 96:13404 (1999)
140 Mueller-Lantzsch et al., AIDS Research and Human Retroviruses 9:343-350 (1993)
141 Herbst et al., Amer. J. Pathol. 149:1727 (1996)
142 U.S. Pat. No. 5,858,723
143 Löwer et al., Proc. Natl. Acad. Sci USA 93:5177 (1996)
144 Löwer et al., Virology 192:501 (1993)
145 Genbank accession number AB047240
146 Andersson et al. (1999) *J. Gen. Virol.* 80:255-260.
147 Zsiros et al. (1998) *J. Gen. Virol.* 79:61-70.
148 Tönjes et al. (1999) *J. Virol.* 73:9187-9195.
149 Johnston et al. (2001) *Ann Neurol* 50(4):434-42.
150 Medstrand et al. (1998) *J Virol* 72(12):9782-7.
151 U.S. Pat. No. 5,010,175
152 International patent application WO 91/17823.
153 U.S. Pat. No. 4,816,567.
154 Merrifeld, *J. Am. Chem. Soc.* 85:2149, 1963
155 Caprin and Han, *J. Org. Chem.* 37:3404, 1972
156 Milstein and Kohler, *Nature* 256:495-497, 1975
157 Gulfre and Milstein, *Methods in Enzymology: Immunochemical Techniques* 73:1-46
158 Langone and Banatis eds., Academic Press, 1981
159 Altschul et al. *Nucleic Acids Res.* (1997) 25:3389-3402
160 Brutlag et al. *Comp. Chem.* (1993) 17:203
161 Schena et al. (1996) Proc Natl Acad Sci USA. 93(20): 10614-9
162 Schena et al. (1995) Science 270(5235):467-70
163 Shalon et al. (1996) Genome Res. 6(7):639-45
164 U.S. Pat. No. 5,807,522
165 European patent application 0799897
166 WO 97/29212
167 WO 97/27317
168 European patent application 0785280
169 WO 97/02357
170 U.S. Pat. No. 5,593,839
171 U.S. Pat. No. 5,578,832
172 European patent application 0728520
173 U.S. Pat. No. 5,599,695
174 European patent application 0721016.
175 U.S. Pat. No. 5,556,752
176 WO 95/22058
177 U.S. Pat. No. 5,631,734
178 Pappalarado et al., *Sem. Radiation Oncol.* (1998) 8:217
179 Ramsay *Nature Biotechnol.* (1998) 16:40
180 U.S. Pat. No. 5,134,854
181 U.S. Pat. No. 5,445,934
182 WO 95/35505
183 U.S. Pat. No. 5,631,734
184 U.S. Pat. No. 5,800,992
185 WO92/02526.
186 U.S. Pat. No. 5,124,246.
187 Mullis et al., *Meth. Enzymol.* (1987)155:335
188 U.S. Pat. No. 4,683,195
189 U.S. Pat. No. 4,683,202
190 Saiki et al. (1985) *Science* 239:487
191 Hanahan et al. Cell 100:57-70 (2000)
192 Weissman S M Mol Biol. Med. 4(3), 133-143 (1987
193 Patanjali, et al. Proc. Natl. Acad. Sci. USA 88 (1991)
194 Simone et al. Am J Pathol. 156(2):445-52 (2000)
195 Clayerie (1996) Meth. Enzymol. 266:212-227.
196 *Automated DNA Sequencing and Analysis Techniques* Adams et al., eds., Chap. 36, p. 267 Academic Press, San Diego, 1994
197 Clayerie et al. *Comput. Chem.* (1993) 17:191
198 Altschul et. al, J. Mol. Biol., 215:403-410, 1990
199 Pearson & Lipman, PNAS, 85:2444, 1988
200 Luo et al. (1999) *Nature Med* 5:117-122
201 Higgins & Sharp CABIOS 5; 151-153 (1989)
202 Delli Bovi et al. (1986, Cancer. Res. 46:6333-6338)
203 Cesarone, C. et al., Anal Biochem 100:188-197 (1979)
204 Southern, E. M., J. Mol. Biol. 98:503-517 (1975)
205 Feinberg, A. P., et al., 1983, Anal. Biochem. 132:6-13
206 Wright and Manos (1990, in "PCR Protocols", Innis et al., eds., Academic. Press, pp. 153-158)
207 Keown et. al., Methods in Enzymology 185:527-537 (1990)
208 Marks, et al., Brit. J. Urol. 75:225 (1995)
209 Skea, et al., J. Immunol. 151:3557 (1993)
210 Mather, et al., J. Nucl. Med. 31:692 (1990)
211 Zhang et al., Nucl. Med. Biol. 19:607 (1992)

The invention claimed is:

1. A method of screening for early stage prostate cancer, the method comprising a step of assaying, in a patient sample comprising prostate cells, an RNA comprising a Gag or Pol encoding sequence of a human endogenous mouse mammary tumor virus (MMTV)-like subgroup 2 (HML-2) retrovirus, HERV-K (CH), wherein an increased level of said RNA of at least 150% relative to a control sample level of RNA from cells that are not prostate tumor cells indicates that the patient should undergo further testing for the presence of prostate cancer.

2. The method of claim 1 wherein the RNA comprises a Pol encoding sequence of HERV-K(CH).

3. The method of claim 2 wherein the RNA comprises a nucleotide sequence corresponding to a DNA sequence of SEQ ID NO:26.

4. The method of claim 1 wherein the step of assaying is preceded by a step of enriching RNA in the patient sample.

5. The method of claim 1 wherein the expression product is detected using Polymerase Chain Reaction (PCR), Strand Displacement Amplification (SDA), Self Sustaining Sequence Replication (SSSR), Ligase Chain Reaction (LCR), Transcription Mediated Amplification (TMA) or Nucleic Acid Sequence Based Amplification (NASBA).

6. The method of claim 5 wherein the PCR is Reverse-Transcription PCR (RT-PCR).

7. The method of claim 1 wherein the RNA comprises a Gag encoding sequence of HERV-K(CH).

* * * * *